United States Patent
Finke et al.

(10) Patent No.: US 7,091,211 B2
(45) Date of Patent: Aug. 15, 2006

(54) CYCLOPENTYL MODULATORS OF CHEMOKINE RECEPTOR ACTIVITY

(75) Inventors: Paul E. Finke, Milltown, NJ (US);
Jennifer L. Loebach, Westfield, NJ (US); Kerry A. Parker, Edison, NJ (US); Christopher W. Plummer, Hoboken, NJ (US); Sander G. Mills, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 55 days.

(21) Appl. No.: 10/901,414

(22) Filed: Jul. 28, 2004

(65) Prior Publication Data

US 2005/0070609 A1    Mar. 31, 2005

Related U.S. Application Data

(60) Provisional application No. 60/491,481, filed on Jul. 31, 2003.

(51) Int. Cl.
*A61K 31/438* (2006.01)
*C07D 401/04* (2006.01)

(52) U.S. Cl. ........................................ 514/278; 546/18

(58) Field of Classification Search ................ 546/18; 514/278

See application file for complete search history.

(56) References Cited

U.S. PATENT DOCUMENTS

| | | | |
|---|---|---|---|
| 5,468,469 A | 11/1995 | Aszalos et al. |
| 5,607,936 A | 3/1997 | Chiang et al. |
| 5,869,496 A | 2/1999 | Hale et al. |
| 5,962,462 A | 10/1999 | Mills et al. |
| 6,013,644 A | 1/2000 | Mills et al. |
| 6,358,979 B1 | 3/2002 | Finke et al. |
| 6,432,981 B1 | 8/2002 | Finke et al. |
| 6,472,410 B1 | 10/2002 | Finke et al. |
| 6,500,844 B1 | 12/2002 | Finke et al. |
| 6,506,777 B1 | 1/2003 | Finke et al. |
| 6,538,002 B1 | 3/2003 | Finke et al. |
| 6,593,346 B1 | 7/2003 | Finke et al. |

FOREIGN PATENT DOCUMENTS

| | | |
|---|---|---|
| WO | WO 94/17045 A1 | 8/1994 |
| WO | WO 94/29309 A1 | 12/1994 |
| WO | WO 96/10568 A1 | 4/1996 |
| WO | WO 01/78707 A1 | 10/2001 |

OTHER PUBLICATIONS

Devalaraj et al Multiple Chemotactic factors : fine control or redundancy , 1999.*
Dean et al Genetic Restrictions of HIV-1 Infection and Progression to AIDS by a Deletion Allele of the CKR5 Structural Gene 1996.*
Fauci Anthony et al Acquired Immunodeficiency Syndrome—1984.*
Choe et al The B- Chemokine Receptors CCR3 and CCR5 Facilitate Infection by Primary HIV-1 Isolates-1996.*
Murphy, P., et al., "The Molecular Biology of Leukocyte Chemoattractant Receptors", Annual Review of Immunology, vol. 12, No. 1, pp. 593-633 (1994).
Schall, T.J. "Biology of the RANTES/SIS Cytokine Family", Cytokine, vol. 3, No. 3, pp. 165-183 (1991).
Deng, H., et al., "Identification of a Major Co-receptor for Primary Isolates of HIV-1", Nature, vol. 381, pp. 661-666 (1996).
Horuk, R., "Molecular Properties of the Chemokine Receptor Family", Trends in Pharmaceutical Science, vol. 15, pp. 159-165 (1994).
Ben-Baruch, A., et al., "Monocyte Chemotactic Protein-3 (MCP3) Interacts with Multiple Leukocyte Receptors", Journal of Biological Chemistry, vol. 270, No. 38, pp. 22123-22128 (1995).
Neote, K., et al., "Molecular Cloning, Functional Expression, and Signaling Chracteristics of a C-C Chemokine Receptor", Cell, vol. 72, pp. 145-425 (1993).
Combadiere, C., et al., "Cloning and Functional Expression of a Human Eosinophil CC Chemokine Receptor", Journal of Biological Chemistry, vol. 270, No. 27, pp. 16491-16494 (1995).
Power, C.A., et al., "Molecular Cloning and Functional Expression of a Novel CC Chemokine Receptor cDNA from a Human Basophilic Cell Line", Journal of Biological Chemistry, vol. 270, No. 33, pp. 19495-19500 (1995).

(Continued)

*Primary Examiner*—Rita Desai
(74) *Attorney, Agent, or Firm*—Kenneth R. Walton; Valerie J. Camara

(57) ABSTRACT

Cyclopentyl compounds of Formula (I) are modulators of chemokine receptor activity:

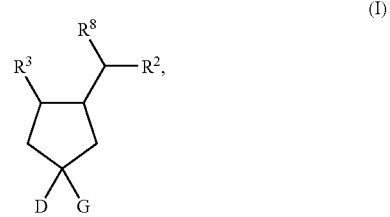

wherein D, G, $R^2$, $R^3$ and $R^8$ in Formula (I) are defined herein. The compounds, and pharmaceutically acceptable salts and individual diastereomers thereof, are useful in the treatment and prevention of HIV infection, in delaying the onset of AIDS, and in the treatment of AIDS. The compounds are also useful for treating other diseases and conditions mediated by chemokine receptors.

20 Claims, No Drawings

OTHER PUBLICATIONS

Samson, M., et al., "Molecular Cloning and Functional Expression of a New Human CC-Chemokine Receptor Gene", vol. 35, pp. 3362-3367 (1996).

Chaudhuri, A., et al., "Expression of the Duffy Antigen in K562 Cells", Journal of Biological Chemistry, vol. 269, No. 11, pp. 7835-7838 (1994).

Kita, H., et al., "Chemokines Active on Eosiniphils: Potential Roles in Allergic Inflammation", J. Exp. Med., vol. 183, pp. 2421-2126 (1996).

Smith, D.H., et al., "Blocking of HIV-1 Infectivity by a Soluble, Secreted Form of the CD4 Antigen", vol. 238, pp. 1704-1707 (1987).

Levy, J.A., "Infection by Human Immunodeficiency Virus—CD4 is Not Enough", N. Engl. J. Med., vol. 335, No. 20, pp. 1528-1530 (1996).

Dragic, T., et al., "HIV-1 Entry into CD4+ Cells is Mediated by the Chemokine Receptor CC-CKR-5", Nature, vol. 381, pp. 667-673 (1996).

Wu, L., et al., "CD4-induced Interaction of Primary HIV-1 gp120 Glycoproteins with the Chemokine Receptor CCR-5", Nature, vol. 384, pp. 179-183 (1996).

Trkola, A., et al., "CD4-dependent, Antibody-sensitive, Interactions Between HIV-1 and its Co-receptor CCR-5", Nature, vol. 384, pp. 184-187 (1996).

Samson, M., et al., "Resistance to HIV-1 Infection in Caucasian Individuals Bearing Mutant Alleges of the CCR-5 Chemokine Receptor Gene", Nature, vol. 382, pp. 722-725 (1996).

Hill, M.C., et al., "Natural Resistance to HIV?", Nature, vol. 382, pp. 668-669 (1996).

Huang, Y., et al., "The Role of a Mutant CCR5 Allele in HIV-1 Transmission and Disease Progression", Nature Medicine, vol. 2, No. 11, pp. 1240-1243 (1996).

Zhang, L., et al., "HIV-1 subtype and Seond-receptor Use", Nature, vol. 383, p. 768 (1996).

* cited by examiner

CYCLOPENTYL MODULATORS OF CHEMOKINE RECEPTOR ACTIVITY

This application claims the benefit of U.S. Provisional Application No. 60/491,481, filed Jul. 31, 2003, the disclosure of which is hereby incorporated by reference in its entirety.

FIELD OF THE INVENTION

The present invention is directed to cyclopentyl compounds that can modulate the activity of chemokine receptors such as CCR3 and CCR5 chemokine receptors. The compounds can be used to prevent or treat diseases and conditions in which chemokine receptors are involved. The compounds are useful, for example, for preventing or treating HIV infection and AIDS.

BACKGROUND OF THE INVENTION

The references cited throughout the present application are not admitted to be prior art to the claimed invention. Information presented in this section of the application is not admitted to be prior art to the claimed invention.

Chemokines are chemotactic cytokines that are released by a wide variety of cells to attract macrophages, T cells, eosinophils, basophils and neutrophils to sites of inflammation (reviewed in Schall, Cytokine, 3, 165–183 (1991) and Murphy, Rev. Immun., 12, 593–633 (1994)). There are two classes of chemokines, C-X-C ($\alpha$) and C—C ($\beta$), depending on whether the first two cysteines are separated by a single amino acid (C-X-C) or are adjacent (C—C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng et al., Nature, 381, 661–666 (1996)).

The chemokines bind specific cell-surface receptors belonging to the family of G-protein-coupled seven-transmembrane-domain proteins (reviewed in Horuk, Trends Pharm. Sci., 15, 159–165 (1994)) which are termed "chemokine receptors." On binding their cognate ligands, chemokine receptors transduce an intracellular signal through the associated trimeric G protein, resulting in a rapid increase in intracellular calcium concentration. There are at least sixteen human chemokine receptors that bind or respond to $\beta$-chemokines with the following characteristic pattern: CCR1 (or "CKR-1" or "CC-CKR-1") [MIP-1$\alpha$, MIP-1$\beta$, MCP-3, RANTES] (Ben-Barruch et al., J. Biol. Chem., 270, 22123–22128 (1995); Beote, et al, Cell, 72, 415–425 (1993)); CCR2A and CCR2B (or "CKR-2A"/"CKR-2B" or "CC-CKR-2A"/"CC-CKR-2B") [MCP-1, MCP-3, MCP4]; CCR3 (or "CKR-3" or "CC-CKR-3") [eotaxin, RANTES, MCP-3] (Combadiere et al., J. Biol. Chem., 270, 16491–16494 (1995); CCR4 (or "CKR-4" or "CC-CKR-4") [MIP-1$\alpha$, RANTES, MCP-1] (Power et al., J. Biol. Chem., 270, 19495–19500 (1995)); CCR5 (or "CKR-5" or "CC-CKR-5") [MIP-1$\alpha$, RANTES, MIP-1$\beta$] (Sanson et al., Biochemistry, 35, 3362–3367 (1996)); and the Duffy blood-group antigen [RANTES, MCP-1] (Chaudhun et al., J. Biol. Chem., 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR1, CCR2, CCR2A, CCR2B, CCR3, CCR4, CCR5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita et al., J. Exp. Med. 183, 2421–2426 (1996). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. Certain compounds have been demonstrated to inhibit the replication of HIV, including soluble CD4 protein and synthetic derivatives (Smith et al., Science, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells; however, fusin does not promote entry of macrophagetropic viruses which are believed to be the key pathogenic strains of HIV in vivo. It has been recognized that for efficient entry into target cells, human immunodeficiency viruses require a chemokine receptor, most probably CCR5 or CXCR-4, as well as the primary receptor CD4 (Levy, N. Engl. J. Med., 335(20), 1528–1530 (Nov. 14 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng et al., Nature, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that $\beta$-chemokine ligands prevent HIV-1 from fusing with the cell (Dragic et al., Nature, 381, 667–673 (1996)). It has further been demonstrated that a complex of gp120 and soluble CD4 interacts specifically with CCR5 and inhibits the binding of the natural CCR5 ligands MIP-1$\alpha$ and MIP-1$\beta$ (Wu et al., Nature, 384, 179–183 (1996); Trkola et al., Nature, 384, 184–187 (1996)).

Humans who are homozygous for mutant CCR5 receptors which are not expressed on the cell surface appear to be unusually resistant to HIV-1 infection and are not immunocompromised by the presence of this genetic variant (Nature, 382, 722–725 (1996)). Absence of CCR5 appears to confer substantial protection from HIV-1 infection (Nature, 382, 668–669 (1996)). Other chemokine receptors may be used by some strains of HIV-1 or may be favored by non-sexual routes of transmission. Although most HIV-1 isolates studied to date utilize CCR5 or fusin, some can use both as well as the related CCR2B and CCR3 as co-receptors (*Nature Medicine,* 2(11), 1240–1243 (1996)). Nevertheless, drugs targeting chemokine receptors may not be unduly compromised by the genetic diversity of HIV-1 (Zhang et al., *Nature,* 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β.

The present invention is directed to certain 3-(aryl or heteroaryl)-4-((spiropiperidin-1-yl)alkyl)cyclopentyl compounds that are modulators of chemokine receptor activity and the uses of these compounds for preventing or treating conditions or diseases in which chemokine receptors are involved. References of interest with respect to the present invention include the following:

WO 94/17045, WO 94/29309, and WO 96/10568 disclose certain spiro-substituted azacycles as tachykinin antagonists.

U.S. Pat. Nos. 5,962,462 and 6,013,644 disclose certain spiro-substituted azacycles which are modulators of chemokine receptor activity.

U.S. Pat. Nos. 6,500,844, 6,538,002, 6,472,410, 6,358,979, 6,506,777 and 6,432,981 disclose certain cyclopentyl compounds which are modulators of chemokine receptor activity.

WO 01/78707 discloses a method for inhibiting the rejection of transplanted grafts by administration of an antagonist of CCR5 function to the graft recipient.

SUMMARY OF THE INVENTION

The present invention is directed to compounds and pharmaceutically acceptable salts thereof which inhibit the entry of HIV into target cells and are of value in the treatment and/or prevention of infection by HIV and in the delay in the onset, treatment, and/or prevention of AIDS. These compounds are modulators of chemokine receptor activity and are also useful in delaying the onset of, treating, or preventing certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. More particularly, the present invention includes compounds of Formula I:

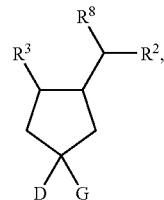

or a pharmaceutically acceptable salt and/or an individual diastereomer thereof, wherein:

D and G are defined as follows:

(A) D is —H and G is

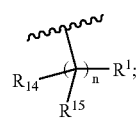

(B) D is $R^7$ and G is

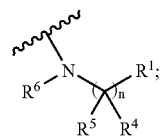

or (C) D is $R^{15}$ and G is $R^1$;

(D) D is —H and G is

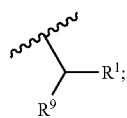

or (E) D and G together form

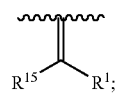

$R^1$ is:
(1) —$CO_2H$,
(2) —$C(=O)NR^yR^z$,
(3) tetrazolyl,
(4) —$SO_2NHCO$—$R^u$, or
(5) —$P(O)(OH)_2$;

$R^2$ is:

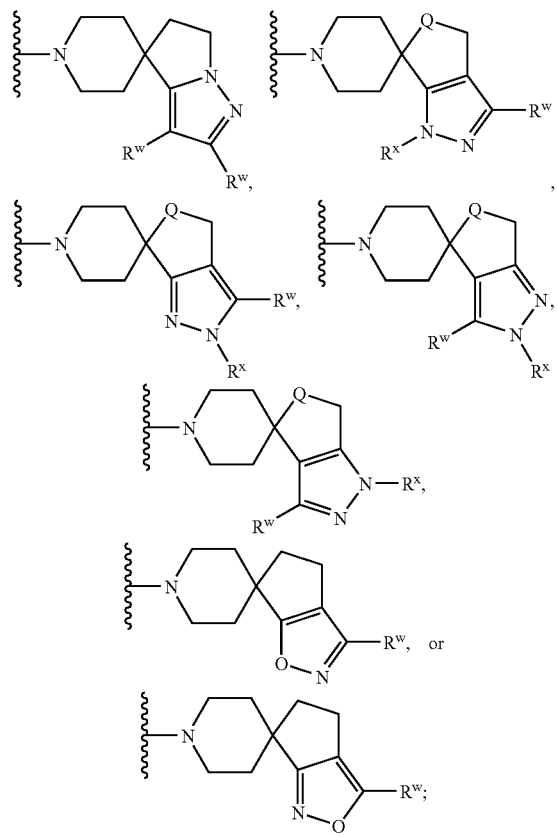

wherein Q is O or $CH_2$;

$R^3$ is phenyl or a 5- or 6-membered heteroaromatic ring containing from 1 to 4 heteroatoms each of which is independently N, O or S; wherein the phenyl or the heteroaromatic ring is optionally substituted with from 1 to 5 substituents each of which is independently:
(a) halo,
(b) —$C_{1-3}$ haloalkyl,
(c) —OH,
(d) —$C_{1-3}$ alkyl,
(e) —O—$C_{1-3}$ alkyl,
(f) —$CO_2R^u$,
(g) —$NR^uR^v$, or
(h) —C(=O)$NR^uR^v$;

$R^4$, $R^5$ and $R^6$ are defined as follows:
(A) each of $R^4$, $R^5$ and $R^6$ is independently —H, —$C_{1-10}$ alkyl, —$C_{3-8}$ cycloalkyl, —$C_{2-10}$ alkenyl, —$C_{2-10}$ alkynyl, phenyl, —$C_{1-6}$ alkyl-phenyl, —$C_{1-6}$ alkyl-$C_{3-8}$ cycloalkyl, naphthyl, biphenyl, HetA, or HetB; wherein HetA is a 5- or 6-membered heteroaromatic ring containing from 1 to 4 heteroatoms each of which is independently N, O or S; and HetB is a 5- or 6-membered unsaturated, non-aromatic heterocyclic ring containing from 1 to 4 heteroatoms each of which is independently N, O, or S; and wherein the alkyl, cycloalkyl, alkenyl, alkynyl, phenyl, phenylalkyl, cycloalkylalkyl, naphthyl, biphenyl, HetA, or HetB is optionally subsituted with from 1 to 5 substituents each of which is independently:

(a) halo,
(b) —$C_{1-3}$ haloalkyl,
(c) —OH,
(d) —$C_{1-3}$ alkyl,
(e) —O—$C_{1-3}$ alkyl,
(f) —$CO_2R^u$,
(g) —$NR^uR^v$, or
(h) —C(=O)$NR^uR^v$;

(B) with the proviso that n is 1, $R^6$ is as defined in (A); and $R^4$ and $R^5$ are joined together to form with the carbon atom to which both are attached a 3- to 8-membered saturated carbocyclic ring which is optionally substituted with from 1 to 5 substituents each of which is independently:
(a) halo,
(b) —$C_{1-3}$ haloalkyl,
(c) —OH,
(d) —$C_{1-3}$ alkyl,
(e) —O—$C_{1-3}$ alkyl,
(f) —$CO_2R^u$,
(g) —$NR^uR^v$, or
(h) —C(=O)$NR^uR^v$; or (C) with the proviso that n is 1, $R^4$ is as defined in (A); and $R^5$ and $R^6$ are joined together to form with the carbon to which $R^5$ is attached and the nitrogen to which $R^6$ is attached a 3- to 8-membered saturated monoazacarbocyclic ring which has $R^1$ as a substituent on a ring carbon alpha to the ring nitrogen and which is optionally substituted with from 1 to 5 substituents each of which is independently:
(a) halo,
(b) —$C_{1-3}$ haloalkyl,
(c) —OH,
(d) —$C_{1-3}$ alkyl,
(e) —O—$C_{1-3}$ alkyl,
(f) —$CO_2R^u$,
(g) —$NR^uR^v$, or
(h) —C(=O)$NR^uR^v$;

$R^7$ is —H or —$C_{1-6}$ alkyl;
$R^8$ is —H or —$C_{1-6}$ alkyl;
$R^9$ is —$NR^sR^t$,
$R^{14}$ is —H or —$C_{1-10}$ alkyl;
$R^{15}$ is —H, —$NR^sR^t$, —$C_{1-10}$ alkyl, —$C_{2-10}$ alkenyl, —$C_{3-8}$ cycloalkyl, —$C_{5-8}$ cycloalkenyl, or —$C_{1-6}$ alkyl-$C_{3-8}$ cycloalkyl; wherein the alkyl, alkenyl, cycloalkyl, cycloalkenyl, or the cycloalkylalkyl is optionally subsituted with from 1 to 5 substituents each of which is independently:
(a) halo,
(b) —$C_{1-3}$ haloalkyl,
(c) —OH,
(d) —$C_{1-3}$ alkyl, or
(e) —O—$C_{1-3}$ alkyl;

$R^s$ and $R^t$ are each independently —H, —$C_{1-6}$ alkyl, or —$C_{1-6}$ alkyl-$C_{3-8}$ cycloalkyl;
each $R^u$ is independently —H, —$C_{1-6}$ alkyl, —$C_{5-6}$ cycloalkyl, benzyl or phenyl, wherein the alkyl, cycloalkyl, benzyl, or phenyl is optionally substituted with from 1 to 3 substituents each of which is independently halo, —$C_{1-3}$ alkyl, —O—$C_{1-3}$ alkyl, or —$C_{1-3}$ haloalkyl;
each $R^v$ is independently —H, —$C_{1-6}$ alkyl, —$C_{5-6}$ cycloalkyl, benzyl or phenyl, wherein the alkyl, cycloalkyl, benzyl, or phenyl is optionally substituted with from 1 to 3 substituents each of which is independently halo, —$C_{1-3}$ alkyl, —O—$C_{1-3}$ alkyl, or —$C_{1-3}$ haloalkyl;

each $R^w$ is independently —H, —$C_{1-6}$ alkyl, —$C_{1-6}$ haloalkyl, —O—$C_{1-6}$ alkyl, —O—$C_{1-6}$ haloalkyl, or —$C_{1-6}$ alkyl-aryl; wherein the aryl in the arylalkyl group is optionally substituted with from 1 to 5 substituents each of which is independently halo, —$C_{1-6}$ alkyl, or —O—$C_{1-6}$ alkyl;

$R^x$ is —H, —$C_{1-6}$ alkyl, —$C_{1-6}$ haloalkyl, or —$C_{1-6}$ alkyl-aryl; wherein the aryl in the arylalkyl group is optionally substituted with from 1 to 5 substituents each of which is independently halo, —$C_{1-6}$ alkyl, or —O—$C_{1-6}$ alkyl;

$R^y$ and $R^z$ are each independently —H or —$C_{1-6}$ alkyl; and n is an integer which is equal to 1, 2, 3, or 4.

The present invention also includes pharmaceutical compositions comprising a compound of Formula I, or a pharmaceutically acceptable salt and/or an individual diastereomer thereof, and a pharmaceutically acceptable carrier, and optionally one or more other excipients and/or one or more other active agents suitable for delaying the onset of, treating or preventing HIV infection or AIDS or other diseases or conditions in which chemokine receptors are involved.

Other embodiments, aspects and features of the present invention are either further described in or will be apparent from the ensuing description, examples and appended claims.

DETAILED DESCRIPTION OF THE INVENTION

The present invention includes cyclopentyl compounds of Formula I above. These compounds (including diastereomers) and their pharmaceutically acceptable salts are modulators of chemokine receptor activity, including but not limited to, the activity of CCR3 and CCR5 chemokine receptors. In particular, many of the compounds are antagonists of CCR5 chemokine receptor activity.

A first embodiment of the present invention is a compound of Formula I, or a pharmaceutically acceptable salt and/or an individual diastereomer thereof, wherein $R^1$ is —$CO_2H$, —C(=O)$NR^yR^z$, or tetrazolyl; and all other variables are as originally defined above.

A second embodiment of the present invention is a compound of Formula I, or a pharmaceutically acceptable salt and/or an individual diastereomer thereof, wherein $R^1$ is —$CO_2H$ or —C(=O)$NH_2$; and all other variables are as originally defined above.

A third embodiment of the present invention is a compound of Formula I, or a pharmaceutically acceptable salt and/or an individual diastereomer thereof, wherein $R^1$ is —$CO_2H$; and all other variables are as originally defined above.

A fourth embodiment of the present invention is a compound of Formula I, or a pharmaceutically acceptable salt and/or an individual diastereomer thereof, wherein $R^2$ is:

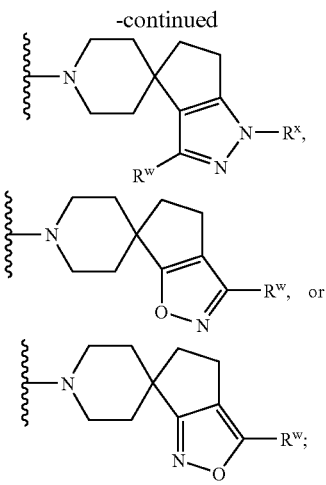

and all other variables are as originally defined above.

A fifth embodiment of the present invention is a compound of Formula I, or a pharmaceutically acceptable salt and/or an individual diastereomer thereof, wherein $R^2$ is:

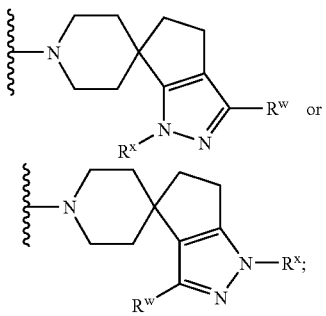

and all other variables are as originally defined above.

Aspects of the present invention include a compound of Formula I, or a pharmaceutically acceptable salt and/or an individual diastereomer thereof, as defined in either one of the fourth and fifth embodiments, wherein:

$R^w$ is —H, —$C_{1-4}$ alkyl, —$C_{1-4}$ fluoroalkyl, —O—$C_{1-4}$ alkyl, —O—$C_{1-4}$ fluoroalkyl, or —$C_{1-3}$ alkyl-phenyl; wherein the phenyl in the phenylalkyl group is optionally substituted with from 1 to 4 substituents each of which is independently halo, —$C_{1-4}$ alkyl, or —O—$C_{1-4}$ alkyl; and $R^x$ is —H, —$C_{1-4}$ alkyl, —$C_{1-4}$ fluoroalkyl, or —$C_{1-3}$ alkyl-phenyl; wherein the phenyl in phenylalkyl group is optionally substituted with from 1 to 4 substituents each of which is independently halo, —$C_{1-4}$ alkyl, or —O—$C_{1-4}$ alkyl.

Other aspects of the present invention include a compound of Formula I, or a pharmaceutically acceptable salt and/or an individual diastereomer thereof, as defined in either one of the fourth and fifth embodiments, wherein:

$R^w$ is —H, —$C_{1-3}$ alkyl, —$CF_3$, —O—$C_{1-3}$ alkyl, —O—$CF_3$, or benzyl; wherein the benzyl ring is optionally substituted with from 1 to 3 substituents each of which is independently bromo, chloro, fluoro, —$C_{1-3}$ alkyl, or —O—$C_{1-3}$ alkyl; and $R^x$ is —H, —$C_{1-3}$ alkyl, or —$CF_3$.

Still other aspects of the present invention include a compound of Formula I, or a pharmaceutically acceptable salt and/or an individual diastereomer thereof, wherein $R^1$ is as defined in any one of the first, second and third embodiments; $R^2$ is as defined in either one of the fourth and fifth embodiments; and all other variables are as originally defined above or as defined in a preceding aspect.

A sixth embodiment of the present invention is a compound of Formula I, or a pharmaceutically acceptable salt and/or an individual diastereomer thereof, wherein $R^3$ is phenyl or a 5- or 6-membered heteroaromatic ring containing a total of from 1 to 4 heteroatoms independently selected from zero to 4 N atoms, from zero to 2 O atoms, and from zero to 2 S atoms; wherein the phenyl or the heteroaromatic ring is optionally substituted with from 1 to 3 substituents each of which is independently:
(a) halo,
(b) —$C_{1-3}$ fluoroalkyl,
(c) —OH,
(d) —$C_{1-3}$ alkyl, or
(e) —O—$C_{1-3}$ alkyl;
and all other variables are as originally defined above.

A seventh embodiment of the present invention is a compound of Formula I, or a pharmaceutically acceptable salt and/or an individual diastereomer thereof, wherein $R^3$ is phenyl or thienyl; and wherein the phenyl or thienyl is optionally substituted with from 1 to 3 substituents each of which is independently:
(a) halo,
(b) —$CF_3$,
(c) —OH,
(d) —$C_{1-3}$ alkyl, or
(e) —O—$C_{1-3}$ alkyl;
and all other variables are as originally defined above.

An eighth embodiment of the present invention is a compound of Formula I, or a pharmaceutically acceptable salt and/or an individual diastereomer thereof, wherein $R^3$ is phenyl or thienyl; and wherein the phenyl or thienyl is optionally substituted with from 1 to 3 substituents each of which is independently:
(a) fluoro,
(b) chloro,
(c) —$CF_3$,
(d) —OH, or
(e) —$C_{1-3}$ alkyl;
and all other variables are as originally defined above.

A ninth embodiment of the present invention is a compound of Formula I, or a pharmaceutically acceptable salt and/or an individual diastereomer thereof, wherein $R^3$ is:
(1) phenyl optionally substituted with from 1 to 4 substituents each of which is independently fluoro or chloro, or
(2) thienyl;
and all other variables are as originally defined.

A tenth embodiment of the present invention is a compound of Formula I, or a pharmaceutically acceptable salt and/or an individual diastereomer thereof, wherein $R^3$ is phenyl, 3-fluorophenyl, 3,4-difluorophenyl, or 3,5-difluorophenyl; and all other variables are as originally defined above.

Further aspects of the present invention include a compound of Formula I, or a pharmaceutically acceptable salt and/or an individual diastereomer thereof, wherein $R^1$ is as defined in any one of the first, second and third embodiments; $R^2$ is as defined in either one of the fourth and fifth embodiments; $R^3$ is as defined in any one of sixth, seventh, eighth, ninth and tenth embodiments; and all other variables are as originally defined above or as defined in a preceding aspect.

An eleventh embodiment of the present invention is a compound of Formula I, or a pharmaceutically acceptable salt and/or an individual diastereomer thereof, wherein $R^8$ is —H or —$CH_3$; and all other variables are as originally defined above.

A twelfth embodiment of the present invention is a compound of Formula I, or a pharmaceutically acceptable salt and/or an individual diastereomer thereof, wherein $R^8$ is —H; and all other variables are as originally defined above.

Further aspects of the present invention include a compound of Formula I, or a pharmaceutically acceptable salt and/or an individual diastereomer thereof, wherein $R^1$ is as defined in any one of the first, second and third embodiments; $R^2$ is as defined in either one of the fourth and fifth embodiments; $R^3$ is as defined in any one of sixth, seventh, eighth, ninth and tenth embodiments; $R^8$ is as defined in either one of the eleventh and twelfth embodiments; and all other variables are as originally defined above or as defined in a preceding aspect.

A thirteenth embodiment of the present invention is a compound of Formula II, or a pharmaceutically acceptable salt and/or an individual diastereomer thereof:

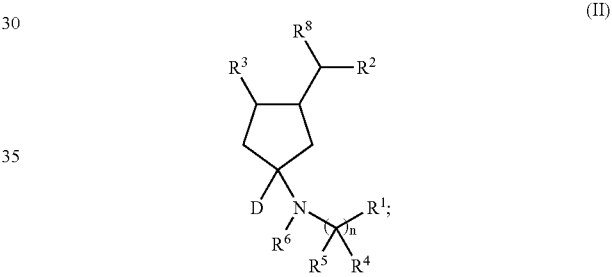

wherein all the variables are as originally defined above.

A fourteenth embodiment of the present invention is a compound of Formula II, or a pharmaceutically acceptable salt and/or an individual diastereomer thereof, wherein $R^1$ is —$CO_2H$; and all other variables are as defined in the thirteenth embodiment.

A fifteenth embodiment of the present invention is a compound of Formula II, or a pharmaceutically acceptable salt and/or an individual diastereomer thereof, wherein $R^2$ is as defined in the fourth embodiment; and all other variables are as defined in the thirteenth embodiment. In an aspect of this embodiment, $R^1$ is —$CO_2H$.

A sixteenth embodiment of the present invention is a compound of Formula II, or a pharmaceutically acceptable salt and/or an individual diastereomer thereof, wherein $R^2$ is as defined in the fifth embodiment; and all other variables are as defined in the thirteenth embodiment. In an aspect of this embodiment, $R^1$ is —$CO_2H$.

Aspects of the present invention include a compound of Formula II, or a pharmaceutically acceptable salt and/or an individual diastereomer thereof, as defined in either one of the fifteenth and sixteenth embodiments, wherein:

$R^w$ is —H, —$C_{1-4}$ alkyl, —$C_{1-4}$ fluoroalkyl, —O—$C_{1-4}$ alkyl, —O—$C_{1-4}$ fluoroalkyl, or —$C_{1-3}$ alkyl-phenyl;
wherein the phenyl in the phenylalkyl group is optionally substituted with from 1 to 4 substituents each of which is independently halo, —$C_{1-4}$ alkyl, or —O—$C_{1-4}$ alkyl; and $R^x$ is —H, —$C_{1-4}$ alkyl, —$C_{1-4}$ fluoroalkyl, or —$C_{1-3}$ alkyl-phenyl; wherein the phenyl in phenylalkyl group is optionally substituted with from 1 to 4 substituents each of which is independently halo, —$C_{1-4}$ alkyl, or —O—$C_{1-4}$ alkyl.

Other aspects of the present invention include a compound of Formula II, or a pharmaceutically acceptable salt and/or an individual diastereomer thereof, as defined in either one of the fifteenth and sixteenth embodiments, wherein:

$R^w$ is —H, —$C_{1-3}$ alkyl, —$CF_3$, —O—$C_{1-3}$ alkyl, —O—$CF_3$, or benzyl; wherein the benzyl ring is optionally substituted with from 1 to 3 substituents each of which is independently bromo, chloro, fluoro, —$C_{1-3}$ alkyl, or —O—$C_{1-3}$ alkyl; and $R^x$ is —H, —$C_{1-3}$ alkyl, or —$CF_3$.

A seventeenth embodiment of the present invention is a compound of Formula II, or a pharmaceutically acceptable salt and/or an individual diastereomer thereof, wherein $R^3$ is as defined in the sixth embodiment; and all other variables are as defined in the thirteenth embodiment.

An eighteenth embodiment of the present invention is a compound of Formula II, or a pharmaceutically acceptable salt and/or an individual diastereomer thereof, wherein $R^3$ is phenyl which is optionally substituted with from 1 to 3 substituents each of which is independently:
(a) halo,
(b) —$CF_3$,
(c) —OH,
(d) —$C_{1-3}$ alkyl, or
(e) —O—$C_{1-3}$ alkyl;

and all other variables are as defined in the thirteenth embodiment.

A nineteenth embodiment of the present invention is a compound of Formula II, or a pharmaceutically acceptable salt and/or an individual diastereomer thereof, wherein $R^3$ is phenyl which is optionally substituted with from 1 to 3 substituents each of which is independently:
(a) halo,
(b) —$CF_3$,
(c) —OH,
(d) —$C_{1-3}$ alkyl, or
(e) —O—$C_{1-3}$ alkyl;

and all other variables are as defined in the thirteenth embodiment.

A twentieth embodiment of the present invention is a compound of Formula II, or a pharmaceutically acceptable salt and/or an individual diastereomer thereof, wherein $R^3$ is phenyl, 3-fluorophenyl, 3,4-difluorophenyl, or 3,5-difluorophenyl; and all other variables are as defined in the thirteenth embodiment.

Further aspects of the present invention include a compound of Formula II, or a pharmaceutically acceptable salt and/or an individual diastereomer thereof, wherein $R^1$ is —$CO_2H$; $R^2$ is as defined in either one of the fifteenth and sixteenth embodiments; $R^3$ is as defined in any one of seventeenth, eighteenth, nineteenth and twentieth embodiments; and all other variables are as defined in the thirteenth embodiment or as defined in a preceding aspect.

A twenty-first embodiment of the present invention is a compound of Formula II, or a pharmaceutically acceptable salt and/or an individual diastereomer thereof, wherein $R^4$ is —H or —$C_{1-3}$ alkyl; and all other variables are as defined in the thirteenth embodiment.

A twenty-second embodiment of the present invention is a compound of Formula II, or a pharmaceutically acceptable salt and/or an individual diastereomer thereof, wherein $R^4$ is —H; and all other variables are as defined in the thirteenth embodiment.

Further aspects of the present invention include a compound of Formula II, or a pharmaceutically acceptable salt and/or an individual diastereomer thereof, wherein $R^1$ is —$CO_2H$; $R^2$ is as defined in either one of the fifteenth and sixteenth embodiments; $R^3$ is as defined in any one of seventeenth, eighteenth, nineteenth and twentieth embodiments; $R^4$ is as defined in either one of the twenty-first and twenty-second embodiments; and all other variables are as defined in the thirteenth embodiment or as defined in a preceding aspect.

A twenty-third embodiment of the present invention is a compound of Formula II, or a pharmaceutically acceptable salt and/or an individual diastereomer thereof, wherein $R^5$ is —H, —$C_{1-6}$ alkyl, —$C_{3-8}$ cycloalkyl, —$C_{1-6}$ alkyl-$C_{3-8}$ cycloalkyl, or phenyl; and all other variables are as defined in the thirteenth embodiment.

A twenty-fourth embodiment of the present invention is a compound of Formula II, or a pharmaceutically acceptable salt and/or an individual diastereomer thereof, wherein $R^5$ is —H, methyl, n-propyl, isopropyl, n-butyl, t-butyl, isobutyl, sec-butyl, cyclohexyl, —$CH_2$-cyclopropyl, —$CH_2$-cyclobutyl, or phenyl; and all other variables are as defined in the thirteenth embodiment.

A twenty-fifth embodiment of the present invention is a compound of Formula II, or a pharmaceutically acceptable salt and/or an individual diastereomer thereof, wherein $R^5$ is isopropyl, isobutyl, sec-butyl, or cyclohexyl.

Further aspects of the present invention include a compound of Formula II, or a pharmaceutically acceptable salt and/or an individual diastereomer thereof, wherein $R^1$ is —$CO_2H$; $R^2$ is as defined in either one of the fifteenth and sixteenth embodiments; $R^3$ is as defined in any one of seventeenth, eighteenth, nineteenth and twentieth embodiments; $R^4$ is as defined in either one of the twenty-first and twenty-second embodiments; $R^5$ is as defined in any one of the twenty-third, twenty-fourth and twenty-fifth embodiments; and all other variables are as defined in the thirteenth embodiment or as defined in a preceding aspect.

A twenty-sixth embodiment of the present invention is a compound of Formula II, or a pharmaceutically acceptable salt and/or an individual diastereomer thereof, wherein $R^6$ is —H, —$C_{1-6}$ alkyl, —$C_{3-8}$ cycloalkyl, —$C_{1-6}$ alkyl-$C_{3-8}$ cycloalkyl, phenyl, or benzyl; and all other variables are as defined in the thirteenth embodiment.

A twenty-seventh embodiment of the present invention is a compound of Formula II, or a pharmaceutically acceptable salt and/or an individual diastereomer thereof, wherein $R^6$ is —H, methyl, n-butyl, t-butyl, isobutyl, sec-butyl, —$CH_2$-cyclopropyl, —$CH_2$-cyclobutyl, or cyclohexyl; and all other variables are as defined in the thirteenth embodiment.

Further aspects of the present invention include a compound of Formula II, or a pharmaceutically acceptable salt and/or an individual diastereomer thereof, wherein $R^1$ is —$CO_2H$; $R^2$ is as defined in either one of the fifteenth and sixteenth embodiments; $R^3$ is as defined in any one of seventeenth, eighteenth, nineteenth and twentieth embodiments; $R^4$ is as defined in either one of the twenty-first and twenty-second embodiments; $R^5$ is as defined in any one of the twenty-third, twenty-fourth and twenty-fifth embodiments; $R^6$ is as defined in either one of the twenty-sixth and twenty-seventh embodiments; and all other variables are as defined in the thirteenth embodiment or as defined in a preceding aspect.

A twenty-eighth embodiment of the present invention is a compound of Formula II, or a pharmaceutically acceptable salt and/or an individual diastereomer thereof, wherein $R^7$ is —H or —$CH_3$; and all other variables are as defined in the thirteenth embodiment.

A twenty-ninth embodiment of the present invention is a compound of Formula II, or a pharmaceutically acceptable salt and/or an individual diastereomer thereof, wherein $R^7$ is —H; and all other variables are as defined in the thirteenth embodiment.

Further aspects of the present invention include a compound of Formula II, or a pharmaceutically acceptable salt and/or an individual diastereomer thereof, wherein $R^1$ is —$CO_2H$; $R^2$ is as defined in either one of the fifteenth and sixteenth embodiments; $R^3$ is as defined in any one of seventeenth, eighteenth, nineteenth and twentieth embodiments; $R^4$ is as defined in either one of the twenty-first and twenty-second embodiments; $R^5$ is as defined in any one of the twenty-third, twenty-fourth and twenty-fifth embodiments; $R^6$ is as defined in either one of the twenty-sixth and twenty-seventh embodiments; $R^7$ is as defined in either one of the twenty-eighth and twenty-ninth embodiments; and all other variables are as defined in the thirteenth embodiment or as defined in a preceding aspect.

A thirtieth embodiment of the present invention is a compound of Formula II, or a pharmaceutically acceptable salt and/or an individual diastereomer thereof, wherein n is an integer which is 1; and all other variables are as defined in the thirteenth embodiment.

Further aspects of the present invention include a compound of Formula II, or a pharmaceutically acceptable salt and/or an individual diastereomer thereof, wherein $R^1$ is —$CO_2H$; $R^2$ is as defined in either one of the fifteenth and sixteenth embodiments; $R^3$ is as defined in any one of seventeenth, eighteenth, nineteenth and twentieth embodiments; $R^4$ is as defined in either one of the twenty-first and twenty-second embodiments; $R^5$ is as defined in any one of the twenty-third, twenty-fourth and twenty-fifth embodiments; $R^6$ is as defined in either one of the twenty-sixth and twenty-seventh embodiments; $R^7$ is as defined in either one of the twenty-eighth and twenty-ninth embodiments; n is an integer which is 1; and all other variables are as defined in the thirteenth embodiment or as defined in a preceding aspect.

A first class of compounds of the present invention are compounds of Formula IIA or IIB:

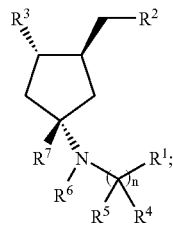

(IIA)

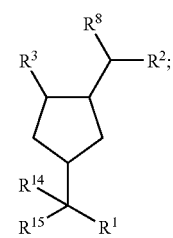

(IIB)

and pharmaceutically acceptable salts thereof; wherein each of the variables is as defined in the thirteenth embodiment. Sub-classes of the first class include the groups of compounds in which one of the variables $R^1$, $R^2$, $R^3$, $R^4$, etc. directly or indirectly depicted in Formula IIA or IIB is as defined in any one of the preceding embodiments. Other sub-classes include the groups of compounds in which two or more of the variables $R^1$, $R^2$, $R^3$, $R^4$, etc. directly or indirectly depicted in Formula IIA or IIB are as defined in any one of the preceding embodiments.

A thirty-first embodiment of the present invention is a compound of Formula III, or a pharmaceutically acceptable salt and/or an individual diastereomer thereof:

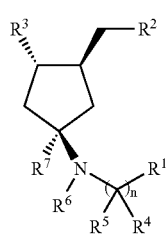

(III)

wherein all the variables are as originally defined above.

A thirty-second embodiment of the present invention is a compound of Formula III, or a pharmaceutically acceptable salt and/or an individual diastereomer thereof, wherein $R^1$ is —$CO_2H$; and all other variables are as defined in the thirty-first embodiment.

A thirty-third embodiment of the present invention is a compound of Formula III, or a pharmaceutically acceptable salt and/or an individual diastereomer thereof, wherein $R^{14}$ is —H or —$C_{1-3}$ alkyl; and all other variables are as defined in the thirty-first embodiment. In an aspect of this embodiment, $R^1$ is —$CO_2H$.

A thirty-fourth embodiment of the present invention is a compound of Formula m, or a pharmaceutically acceptable salt and/or an individual diastereomer thereof, wherein $R^{14}$ is —H; and all other variables are as defined in the thirty-first embodiment. In an aspect of this embodiment, $R^1$ is —$CO_2H$.

Further aspects of the present invention include a compound of Formula III, or a pharmaceutically acceptable salt and/or an individual diastereomer thereof, wherein $R^1$ is —$CO_2H$; $R^{14}$ is as defined in either one of the thirty-third and thirty-fourth embodiments; and all other variables are as defined in the thirty-first embodiment.

A thirty-fifth embodiment of the present invention is a compound of Formula III, or a pharmaceutically acceptable salt and/or an individual diastereomer thereof, wherein $R^{15}$ is —NR$^s$R$^t$ or —C$_{1-6}$ alkyl; and R$^s$ and R$^t$ are each independently —H, —C$_{1-6}$ alkyl, or —C$_{1-4}$ alkyl-C$_{3-6}$ cycloalkyl, with the proviso that R$^s$ and R$^t$ are not both —H; and all other variables are as defined in the thirty-first embodiment.

A thirty-sixth embodiment of the present invention is a compound of Formula III, or a pharmaceutically acceptable salt and/or an individual diastereomer thereof, wherein R$^{15}$ is —NH(—C$_{1-4}$ alkyl), —N(—C$_{1-4}$ alkyl)$_2$, or —C$_{1-4}$ alkyl; and all other variables are as defined in the thirty-first embodiment.

Further aspects of the present invention include a compound of Formula III, or a pharmaceutically acceptable salt and/or an individual diastereomer thereof, wherein R$^1$ is —CO$_2$H; R$^{14}$ is as defined in either one of the thirty-third and thirty-fourth embodiments; R$^{15}$ is as defined in either one of the thirty-fifth and thirty-sixth embodiments; and all other variables are as defined in the thirty-first embodiment.

A second class of compounds of the present invention are compounds of Formula IIIA or IIIB:

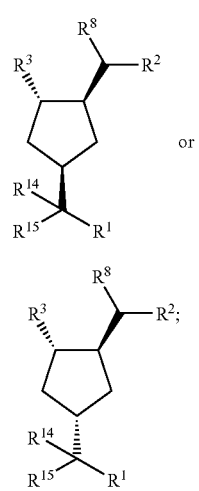

(IIIA)

or (IIIB)

and pharmaceutically acceptable salts thereof, wherein each variable is as defined in the thirty-first embodiment. Subclasses of the second class include the groups of compounds in which one of the variables R$^1$, R$^2$, R$^3$, R$^8$, R$^{14}$, R$^{15}$, etc. directly or indirectly depicted in Formula IIIA or IIIB is as defined in any one of the preceding embodiments. Other sub-classes include the groups of compounds in which two or more of the variables R$^1$, R$^2$, R$^3$, R$^8$, R$^{14}$, R$^{15}$, etc. directly or indirectly depicted in Formula IIIA or IIIB are as defined in any one of the preceding embodiments. A subclass of particular interest includes compounds of Formula IIIA1 and IIIB1:

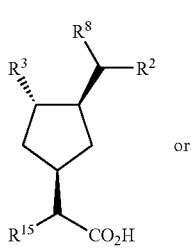

(IIIA1)

or (IIIB1)

and pharmaceutically acceptable salts thereof, wherein each variable is as defined in the thirty-first embodiment.

A thirty-seventh embodiment of the present invention is a compound of Formula IV, or a pharmaceutically acceptable salt and/or an individual diastereomer thereof:

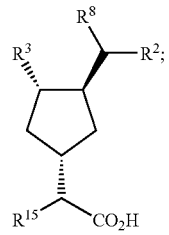

(IV)

wherein all the variables are as originally defined above.

A thirty-eighth embodiment of the present invention is a compound of Formula IV, or a pharmaceutically acceptable salt and/or an individual diastereomer thereof, wherein R$^1$ is —CO$_2$H; and all other variables are as defined in the thirty-seventh embodiment.

A thirty-ninth embodiment of the present invention is a compound of Formula IV, or a pharmaceutically acceptable salt and/or an individual diastereomer thereof, wherein R$^{15}$ is —NR$^s$R$^t$ or —C$_{1-6}$ alkyl; R$^s$ and R$^t$ are each independently —H, —C$_{1-6}$ alkyl, or —C$_{1-4}$ alkyl-C$_{3-6}$ cycloalkyl, with the proviso that R$^s$ and R$^t$ are not both —H; and all other variables are as defined in the thirty-seventh embodiment.

A fortieth embodiment of the present invention is a compound of Formula IV, or a pharmaceutically acceptable salt and/or an individual diastereomer thereof, wherein R$^{15}$ is —NH(—C$_{1-4}$ alkyl), —N(—C$_{1-4}$ alkyl)$_2$, or —C$_{1-4}$ alkyl; and all other variables are as defined in the thirty-seventh embodiment.

Further aspects of the present invention include a compound of Formula IV, or a pharmaceutically acceptable salt and/or an individual diastereomer thereof, wherein R$^1$ is —CO$_2$H; R$^{15}$ is as defined in either one of the thirty-ninth and fortieth embodiments; and all other variables are as defined in the thirty-seventh embodiment.

A third class of compounds of the present invention are compounds of Formula IVA or IVB:

(IVA)

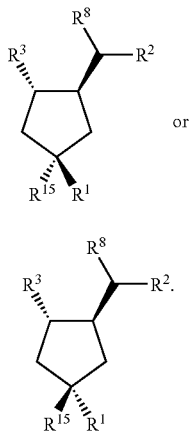

or (IVB)

and pharmaceutically acceptable salts thereof, wherein each variable is as defined in the thirty-seventh embodiment. Sub-classes of the third class include the groups of compounds in which one of the variables $R^1$, $R^2$, $R^3$, $R^8$, $R^{15}$, etc. directly or indirectly depicted in Formula IVA or IVB is as defined in any one of the preceding embodiments. Other sub-classes include the groups of compounds in which two or more of the variables $R^1$, $R^2$, $R^3$, $R^8$, $R^{15}$, etc. directly or indirectly depicted in Formula IVA or IVB are as defined in any one of the preceding embodiments.

A fourth class of compounds of the present invention are compounds of Formula V:

(V)

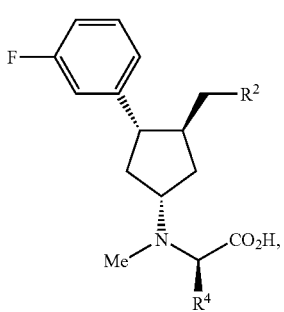

and pharmaceutically acceptable salts thereof, wherein:

$R^2$ is:

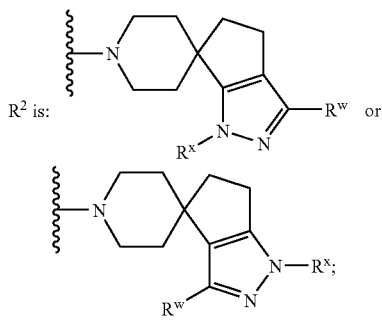

-continued

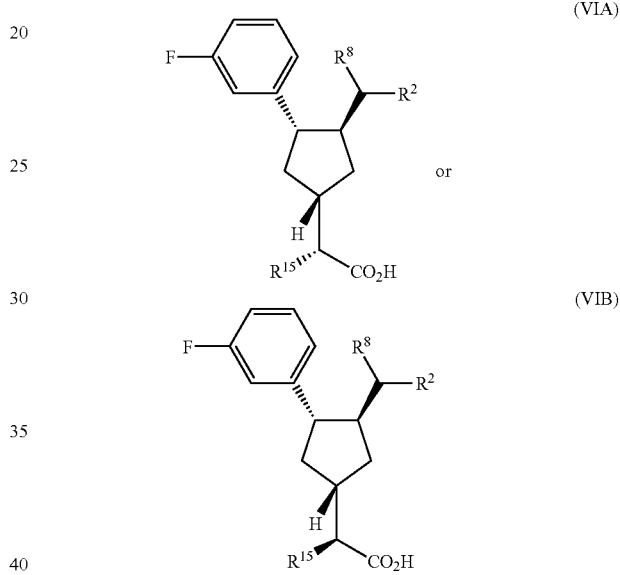

$R^w$ is —H, —$C_{1-3}$ alkyl, —$CF_3$, —O—$C_{1-3}$ alkyl, or benzyl; wherein the benzyl ring is optionally substituted with from 1 to 3 substituents each of which is independently bromo, chloro, fluoro, —$C_{1-3}$ alkyl, or —O—$C_{1-3}$ alkyl; and $R^x$ is —H, —$C_{1-3}$ alkyl, or —$CF_3$.

A fifth class of compounds of the present invention are compounds of Formula VI:

(VIA)

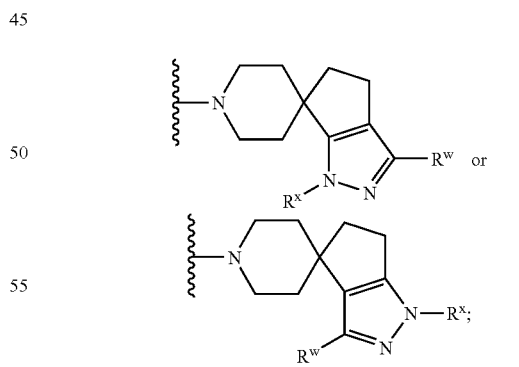

or (VIB)

and pharmaceutically acceptable salts thereof, wherein:
$R^2$ is:

$R^{15}$ is —$NR^sR^t$, —$C_{1-6}$ alkyl, —$CH_2$-cyclopropyl, —$CH_2$-Cyclobutyl, —$CH_2$-cyclopentyl, or —$CH_2$-cyclohexyl;
$R^8$ is —H or methyl;
$R^s$ is —H or —$C_{1-6}$ alkyl;
$R^t$ is —$C_{1-6}$ alkyl;
$R^w$ is —H, —$C_{1-3}$ alkyl, —$CF_3$, —O—$C_{1-3}$ alkyl, —O—$CF_3$, or benzyl; wherein the benzyl ring is optionally substituted with from 1 to 3 substituents each of which is independently bromo, chloro, fluoro, —$C_{1-3}$ alkyl, or —O—$C_{1-3}$ alkyl; and $R^x$ is —H, —$C_{1-3}$ alkyl, or —$CF_3$.

A sixth class of compounds of the present invention are compounds of Formula VIIA or VIIB:

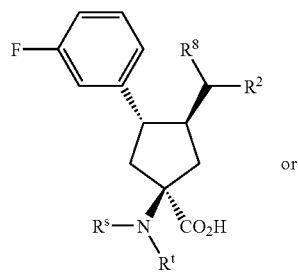

(VIIA)

or

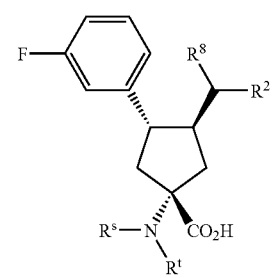

(VIIB)

and pharmaceutically acceptable salts thereof, wherein $R^2$, $R^8$, $R^s$, $R^t$, $R^w$, and $R^x$ are each as defined in the fifth class.

A forty-first embodiment of the present invention is a compound of Formula I, or a pharmaceutically acceptable salt and/or an individual diastereomer thereof, wherein $R^{15}$ is —$NR^sR^t$, —$C_{1-10}$ alkyl, or —$C_{1-6}$ alkyl-$C_{3-8}$ cycloalkyl; wherein the alkyl or the cycloalkylalkyl is optionally substituted with from 1 to 5 substituents each of which is independently:

(a) halo,
(b) —$C_{1-3}$ haloalkyl,
(c) —OH,
(d) —$C_{1-3}$ alkyl, or
(e) —O—$C_{1-3}$ alkyl;

and all other variables are as originally defined above.

Still further aspects of the present invention include a compound of Formula I, or a pharmaceutically acceptable salt and/or an individual diastereomer thereof, wherein $R^1$ is as defined in any one of the first, second and third embodiments; $R^2$ is as defined in either one of the fourth and fifth embodiments; $R^{15}$ is as defined in the forty-first embodiment; and all other variables are as originally defined above or as defined in a preceding aspect.

A forty-second embodiment of the present invention is a compound of Formula VIIIA or VIIIB, or a pharmaceutically acceptable salt and/or an individual diastereomer thereof:

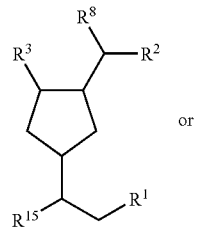

(VIIIA)

or

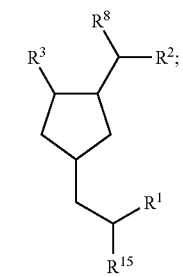

(VIIIB)

wherein all the variables are as originally defined above.

A forty-third embodiment of the present invention is a compound of Formula VIIIA or VIIIB, or a pharmaceutically acceptable salt and/or an individual diastereomer thereof, wherein $R^1$ is —$CO_2H$; and all other variables are as defined in the forty-second embodiment.

A forty-fourth embodiment of the present invention is a compound of Formula IX, or a pharmaceutically acceptable salt and/or an individual diastereomer thereof:

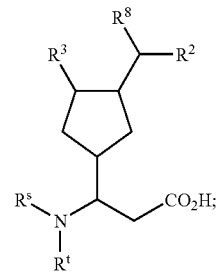

(IX)

wherein all the variables are as originally defined above.

Still further aspects of the present invention include a compound of Formula IX, or a pharmaceutically acceptable salt and/or an individual diastereomer thereof, wherein $R^1$ is —$CO^2H$; $R^2$ is as defined in either one of the fourth and fifth embodiments; and all other variables are as originally defined above or as defined in a preceding aspect.

It is to be understood that additional embodiments of the present invention include, but are not limited to, compounds of any of Formulas I to IX, wherein each of two or three or more of the variables contained therein (e.g., $R^1$, $R^2$, $R^3$, $R^8$, and so forth) is independently defined in accordance with its definition in any one of the embodiments or aspects as set forth above, or in accordance with its definition in any one of the foregoing classes set forth above or a sub-class thereof. Any and all possible combinations of these variables in each of Formulas I to IX are additional embodiments within the scope of the present invention.

Another aspect of the present invention is a compound selected from the group consisting of N-methyl-N-(1-(R)-3-(S)-((2'-benzyl-5',6'-dihydrospiro[piperidin-1-yl-4,4'-[4H]pyrrolo[1,2-b]pyrazole])methyl)-4-(S)-(3-fluorophenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((2-ethyl-5,6 dihydrospiro[cyclopentapyrazole-4(2H),4'-piperidin-1'-yl])methyl)-4-(S)-(3-fluorophenyl)cyclopent-1-yl)-(R)-valine;

N-methyl-N-(1-(R)-3-(S)-((2,3-diethyl-4,5-dihydrospiro[cyclopentapyrazole-6(2H),4'-piperidin-1'-yl])methyl)-4-(S)-(3-fluorophenyl)cyclopent-1-yl)-(R)-valine;

N-methyl-N-(1-(R)-3-(S)-((1-ethyl-5,6 dihydrospiro[cyclopentapyrazole-4(1H),4'-piperidin-1'-yl])methyl)-4-(S)-(3-fluorophenyl)cyclopent-1-yl)-(R)-valine;

N-methyl-N-(1-(R)-3-(S)-((1-ethyl-3-methyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((1,3-dimethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((3-methyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((2,3-diethyl-5,6 dihydrospiro[cyclopentapyrazole-4(1H),4'-piperidin-1'-yl])methyl)-4-(S)-(3-fluorophenyl)cyclopent-1-yl)-(R)-valine;

N-methyl-N-(1-(R)-3-(S)-((1,3-diethyl-5,6 dihydrospiro[cyclopentapyrazole-4(1H),4'-piperidin-1'-yl])methyl)-4-(S)-(3-fluorophenyl)cyclopent-1-yl)-(R)-valine;

N-methyl-N-(1-(R)-3-(S)-((3-ethyl-1-methyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R,S)-α-methylvaline;

N-methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-t-butylglycine;

N-methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-leucine;

N-ethyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3,5-difluorophenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3,4-difluorophenyl)cyclopent-1-yl)-(R)-valine;

N-methyl-N-(1-(R)-3-(S)-((1-ethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((1-methyl-3-ethyl-4,5-dihydrospiro[cyclopentapyrazole-6(1H),4'-piperidin-1'-yl])methyl)-4-(S)-(3-fluorophenyl)cyclopent-1-yl)-(R)-t-butylglycine;

N-methyl-N-(1-(R)-3-(S)-((3-ethyl-1-methyl-4,5-dihydrospiro[cyclopentapyrazole-6(1H),4'-piperidin-1'-yl])methyl)-4-(S)-(3,5-difluorophenyl)cyclopent-1-yl)-(R)-valine;

N-methyl-N-(1-(R)-3-(S)-((3-ethyl-4,5-dihydrospiro[6H-cyclopent[d]isoxazole-6,4'-piperidin-1'-yl])methyl)-4-(S)-(3-fluorophenyl)cyclopent-1-yl)-(R)-valine;

N-methyl-N-(1-(R)-3-(S)-((3-ethyl-4,5-dihydrospiro[6H-cyclopent[c]isoxazole-6,4'-piperidin-1'-yl])methyl)-4-(S)-(3-fluorophenyl)cyclopent-1-yl)-(R)-valine;

N-methyl-N-(1-(R)-3-(S)-((1-ethyl-3-methoxy-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((2-ethyl-3-methoxy-4,5-dihydrospiro[cyclopentapyrazole-6(2H),4'-piperidin-1'-yl])methyl)-4-(S)-(3-fluorophenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3-fluoro-4-methylphenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3,4-dichlorophenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3,5-difluorophenyl)cyclopent-1-yl)-(R)-t-butylglycine;

N-methyl-N-(1-(R)-3-(S)-((1,3-diethyl-4,5-dihydrospiro[cyclopentapyrazole-6(1H),4'-piperidin-1'-yl])methyl)-4-(S)-(4-fluorophenyl)cyclopent-1-yl)-(R)-valine;

N-methyl-N-(1-(R)-3-(S)-((1-ethyl-3-methoxy-5,6-dihydrospiro[cyclopenta-pyrazole-4(2H),4'-piperidin-1'-yl])methyl)-4-(S)-(3-fluorophenyl)cyclopent-1-yl)-(R)-valine;

N-methyl-N-(1-(R)-3-(S)-((2-ethyl-3-methoxy-5,6-dihydrospiro[cyclopenta-pyrazole-4(2H),4'-piperidin-1'-yl])methyl)-4-(S)-(3-fluorophenyl)cyclopent-1-yl)-(R)-valine;

N-methyl-N-(1-(R)-3-(S)-((1-methyl-3-methoxy-4,5-dihydrospiro[cyclopenta-pyrazole-6(1H),4'-piperidin-1'-yl])methyl)-4-(S)-(3-fluorophenyl)cyclopent-1-yl)-(R)-valine;

N-methyl-N-(1-(R)-3-(S)-((1-ethyl-3-methoxy-4,5-dihydrospiro[cyclopentapyrazole-6(1H),4'-piperidin-1'-yl])methyl)-4-(S)-(3,5-difluorophenyl)cyclopent-1-yl)-(R)-t-butylglycine;

N-methyl-N-(1-(R)-3-(S)-((3-ethyl-1-methyl-4,5-dihydrospiro[cyclopentapyrazole-6(1H),4'-piperidin-1'-yl])methyl)-4-(S)-(3,5-difluorophenyl)cyclopent-1-yl)-(R)-t-butylglycine;

N-methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-valine;

N-methyl-N-(1-(S)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-valine;

N-methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-t-butylglycine;

N-methyl-N-(1-(S)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-t-butylglycine;

N-methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3,5-difluorophenyl)cyclopent-1-yl)-(R)-valine;

N-methyl-N-(1-(S)-3-(S)-(1-(R)-(1,3-diethyl-4,5-dihydrospiro[cyclopentapyrazole-6(1H),4'-piperidin-1'-yl])eth-1-yl)-4-(S)-(3,5-difluorophenyl)cyclopent-1-yl)-(R)-valine;

N-methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3,5-difluorophenyl)cyclopent-1-yl)-(R)-t-butylglycine;

N-methyl-N-(1-(S)-3-(S)-(1-(R)-(1,3-diethyl-4,5-dihydrospiro[cyclopentapyrazole-6(1H),4'-piperidin-1'-yl])eth-1-yl)-4-(S)-(3,5-difluorophenyl)cyclopent-1-yl)-(R)-t-butylglycine;

N-methyl-N-(1-(R)-methyl-3-(S)-(1-(R)-(1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(S)-methyl-3-(S)-(1-(R)-(1,3-diethyl-4,5-dihydrospiro[cyclopentapyrazole-6(1H),4'-piperidin-1'-yl])methyl)4-(S)-(3-fluorophenyl)cyclopent-1-yl)-(R)-valine;

N-(1-(R)-methyl-3-(S)-(1-(R)-(1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-(1-(S)-methyl-3-(S)-(1-(R)-(1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R,S)-α-methylvaline;

N-(1-(S)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R,S)-α-methylvaline;

N-methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valinamide;

N-methyl-N-(1-(S)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valinamide;

N-methyl-N-(1-(R)-3-(S)-((2'-ethyl-5',6'-dihydrospiro[piperidin-1-yl-4,4'-[4H]pyrrolo[1,2-b]pyrazole])methyl)-4-(S)-(3-fluorophenyl)cyclopent-1-yl)-(R)-valine;

N-methyl-N-(1-(R)-3-(S)-((1,3-diethyl-4,6-dihydrospiro[furo[3,4-c]pyrazole-6(1H),4'-piperidin-1'-yl])methyl)-4-(S)-(3-fluorophenyl)cyclopent-1-yl)-(R)-valine;

N-methyl-N-(1-(R)-3-(S)-((2,3-diethyl-4,6-dihydrospiro[furo[3,4-c]pyrazole-6(1H),4'-piperidin-1'-yl])methyl)-4-(S)-(3-fluorophenyl)cyclopent-1-yl)-(R)-valine;

2-(S)-(1-(R)-3-(S)-((1,3-diethyl-4,5-dihydrospiro[cyclopentapyrazole-6(1H),4'-piperidin-yl])methyl)-4-(S)-(3-fluorophenyl)cyclopent-1-yl)-2-(1,1-dimethylprop-1-ylamino)acetic acid;

2-(S)-(1-(R)-3-(S)-((1,3-diethyl-4,5-dihydrospiro[cyclopentapyrazole-6(1H),4'-piperidin-yl])methyl)-4-(S)-(3-fluorophenyl)cyclopent-1-yl)-2-((1,1-dimethylprop-1-yl)methylamino)acetic acid;

2-(S)-(1-(R)-3-(S)-((1,3-diethyl-4,5-dihydrospiro[cyclopentapyrazole-6(1H),4'-piperidin-yl])methyl)-4-(S)-(3-fluorophenyl)cyclopent-1yl)-3-(cyclopropyl)propionic acid;

2-(R)-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-3-(cyclopropyl)propionic acid;

1-(R or S)-(2,2-dimethylprop-1-ylamino)-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylic acid;

1-(R or S)-((2,2-dimethylprop-1-yl)methylamino)-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylic acid;

1-(S)-((2,2-dimethylprop-1-yl)amino)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylic acid;

1-(R)-((2,2-dimethylprop-1-yl)amino)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylic acid;

1-(R)-(dimethylamino)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylic acid;

1-(S)-(dimethylamino)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylic acid;

and pharmaceutically acceptable salts thereof.

The compounds of the instant invention have at least two asymmetric centers at the cyclopentyl ring carbons bearing the spiropiperidinylmethyl substituent and the $R^3$ substituent. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. In an aspect of the present invention, the relative orientation between the spiropiperidinylmethyl and $R^3$ groups is trans; that is:

(XA)

or

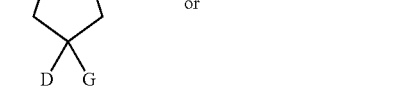

(XB)

A preferred aspect of the present invention is a compound of Formula XA, or a pharmaceutically acceptable salt and/or an individual diastereomer thereof.

The independent syntheses of the diastereomers described above or their chromatographic separations may be achieved as known in the art by appropriate modification of the methodologies disclosed herein. Their absolute stereochemistry may be determined by the x-ray crystallography of crystalline products or crystalline intermediates which are derivatized, if necessary, with a reagent containing an asymmetric center of known absolute configuration.

The compounds of the present invention can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. When the compounds of the invention carry an acidic moiety, suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of a carboxylic acid (—COOH) group or an alcohol group being present, pharmaceutically acceptable esters can be employed to modify the solubility or hydrolysis characteristics of the compound.

Other embodiments of the present invention include the following:

(a) A pharmaceutical composition comprising an effective amount of a compound of Formula I and a pharmaceutically acceptable carrier.

(b) A pharmaceutical composition which comprises the product prepared by combining (e.g., mixing) an effective amount of a compound of Formula I and a pharmaceutically acceptable carrier.

(c) The pharmaceutical composition of (a) or (b), wherein the compound of Formula I is employed in an amount effective for modulating CCR3 or CCR5 chemokine receptor activity.

(d) The pharmaceutical composition of (a) or (b), wherein the compound of Formula I is employed in an amount effective for treating infection by HIV, delaying the onset of or preventing infection by HIV, delaying the onset of AIDS, treating AIDS, or preventing AIDS.

(e) The pharmaceutical composition of (d), further comprising an effective amount of an HIV infection/AIDS treatment agent selected from the group consisting of HIV/ AIDS antiviral agents, immunomodulators, and anti-infective agents.

(f) The pharmaceutical composition of (e), wherein the HIV infection/AIDS treatment agent is an antiviral selected from the group consisting of HIV protease inhibitors, non-nucleoside HIV reverse transcriptase inhibitors, nucleoside HIV reverse transcriptase inhibitors, and HIV integrase inhibitors.

(g) A method for modulating chemokine receptor activity (e.g., CCR3 or CCR5 activity) in a subject in need of such modulation, which comprises administering to the subject an effective amount of a compound of Formula I.

(h) A method for treating infection by HIV, delaying of the onset of AIDS, or treating AIDS in a subject in need thereof, which comprises administering to the subject an effective amount of a compound of Formula I.

(i) A method for preventing infection by HIV or for preventing AIDS in a subject in need thereof, which comprises administering to the subject an effective amount of a compound of Formula I.

(j) A method for blocking the entry of HIV into target cells of a subject in need of such blocking which comprises administering to the subject a compound of Formula I in an amount effective to block HIV from binding to surface receptors of the target cells.

(k) The method of (j), wherein blocking the entry of HIV into target cells prevents infection of the subject by HIV.

(l) The method of (j), wherein blocking the entry of HIV into target cells prevents infectious spread of HIV in the subject.

(m) The method of (j), wherein blocking the entry of HIV into target cells delays the onset of AIDS in the subject.

(n) The method of (j), wherein blocking the entry of HIV into target cells treats the pathological conditions of AIDS in the subject.

(o) A method for the treatment or prevention of asthma, allergic rhinitis, dermatitis, conjunctivitis, atherosclerosis or rheumatoid arthritis in a subject in need thereof, which comprises administering to the subject an effective amount of a compound of Formula I.

(p) A combination useful for treating or preventing infection by HIV, or for preventing, treating or delaying the onset of AIDS, which is an effective amount of a compound of Formula I and an effective amount of an HIV infection/ AIDS antiviral agent selected from the group consisting of HIV protease inhibitors, non-nucleoside HIV reverse transcriptase inhibitors, nucleoside HIV reverse transcriptase inhibitors, HIV integrase inhibitors and HIV fusion inhibitors.

(q) A method of blocking entry of HIV into target cells of a subject in need of such blocking which comprises administering to the subject the pharmaceutical composition of (a), (b), (c), (d), (e) or (f) or the combination of (p).

(r) A method of preventing or treating infection by HIV in a subject in need thereof which comprises administering to the subject the pharmaceutical composition of (a), (b), (c), (d), (e) or (f) or the combination of (p).

(s) A method of preventing, treating or delaying the onset of AIDS in a subject in need thereof which comprises administering to the subject the pharmaceutical composition of (a), (b), (c), (d), (e) or (f)or the combination of (p).

(t) A method for the prevention or treatment of asthma, allergic rhinitis, dermatitis, conjunctivitis, atherosclerosis or rheumatoid arthritis in a subject in need thereof, which comprises administering to the subject the pharmaceutical composition of (a), (b) or (c).

The present invention also includes a compound of the present invention (i) for use in, (ii) for use as a medicament for, or (iii) for use in the preparation of a medicament for: (a) modulating chemokine receptor activity (e.g., CCR3 or CCR5 activity), (b) blocking entry of HIV into target cells, (c) preventing or treating infection by HIV, (c) preventing, treating or delaying the onset of AIDS, or (e) preventing or treating asthma, allergic rhinitis, dermatitis, conjunctivitis, atherosclerosis or rheumatoid arthritis. In the HIV/AIDS-related uses, the compounds of the present invention can optionally be employed in combination with one or more other HIV/AIDS treatment agents selected from HIV/AIDS antiviral agents, anti-infective agents, and immunomodulators.

Additional embodiments of the invention include the pharmaceutical compositions, combinations and methods set forth in (a)–(t) above and the uses set forth in the preceding paragraph, wherein the compound of the present invention employed therein is a compound of one of the embodiments, aspects, classes, or sub-classes of the compounds described above. In all of these embodiments, the compound may optionally be used in the form of a pharmaceutically acceptable salt and/or an individual diastereomer.

As used herein, the term "alkyl" refers to any linear or branched chain alkyl group having a number of carbon atoms in the specified range. Thus, for example, "$C_{1-6}$ alkyl" (or "$C_1$–$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "alkenyl" means any linear or branched chain alkenyl group having a number of carbon atoms in the specified range. Thus, for example, "$C_{2-6}$ alkenyl" (or "$C_2$–$C_6$ alkenyl") refers to all of the hexenyl and pentenyl isomers as well as 1-butenyl, 2-butenyl, 3-butenyl, isobutenyl, 1-propenyl, 2-propenyl, and ethenyl (or vinyl).

The term "alkynyl" means any linear or branched chain alkynyl group having a number of carbon atoms in the specified range. Thus, for example, "$C_{2-6}$ alkynyl" (or "$C_2$–$C_6$ alkynyl") refers to all of the hexynyl and pentynyl isomers as well as 1-butynyl, 2-butynyl, 3-butynyl, 1-propynyl, 2-propynyl, and ethynyl (or acetylenyl).

The terms "cycloalkyl" and "saturated carbocyclic ring" have the same meaning and each refers to any cyclic ring of an alkane having a number of carbon atoms in the specified range. Thus, for example, "$C_{3-8}$ cycloalkyl" (or "$C_3$–$C_8$ cycloalkyl") refers to cyclopropyl, cyclobutyl, cyclopentyl, cyclohexyl, cycloheptyl, and cyclooctyl.

The term "cycloalkenyl" means any cyclic ring of an alkene having a number of carbon atoms in the specified range. Thus, for example, "$C_{5-8}$ cycloalkenyl" (or "$C_5$–$C_8$ cycloalkenyl") refers to cyclopentenyl, cyclohexenyl, cycloheptenyl, and cyclooctenyl.

The term "saturated monoazacyclic ring" means any saturated cyclic ring containing a nitrogen atom and the rest carbon atoms wherein the total number of ring atoms is in the specified range. Thus, for example, a "3- to 8-membered saturated monoazacyclic ring" refers to aziridinyl, azetidinyl, pyrrolidinyl, piperidinyl, azepanyl (or cycloazaheptyl or hexahydroazepinyl), and octahydroazocinyl (or cycloazaoctyl).

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms has been replaced with a halogen (i.e., F, Cl, Br and/or I). Thus, for example, "$C_{1-6}$ haloalkyl" (or "$C_1$–$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "aryl" refers to aromatic mono- and polycarbocyclic ring systems, wherein the individual carbocyclic rings in the polyring systems may be fused or attached to each other via a single bond. Suitable aryl groups include, but are not limited to, phenyl, naphthyl, and biphenylenyl.

Compounds of the present invention can contain heterocyclic moieties. The term "heterocyclic" (and variations thereof such as "heterocycle" or "heterocyclyl") generally refers to (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of, bridged with, or fused to the other ring or rings and each ring is saturated or unsaturated, and the monocyclic ring, bicyclic ring system, or tricyclic ring system contains one or more heteroatoms (e.g., from 1 to 6 heteroatoms, from 1 to 5 heteroatoms, from 1 to 4 heteroatoms, from 1 to 3 heteroatoms, 1 or 2 heteroatoms, or 1 heteroatom) independently selected from N, O and S and a balance of carbon atoms (the monocylic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. The heterocyclic ring may be attached to the rest of the molecule via any heteroatom or carbon atom in the ring, provided that attachment results in the creation of a stable structure. When the heterocyclic ring has substituents, it is understood that the substituents may be attached to any atom in the ring, whether a heteroatom or a carbon atom, provided that a stable chemical structure results.

Heteroaromatics form a subset of the heterocycles of interest with respect to the invention; i.e., the term "heteroaromatic" (alternatively "heteroaryl") generally refers to a heterocycle as defined above in which the entire ring system (whether mono- or poly-cyclic) is an aromatic ring system. Of particular interest are heteroaromatic rings. The term "heteroaromatic ring" refers herein to any 5- or 6-membered monocyclic aromatic ring which consists of carbon atoms and one or more (e.g., from 1 to 4, or from 1 to 3, or 1 or 2, or 1) heteroatoms independently selected from N, O and S. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Unsaturated, non-aromatic heterocycles form another subset of the heterocycles of interest with respect to the invention. Of particular interest are 5- or 6-membered unsaturated, non-aromatic heterocyclic rings containing from 1 to 4 heteroatoms each of which is independently N, O, or S. Representative examples of such rings include the dihydro derivatives of the 5-membered heteroaromatics and the dihydro and tetrahydro derivatives of the 6-membered heteroaromatics set forth in the preceding paragraph.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable (e.g., $R^u$ and $R^v$) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "heteroaromatic ring is optionally substituted with from 1 to 5 substituents . . . ") includes mono- and poly-substitution by a named substituent to the extent such single and multiple substitution (including multiple substitution at the same site) is chemically allowed.

The symbol "〰" in front of an open bond in the structural formula of a group marks the point of attachment of the group to the rest of the molecule.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. These compounds are, for example, typically useful as modulators of the CCR3 and/or CCR5 chemokine receptors. More particularly, the compounds of the present invention are typically useful as inhibitors of CCR5.

The utility of the compounds in accordance with the present invention as modulators of chemokine receptor activity may be demonstrated by methodologies known in the art, such as the assay for chemokine binding as disclosed by Van Riper et al., *J. Exp. Med.*, 177, 851–856 (1993) which may be readily adapted for measurement of CCR-5 binding, and the assay for CCR-3 binding as disclosed by Daugherty et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, or HEK-293. For example, a CCR3 transfected AML14.3D10 cell line has been placed on restricted deposit with American Type Culture Collection as ATCC No. CRL-12079. The utility of the compounds in accordance with the present invention as inhibitors of the spread of HIV infection in cells may be demonstrated by methodologies known in the art, such as the HIV quantitation assay disclosed by Nunberg et al., *J. Virology*, 65 (9), 4887–4892 (1991).

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be prevented or treated using the methods of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due to congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migrans (e.g., *Toxocara*), eosinophilic gastroenteritis (e.g., *Anisaki* spp., *Phocanema* ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of chemokine receptors, including CCR5 and/or CCR3. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR5 and/or CCR3. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to the use of these compounds in the prevention or treatment of infection by a retrovirus, in particular, the human immunodeficiency virus (HIV) and the treatment of, and delaying of the onset of, consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR5 or CCR3, of a target cell, which comprises contacting the target cell with an amount of the compound which is effective at inhibiting the binding of the chemokine to the chemokine receptor.

The present invention also includes methods for treating or preventing a stress response via administration of an effective amount of a compound of Formula I, or a pharmaceutically acceptable salt and/or an individual diastereomer thereof, to a subject suffering from a stress response or at risk to suffer from a stress response. More particularly, the present invention includes a method of treating or preventing stress response in a subject in need thereof, which comprises administering an effective amount of a compound of Formula I, or a pharmaceutically acceptable salt and/or an individual diastereomer thereof, to the subject. Treatment or prevention of the stress response can hasten the subject's return to normal activity with a reduced requirement for narcotic analgesics and/or with a lower complication rate. The subject can be a surgical patient who has pre-existing infection (e.g., sepsis from abscess or empyema) or inflammation (e.g, rheumatoid arthritis or acute myocardial infarction). More particularly, the subject can be a cardiac surgery patient, such as a patient who has recently experienced a myocardial infarction or who has a lung infection or liver disease.

The term "stress response" refers to any response (i.e., physiological change) seen in a subject exposed to an insult. An insult is a trauma (e.g., physical injury, wounds, surgery, burns) or a physiopathological state (e.g., infection such as bacteremia or endotoxin infusion) that results in changes to existing rhythmical processes which are homeostatic in nature. Stress response includes, but is not limited to, any one or more of the following conditions: hyperthermia, hypothermia, hypertension, hypotension, inflammation, malaise (i.e., discomfort or debility typically characterized by decreased activity and/or loss of appetite), shock (e.g., septic shock), tissue damage, organ damage and/or failure, and sepsis.

The present invention also includes a method of treating or preventing hyperthermia in a subject in need thereof, which comprises administering an effective amount of a compound of Formula I, or a pharmaceutically acceptable salt and/or an individual diastereomer thereof, to the subject. The subject can be, for example, a surgical patient such as a cardiac surgery patient.

The term "hyperthermia" refers herein to the elevation of the temperature of a subject's body, or a part of a subject's body, compared to the normal temperature of the subject. In mammals, a normal body temperature is ordinarily maintained due to the thermoregulatory center in the anterior hypothalamus, which acts to balance heat production by body tissues with heat loss. The terms "fever" and "hyperthermia" are sometimes distinguished from each other, wherein fever refers to a regulated elevation in a subject's thermal set point (in response, e.g., to an infection or other insult), and hyperthermia refers to an unregulated rise in body temperature that is not triggered by an increased thermal set point but is instead in response to an internal (e.g., exercise) or external (e.g., hot ambient conditions) source of heat. The terms "fever" and "hyperthermia" are used interchangeably herein, and both refer to a regulated rise in body temperature in response to an insult or other inflammatory stimulus.

The present invention also includes a method of treating or preventing hypothermia in a subject in need thereof, which comprises administering an effective amount of a compound of Formula I, or a pharmaceutically acceptable salt and/or an individual diastereomer thereof, to the subject. The subject can be, for example, a surgical patient such as a cardiac surgery patient. The term "hypothermia" refers to a decrease in the temperature of a subject's body, or a part of a subject's body, compared to the normal temperature of the subject. The decrease is typically a regulated decrease in the subject's thermal set point, such as in response to an insult (e.g., infection).

It is believed that the compounds of the present invention are inhibiting CCR5 chemokine receptor activity in preventing and treating stress response including (but not limited to) hyperthermia and hypothermia. Further description of the use of CCR5 receptor inhibitors in the treatment and prevention of a stress response is found in International Patent Application No. PCT/US 03/01874, filed on Jan. 22, 2003 and published as WO 03/061659,the disclosure of which is incorporated herein by reference in its entirety.

With respect to the various uses and methods described above and elsewhere herein, the term "subject" refers to an animal, preferably a mammal, most preferably a human, who is the object of treatment, observation or experiment and in whom modulation of chemokine receptor activity is desired.

The term "modulation" as used herein encompasses antagonism, agonism, partial antagonism, inverse agonism and/or partial agonism. In a preferred aspect of the present invention, modulation refers to antagonism of chemokine receptor activity (e.g., antagonsim of CCR3 or CCR5 receptors).

The term "patient" can be used interchangeably with "subject", and typically refers to a subject who/which is awaiting or receiving medical care or is or will be the object of a medical procedure (e.g., surgery).

The term "cardiac surgery patient" refers to a patient who has or will have open heart surgery using cardiopulmonary bypass. "Cardiopulmonary bypass", or a variant thereof (e.g., "bypass" or "circulatory bypass") refers to circulatory bypass of the heart and lungs; i.e., the condition wherein the heartbeat is stopped for the purpose of surgery on the still heart, and the blood supply to the brain and the remainder of the body, excluding the heart and lungs, is provided by an extracorporeal machine that oxygenates and pumps the blood.

The term "transplant" refers to the grafting, implantation or transplantation of organs, tissues, cells (e.g., bone marrow) and/or biocompatible materials onto or into the body of a subject. The term encompasses the transfer of tissues from one part of the subject's body to another part and the transfer of organs, tissues, and/or cells obtained from a donor animal (either directly or indirectly such as an organ or tissue produced in vitro by culturing cells obtained from the animal) into the subject. The term "transplant rejection" means any immune reaction in the recipient directed against grafted organs, tissues, cells, and/or biocompatible materials.

The term "treating", or a variant thereof (e.g., "treatment"), refers to reducing or ameliorating an existing undesirable or adverse condition, symptom or disease (e.g., stress response due to exposure to a stressor) or delaying its onset in a subject in need of such reduction, amelioration or delay.

The term "preventing", or a variant thereof (e.g., "prevention"), refers to prophylaxis of an undesirable or adverse condition, symptom or disease in a subject who is at increased risk of acquiring such a condition, symptom, or disease as a result of being subjected or exposed to the causative agent of said condition, symptom or disease. "Increased risk" means a statistically higher frequency of occurrence of the condition, symptom, or disease in the subject as a result of exposure to the causative agent (e.g., an insult as defined above) in comparison to the frequency of its occurrence in the general population (e.g., an individual about to have surgery would be at a substantially increased risk for hyperthermia and inflammation subsequent to the surgery).

The term "effective amount" as used herein means that amount of active agent or active ingredient (e.g., chemokine receptor CCR5 modulator, especially a CCR5 antagonist) that elicits the biological or medicinal response in a tissue, system, animal or human that is being sought by a researcher, veterinarian, physician or other clinician, which includes alleviation of the symptoms of the disease or condition being treated. The term "therapeutically effective amount" refers to an amount of active agent suitable for treating the disease or condition of interest subsequent to detection or diagnosis of the disease or condition and/or subsequent to the development of symptoms thereof. The term "prophylactically effective amount" refers to an amount of active agent suitable for prevention of the disease or condition of interest (e.g., a subject who has been or soon will be exposed to the causative agent of a disease or condition but has not yet developed symptoms thereof).

The term "administration", or a variant thereof (e.g., "administering"), means providing the active agent or active ingredient (e.g., a CCR5 antagonist), alone or as part of a pharmaceutically acceptable composition, to the subject (e.g., warm-blooded vertebrate) in whom/which the condition, symptom, or disease is to be treated or prevented. When the salt of a chemical compound is administered, references to the amount of active ingredient are to the free acid or free base form of the compound. Actual dosage levels of active ingredients in a composition employed in a method of the present invention can be varied so as to administer an amount of the active compound(s) that is effective to achieve the desired therapeutic or prophylactic response for a particular subject and/or application.

By "pharmaceutically acceptable" is meant that the ingredients of a pharmaceutical composition are compatible with each other and not deleterious to the recipient thereof.

The term "composition" as used herein refers to a product comprising the specified ingredients in the specified amounts, as well as any product which results, directly or indirectly, from combination of the specified ingredients in the specified amounts.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR-4, CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of compounds of Formula I with one or more agents useful in the prevention or treatment of AIDS. For example, the compounds of this invention may be effectively administered, whether at periods of pre-exposure and/or post-exposure, in combination with effective amounts of the antiviral agents, immunomodulators, anti-infectives, or vaccines suitable for treating HIV infection and AIDS, and known to those of ordinary skill in the art, including the antiviral agents listed in the following Table.

Antivirals

| Drug Name | Manufacturer (Tradename and/or Location) | Indication (Activity) |
|---|---|---|
| abacavir GW 1592 1592U89 | Glaxo Welcome (ZIAGEN ®) | HIV infection, AIDS, ARC (nucleoside reverse transcriptase inhibitor) |
| abacavir + lamivudine + zidovudine | GlaxoSmithKline (TRIZIVIR ®) | HIV infection, AIDS, ARC (nucleoside reverse transcriptase inhibitors) |
| acemannan | Carrington Labs (Irving, TX) | ARC |
| ACH 126443 | Achillion Pharm. | HIV infections, AIDS, ARC (nucleoside reverse transcriptase inhibitor) |
| acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| adefovir dipivoxil GS 840 | Gilead | HIV infection, AIDS, ARC (reverse transcriptase inhibitor) |
| AL-721 | Ethigen (Los Angeles, CA) | ARC, PGL, HIV positive, AIDS |
| alpha interferon | GlaxoSmithKline | Kaposi's sarcoma, HIV, in combination w/Retrovir |
| AMD3100 | AnorMed | HIV infection, AIDS, ARC (CXCR4 antagonist) |
| amprenavir 141 W94 GW 141 VX478 (Vertex) | GlaxoSmithKline (AGENERASE ®) | HIV infection, AIDS, ARC (protease inhibitor) |
| ansamycin | Adria Laboratories | ARC |

-continued

| Drug Name | Manufacturer (Tradename and/or Location) | Indication (Activity) |
|---|---|---|
| LM 427 | (Dublin, OH) Erbamont (Stamford, CT) | |
| antibody which neutralizes pH labile alpha aberrant interferon | Advanced Biotherapy Concepts (Rockville, MD) | AIDS, ARC |
| AR177 | Aronex Pharm | HIV infection, AIDS, ARC |
| atazanavir (BMS 232632) | Bristol-Myers Squibb (REYATAZ ™) | HIV infection, AIDS, ARC (protease inhibitor) |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| capravirine (AG-1549, S-1153) | Pfizer | HIV infection, AIDS, ARC (non-nucleoside reverse transcriptase inhibitor) |
| CI-1012 | Warner-Lambert | HIV-1 infection |
| cidofovir | Gilead Science | CMV retinitis, herpes, papillomavirus |
| curdlan sulfate | AJI Pharma USA | HIV infection |
| cytomegalovirus immune globin | MedImmune | CMV retinitis |
| cytovene ganciclovir | Syntex | sight threatening CMV peripheral CMV retinitis |
| delavirdine | Pharmacia-Upjohn (RESCRIPTOR ®) | HIV infection, AIDS, ARC (non-nucleoside reverse transcriptase inhibitor) |
| dextran Sulfate | Ueno Fine Chem. Ind. Ltd. (Osaka, Japan) | AIDS, ARC, HIV positive asymptomatic |
| ddC (zalcitabine, dideoxycytidine) | Hoffman-La Roche (HIVID ®) | HIV infection, AIDS, ARC (nuclesodie reverse transcriptase inhibitor) |
| ddI (didanosine, dideoxyinosine) | Bristol-Myers Squibb (VIDEX ®) | HIV infection, AIDS, ARC; combination with AZT/d4T (nucleoside reverse transcriptase inhibitor) |
| DPC 681 & DPC 684 | DuPont | HIV infection, AIDS, ARC (protease inhibitors) |
| DPC 961 & DPC 083 | Bristol-Myers Squibb (from DuPont Pharma) | HIV infection AIDS, ARC (non-nucleoside reverse transcriptase inhibitors) |
| EL10 | Elan Corp, PLC (Gainesville, GA) | HIV infection |
| efavirenz (DMP 266) | Bristol-Myers Squibb (SUSTIVA ®) Merck (STOCRIN ®) | HIV infection, AIDS, ARC (non-nucleoside RT inhibitor) |
| famciclovir | Novartis (FAMVIR ®) | herpes zoster, herpes simplex |
| emtricitabine FTC | Gilead (from Triangle Pharmaceuticals) (COVIRACIL ®) Emory University | HIV infection, AIDS, ARC (nucleoside reverse transcriptase inhibitor) |
| emvirine | Gilead (from Triangle Pharmaceuticals) (COACTINON ®) | HIV infection, AIDS, ARC (non-nucleoside reverse transcriptase inhibitor) |
| enfuvirtide T-20 | Trimeris & Roche (FUZEON ®) | HIV infection, AIDS, ARC (fusion inhibitor) |
| HBY097 | Hoechst Marion Roussel | HIV infection, AIDS, ARC (non-nucleoside reverse transcriptase inhibitor) |
| fosamprenavir | Glaxo Smith Kline | HIV infection, AIDS, ARC (prodrug of amprenavir) |
| hypericin | VIMRx Pharm. | HIV infection, AIDS, ARC |
| recombinant human interferon beta | Triton Biosciences (Almeda, CA) | AIDS, Kaposi's sarcoma, ARC |
| interferon alfa-n3 | Interferon Sciences | ARC, AIDS |
| indinavir | Merck (CRIXIVAN ®) | HIV infection, AIDS, ARC, asymptomatic HIV positive, (protease inhibitor) |
| ISIS 2922 | ISIS Pharmaceuticals | CMV retinitis |
| JE2147/AG1776 | Agouron | HIV infection, AIDS, ARC (protease inhibitor) |
| KNI-272 | Nat'l Cancer Institute | HIV-assoc. diseases |

| Drug Name | Manufacturer (Tradename and/or Location) | Indication (Activity) |
|---|---|---|
| lamivudine, 3TC | GlaxoSmithKline (EPIVIR ®) | HIV infection, AIDS, ARC (nucleoside reverse transcriptase inhibitor) |
| lamivudine + zidovudine | GlaxoSmithKline (COMBIVIR ®) | HIV infection, AIDS, ARC (nucleoside reverse transcriptase inhibitor) |
| lobucavir | Bristol-Myers Squibb | CMV infection |
| lopinavir (ABT-378) | Abbott | HIV infection, AIDS, ARC (protease inhibitor) |
| lopinavir + ritonavir (ABT-378/r) | Abbott (KALETRA ®) | HIV infection, AIDS, ARC (protease inhibitor) |
| mozenavir (DMP-450) | AVID (Camden, NJ) | HIV infection, AIDS, ARC (protease inhibitor) |
| nelfinavir | Agouron (VIRACEPT ®) | HIV infection, AIDS, ARC (protease inhibitor) |
| nevirapine | Boeheringer Ingleheim (VIRAMUNE ®) | HIV infection, AIDS, ARC (non-nucleoside reverse transcriptase inhibitor) |
| novapren | Novaferon Labs, Inc. (Akron, OH) | HIV inhibitor |
| peptide T octapeptide sequence | Peninsula Labs (Belmont, CA) | AIDS |
| PRO 140 | Progenics | HIV infection, AIDS, ARC (CCR5 co-receptor inhibitor) |
| PRO 542 | Progenics | HIV infection, AIDS, ARC (attachment inhibitor) |
| trisodium phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| probucol | Vyrex | HIV infection, AIDS |
| RBC-CD4 | Sheffield Med. Tech (Houston TX) | HIV infection, AIDS, ARC |
| ritonavir (ABT-538) | Abbott (NORVIR ®) | HIV infection, AIDS, ARC (protease inhibitor) |
| saquinavir | Hoffmann-LaRoche (FORTOVASE ®) | HIV infection, AIDS, ARC (protease inhibitor) |
| stavudine; d4T didehydrodeoxy- thymidine | Bristol-Myers Squibb (ZERIT ®) | HIV infection, AIDS, ARC (nucleoside reverse transcriptase inhibitor) |
| T-1249 | Trimeris | HIV infection, AIDS, ARC (fusion inhibitor) |
| TAK-779 | Takeda | HIV infection, AIDS, ARC (injectable CCR5 receptor antagonist) |
| tenofovir | Gilead (VIREAD ®) | HIV infection, AIDS, ARC (nucleotide reverse transcriptase inhibitor) |
| tipranavir (PNU-140690) | Boehringer Ingelheim | HIV infection, AIDS, ARC (protease inhibitor) |
| TMC-120 & TMC-125 | Tibotec | HIV infections, AIDS, ARC (non-nucleoside reverse transcriptase inhibitors) |
| TMC-126 | Tibotec | HIV infection, AIDS, ARC (protease inhibitor) |
| valaciclovir | GlaxoSmithKline | genital HSV & CMV infections |
| virazole ribavirin | Viratek/ICN (Costa Mesa, CA) | asymptomatic HIV positive, LAS, ARC |
| zidovudine; AZT | GlaxoSmithKline (RETROVIR ®) | HIV infection, AIDS, ARC, Kaposi's sarcoma in combination with other therapies (nucleoside reverse transcriptase inhibitor) |

The HIV/AIDS antiviral agents, immunomodulators, and anti-infectives listed in the Table in US-2003-0055071 A1, the disclosure of which is hereby incorporated by reference in its entirety, are also suitable for use in combination with compounds of the present invention. It will be understood that the scope of combinations of the compounds of this invention with the HIV/AIDS antivirals, immunomodulators, anti-infectives or vaccines is not limited to the list in the above Table and in the Table in US-2003-0055071 A1, but includes in principle any combination with any pharmaceutical composition useful for the treatment of HIV infection or AIDS. When employed in combination with the compounds of the invention, the HIV/AIDS antivirals and other agents are typically employed in their conventional dosage ranges and regimens as reported in the art, including the dosages described in the *Physicians' Desk Reference*, 54th edition, Medical Economics Company, 2000. The dosage ranges for a compound of the invention in these combinations are the same as those set forth above herein.

In such combinations the compound of the present invention and other active agents may be administered together in a single composition or separately. Where separate administration is employed, the administration of one element may be prior to, concurrent with, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. No. 4,256,108, U.S. Pat. No. 4,166,452, and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically or prophylactically active compounds as noted herein which are usually applied in the treatment or prevention of the above mentioned pathological conditions.

In the treatment or prevention of conditions which require chemokine receptor modulation an appropriate dosage level will generally be about 0.01 to 500 mg per kg patient body weight per day which can be administered in single or multiple doses. In one embodiment, the dosage level is from about 0.1 to about 250 mg/kg per day, and in an aspect of this embodiment, the dosage level is from about 0.5 to about 100 mg/kg per day. A suitable dosage level can be from about 0.01 to about 250 mg/kg per day, from about 0.05 to about 100 mg/kg per day, or from about 0.1 to about 50 mg/kg per day. Within this range the dosage may be from about 0.05 to about 0.5, from about 0.5 to about 5, or from about 5 to about 50 mg/kg per day. For oral administration, the compositions can be provided in the form of capsules or tablets containing from about 1 to about 1000 milligrams of the active ingredient, particularly 1, 5, 10, 15, 20, 25, 50, 75, 100, 150, 200, 250, 300, 400, 500, 600, 750, 800, 900 and 1000 milligrams of the active ingredient for the symptomatic adjustment of the dosage to the patient to be treated. The compounds can be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Abbreviations used in the instant specification, particularly the Schemes and Examples, include the following:
AIDS=acquired immunodeficiency syndrome
ARC=AIDS related complex
Bn=benzyl
BOC or Boc=t-butyloxycarbonyl
BOP=benzotriazol-1-yloxytris-(dimethylamino)phosphonium hexafluorophosphate
Bu=butyl
CBZ=carbobenzoxy (alternatively, benzyloxycarbonyl)
DBU=1,8-diazabicyclo[5.4.0]undec-7-ene
DCE=1,2-dichloroethane
DCM=dichloromethane (or methylene chloride)
DIPEA=diisopropylethylamine (or Hunig's base)
DMF=dimethylformamide
DMSO=dimethyl sulfoxide
DPPE (or dppe)=1,2-bis(diphenylphosphino)ethane
Et=ethyl
EtOAc=ethyl acetate
h=hour(s)
HIV=human immunodeficiency virus
HMPA=hexamethylphosphoramide
LAH=lithium aluminum hydride
LDA=lithium diisopropylamide
LHMDS=lithium hexamethyldisilazide
Me=methyl
MeOH=methanol
Ph=phenyl
PMB=p-methoxybenzyl
Pr=propyl
rt=room temperature
TBAF=tetrabutylammonium fluoride
TDMS (or TBS)=t-butyl-dimethylsilyl
TEA=triethylamine
TFA=trifluoroacetic acid
$Tf_2O$=triflic anhydride
THF=tetrahydrofuran
TPAP=tetrapropylammonium perruthenate The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

The preparation of cinnamate esters such as 1-3 as intermediates that can be used for the synthesis of compounds within the scope of the instant invention is detailed in Scheme 1. Cinnamate esters of structure 1-3 can be obtained commercially or can be synthesized by reacting a suitable aromatic or heteroaromatic aldehyde 1-1 with a phosphonoacetate such as 1-2 in the presence of sodium hydride or other bases such as sodium, lithium or potassium bis(trimethylsilyl)amide, potassium t-butoxide, and the like. The aldehyde 1-1 can be obtained commercially or can be prepared in a variety of ways from commercial materials (see March J. "Advanced Organic Chemistry", 4th ed., John Wiley & Sons, New York, pp. 1270–1271 (1992)).

SCHEME 1

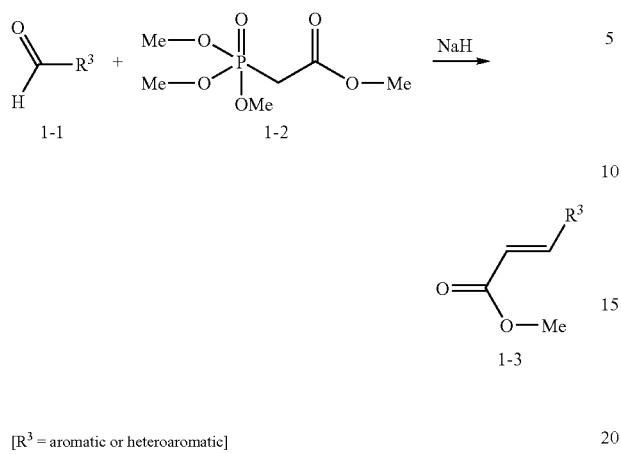

[R³ = aromatic or heteroaromatic]

A preparation of cyclopentane intermediates having a C-4 aryl or heteroaryl substituent within the scope of the instant invention is shown in Scheme 2A and can be used to prepare non-racemic cyclopentane derivatives when the resolution steps are done. Treatment of a trans-cinnamate ester such as 2-1 (see Scheme 1) with 2-((trimethylsilyl)methyl)-2-propen-1-yl acetate (2-2) in the presence of a catalytic amount of tetrakis(triphenylphosphine) palladium (0) and 1,2-bis (diphenylphosphino)ethane in THF at reflux can afford the exo-methylene cyclopentane 2-3. Hydrolysis of the ester can be done several ways, such as with aqueous sodium or lithium hydroxide in methanol or THF, to obtain the racemic acid 2-4. Resolution of the enantiomers can be accomplished by fractional crystallization from isopropanol, or other suitable solvents, of the salts with either (S)-(−)-α- or (R)-(+)-α-methylbenzyl amine to give the salts 2-5 and 2-6. The non-racemic acids 2-7 and 2-8 are recovered by acidification and extraction. Reesterification to non-racemic 2-9 and 2-10 can be done in a variety of ways, such as with trimethylsilyl-diazomethane or acid catalyzed esterification in methanol.

SCHEME 2A

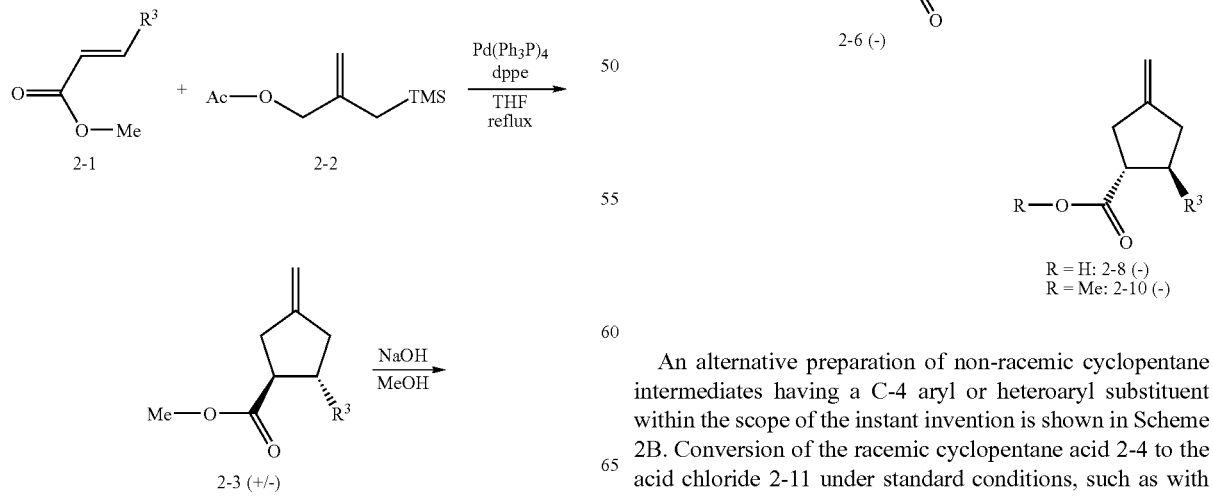

An alternative preparation of non-racemic cyclopentane intermediates having a C-4 aryl or heteroaryl substituent within the scope of the instant invention is shown in Scheme 2B. Conversion of the racemic cyclopentane acid 2-4 to the acid chloride 2-11 under standard conditions, such as with oxalyl chloride in methylene chloride with a catalytic amount of DMF, or to the mixed anhydride 2-12, prepared in situ with trimethylacetyl chloride in ether with TEA as base, followed by reaction with the preformed lithium salt of (S)-(−)-4-benzyl-2-oxazolidinone 2-13 (obtained, e.g., by treating the oxazolidinone with n-BuLi in THF), affords the two diastereomeric products 2-14 and 2-15, which can then be separated by chromatography. Hydrolysis of each diastereomer under standard conditions, such as with lithium hydroxide and hydrogen peroxide or trimethylamine-N-oxide, affords the two non-racemic acids 2-7 and 2-8. Alternatively, in order to obtain an enhanced amount of the desired diastereomer 2-14 before separation, similar conversion of the starting trans-cinnamic acid 2-16 (Scheme 1) to the chiral trans-cinnamate 2-17 followed by the ring formation reaction with 2-((trimethylsilyl)methyl)-2-propen-1-yl acetate (2-2) as detailed in Scheme 2A affords a 60:40 product mixture of 2-14:2-15.

Preparation of some 1,3,4-trisubstituted cyclopentanes within the scope of the instant invention is given in Scheme 3. Reduction of ester 3-1 (either racemic or non-racemic) (Scheme 2A), for example, with lithium borohydride, diisobutylaluminum hydride, lithium aluminium hydride, or sodium bis(2-methoxyethoxy)aluminum hydride in a suitable solvent, such as ether or THF, provides the primary alcohol 3-3. Alternatively, reduction of the acid 3-2 (either racemic or non-racemic) (Scheme 2A or 2B), for example with lithium aluminium hydride in THF, will also afford the alcohol 3-3. In cases where the $R^3$ moiety is not amenable to resolution as detailed in Scheme 2A or 2B, an alternative resolution can often be achieved using chiral HPLC methods to separate the enantiomers of 3-3. Oxidation of 3-3 to the aldehyde 3-4 can be carried out under numerous conditions, such as with DMSO and oxalyl chloride at low temperature, followed by TEA or DIPEA (Swern oxidation), with the

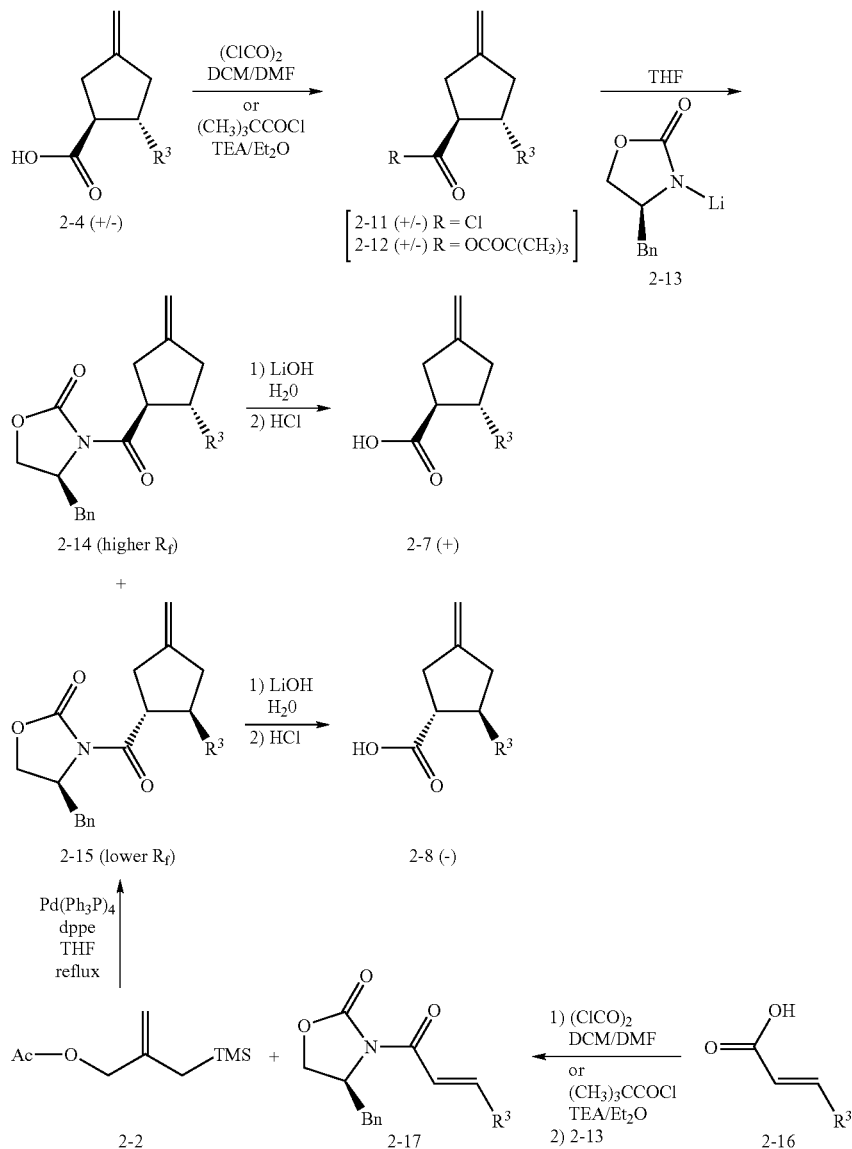

Dess-Martin periodinane, with N-methylmorpholine in the presence of a catalytic amount of TPAP, or with various chromium trioxide-based reagents (see March J. "Advanced Organic Chemistry", 4th ed., John Wiley & Sons, New York, pp. 1167–1171 (1992)). Reductive alkylation of a cyclic amine, such as spiropiperidine 3-5 (see Schemes 23 to 31 for the preparation of representative examples as shown in the brackets in Scheme 3), using for example sodium triacetoxyborohydride or sodium cyanoborohydride in a suitable solvent such as methylene chloride, 1,2-dichloroethane, THF, acetonitrile or methanol, with 3-4 can then provide a 3-((4-spiropiperidin-1-yl)methyl)cyclopentane derivative 3-6. In the cases where the spiropiperidine is stable to ozone, ozonolysis of the exo-methylene at low temperature (e.g., about −70° C. in methanol) followed by a reductive work-up with dimethyl sulfide can afford the ketone 3-7. (Note: In the cases where the spiro moiety contains a basic heterocycle, addition of excess HCl prior to ozonolysis can protect the heterocycle from oxidation during the ozonolysis.) Alternatively, 3-7 can be obtained from 3-6 through a stepwise oxidation using catalytic osmium tetroxide in the presence of N-methylmorpholine-N-oxide followed by sodium periodate cleavage of the intermediate diol. A second reductive alkylation of a D- and/or L-amino-acid ester 3-8 (R'=methyl, ethyl, t-butyl, benzyl or PMB) such as glycine ($R^5$=H), alanine ($R^5$=Me), ethylglycine ($R^5$=Et), valine ($R^5$=iso-Pr), leucine ($R^5$=iso-Bu), isoleucine ($R^5$=sec-Bu), t-butylglycine ($R^5$=t-Bu), cyclopropylalanine ($R^5$=CH$_2$cycPr), cyclobutylalanine ($R^5$=CH$_2$cycBu), cyclohexylglycine ($R^5$=cycHex), phenylglycine ($R^5$=Ph) or a N-alkyl amino-acid, such as N-methyl glycine ($R^6$=Me), or a cyclic amino-acid, such as proline ($R^5$–$R^6$=—(CH$_2$)$_3$—), with 3-7 as described above with sodium triacetoxyborohydride or sodium cyanoborohydride can afford 3-9. Final deprotection of the ester under conditions to which the spiropiperidine is stable, such as HCl in ether, TFA or formic acid for t-butyl and PMB esters, hydrogenation for benzyl or PMB esters, or standard hydrolysis for alkyl or benzyl esters, can afford the final product(s) 3-10 which are within the scope of the instant invention and which can be chemokine receptor modulators. The two individual C-1 isomers (four diastereomers when either the cyclopentyl scaffold or the amino-acid are racemic) can be separated by flash chromatography, Prep TLC, or HPLC methods as either the penultimate esters 3-9 and/or the final compounds 3-10.

SCHEME 3

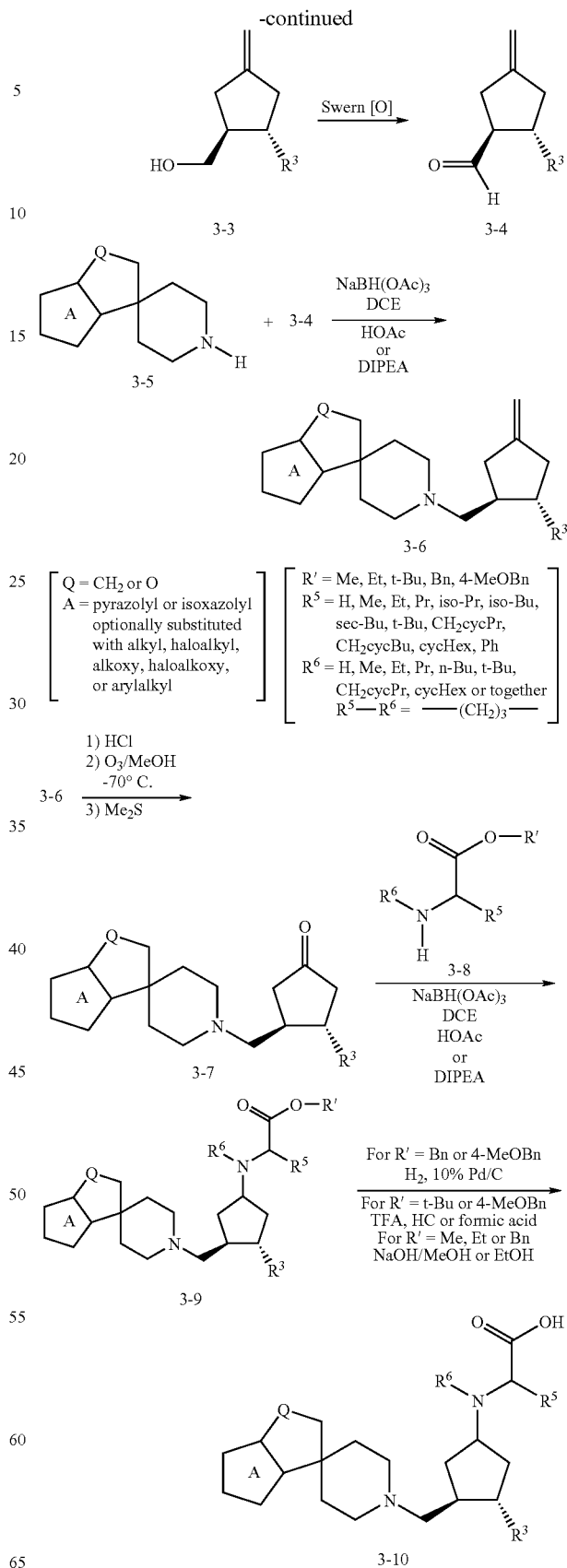

An alternative route for the preparation of some 1,3,4-trisubstituted cyclopentanes within the scope of the instant invention is given in Scheme 4. Scheme 4 is also amenable to the cases where the spiropiperidine in Scheme 3 is not stable to ozone or the osmium tetroxide/sodium periodate sequence, since the oxidation of the exo-methylene can be done prior to the reductive alkylation of the spiropiperidine. Thus, ozonolysis of the alcohol 4-1 (Scheme 3) followed by a reductive work-up with dimethyl sulfide can afford the ketone-alcohol 4-2. Oxidation to the ketone-aldehyde 4-3 can be done as described for Scheme 3 with N-methylmorpholine/TPAP or under Swern conditions. Selective reductive alkylation of the 4-spiropiperidine 4-4 (see Schemes 23 to 31) with the aldehyde of 4-3, using for example sodium triacetoxyborohydride or sodium cyanoborohydride in a suitable solvent such as methylene chloride, 1,2-dichloroethane, THF, acetonitrile or methanol, can then provide the 3-((4-spiropiperidin-1-yl)methyl)cyclopentanone derivative 4-5 (same as 3-7). This can then be converted to the final product(s) 4-6 as described in Scheme 3.

SCHEME 4

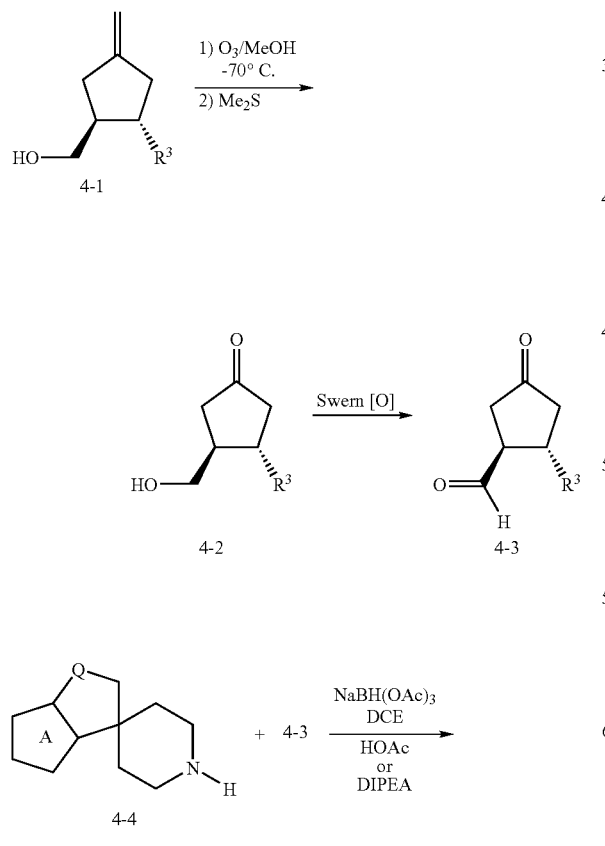

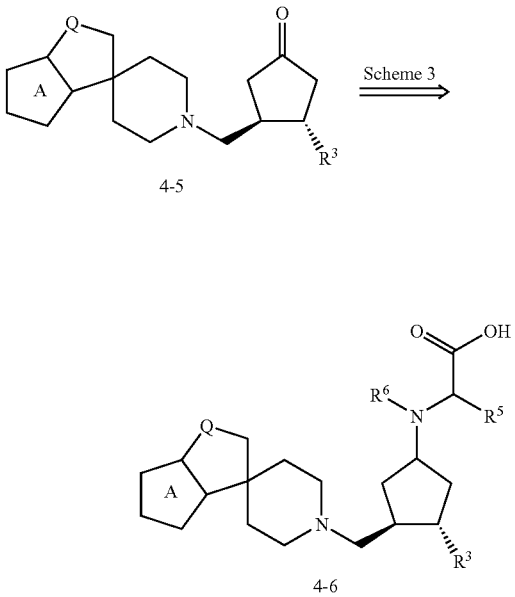

The 3-hydroxymethyl-4-arylcyclopentanone 4-2 can alternatively be prepared via nucleophilic addition to a suitable trans-bicyclo[3.1.0]hexane, as described in U.S. Pat. No. 6,506,908.

An alternative route for the preparation of some 1,3,4-trisubstituted cyclopentanes within the scope of the instant invention is given in Scheme 5A. Reductive alkylation with ketone alcohol 5-1 (Scheme 4) of a variety of amino-acid esters 5-2 (see Scheme 3) affords the alcohols 5-3 and 5-4, of which 5-3 is the major product (lower $R_f$ when $R^5$ is (S), higher $R_f$ when $R^5$ is (R)) and 5-4 is the minor product (higher $R_f$ when $R^5$ is (S), lower $R_f$ when $R^5$ is (R)). Separation of the individual diastereomers (2 when both reactants are non-racemic, 4 when only one is non-racemic) can be done at this intermediate or at a later step. Oxidation of 5-3 and/or 5-4 to the aldehyde(s) 5-5 and 5-6 can be done as described in Scheme 3, preferably with N-methylmorpholine/TPAP when in the presence of the secondary N—H ($R^6$=H). Reductive alkylation of a 4-spiropiperidine 5-7 (see Schemes 23 to 31) with the aldehyde(s) 5-5 and/or 5-6, using for example sodium triacetoxyborohydride or sodium cyanoborohydride in a suitable solvent such as methylene chloride, 1,2-dichloroethane, THF, acetonitrile or methanol, can then provide the 3-((4-spiropiperidin-1-yl)methyl)cyclopentane derivative(s) 5-8 and/or 5-9. The intermediate ester(s) can then be converted to the final product(s) 5-10 and/or 5-11 as described in Scheme 3.

SCHEME 5A
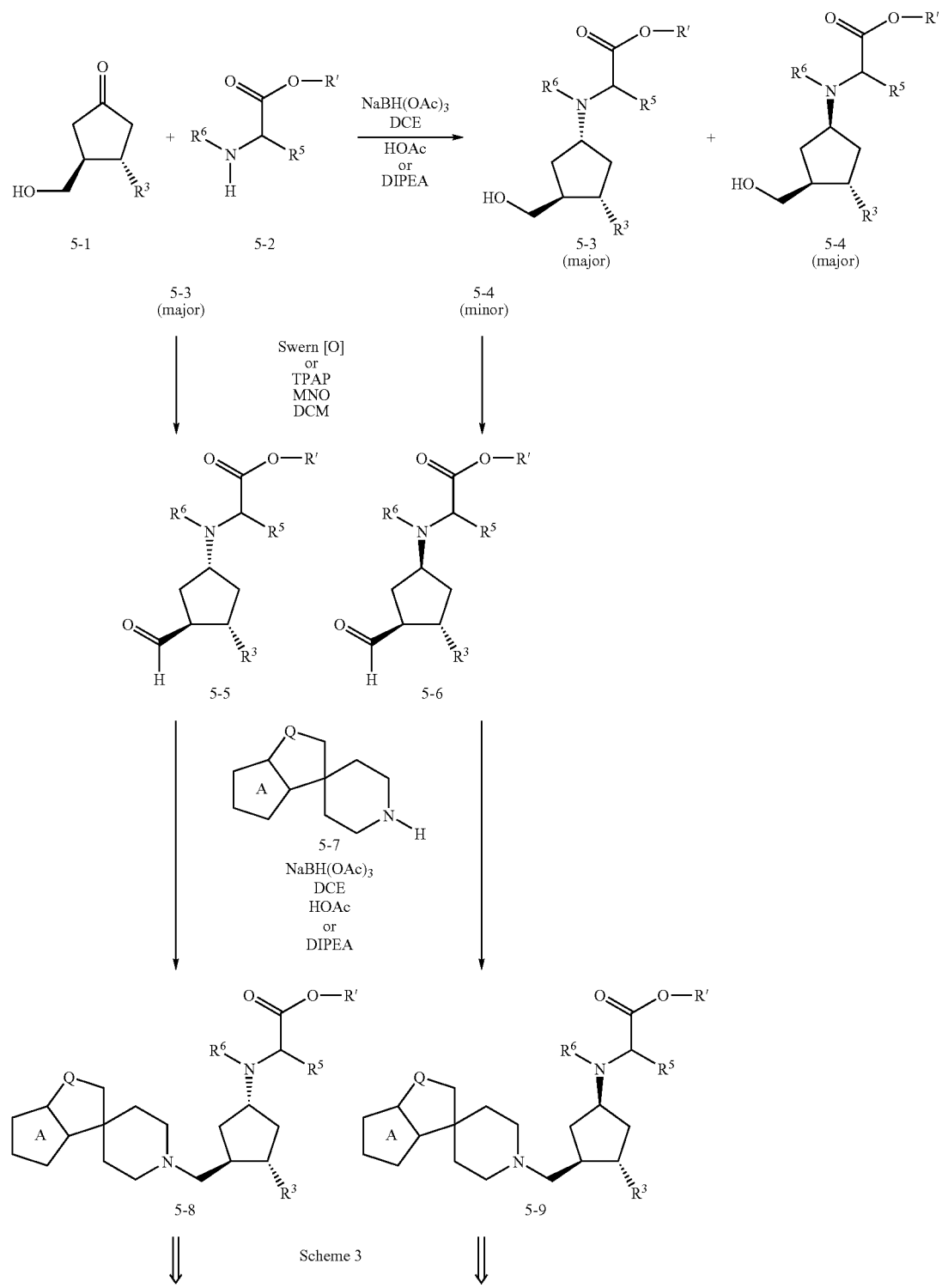

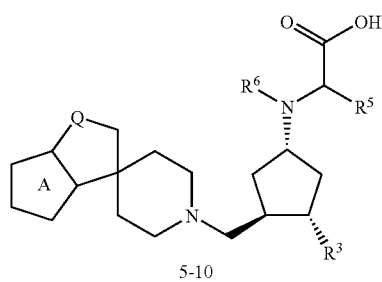

5-10

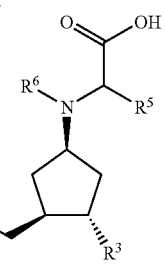

5-11

An alternative preparation of the intermediates 5-3 and 5-4 in Scheme 5A which reverses the C-1 isomeric selectivity is shown in Scheme 5B. Silylation of the alcohol moiety of ketone 5-1 (Scheme 4) gives the silyl ether 5-14. Alternatively, silylation of the alcohol 5-12 (Scheme 3) gives 5-13 which on ozonolysis can also afford the silyl ether 5-14. Reductive alkylation of the aforementioned amino-acid esters 5-2 now using the silyl ether 5-14 affords the products 5-15 and 5-16 in an essentially opposite ratio as is obtained in Scheme 5 for 5-3 and 5-4. TBAF desilylation then affords primarily 5-4. Thus, the preferred C-1 orientation can be selected for depending on the requirements of the desired final compounds.

SCHEME 5B

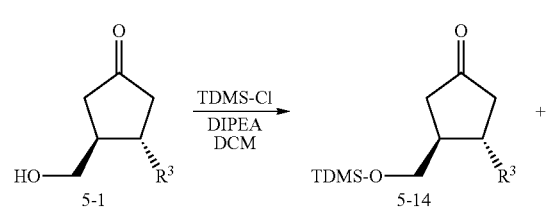

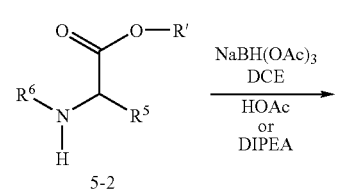

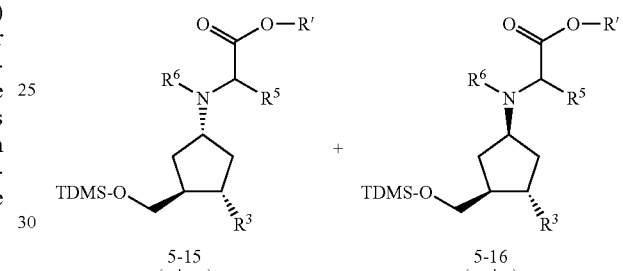

5-15 (minor)    5-16 (major)

↓    ↓

5-3 (minor)    5-4 (major)

An alternative preparation of the intermediates 5-3 or 5-4 in Scheme 5A and intermediates 5-15 and 5-16 in Scheme 5B when $R^6$ is Me is shown in Scheme 5C. When 5-3 ($R^6$=H) is formed in the reductive amination with ketone 5-1 or 5-15 ($R^6$=H), a second reductive amination with formaldehyde, either in the presence of hydrogen and a suitable catalyst, such as 10% Pd/C or Pearlman's catalyst, in methanol or standard reaction with sodium triacetoxyborohydride in 1,2-dichloroehthane, affords the methylated intermediates 5-17 and 5-18 or 5-19 and 5-20. In the latter case, the reaction can be done after isolation of the N—H intermediate or without prior isolation in a two-step, one-pot reaction with the addition of formaldehyde and additional sodium triacetoxyborohydride. Use of acetaldehyde in place of formaldehyde affords the N-ethyl products. These intermediates can be further elaborated to the final products as described in Scheme 5A and/or 5B.

Scheme 5C

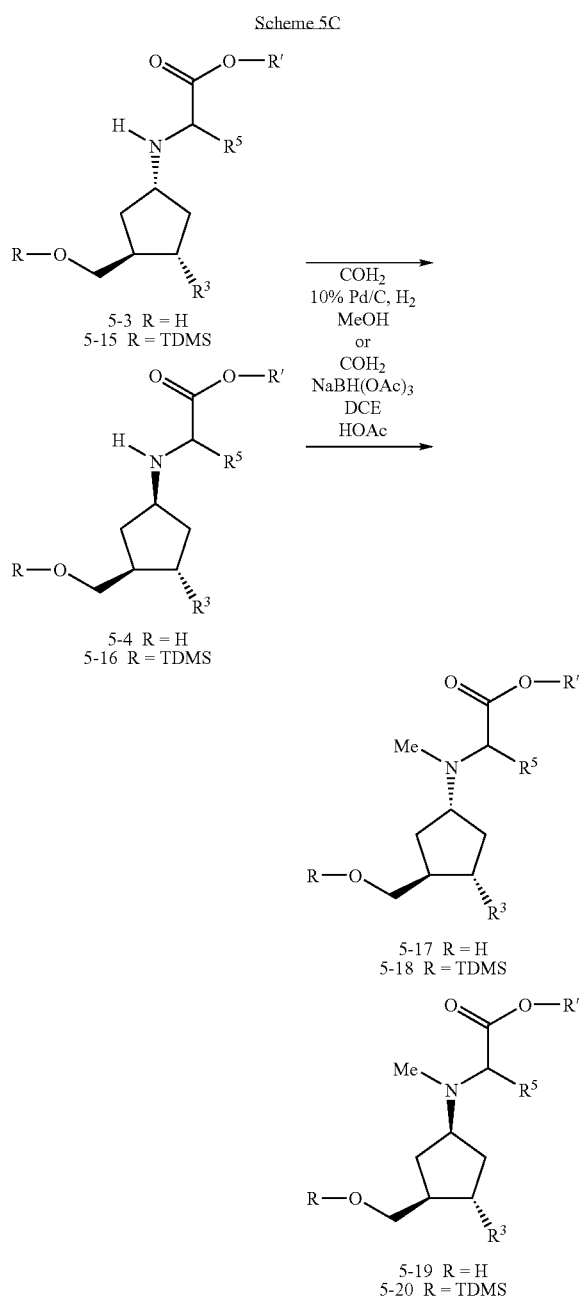

5-3 R = H
5-15 R = TDMS 5-4 R = H
5-16 R = TDMS 5-17 R = H
5-18 R = TDMS 5-19 R = H
5-20 R = TDMS

An alternative route for the preparation of some 1,3,4-trisubstituted cyclopentanes within the scope of the instant invention is given in Scheme 6. Reductive alkylation of benzylamine with ketone-alcohol 6-1 (Scheme 4, either racemic or non-racemic), using for example sodium triacetoxyborohydride or sodium cyanoborohydride, gives 6-2 which can be hydrogenated under standard conditions in methanol in the presence of a palladium catalyst, for example Pd/C or Pearlman's catalyst and using either hydrogen under pressure or ammonium formate at reflux, to afford the primary amine 6-3. Reaction of the amine with CBZ chloride or Boc anhydride gives the amine protected carbamates 6-4 and 6-5 as a mixture of C-1 isomers which can be separated. Oxidation to the aldehydes 6-6 and 6-7 is carried out under Swern conditions or with N-methylmorpholine/TPAP. The relative stereochemistry of the C-1 to the C-3 and C-4 substituents was determined by NMR NOE experiments on either the alcohols 6-4 and 6-5 or the aldehydes 6-6 and 6-7. Reductive alkylation of a 4-spiropiperidine 6-8 (see Schemes 23 to 31) with the individual aldehydes 6-6 and 6-7, using for example sodium triacetoxyborohydride or sodium cyanoborohydride in a suitable solvent such as methylene chloride, 1,2-dichloroethane, THF, acetonitrile or methanol, then provides each of the C-1 amino-protected isomeric 3-((4-spiropiperidin-1-yl)methyl)cyclopentane derivatives 6-9 and 6-10. Deprotection of the C-1 amino with either TFA (for R'=t-butyl) or standard hydrogenation (for R'=Bn) depending on the stability of the spiropiperidine affords the amines 6-11 and 6-12. These amines can then be individually reductively alkylated as above with 2-oxo-acetic acids, such as 2-oxovaleric ($R^5$=n-Pr), 4-methyl-2-oxovaleric ($R^5$=iso-Bu), 2-oxophenylacetic ($R^5$=Ph), to afford the final compounds 6-13 and 6-14 and/or 6-15 and 6-16 as mixtures of the $R^5$ isomers. In the case of $R^5$=iso-Bu and non-racemic cyclopentyl scaffold, comparison of the HPLC of these products with those obtained in Scheme 5 allows the stereochemical assignments of all the final products and intermediates.

SCHEME 6

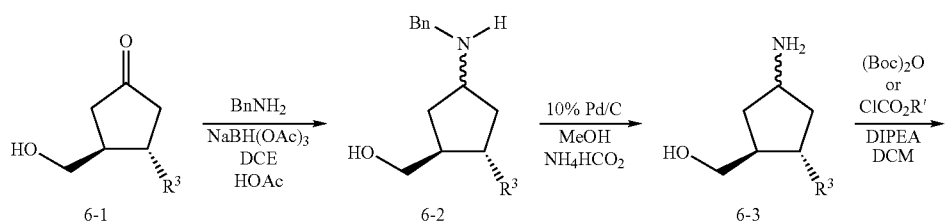

-continued
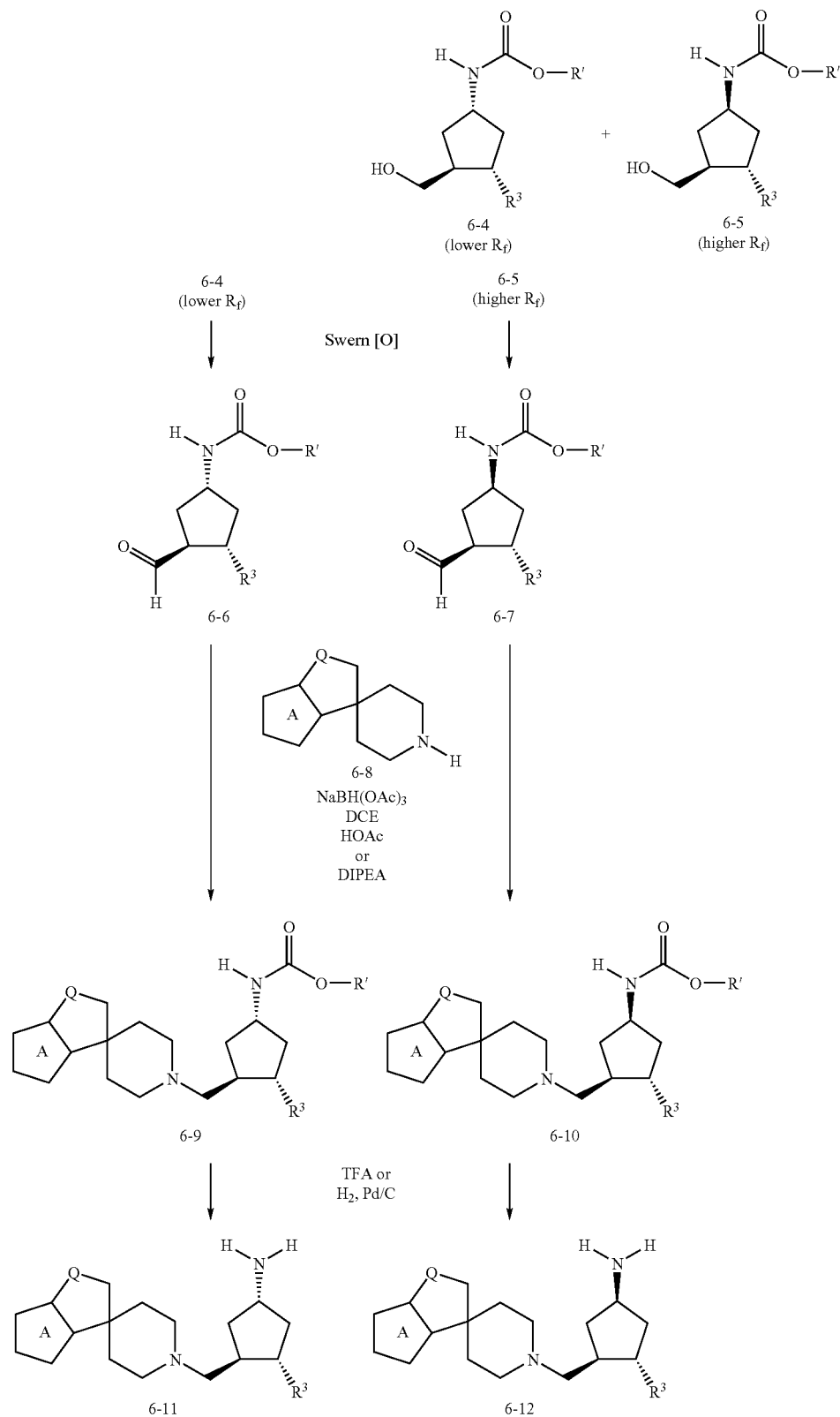

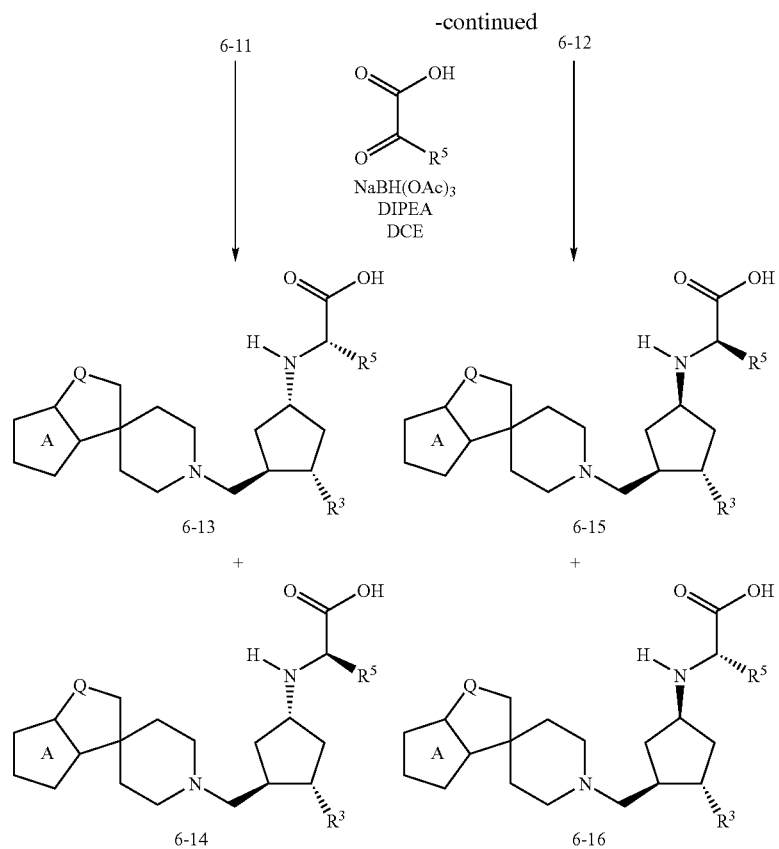

An alternative route for the preparation of some 1,3,4-trisubstituted cyclopentanes within the scope of the instant invention is given in Scheme 7. Reductive alkylation, using for example sodium triacetoxyborohydride or sodium cyanoborohydride, of an alkyl amine with the ketone 7-1 (Schemes 3 or 4) gives 7-2 as a mixture of C-1 isomers which may be separated. Alternatively, carbamate 7-3 (see Scheme 6) can be alkylated with an alkyl or allyl halide, such as 1-bromo-2-methylprop-2-ene, and a strong base, such as sodium hydride in DMF, followed by hydrogenation under standard conditions to reduce the allyl. When R' is Bn, removal of the CBZ can occur simultaneously to give the same amine intermediate 7-2. When R' is t-butyl, a subsequent reaction with TFA is required to give 7-2. Alkylation of the amine with t-butyl or benzyl bromoacetate affords 7-5 which can be converted to the desired final compound(s) 7-6 as described in Scheme 3.

SCHEME 7

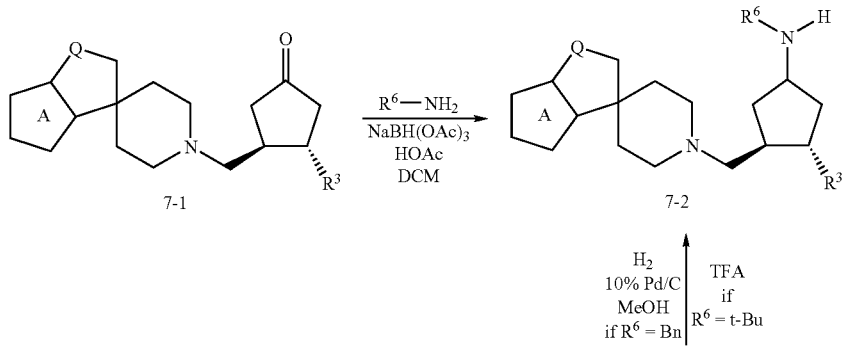

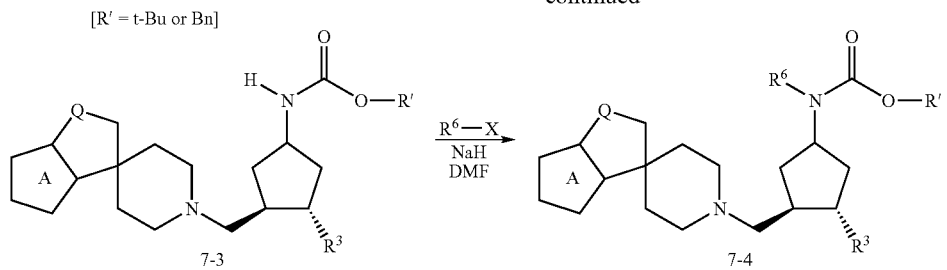

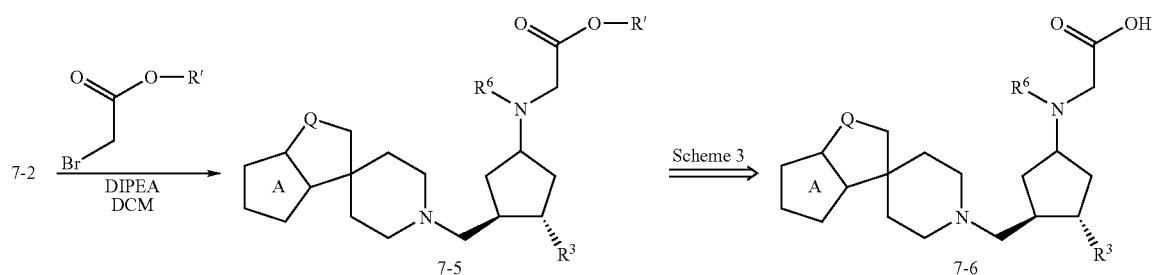

An alternative route for the preparation of some 1,3,4-trisubstituted cyclopentanes within the scope of the instant invention is given in Scheme 8A. Reductive alkylation, using for example sodium triacetoxyborohydride or sodium cyanoborohydride, of glycine t-butyl, benzyl or PMB ester with the ketone-alcohol 8-1 (Scheme 4) gives 8-2 as a mixture of C-1 isomers. A second reductive alkylation with a ketone or aldehyde affords the N-alkyl glycine derivatives 8-3 and 8-4 which can be separated chromatographically either before and/or after the second alkylation. Also, the order of the steps can be reversed such that reductive alkylation of an amine with 8-1 first to give 8-5, followed by alkylation with an alkyl or benzyl bromoacetate as in Scheme 7, affords 8-3 and 8-4. These reactions generally give 8-3 as the predominate product. Individual oxidation of the alcohols 8-3 and 8-4 can be done either under Swern conditions or using the N-methylmorpholine/TPAP method to give the aldehyde intermediate(s) followed by a second or third reductive alkylation of a 4-spiropiperidine which can then be converted to the final product(s) 8-7 and/or 8-8 as described in Scheme 3.

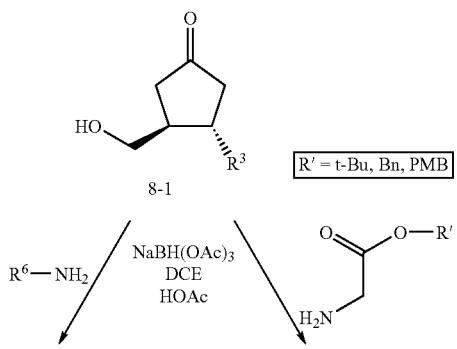

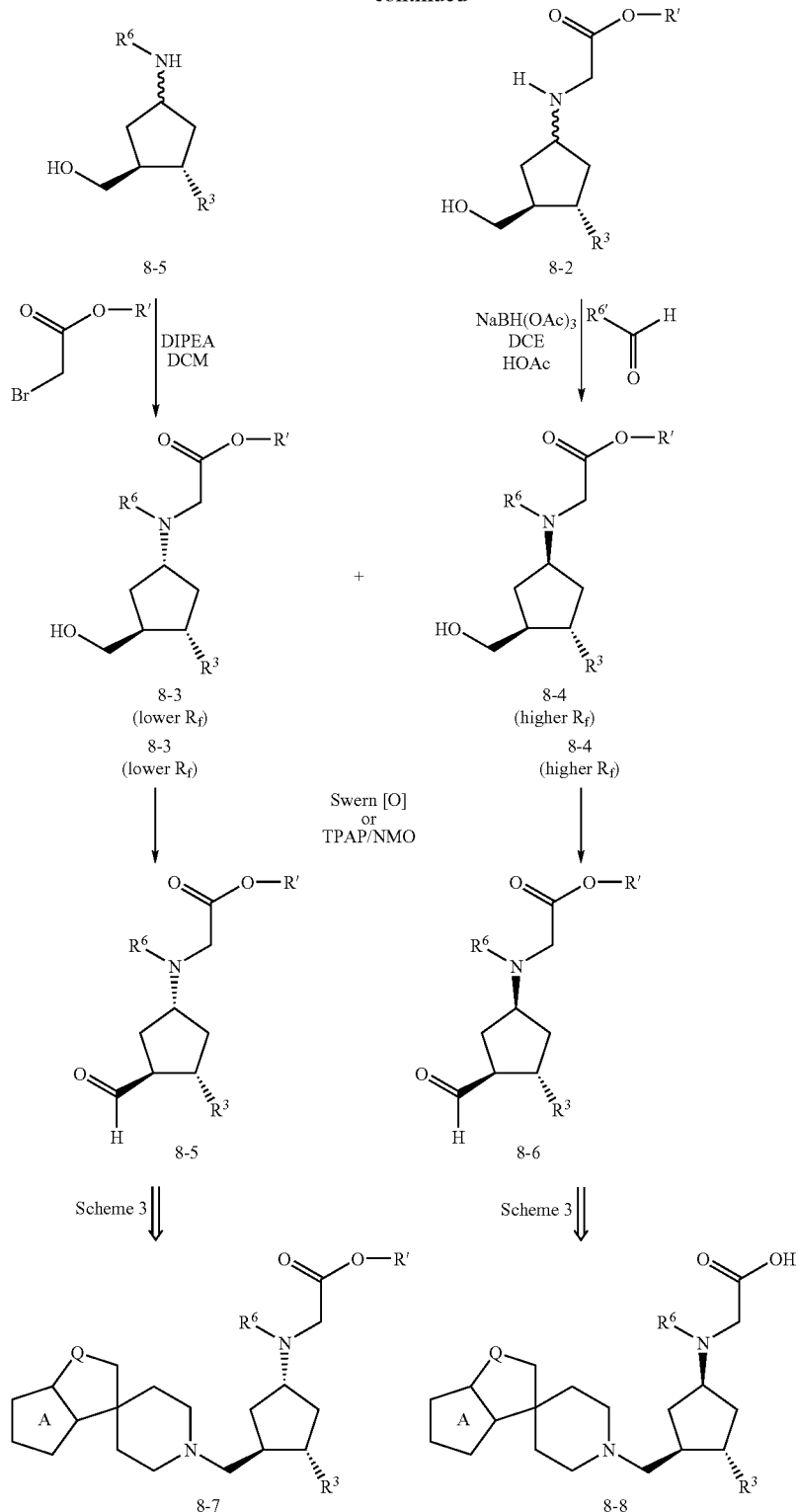

An alternative preparation of the intermediates 8-3 and 8-4 in Scheme 8A which again reverses the C-1 isomeric selectivity is shown in Scheme 8B. Silylation of the alcohol moiety of 8-1 gives the silyl ether 8-9 (see Scheme 5B). Reductive alkylation now using the silyl ether 8-9 gives 8-10 and 8-11 followed by the second reductive alkylation with an aldehyde or ketone affords the products 8-12 and 8-13 in an essentially opposite ratio as is obtained in Scheme 8A for 8-3 and 8-4. TBAF desilylation then affords primarily 8-4. Separation of the C-1 isomers can usually be achieved at one or more of the intermediate steps. Thus, the preferred C-1 orientation can be selected for depending on the requirements of the desired final compounds.

separated and carried on to the final product(s) 9-4 and/or 9-5 individually or as a mixture as detailed in Scheme 5. In cases where the amino-acid ester is too bulky for the reductive amination with sodium triacetoxyborohydride or sodium cyanoborohydride to be effective, an alternative approach is the two step reaction in a suitable titanium(IV) tetraalkoxide followed by reduction with sodium borohydride.

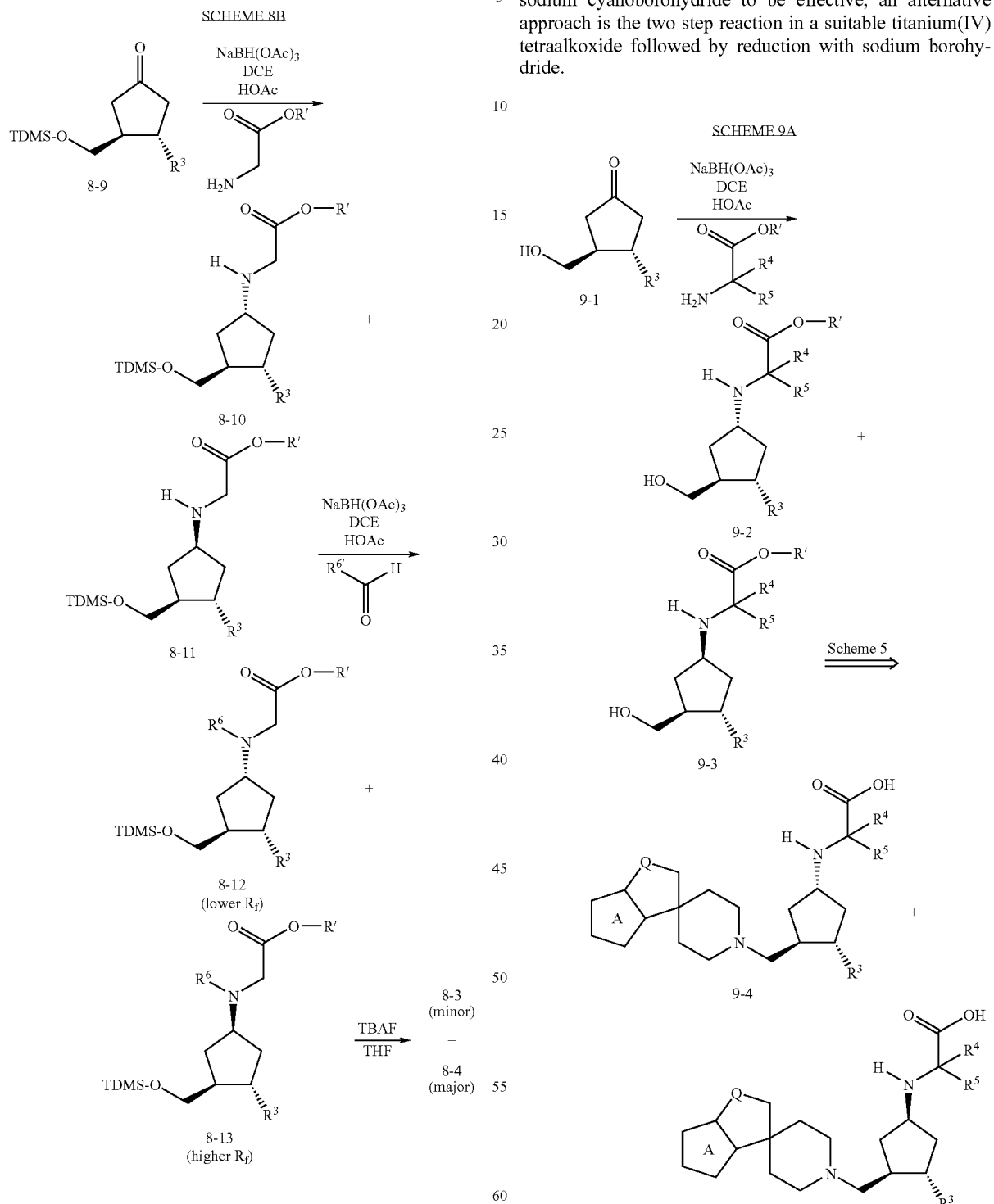

Several other alternative routes for the preparation of some 1,3,4-trisubstituted cyclopentanes within the scope of the instant invention are given in Schemes 9A–C. Reductive alkylation, using for example sodium triacetoxyborohydride or sodium cyanoborohydride, of an amino-acid ester having dialkyl substitution with the ketone-alcohol 9-1 (Scheme 4) gives 9-2 and 9-3 as a mixture of C-1 isomers which may be Furthermore, Scheme 9B shows a second reductive alkylation of 9-2 and/or 9-3 (see Scheme 5C) which affords 9-6 and/or 9-7 which can be separated or used as a mixture to give final product(s) 9-8 and/or 9-9.

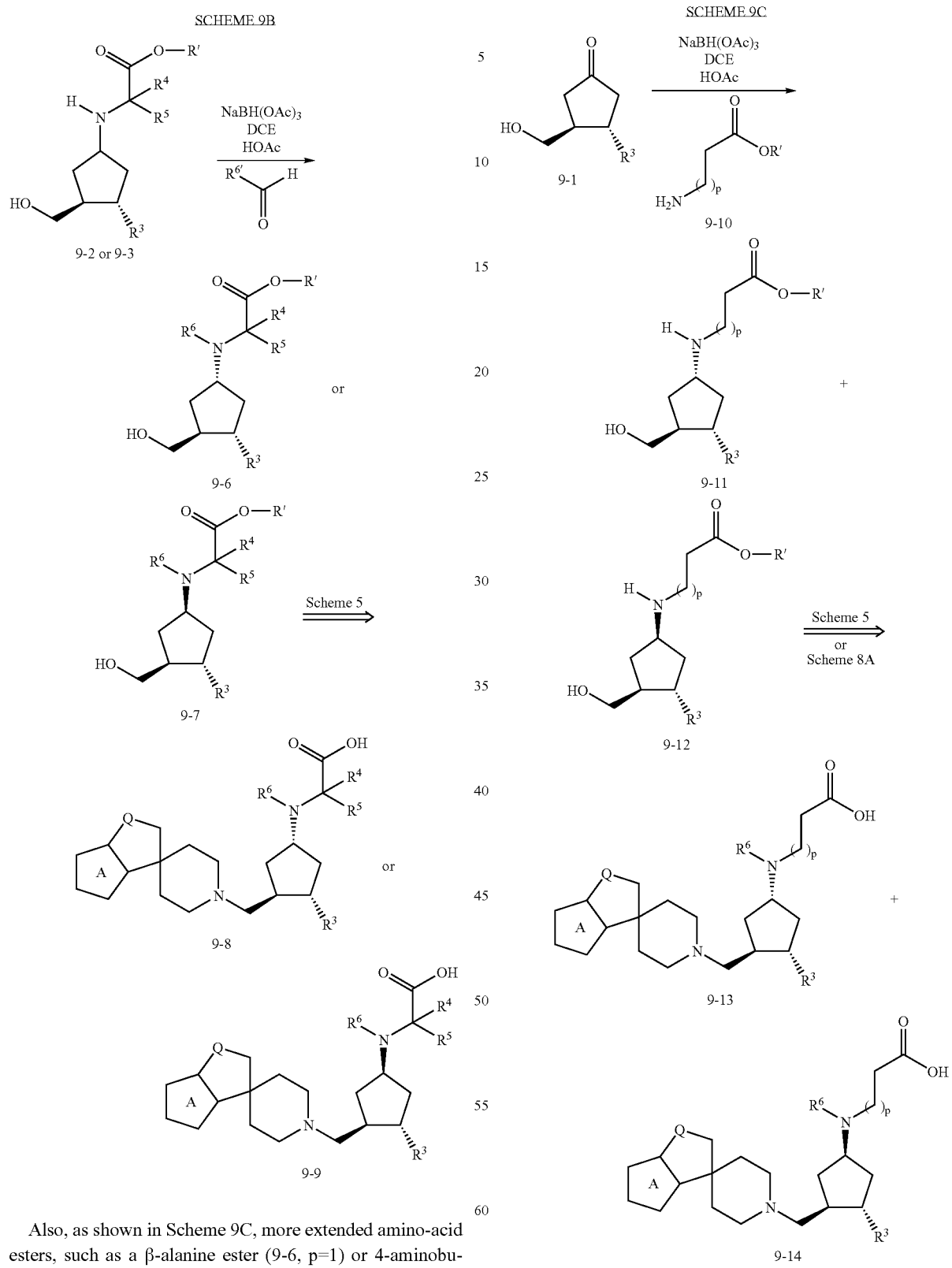

Also, as shown in Scheme 9C, more extended amino-acid esters, such as a β-alanine ester (9-6, p=1) or 4-aminobutyrate (9-10, p=2), which may also be substituted on the chain or on N, can be employed to give 9-11 and 9-12. These intermediates can then be converted to final product(s) 9-13 and 9-14 as described in Schemes 5 and/or 8A.

An alternative route for the preparation of some 1,3,4-trisubstituted cyclopentanes within the scope of the instant invention is given in Scheme 10. Reductive alkylation, using for example sodium triacetoxyborohydride or sodium cyanoborohydride, of a cyclic secondary amino-acid 10-2, such as D- or L-proline t-butyl ester (m=0), β-proline t-butyl ester (m=0), 2-, 3-, and 4-t-butylcarboxypiperidine (m=1), with the ketone-alcohol 10-1 (Scheme 4) gives 10-3 and 10-4 as a mixture of C-1 isomers which may be separated. These intermediates can then be converted to the final product(s) 10-5 and/or 10-6 as described in Scheme 5.

An alternative route for the preparation of some 1,3,4-trisubstituted cyclopentanes within the scope of the instant invention is given in Scheme 11. Reductive alkylation, using for example sodium triacetoxyborohydride or sodium cyanoborohydride, of a cycloalkyl amino-acid 11-2, such as 1-aminocyclopentane carboxylic acid t-butyl ester (Z=single bond) or a heterocyclic amino-acid, such as 4-aminopyran-4-yl carboxylic acid t-butyl ester (Z=O) with the ketone-alcohol 11-1 (Scheme 4) gives 11-3 and 11-4 as a mixture of C-1 isomers which may be separated. These intermediates can then be converted to the final product(s) 11-5 and/or 11-6 as described in Scheme 5.

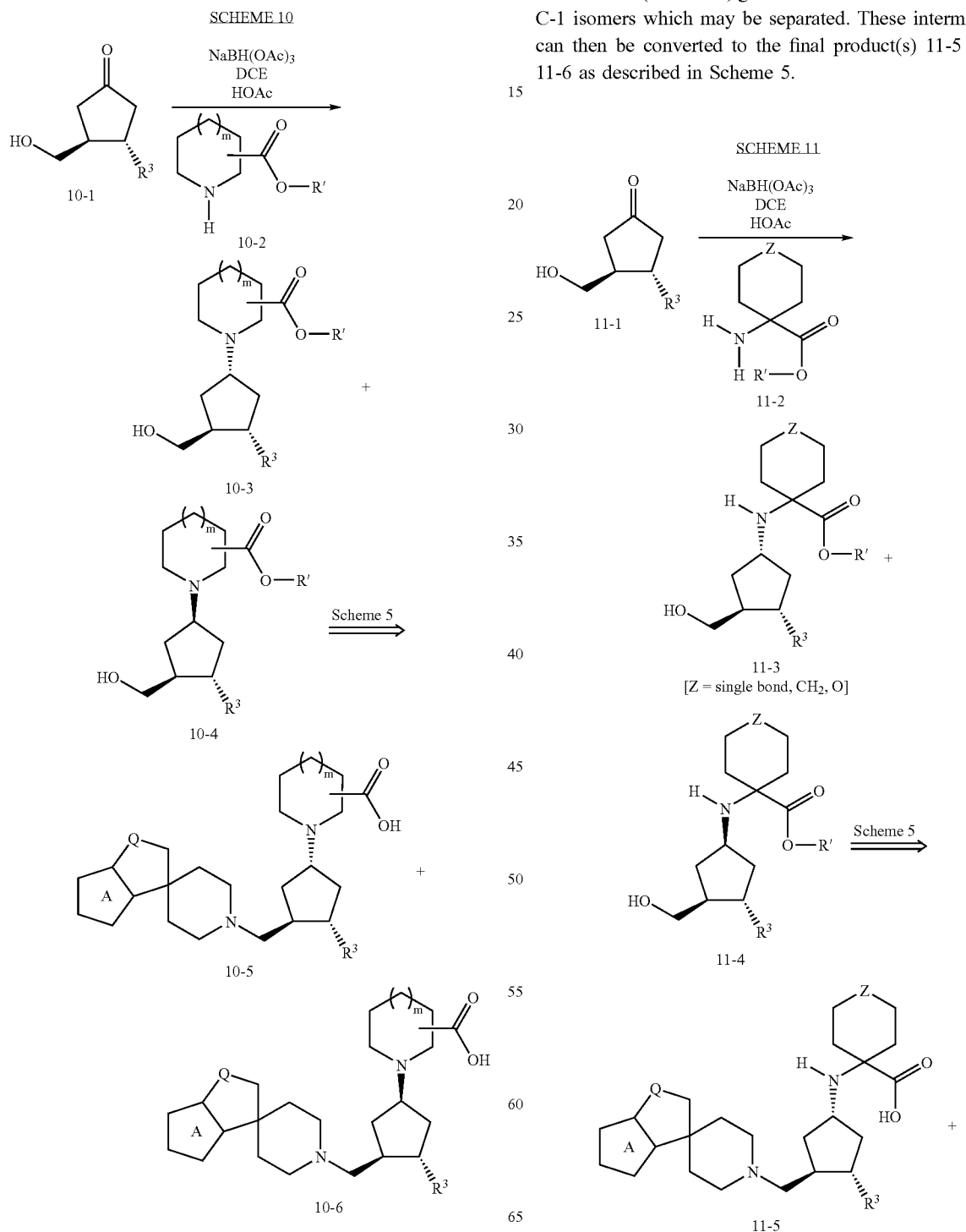

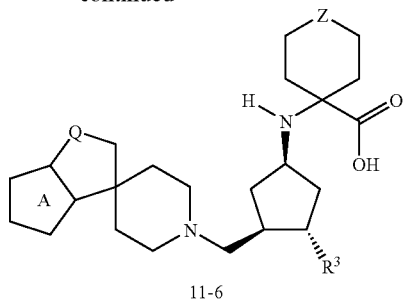

11-6

A route for the preparation of some 1,3,4-trisubstituted cyclopentanes within the scope of the instant invention is given in Scheme 12. Reaction of ketone 12-1 (from Scheme 5B) with a dialkylphosphonoacetic acid ester such as 12-2 (R'=Me, Et, t-Bu, Bn, PMB; R"=Me, Et) (Horner-Wadsworth-Emmons modified ylid reaction) in a suitable solvent, such as THF, dimethylsulfoxide or DMF, in the presence of a strong base, such as sodium hydride or lithium bis(trimethylsilyl)amide, at 0 to 70° C., preferably at about room temperature, affords a mixture of double bond products 12-3 and 12-4. Removal of the TDMS (see below) group allows for the chromatographic separation of these isomers if desired. Normally, these were hydrogenated under standard conditions (e.g., in methanol at atmospheric to 60 psi of hydrogen) in the presence of a Pd catalyst (e.g., 10% palladium on carbon or 20% palladium hydroxide on carbon (Pearlman's catalyst)) to the cyclopentane acetic acid derivatives as a mixture of the C-1 isomers 12-5 and 12-6, with 12-6 usually being the predominant isomeric product, the ratio depending on conditions and the catalyst used. Since the TDMS group is prone to cleavage under these conditions to give 12-7 and 12-8, the hydroxy group can be reprotected using standard conditions with TDMS-Cl (see Scheme 5A). Alternatively, the TDMS group can be completely removed using either acidic alcohol, such as HCl in methanol, or using TBAF in THF, both at about 0° C. to about room temperature, to afford 12-7 and 12-8, which can be separated by chromatography. Alternatively, the TDMS group can be removed prior to the hydrogenation under acidic conditions or with TBAF (see above). Hydrogenation of the intermediate alcohol under standard conditions as above or with a hydroxy directed catalyst, such as (bicyclo [2.2.1]hepta-2,5-diene)[1,4-bis(diphenylphosphino)butane] rhodium(I) tetrafluoroborate or (1,5-cyclooctadiene)(pyridine)(tricyclohexylphosphine)iridium (I) hexafluorophosphate, in methylene chloride or THF, can afford predominantly the other isomeric product 12-7. Oxidation of 12-7 and/or 12-8 to the aldehyde(s) can be carried out under numerous conditions, such as with DMSO and oxalyl chloride at low temperature, followed by triethylamine (Swern oxidation), with the Dess-Martin periodinane, with N-methylmorpholine in the presence of a catalytic amount of TPAP, or with various chromium trioxide-based reagents (see March J. "Advanced Organic Chemistry", 4th ed., John Wiley & Sons, New York, pp. 1167–1171 (1992)). Reductive alkylation of a cyclic amine, such as spiropiperidine 12-9 (see Schemes 23 to 31), using for example sodium triacetoxyborohydride or sodium cyanoborohydride in a suitable solvent such as methylene chloride, 1,2-dichloroethane, THF, acetonitrile or methanol, with the above aldehyde(s) can then provide the 3-((4-spiropiperidin-1-yl)methyl)cyclopentane derivative(s) 12-10 and/or 12-11 which also can be separated by chromatography. When R' is t-Bu or PMB, final deprotection of the acetic acid ester to give 12-12 and/or 12-13 can be done using acidic conditions, such as HCl in ether, formic acid or TFA. When R' is an alkyl ester, standard basic hydrolysis can be used, such as sodium or lithium hydroxide in aq. ethanol, methanol or THF. When R' is Bn or PMB, standard hydrogenation can be used for the deprotection. These acid derivatives are within the scope of the instant invention and can be chemokine receptor modulators. The choice of R' is made depending on the availability of 12-2 or the stability of the spiropiperidine and can be changed during the above sequence by suitable removal and re-esterification, such as hydrolysis of an ethyl ester (12-5 to 12-8, R'=Et) and replacement with a PMB ester (12-5 to 12-8, R'=PMB), using for example PMB-Cl in DMF with TEA as base, after the hydrogenation of 12-3 and/or 124 to 12-5 and 12-6 or 12-7 and 12-8.

SCHEME 12

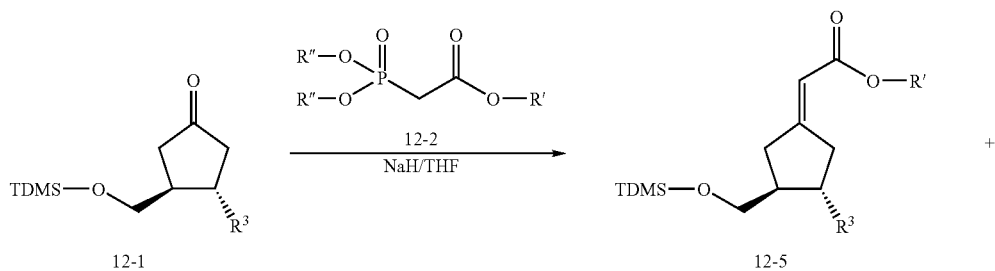

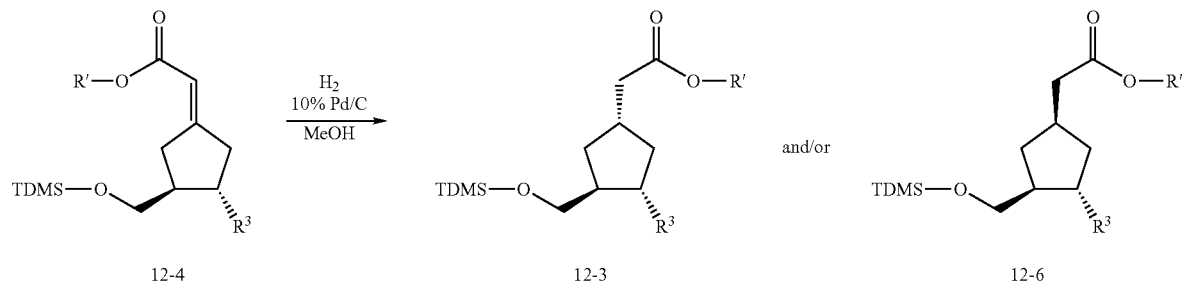
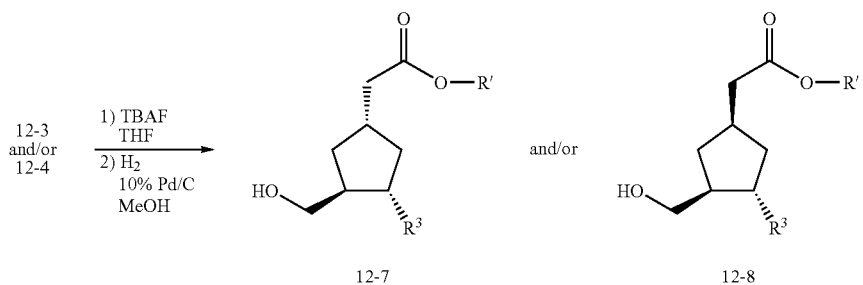
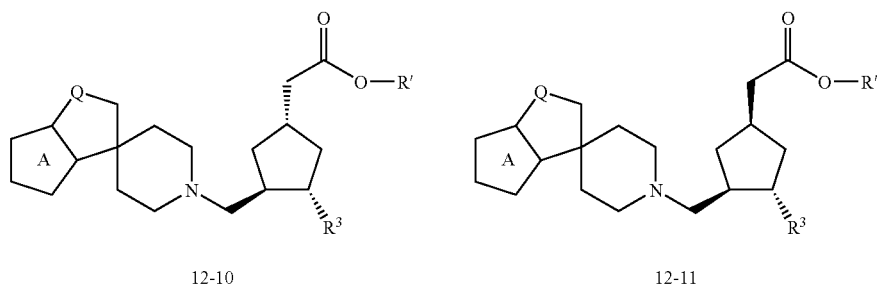

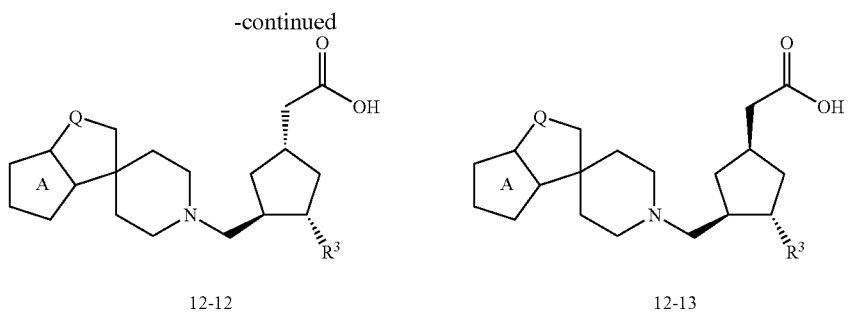

12-12            12-13

An alternative route for the preparation of some 1,3,4-trisubstituted cyclopentanes within the scope of the instant invention is given in Scheme 13. Alkylation of the acetic acid moiety of 13-1 (from Scheme 12), either as racemic or non-racemic and either as a single C-1 isomer or as a mixture, can be done under a variety of conditions with an appropriate alkylating agent, such as an alkyl or allyl halide or sulfonate, in the presence of a strong base, such as sodium hydride in DMF or KHMDS or LDA in THF at low temperature in the presence or absence of an anion stabilizer, such as HMPA, to give the 2 isomeric 2-alkyl acetic acid derivatives 13-2 and 13-3. Removal of the TDMS group with TBAF (see Scheme 12) affords the alcohols 13-4 and 13-5 which can be separated by chromatographic methods. Oxidation to the aldehyde(s), reductive alkylation of a 4-spiropiperidine (see Schemes 23 to 31) and final removal of the acetic acid ester as described for Scheme 12 then affords the final product(s) 13-6 and/or 13-7. When an allyl derivative is used in the above alkylation, it can itself be a chemokine receptor modulator within the scope of the present invention or the double bond can be hydrogenated at the stage of 13-2 and 13-3 or 13-4 and 13-5 or at a point later in the sequence depending on the stability of the spiropiperidine to various conditions.

SCHEME 13

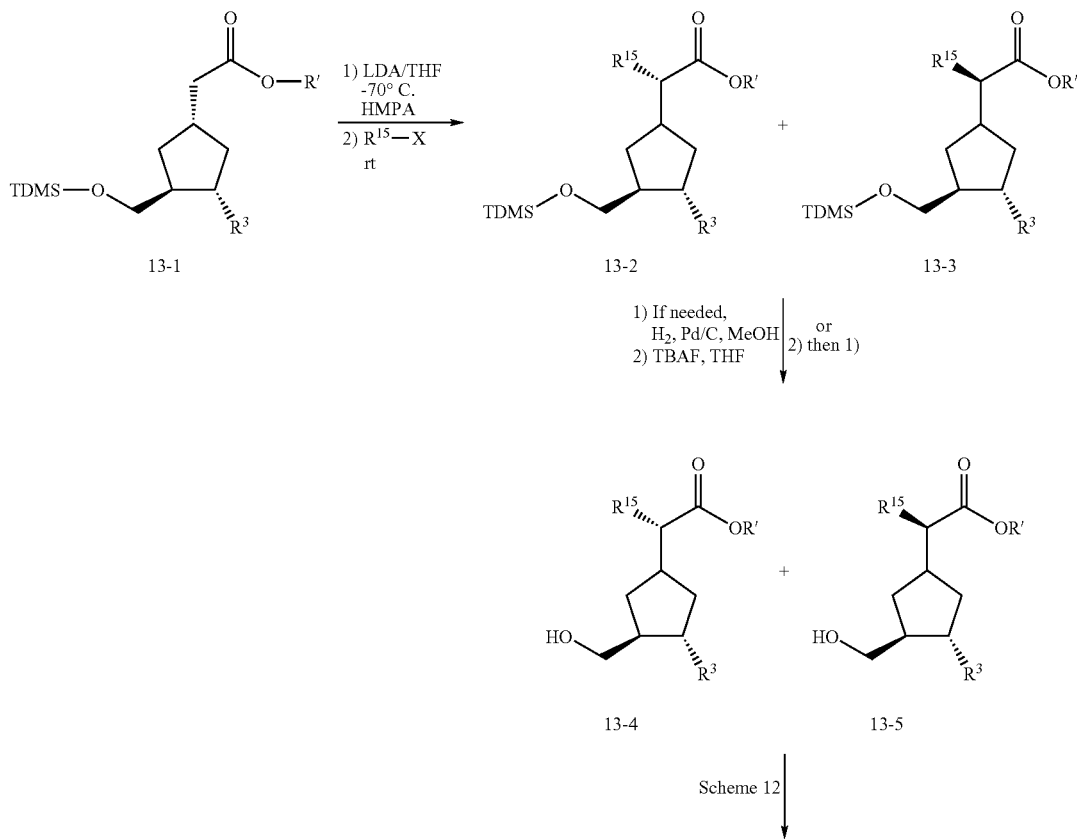

Scheme 12

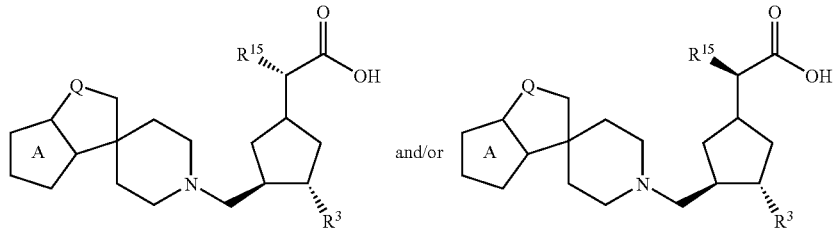

13-6 and/or 13-7

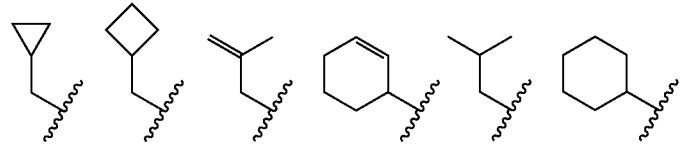

X = Br, I
R' = Me, Et, t-Bu
R^15 = Me, Et, iso-Pr

An alternative route for the preparation of some 1,3,4-trisubstituted cyclopentanes within the scope of the instant invention is given in Scheme 14. The ketone 14-1 (from Scheme 5B) can be reacted with a 2-alkylsubstituted dialkylphosphonoacetic acid ester, such as 14-2 in which $R^{15}$ is Me, Et, cyclohexyl, iso-propyl, iso-butyl, cyclopropylmethyl, cyclobutylmethyl, etc. and fluoro to afford 14-4 and 14-5 which can be separated by chromatographic methods. When the desired dialkylphosphonoacetic acid ester is not commercially available, it can be prepared by alkylation of 14-3 under standard conditions, such as with an alkyl or allyl halide using a strong base, such as sodium hydride or LHMDS, in a suitable solvent, such as DMF, THF or DMSO. Alternatively, 14-3 can be alkylated using sodium hydride as a base in DMF in the presence of CuI at 100° C. The intermediate(s) 14-4 and/or 14-5 can be used as a mixture or may be separated by chromatography into a single double bond isomer at this point or after de-silylation to 14-6 and 14-7. These are then converted to the final product(s) 14-8 and/or 14-9 as described in Scheme 12. When $R^{15}$ in 14-2 contains a double bond, it can be selectively hydrogenated to the corresponding saturated compound, under standard conditions with 10% Pd/C in methanol, as 14-4 to 14-7 or further on in the sequence depending on the compatibility of R', $R^{15}$, and the spiropiperidine.

SCHEME 14

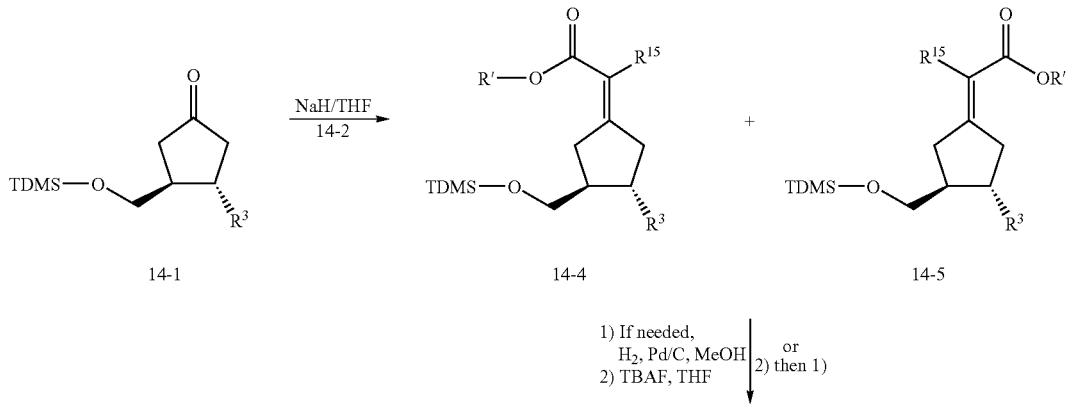

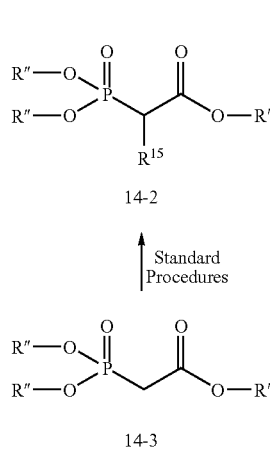

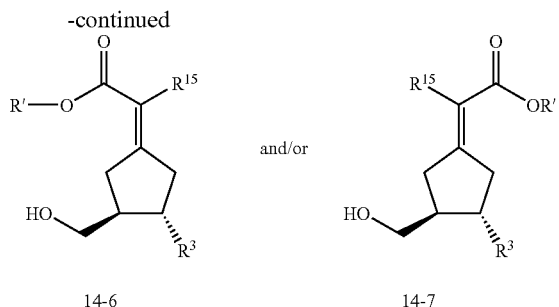

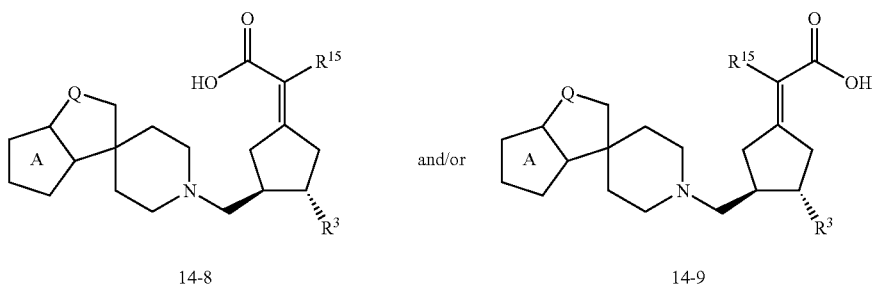

An alternative route for the preparation of some 1,3,4-trisubstituted cyclopentanes within the scope of the instant invention is given in Scheme 15. The C-1 exo-methylene unsaturation of 15-1-154 (Scheme 14) can be hydrogenated either catalytically under standard conditions with Pd (R=H or TDMS) or under alcohol directed conditions with Ir or Rh (R=H) (see Scheme 12) or with chemical reduction, such as with potassium azodicarboxylate in the presence of acetic acid in methanol, to afford the 4 possible stereoisomers 15-5 to 15-8. These isomers can be separated at this step or later in the sequence. The choice of catalyst and whether the reduction is done on the TDMS ether or alcohol can alter the ratio of C-1 epimeric products obtained as described in Scheme 12 and can be used to preferentially obtain the desired isomer(s). These are then converted to the final product(s) 15-9 as described in Scheme 12.

Scheme 15

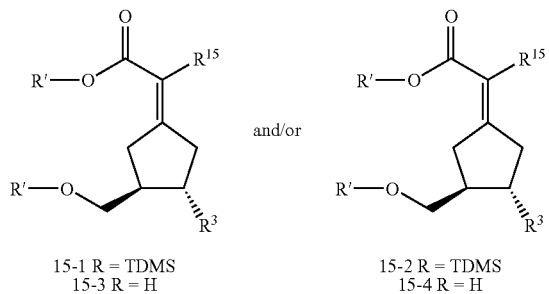

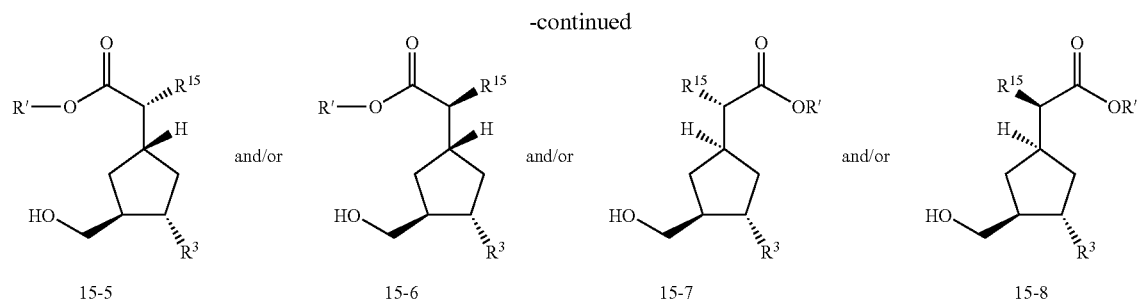

15-5 and/or 15-6 and/or 15-7 and/or 15-8

Scheme 12

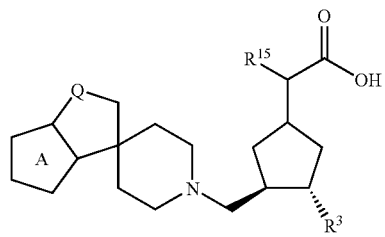

15-9

An alternative route for the preparation of some 1,3,4-trisubstituted cyclopentanes within the scope of the instant invention is given in Scheme 16 in which the C-1 acetic acid moiety can be homolygated. The ester 16-1 (from Scheme 13 or 15, R=OTDMS, Bn, or other suitably protected alcohol group) can be hydrolyzed under standard conditions, such as sodium hydroxide in aqueous methanol, to the acid 16-2. A standard Arndt-Eistert reaction can be used to homolygate the acetic acid to a propionic acid. Thus, the acid can be activated as an acid chloride, for example with oxalyl chloride in the presence of a catalytic amount of DMF in methylene chloride, or as a mixed anhydride with iso-butyl chloroformate or pivaloyl chloride in ether or methylene chloride in the presence of TEA. Subsequent reaction with diazomethane in an inert solvent, such as ether or methylene chloride, affords the diazoketone 16-3 which can be decomposed in methanol in the presence of silver oxide and/or silver nitrate or with irradiation in methanol to give the methyl ester 16-4. If required for conversion to the desired final product, hydrolysis of the methyl ester and reesterification can give a more compatible ester as detailed in the above schemes. Subsequent removal of the silyl or Bn ether (or other suitable alcohol protecting group) leads to the alcohol 16-5 which can be converted to the final product(s) 16-6 as detailed in Scheme 12. Alternatively, if the spiropiperidine in the final product is compatible with the above homolygation sequence, the "R—O" moiety in 16-1 can be replaced with the already functionalized spiropiperidine moiety as obtained in Schemes 12, 13 and 15 above.

SCHEME 16

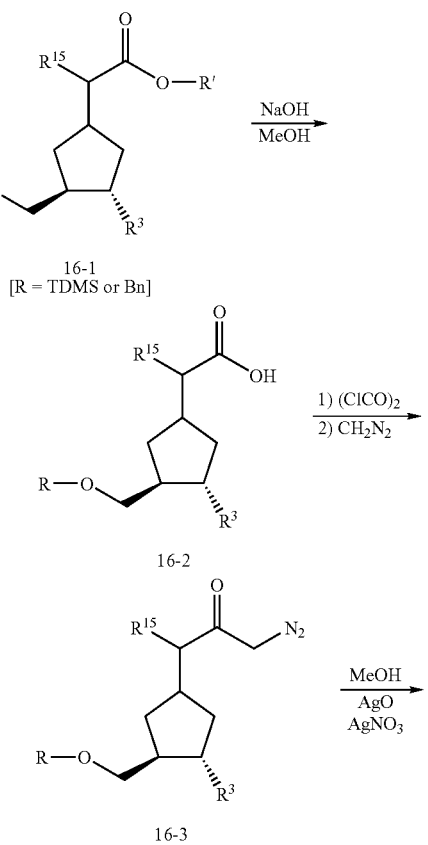

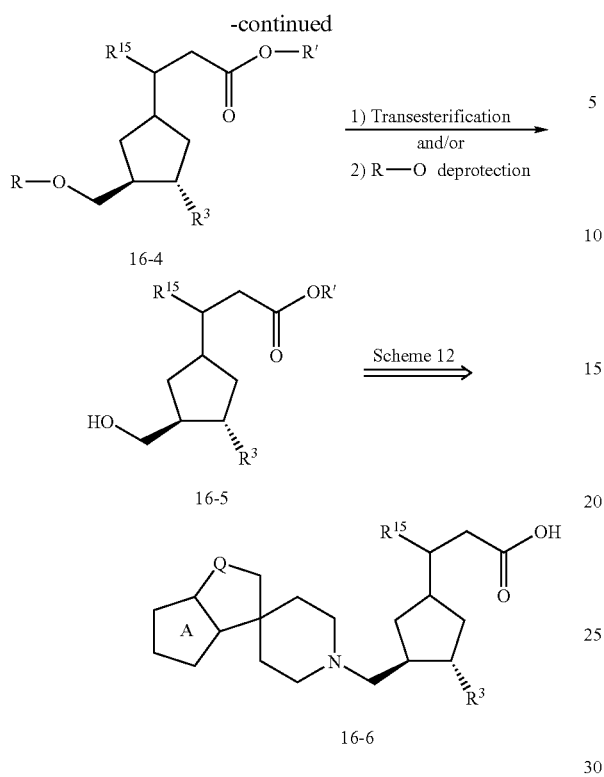

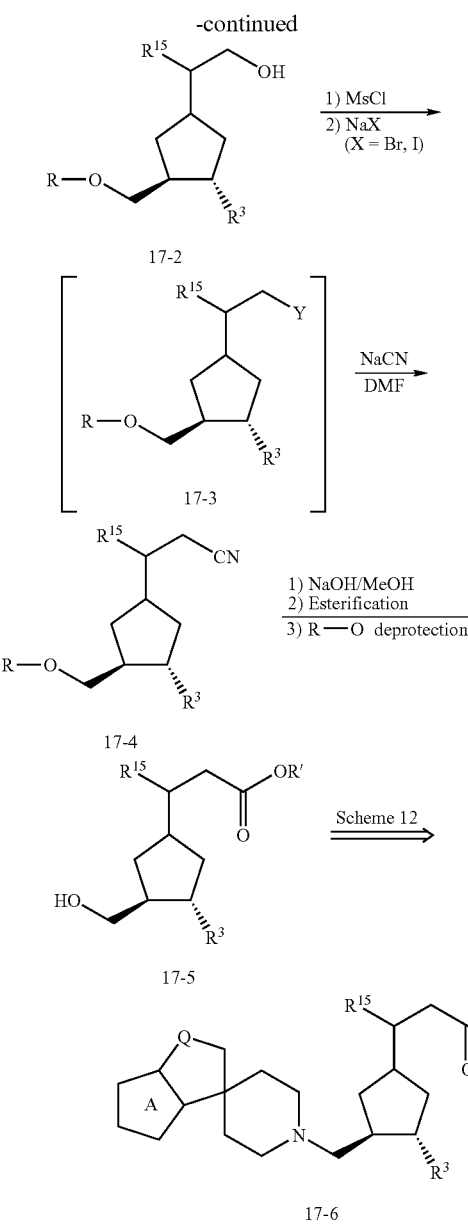

An alternative route for the preparation of some 1,3,4-trisubstituted cyclopentanes within the scope of the instant invention in which the C-1 acetic acid moiety can be homolygated is given in Scheme 17. The homolygation can be achieved through reduction of the ester 17-1 (from Scheme 13 or 15, R=TDMS, Bn, or other suitably protected alcohol group) with an appropriate reducing agent, such as LAH in THF, to give the alcohol 17-2. Activation of the alcohol as its mesylate and/or the bromide or iodide 17-3 (Y=OMs, Br or I) followed by displacement with sodium cyanide would afford the nitrile 17-4. Hydrolysis to the acid, esterification and removal of the C-3 hydroxymethyl protecting group would led to the hydroxymethyl intermediate 17-5 which can be converted to the final product(s) 17-6 as detailed in Scheme 12. Alternatively, if the spiropiperidine in the final product is compatible with the above homolygations, the "R—O" moiety in 17-1 can be the already functionalized spiropiperidine moiety as obtained in Schemes 12, 13 and 15 above.

SCHEME 17

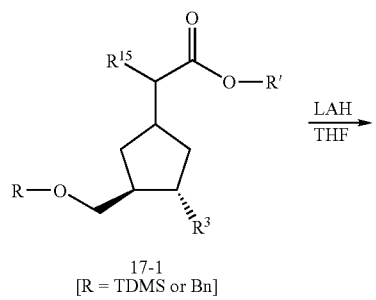

An alternative route for the preparation of some 1,3,4-trisubstituted cyclopentanes within the scope of the instant invention in which the C-1 acetic acid moiety can be homolygated is given in Scheme 18. Standard hydroboration of 18-1 (Scheme 5B, R=TDMS, Bn, or other suitably protected alcohol group), such as with borane-THF complex in THF followed by an oxidative work-up with NaOH and hydrogen peroxide or trimethylamine-N-oxide, affords the alcohol 18-2. Activation of alcohol 18-2 as the mesylate and/or bromo or iodo 18-3 (Y=OMs, Br, or I) and displacement with an acetate anion gives the ester 18-4 in which the $R^{15}$ is now on the β carbon from the cyclopentane ring. Transesterification, if necessary, followed by deprotection at C-3 leads to 18-5. Alternatively, oxidation of 18-2, such as with the Swern method, gives the aldehyde which can be elaborated to 18-5 as shown in Schemes 14-15. The hydroxymethyl intermediate 18-5 can be converted to the final product(s) 18-6 as detailed in Scheme 12. Alternatively, if the spiropiperidine in the final product is compatible with the above homolygations, the "R—O" moiety in 18-2 can be the already functionalized spiropiperidine moiety as obtained in Schemes 12, 13 and 15 above.

invention in which the C-1 acetic acid moiety can be converted to an amino-acid derivative is given in Scheme 19. Hydroxylation of 19-1 (from Scheme 12) can be accomplished by the procedure of Davis, et. al., *J. Org. Chem.*, 1986, 2402. Thus, treatment of 19-1 with a strong base, such as LDA or lithium bis(trimethylsilyl)amide, in THF at a low temperature (e.g., about -70° C.) and quenching of the intermediate anion with (1S)-(+)-(10-camphorsulfonyl)oxaziridine affords a 2.5:1 mixture of primarily 19-2 and a lesser amount of 19-3. Alternatively, use of (1R)-(−)-(10-camphorsulfonyl)oxaziridine affords the opposite ratio of 19-2 and 19-3. The isomeric alcohols can be separated by chiral HPLC utilizing a Chiracel OD column. The stereochemistry of 19-2 (major, longer retention isomer) is assigned by conversion to the hydroxy acid 19-4 by desilylation with TBAF in THF followed by hydrogenation of the PMB ester with Pd/C in methanol. Crystallization of 19-4 afforded a crystal which was amenable to X-ray analysis. Separate treatment of 19-2 with triflic anhydride in THF in the presence of a non-reactive base, such as 2,6-lutidine, can give the triflate 19-5. SN2 displacement of the triflate of 19-5 with a primary amine at elevated temperature, such as 65° C. for 20 hours, gives 19-6 with inverted stereochemistry alpha to the ester. Deprotection of the TDMS with TBAF and oxidation of the hydroxy with TPAP as above (see Scheme 5) can afford the aldehyde which can then be coupled to the spiropiperidine and converted to the final product(s) 19-7 (R'=H) as detailed in Scheme 12. Also, an additional reductive amination of the secondary amine of 19-6 or a later intermediate can then afford the tertiary amine 19-17 (R'=alkyl).

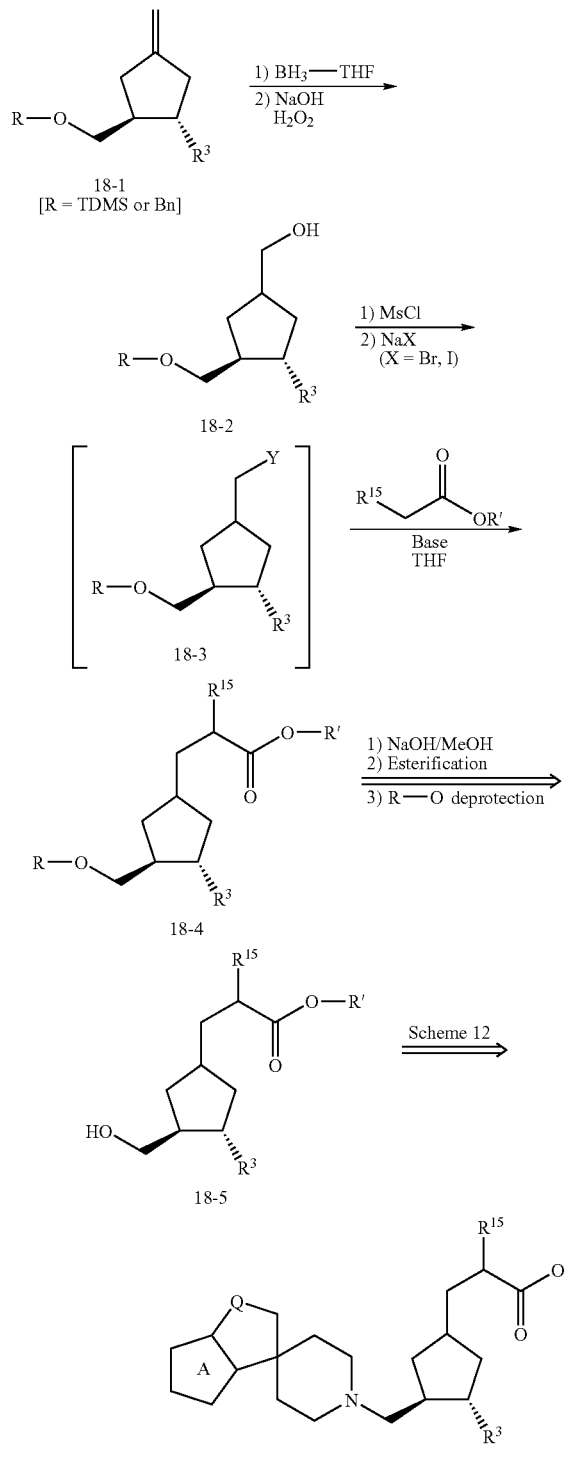

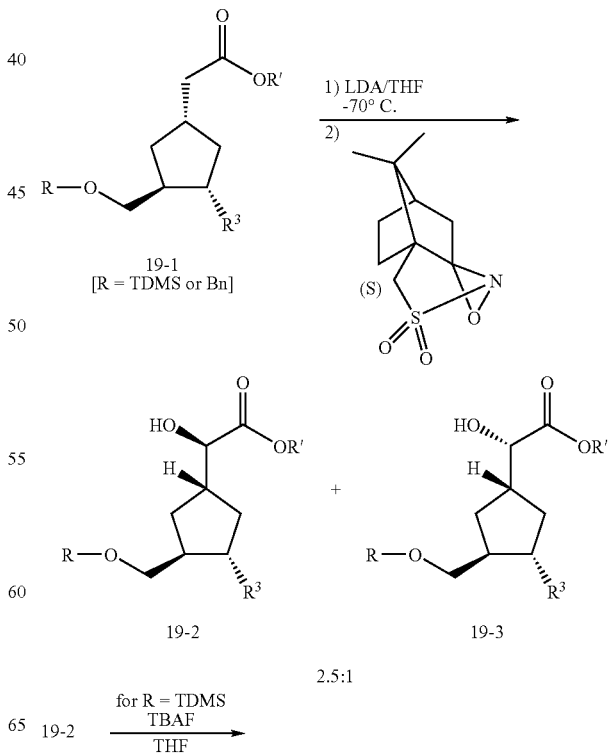

An alternative route for the preparation of some 1,3,4-trisubstituted cyclopentanes within the scope of the instant -continued

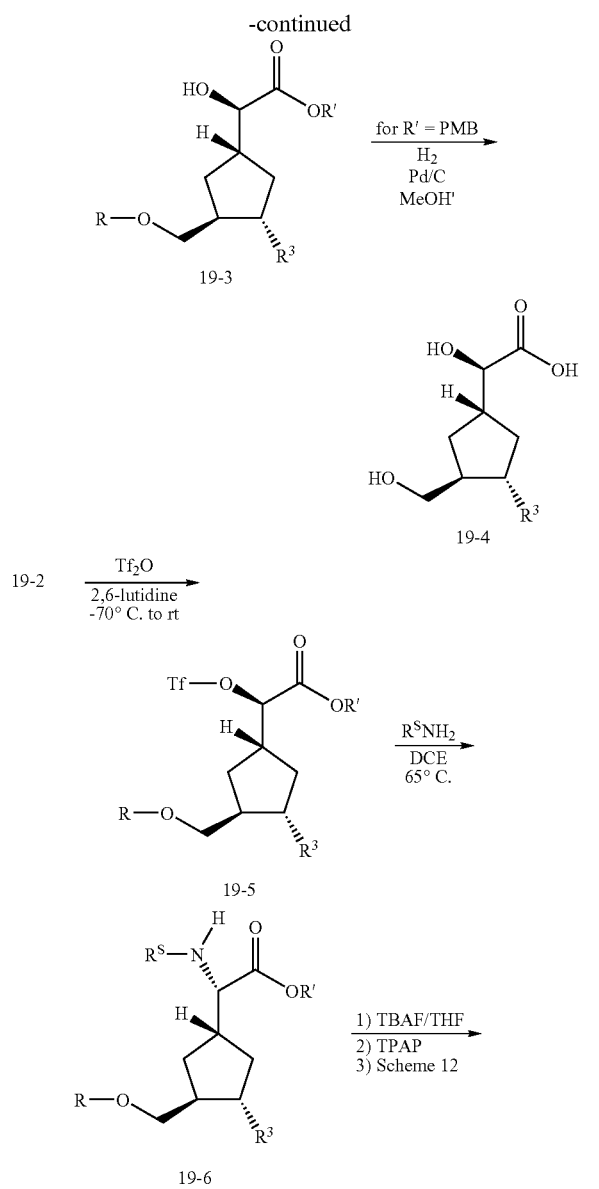

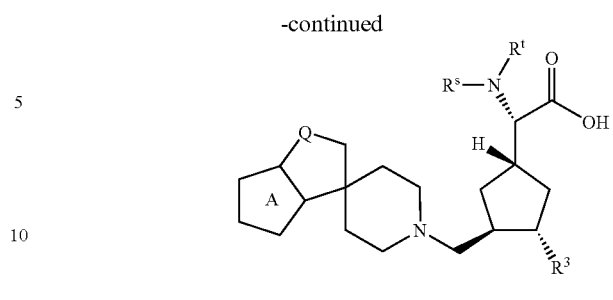

An alternative route for the preparation of some 1,3,4-trisubstituted cyclopentanes within the scope of the instant invention in which the C-1 position is geminally substituted with an amino and carboxylic acid moiety is given in Scheme 20. Addition of the anion of chloroform, formed by treatment with a strong base such as LDA or lithium bis(trimethylsilyl)amide in THF at low temperature (e.g., about −70° C., to 20-1(from Scheme 12) can afford the alcohol 20-2 as a mixture of C-1 diastereomers. Treatment of 20-2 with sodium azide under basic conditions, such as DBU in a suitable solvent such as methanol, affords the azido-acid 20-3. Conversion of the acid to the methyl ester under acidic conditions, such as HCl methanol, can also effect removal of the TDMS group to give the alcohols 20-4 and 20-5 after chromatographic separation. Each diastereomer can then be reacted separately. Swern oxidation to the aldehyde 20-6 and coupling to 4-spiropiperidines 20-7 as described above can give 20-8. Reduction of the azide to the amine 20-9 and either a single reductive alkylation and double alkylation can give 20-10 or 20-12, respectively. Hydrolysis of the methyl esters under basic conditions, such as NaOH or LiOH in methanol, can lead to the desired final product(s) 20-11 and 20-13.

SCHEME 20

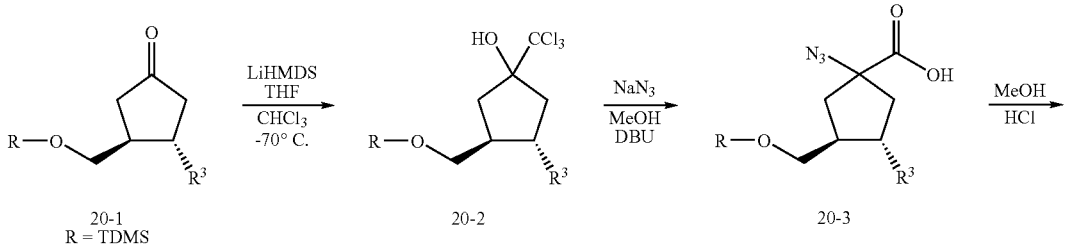

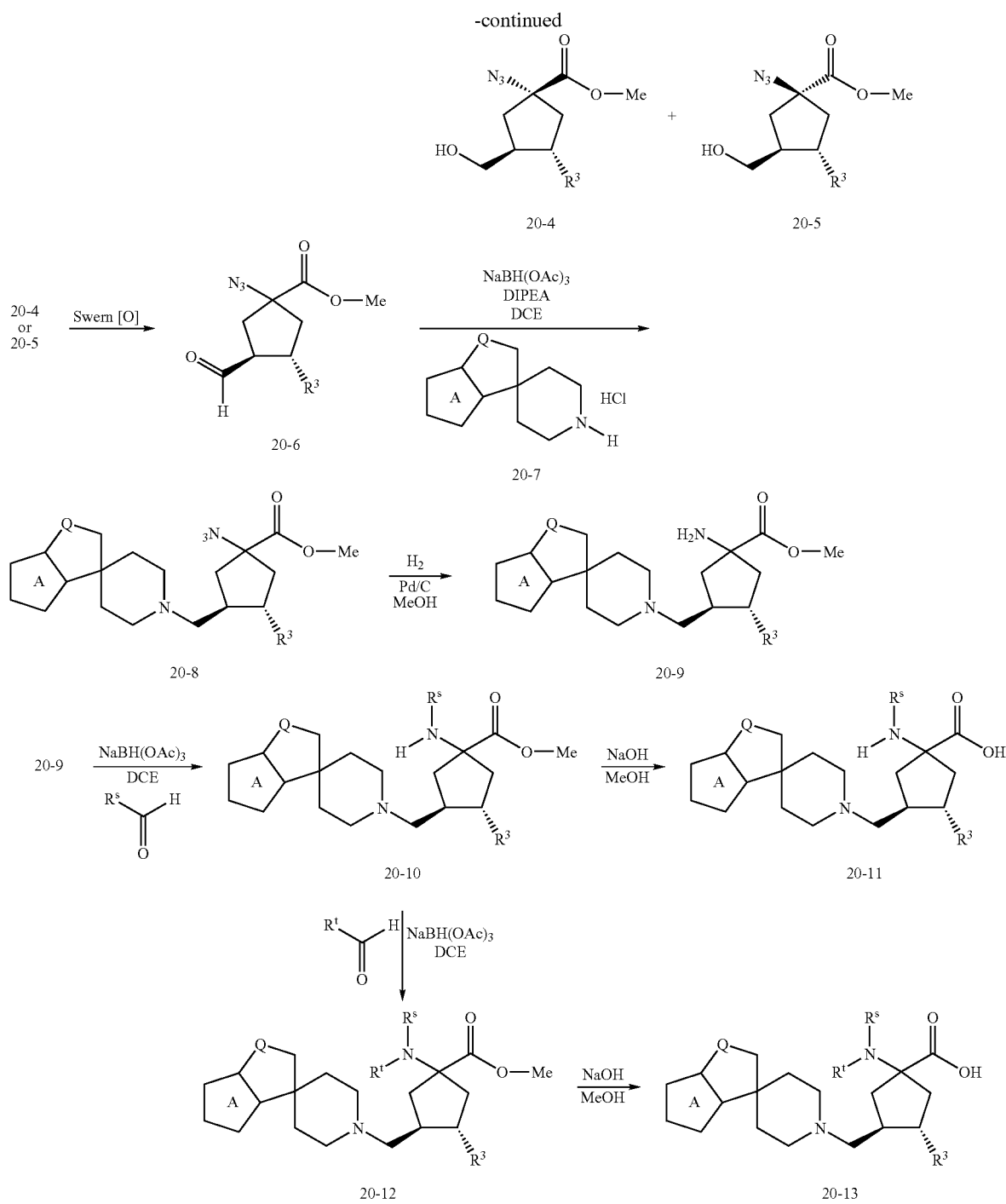

An alternative route for the preparation of some 1,3,4-trisubstituted cyclopentanes within the scope of the instant invention in which the C-1 position is geminally substituted with a methyl and N-substituted amino-acid moiety is given in Scheme 21. The hydroxy of 21-1 (from Scheme 3) can first be protected as the benzyl ether 21-2 using a standard procedure, such as benzyl bromide in DMF with a strong base such as sodium hydride. The exo-methylene of 21-2 can be converted to the ketone of 21-3 as in Scheme 4 with ozone. The addition of the C-1 methyl in 21-4 ($R^7$) can be done with an organometallic reagent, such as methyl lithium or methyl magnesium bromide in THF or ether. The C-1 hydroxy can be exchanged for an acetamido group by treatment with acetonitrile in a strong acid, such as sulfuric acid to give 21-5. The acetate can be cleaved with sodium hydroxide at elevated temperature in ethylene glycol to afford the amine 21-6. Formation of the amino acid moiety of 21-8 can be done stereoselectively by displacement on the triflate 21-7 with inversion α to the ester. The benzyl protecting group can be removed by hydrogenation under standard conditions, such as shaking a methanol solution of 21-8 at 50 psi of hydrogen in the presence of a palladium catalyst. Using procedures described above, the hydroxy can be oxidized to the aldehyde and coupled to the 4-spiropiperidines 21-10 to give 21-11. Hydrolysis of the methyl ester under basic conditions, such as NaOH or LiOH in methanol, with or without alkylation of the amino-acid nitrogen gives the desired final products 21-12 or 21-14.

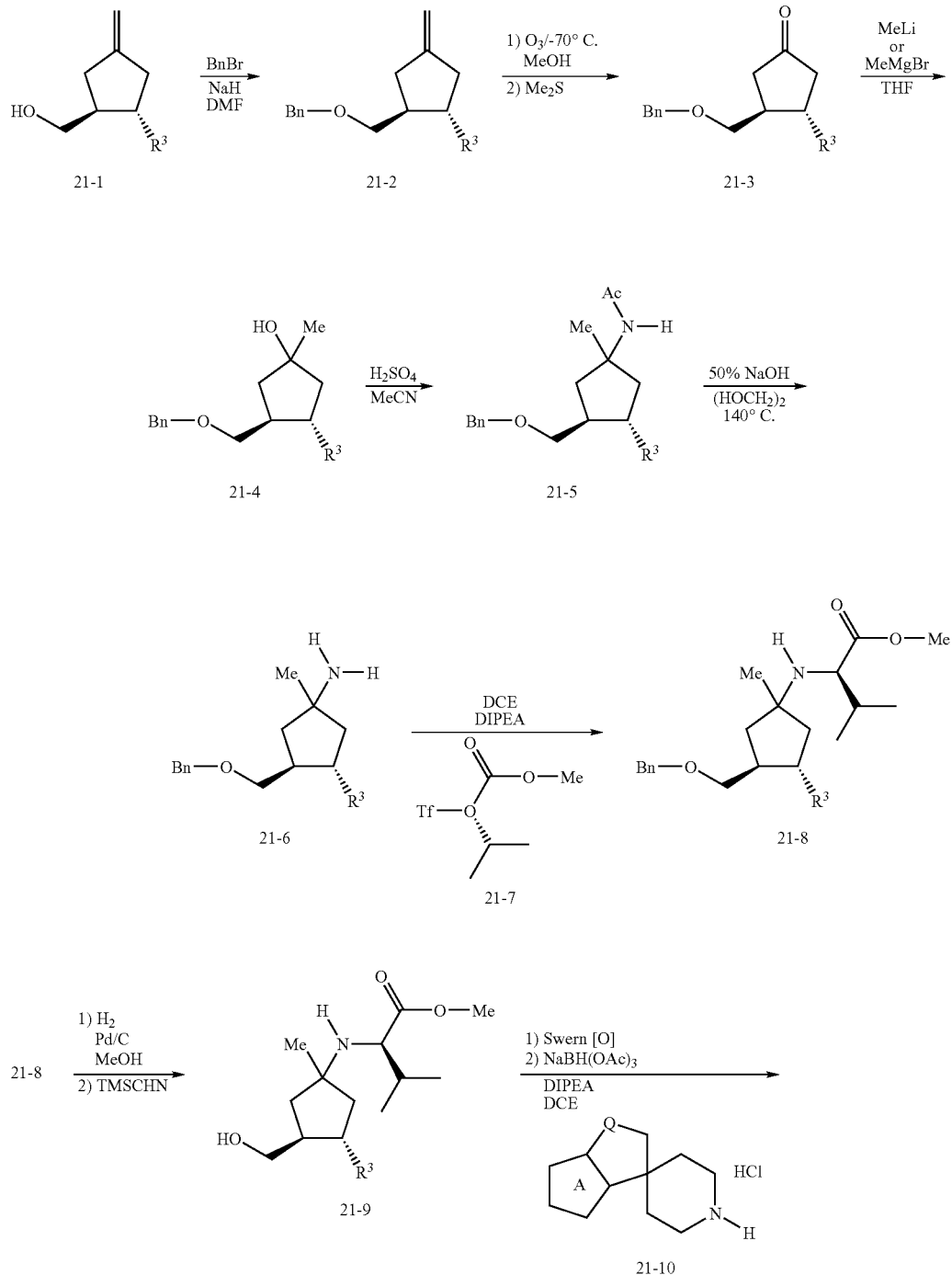

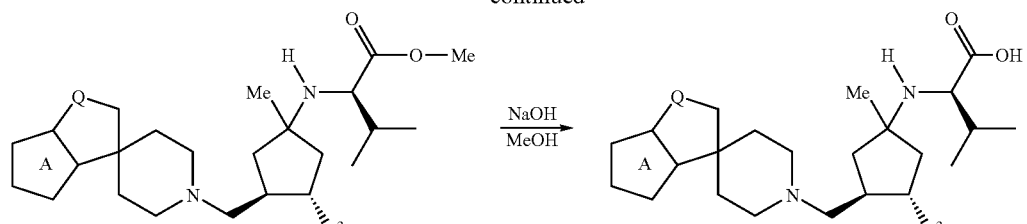

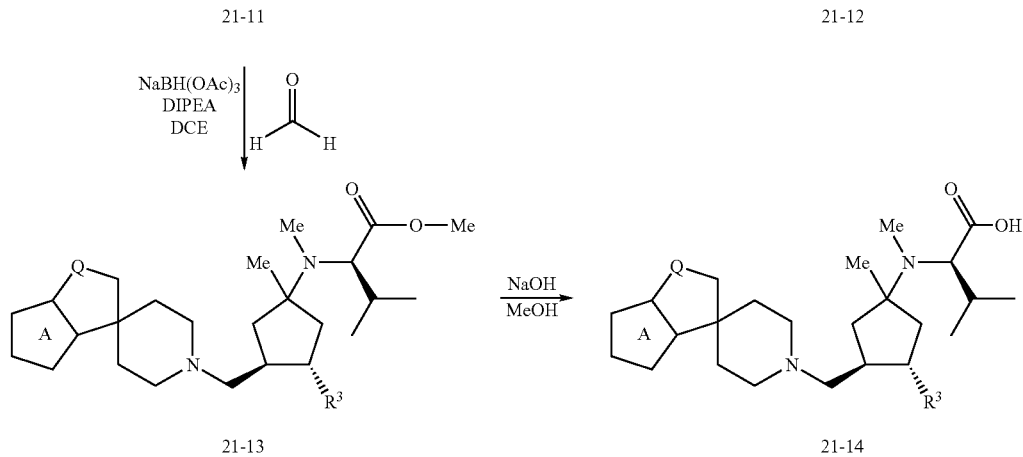

An alternative route for the preparation of some 1,3,4-trisubstituted cyclopentanes within the scope of the instant invention in which there is additional branching alpha to the C-3 position ($R^8$) is given in Scheme 22. The hydroxymethyl 22-1 (from Scheme 3) can be oxidized to the aldehyde 22-2 by several methods, such as the Swern conditions described above. Coupling of the 4-spiropiperidine 22-3 (see Schemes 23 to 31) in the presence of trimethylsilylcyanide in acetic acid can give the nitrile intermediate 22-4. Subsequent treatment of 22-4 with an alkyl magnesium bromide in THF can afford the branched product isomers 22-5, which can be separated here or at a later stage. Conversion to the ketone can be done by ozonolysis under acidic conditions if the spiropiperidine is not stable to ozone. Alternatively, a two-step oxidation can be done with osmium tetroxide/NMO followed by periodate cleavage of the intermediate diol. Introduction of the C-1 amino-acid side chain can be accomplished to give the final product(s) 22-7 and 22-8 using methods described in Scheme 3, 5A, 5B, 5C and the isomers separated at a convenient intermediate. Alternatively, the introduction of other C-1 functionality can be done from 22-5 or 22-6 as described in Schemes 6, 7, 8A, 8B, 9, 10, 11, 12, 13, 14, 15, 16, 17, 18, 19, 20, or 21, depending on the compatibility of the spiropiperidine.

SCHEME 22

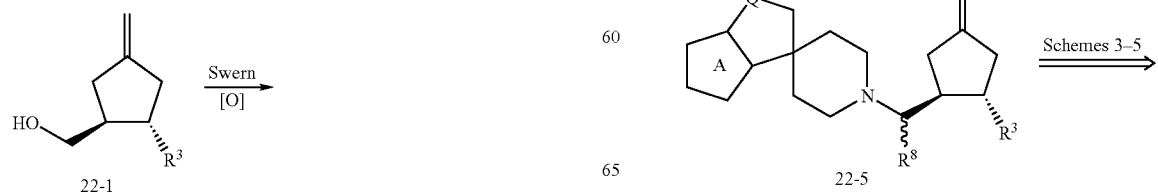

-continued

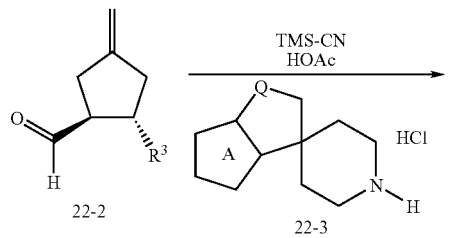

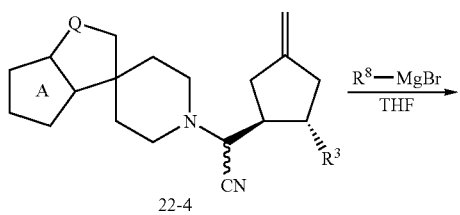

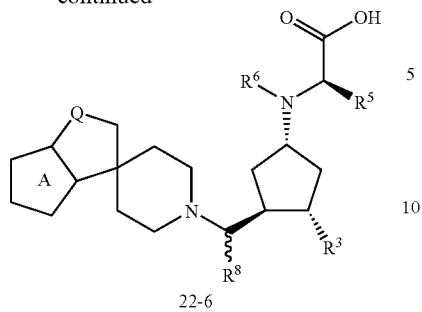

A route for the preparation of some 4-spiropiperidines, which can be used as described in Schemes 3 to 22 for the preparation of the 1,3,4-trisubstituted cyclopentanes within the scope of the instant invention, is given in Scheme 23. BOC-isonipecotic acid (23-1) can be esterified to 23-2 under standard conditions, such as with trimethylsilyldiazomethane in a solvent mixture of methanol and DCM. Alkylation at the 4-position can be done using a strong base, such as LDA or lithium or potassium bis(trimethylsilyl) amide (LHMDS or KHMDS), at low temperature in THF to form the anion and subsequent addition of an appropriate alkyl halide, such as 5-bromo-1-pentene, to give 23-3. Cleavage of the terminal olefin with ozone at low temperature in methanol, followed by a reductive work-up with dimethyl sulfide, can be done to give the aldehyde 23-4. Oxidation to the acid can be done with a variety of reagents, such as chromic acid in acetone (Jones Reagent), which can be esterified as above to give the diester 23-5. Internal cyclization can be accomplished with a strong base, such as LDA, LHMDS or KHMDS, at low temperature to room temperature in THF to give the spiro product 23-6. The ester can be removed by basic hydrolysis at elevated temperature in a protic solvent mixture with concomitant decarboxylation to give the spiro-ketone 23-7. Alkylation to the alcohol 23-8 can be done by formation of the enolate with strong base as above followed by addition of an aldehyde. Oxidation to the diketone 23-9 can be done as above with Jones Reagent. Reaction with an N-alkyl hydrazine can give a mixture of the two possible isomers 23-10 and 23-11 which can be separated by normal or reverse phase chromatography. Final removal of the N—BOC protecting group can be done with strong acid, such as HCl in methanol or in neat TFA, to afford the individual 1,3- and 2,3-dialkyl-4,5-dihydrospiro[cyclopentapyrazole-6(1H and 2H),4'-piperidines] 23-12 and 23-13, respectively, as their di-HCl or di-TFA salts.

SCHEME 23

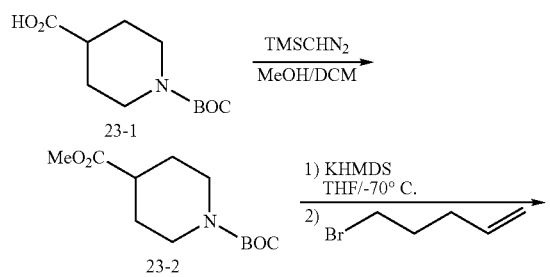

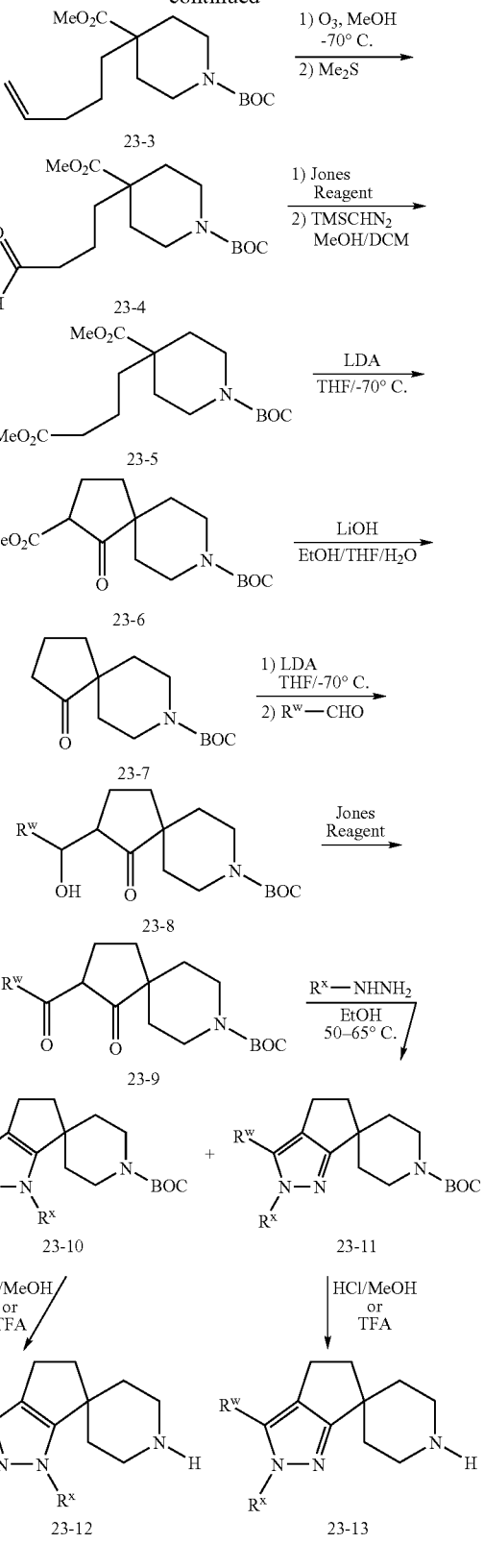

An alternative route for the preparation of some 4-substituted piperidines, which can be used as described in Schemes 3 to 22 for the preparation of the 1,3,4-trisubstituted cyclopentanes within the scope of the instant invention, is given in Scheme 24. Reaction of the spiro-ketone 24-1 (from Scheme 23) with ethyl formate under basic conditions, such as with potassium t-butoxide, gives the keto-aldehyde 24-2, mostly in its enol form. Reaction with an N-alkyl hydrazine can give a mixture of the two possible isomers 24-3 and 24-4 which can be separated by normal or reverse phase chromatography. Final removal of the N—BOC protecting group can be done with strong acid, such as HCl in methanol or in neat TFA, to afford the individual 1- and 2-alkyl-4,5-dihydrospiro[cyclopentapyrazole-6(1H and 2H),4'-piperidines] 24-5 and 24-6, respectively, as their di-HCl or di-TFA salts.

tion, is given in Scheme 25. Reaction of the diketone 25-1 (from Scheme 23) with hydrazine can give the 3-alkyl product 25-2, unsubstituted on the nitrogens. Final removal of the N—BOC protecting group can be done with strong acid, such as HCl in methanol or in neat TFA, to afford the 3-alkyl-4,5-dihydrospiro[cyclopentapyrazole-6,4'-piperidine] 25-3 as the di-HCl or di-TFA salt.

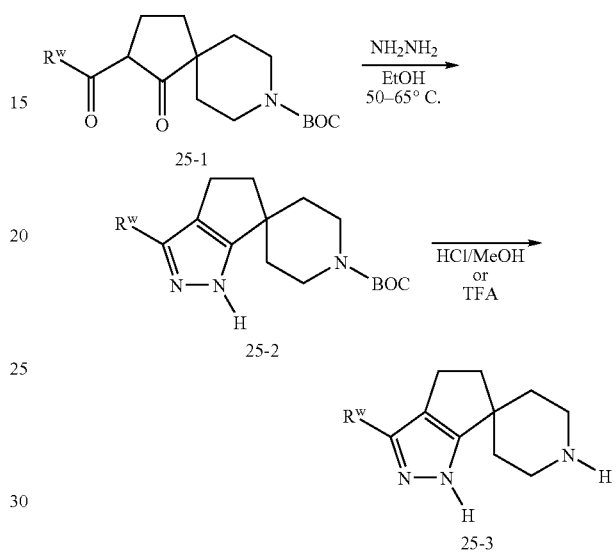

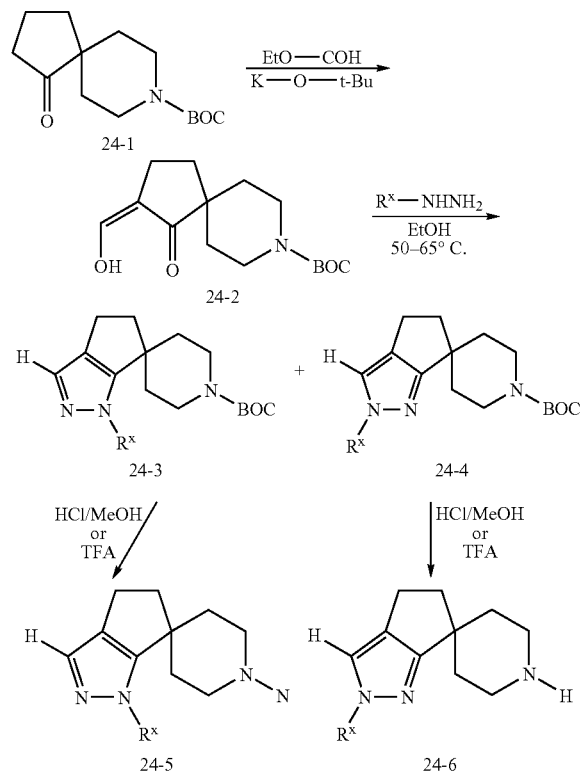

An alternative route for the preparation of some 4-substituted piperidines, which can be used as described in Schemes 3 to 22 for the preparation of the 1,3,4-trisubstituted cyclopentanes within the scope of the instant invention, is given in Scheme 26. Reaction of the keto-ester 26-1 (from Scheme 23) with hydrazine can give 26-2. Methylation with excess trimethylsilyldiazomethane in ether can give a mixture of N- and O-alkylation to give 26-3 and 26-4, from which the BOC can be removed (see scheme 23) to afford 26-5 and 26-6, respectively. Alternatively, the O-alkylation product 26-3 can be N-alkylated in a separate step with an alkyl halide, such as ethyl iodide, under basic conditions, such as sodium hydride in DMF, to afford the pyrazoles having a different R-group than methyl. Separation and acidic removal of the BOC affords the desired piperidines 26-7 and 27-8.

An alternative route for the preparation of some 4-substituted piperidines, which can be used as described in Schemes 3 to 22 for the preparation of the 1,3,4-trisubstituted cyclopentanes within the scope of the instant invention, is given in Scheme 24. Reaction of the spiro-ketone

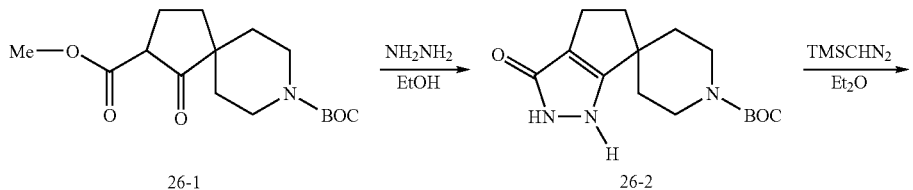

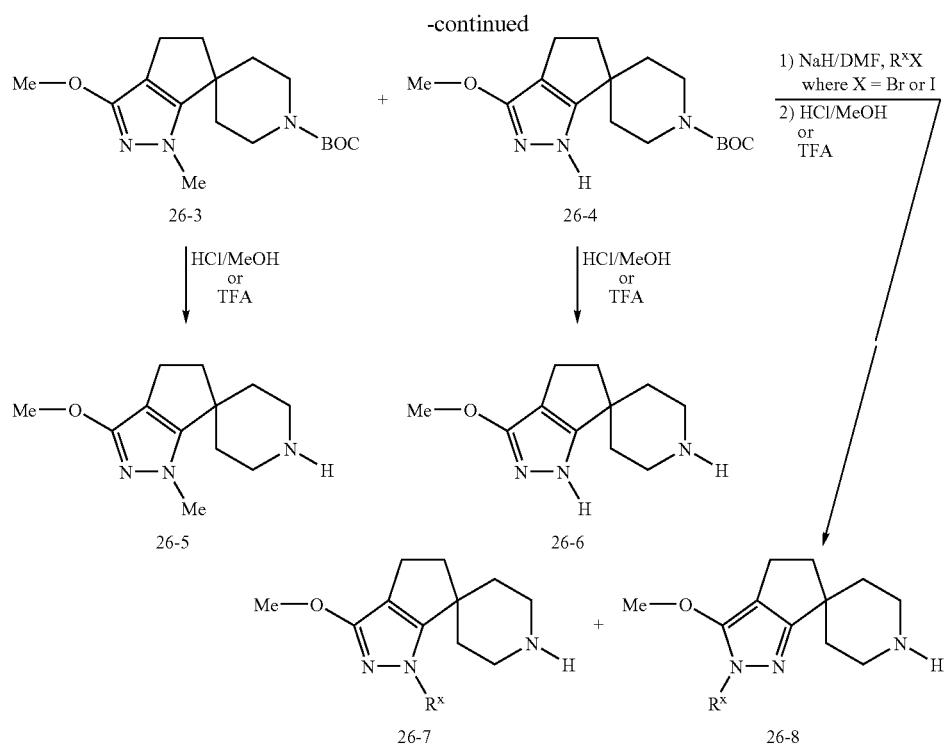

An alternative route for the preparation of some 4-substituted piperidines, which can be used as described in Schemes 3 to 22 for the preparation of the 1,3,4-trisubstituted cyclopentanes within the scope of the instant invention, is given in Scheme 27. Reaction of the diketone 27-1 (from Scheme 23) with hydroxylamine in toluene in the presence of a base, such as DIPEA, followed by treatment with sulfuric acid can give both isoxazole isomers 27-2 and 27-3. Since the acid treatment also removes the BOC, the isomers can be separated by reverse phase chromatography in which the faster isomer is 27-3 and the slower isomer is 27-2.

SCHEME 27

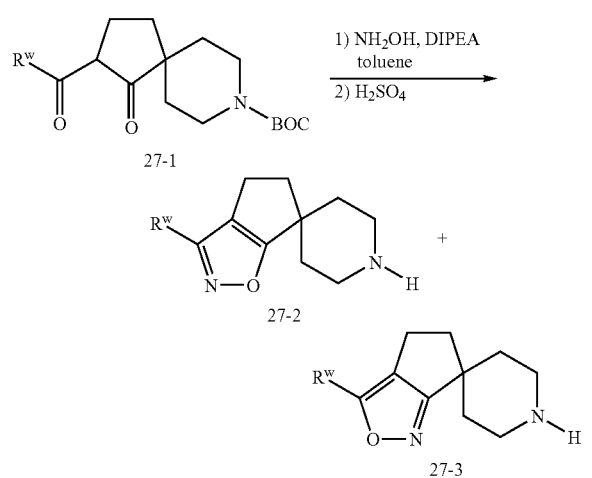

An alternative route for the preparation of some 4-substituted piperidines, which can be used as described in Schemes 3 to 22 for the preparation of the 1,3,4-trisubstituted cyclopentanes within the scope of the instant invention, is given in Scheme 28. Hydroxylation of 28-1 (from Scheme 23) can be done by quenching the ester anion, generated at low temperature with LDA in THF, with $MoO_5$—MoOPh complex to give 28-2. Methylation of the hydroxy can be done with methyl iodide in DMF with sodium hydride as base. The ester-ether 28-3 can be converted to the methyl ketone 28-4 by reaction with the lithium anion of TMS-Me in THF followed by de-silylation with TBAF. Condensation with an aldehyde gives the hydroxyketone 28-5 which can be oxidized to the diketone 28-6 under Swern conditions. Diazotization of 28-6 with mesyl azide affords 28-7 which can be cyclized to 28-8 with rhodium acetate. The pyrazole formation can then be performed as described in Scheme 23 to give a mixture of 28-9 and 28-10. The mixture can then be treated with acid to remove the BOC and afford the desired piperidines 28-11 and 28-12 which were used without separation.

SCHEME 28

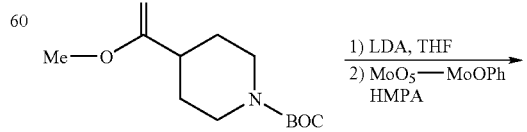

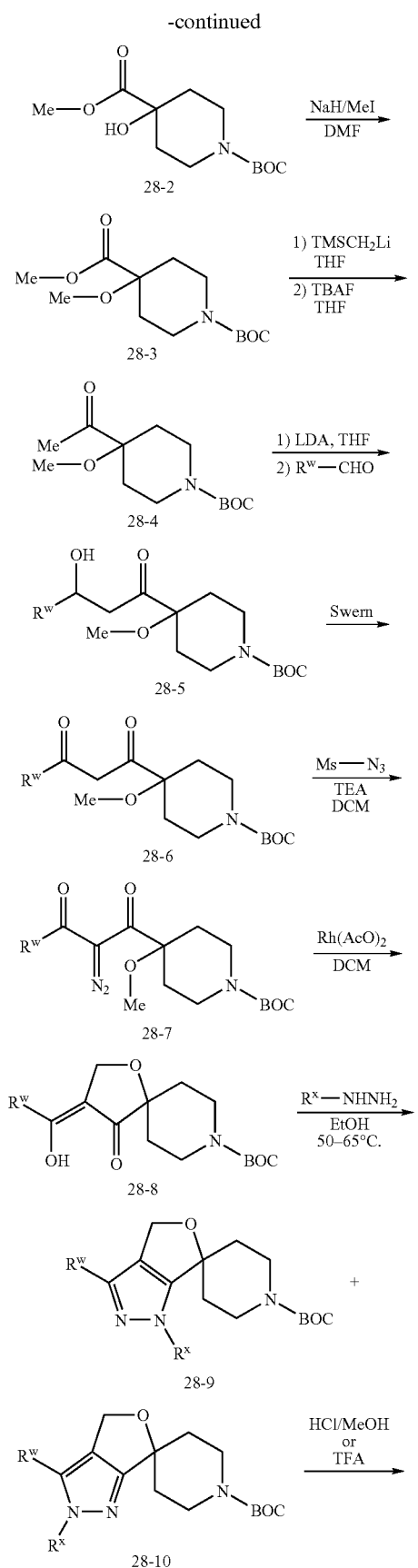
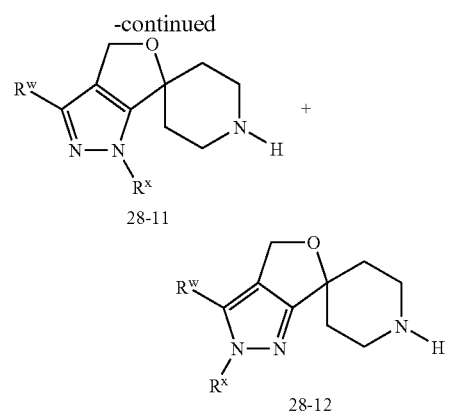

An alternative route for the preparation of some 4-substituted piperidines, which can be used as described in Schemes 3 to 22 for the preparation of the 1,3,4-trisubstituted cyclopentanes within the scope of the instant invention, is given in Scheme 29. Reaction of cyclopropyldiphenylsulfonium tetrafluoroborate (B. Trost, *J. Am. Chem. Soc.,* 1975, 2218) in THF at low temperature (e.g., −40° C.) with solid potassium bis(trimethylsilyl)amide (KHMDS) gives the anion which can then be reacted in situ with Boc-piperidone (29-1) to form an intermediate epoxide 29-2. Treatment with lithium tetrafluoroborate in toluene at elevated temperature (e.g., 80° C.) gives the ring expanded spiro ketone product 29-3. Reaction of 29-3 with allyl tetrahydrothiophenium bromide (prepared from allyl bromide and tetrahydrothiophene in methanol according to *J. Chem. Soc., Perkin Trans. I,* 1993, 2979) and benzyltriethylammonium in the presence of a base such as sodium hydroxide can afford the epoxide 29-4 which on treatment with 4-nitrophenol in the presence of a palladium catalyst such Pd(0) (Ph$_3$P)$_4$ in THF gives the ring expanded spiro-cyclopentanone 29-5. The vinyl group of 29-5 can be cleaved to the aldehyde 29-6 with ozone at low temperature (e.g., −70° C.) in methanol followed by a reductive workup with dimethyl sulfide. The pyrazole formation can then be performed as described in Scheme 23 to give a separable mixture of 29-7 and 29-8. The individual isomers can then be treated with hydrochloric acid in methanol to remove the BOCs and afford the desired piperidines 29-9 and 29-19 as their HCl salts.

SCHEME 29

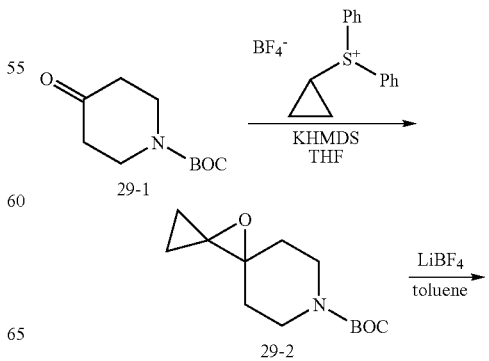

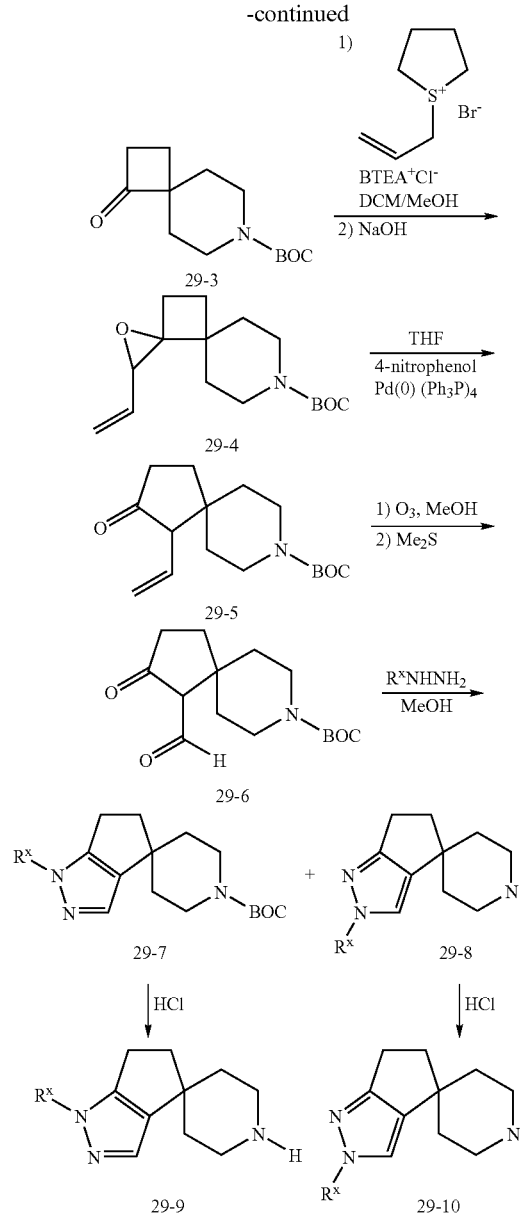

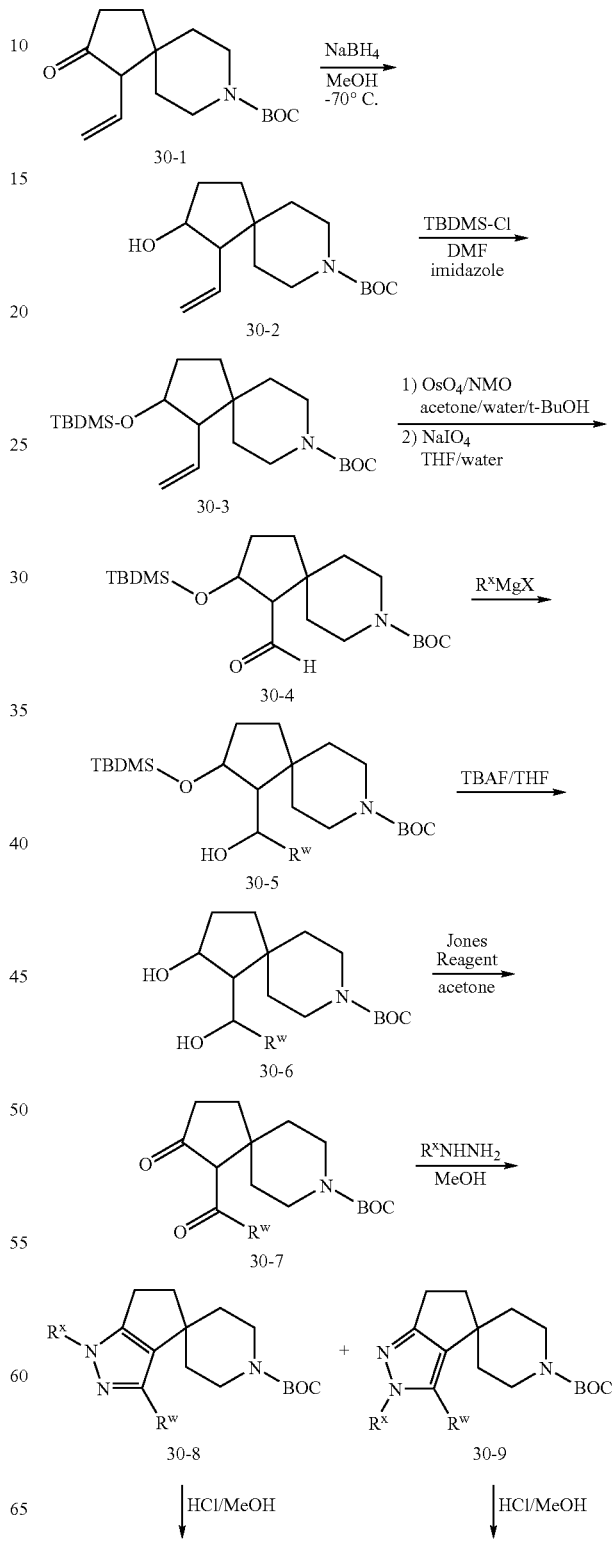

and 30-9. The individual isomers can then be treated with hydrochloric acid in methanol to remove the BOCs and afford the desired piperidines 30-10 and 30-11 as their HCl salts.

An alternative route for the preparation of some 4-substituted piperidines, which can be used as described in Schemes 3 to 22 for the preparation of the 1,3,4-trisubstituted cyclopentanes within the scope of the instant invention, is given in Scheme 30. The intermediate vinyl spirocyclopentanone 30-1 from Scheme 29 can be reduced to the alcohol 30-2 and protected as the t-butyldimethylsilyl ether 30-3. The vinyl can cleaved with ozone as above or in a two-step reaction with catalytic osmium tetroxide in the presence of NMO followed by reaction with sodium periodate to give the aldehyde 30-4. This can be reacted with an alkyl magnesium halide, such as methyl or ethyl magnesium bromide, in THF or ether to afford the alcohol 30-5. Removal of the TBDMS group can be done with TBAF in THF to give the diol 30-6. Oxidation of both alcohol groups to the diketone 30-7 can be done with excess Jones reagent in acetone. The pyrazole formation can then be performed as described in Scheme 23 to give a separable mixture of 30-8

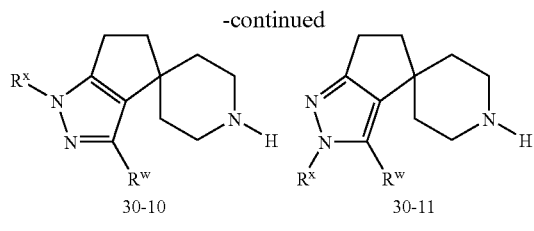

An alternative route for the preparation of some 4-substituted piperidines, which can be used as described in Schemes 3 to 22 for the preparation of the 1,3,4-trisubstituted cyclopentanes within the scope of the instant invention, is given in Scheme 31. N—Boc-4-methoxycarbonylpiperidine (31-1) can be alkylated at the 4-position with 2-bromo-1-trimethylsilyloxyethane via enolate formation with a strong base, such as KHMDS, in THF at from about −70° C. to about room temperature to give 31-2. The ester 31-2 can be reduced to the primary alcohol 31-3 with lithium borohydride in THF at about room temperature. Standard Swern oxidation can give the aldehyde 31-4 which can be reacted with methyl magnesium bromide or iodide in THF to afford the secondary alcohol 31-5. A second Swern oxidation can give the ketone 31-6 which can be alkylated at the methyl position with phenylacetaldehyde via enolate formation with a strong base, such as LHMDS, in THF at from about −70° C. to about room temperature to give 31-7. The resulting alcohol can be oxidized to the diketone 31-8 under Swern conditions or more preferably with Dess-Martin reagent in DCM. The diketone can then be converted to the pyrazole 31-9 by reaction with hydrazine in a protic solvent, such as methanol or ethanol, at elevated temperature (e.g., about 65° C.). Removal of the TBDMS group with TBAF in THF can afford the alcohol 31-10 which can be cyclized to the spiro pyrazole 31-11 with triphenylphosphine in the presence of DEAD. Final removal of the BOC group can be done under standard acid conditions, such as with TFA or with hydrochloric acid in methanol, to afford the desired spiro piperidine 30-12 as the TFA or HCl salt.

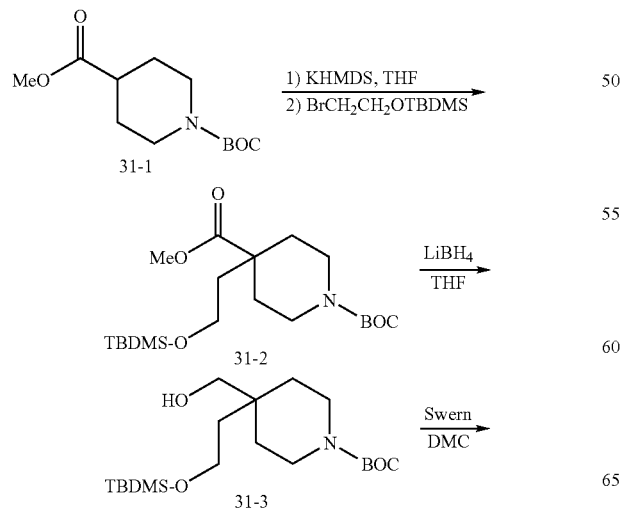

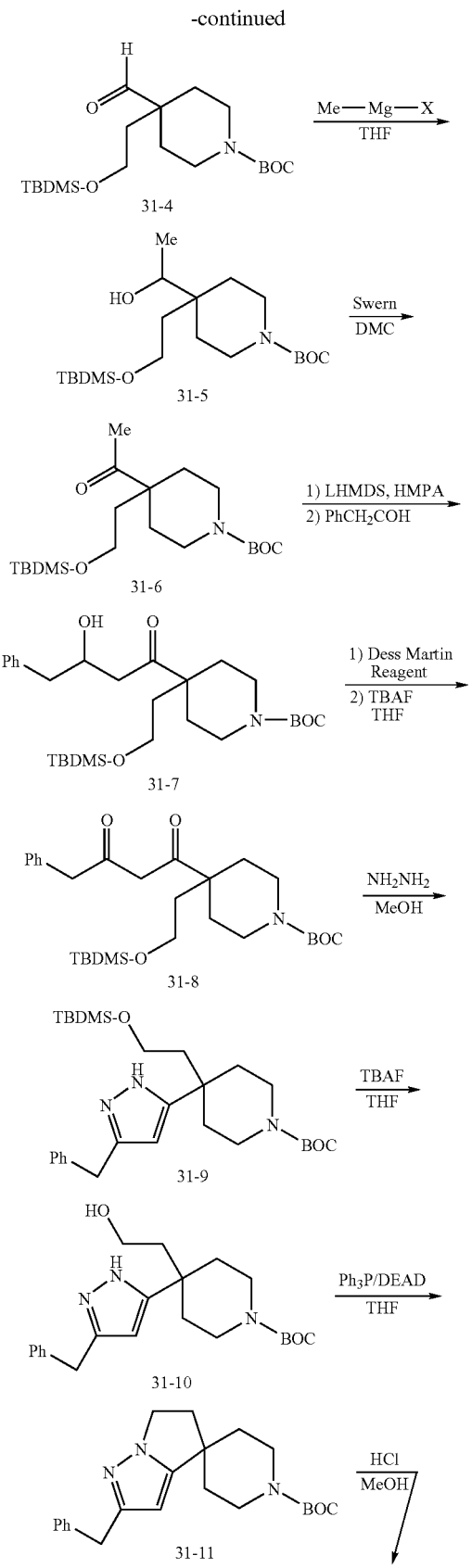

-continued

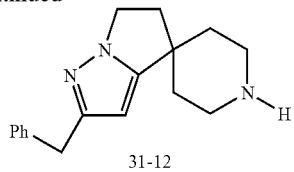
31-12

The following examples serve only to illustrate the invention and its practice. The examples are not to be construed as limitations on the scope or spirit of the invention.

Procedure 1

1,3-Diethyl-4,5-dihydrospiro[cyclopentapyrazole-6 (1H),4'-piperidine]dihydrochloride

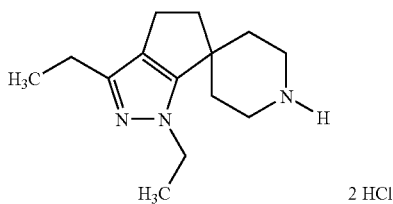
2 HCl

Step A: Methyl 1-(tert-butoxycarbonyl)piperidine-4-carboxylate

To a solution of BOC-isonipecotic acid (45.0 g, 0.20 mol) dissolved in a 3:1 solution of dichloromethane/methanol (1200 mL) at 0° C. was added a solution of trimethylsilyldiazomethane (147 mL, 0.29 mol, 2.0M in hexane) over 30 min via an addition funnel. The reaction mixture was then concentrated to afford the title compound (47 g) as a light yellow oil. This was used directly in the next step without further purification.

$^1$H NMR (400 MHz, CDCl$_3$): δ 1.46 (s, 9 H), 1.58–1.68 (m, 2 H), 1.86–1.91 (m, 2 H), 2.45 (tt, 1 H), 2.81–2.87 (m, 2 H), 3.70 (s, 3 H), 4.00–4.05 (m, 2 H).

Step B: Methyl 4-(pent-4-en-1-yl)-1-(tert-butoxycarbonyl)piperidine-4-carboxylate To a solution of potassium bis(trimethylsilyl)amide (30.7 g, 0.15 mol) in tetrahydrofuran (750 mL) at 0° C. was added a solution of methyl 1-(tert-butoxycarbonyl)piperidine-4-carboxylate (25 g, 0.10 mol) from Step A in tetrahydrofuran (250 mL) and the reaction mixture was stirred for 1 h. 5-Bromo-1-pentene (19.4 mL, 0.164 mol) was added and the reaction mixture was allowed to warm to room temperature for 1.5 h. The reaction mixture was then poured into saturated sodium bicarbonate solution and extracted three times with ethyl acetate. The organic layers were combined and washed with brine, dried over sodium sulfate, filtered, and concentrated to afford the title compound (30.9 g) which was used in the next step without further purification.

$^1$H NMR (400 MHz, CDCl$_3$): δ 1.26–1.40 (m, 4 H), 1.46 (s, 9 H), 1.50–1.54 (m, 2 H), 1.99–2.06 (m, 2 H), 2.11–18 (m, 2 H), 2.80–2.98 (m, 2 H), 3.72 (s, 3 H), 3.87–3.95 (m, 2 H), 4.95–5.02 (m, 2 H), 5.72–5.80 (m, 1 H).

Step C: Methyl 4-(4-oxobut-1-yl)-1-(tert-butoxycarbonyl)piperidine-4-carboxylate A solution of methyl 4-(pent-4-en-1-yl)-1-(tert-butoxycarbonyl)piperidine-4-carboxylate (29.4 g, 0.0945 mol) from Step B in methanol (1000 mL) was cooled to −78° C. in a dry ice/methanol bath and ozone was bubbled into the solution until a blue color persisted. The excess ozone was removed with a stream of nitrogen and then methyl sulfide (69 mL, 0.95 mol) was added, the cooling bath was removed, and the reaction mixture was allowed to warm to room temperature over 1.5 h. The reaction mixture was then concentrated. The residue was then purified by flash chromatography eluting with 2:1 heptane/ethyl acetate to afford the title compound (23.0 g).

$^1$H NMR (400 MHz, CDCl$_3$): δ 1.29–1.40 (m, 2 H), 1.46 (s, 9 H), 1.50–1.57 (m, 4 H), 2.09–2.13 (m, 2 H), 2.41–2.44 (m, 2 H), 2.82–2.95 (m, 2 H), 3.73 (s, 3 H), 3.86–3.89 (m, 2 H), 9.74 (s, 1 H).

Step D: 4-(1-(tert-Butoxycarbonyl)-4-(methoxycarbonyl)piperidin-4-yl)butanoic acid To a solution of methyl 4-(4-oxobut-1-yl)-1-(tert-butoxycarbonyl)piperidine-4-carboxylate (23.0 g, 0.0734 mol) from Step C in acetone (775 mL) at room temperature was added Jones reagent (28.2 mL, 2.6M) via syringe. After 5 min, the reaction mixture was concentrated. The residue was taken up in water and diethyl ether and extracted three times with diethyl ether. The organic layers were combined, washed with brine, dried over sodium sulfate, filtered, and concentrated to give the title compound (23.4 g) which was used in the next step without further purification.

$^1$H NMR (400 MHz, CDCl$_3$): δ 1.33–1.41 (m, 2 H), 1.46 (s, 9 H), 1.50–1.57 (br s, 4 H), 2.09–2.19 (m, 2 H), 2.32–2.34 (m, 2 H), 2.85–2.89 (m, 2 H), 3.73 (s, 3 H), 3.81–3.89 (m, 2 H).

Step E: Methyl 4-(1-(tert-butoxycarbonyl)-4-(methoxycarbonyl)piperidin-4-yl)butanoate To a solution of 4-(1-(tert-butoxycarbonyl)-4-(methoxycarbonyl)piperidin-4-yl)butanoic acid (23.4 g, 0.071 mol) from Step D in 3:1 dichloromethane/methanol (480 mL) at 0° C. was added a solution of trimethylsilyldiazomethane (53 mL, 0.11 mol, 2.0M in hexane). The reaction mixture was stirred for 15 min and then concentrated to afford 25.5 g. The residue was purified by flash chromatography eluting with 20–30% ethyl acetate in hexanes to give the title compound (20.1 g).

$^1$H NMR (400 MHz, CDCl$_3$): δ 1.33–1.42 (m, 2 H), 1.43 (s, 9 H), 1.57–1.59 (m, 4 H), 2.08–2.14 (m, 2 H), 2.26–2.31 (m, 2 H), 2.84–2.94 (m, 2 H), 3.68 (s, 3 H), 3.73 (s, 3 H), 3.83–3.90 (m, 2 H).

Step F: tert-Butyl 2-(methoxycarbonyl)-1-oxo-8-azaspiro[4.5]decane-8-carboxylate To a solution of methyl 4-(1-(tert-butoxycarbonyl)-4-(methoxycarbonyl)piperidin-4-yl)butanoate (20.1 g, 0.058 mol) from Step E in tetrahydrofuran (600 mL) at −78° C. was added lithium diisopropylamide mono(tetrahydrofuran) (47 mL, 0.070 mol, 1.5M solution in cyclohexanes). The reaction mixture was stirred at −78° C. for 25 min. Thin layer chromatography (tlc) analysis (50% ethyl acetate in hexanes) showed that starting material remained. Additional lithium diisopropylamide mono(tetrahydrofuran) (31 mL)

was added and the reaction mixture was stirred for 20 min. The reaction mixture was poured into saturated ammonium chloride and extracted three times with diethyl ether. The organic layers were combined, washed with brine, dried over sodium sulfate, and concentrated to afford the title compound (19.9 g) which was taken on to the next step without further purification.

Step G: tert-Butyl 1-oxo-8-azaspiro[4.5]decane-8-carboxylate

To a solution of tert-butyl 2-(methoxycarbonyl)-1-oxo-8-azaspiro[4.5]decane-8-carboxylate (17.2 g, 0.055 mol) from Step F in a 2:2:1 mixture of ethanol/tetrahydrofuran/water (555 mL) was added pulverized lithium hydroxide (26 g, 1.10 mol). The reaction mixture was heated to 90° C. for 60 h. The reaction mixture was allowed to cool and was then concentrated, dissolved in water and dichloromethane, and extracted three times with dichloromethane. The organic layers were combined, washed with brine, dried over sodium sulfate, filtered, and concentrated to afford 11.4 g. The residue was purified by flash chromatography eluting with 20–30% ethyl acetate in hexanes to give the title compound (9.41 g).

$^1$H NMR (400 MHz, CDCl$_3$): δ 1.29–1.37 (m, 2 H), 1.47 (s, 9 H), 1.62–1.69 (m, 2 H), 1.92–1.95 (m, 4 H), 2.30–2.34 (m, 2 H), 3.05–3.10 (m, 2 H), 3.87–3.92 (m, 2 H).

Step H: tert-Butyl 2-(1-hydroxyprop-1-yl)-1-oxo-8-azaspiro[4.5]decane-8-carboxylate tert-Butyl 1-oxo-8-azaspiro[4.5]decane-8-carboxylate from Step G (4.5 g, 17.8 mmol) was dried by evaporating with toluene (10 mL) three times in vacuo, dissolved in tetrahydrofuran (100 mL), and cooled to −78° C. To this solution was added lithium diisopropylamide mono(tetrahydrofuran) (24 mL, 36 mmol, 1.5 M in cyclohexane). The reaction mixture was stirred for 30 min at −78° C. before adding propionaldehyde (2.6 mL, 36 mmol). After 5 min, the reaction mixture was diluted with diethyl ether, poured into saturated ammonium chloride, and extracted three times with diethyl ether. The organic layers were combined, washed with brine, dried over sodium sulfate, filtered, and concentrated to afford 6.7 g of a clear oil. The residue was purified by flash chromatography eluting with 20–30% ethyl acetate in hexanes to give the title compound (4.75 g).

$^1$H NMR (400 MHz, CDCl$_3$): δ 0.97 (t, 3 H), 1.33–1.37 (m, 2 H), 1.47 (s, 9 H), 1.54–1.68 (m, 5 H), 1.75–1.78 (m, 1 H), 2.07–2.13 (m, 2 H), 2.30–2.33 (m, 1 H), 2.95–3.15 (m, 2 H), 3.62–3.63 (m, 1 H), 3.84–3.94 (m, 2 H).

Step I: tert-Butyl 2-(1-oxoprop-1-yl)-1-oxo-8-azaspiro[4.5]decane-8-carboxylate To a solution of oxalyl chloride (1.6 mL, 18.3 mmol) in dichloromethane (150 mL) at −78° C. was slowly added dimethyl sulfoxide (2.6 mL, 37 mmol). After 5 min, a solution of tert-butyl 2-(1-hydroxyprop-1-yl)-1-oxo-8-azaspiro[4.5]decane-8-carboxylate (4.75 g, 15.3 mmol) from Step H in dichloromethane (40 mL) was added via an addition funnel. The reaction mixture was stirred for 45 min at −78° C. and then triethylamine (10.2 mL, 73.2 mmol) was added. After 5 min, the reaction mixture was removed from the cooling bath, allowed to warm to room temperature for 1.5 h, poured into water, and extracted three times with dichloromethane. The organic layers were combined, washed with brine, dried over sodium sulfate, filtered and concentrated to afford 4.65 g. The residue was purified by flash chromatography eluting with 15% ethyl acetate in hexanes to give the title compound (3.98 g) as a pink oil.

Step J: 1'-(tert-Butoxycarbonyl)-1,3-diethyl-4,5-dihydrospiro[cyclopentapyrazole-6(1H),4'-piperidine] (faster HPLC isomer) and 1'-(tert-butoxycarbonyl)-2,3-diethyl-4,5-dihydrospiro[cyclopentapyrazole-6(2H),4'-piperidine] (slower HPLC isomer)

To a solution of tert-butyl 2-(1-oxoprop-1-yl)-1-oxo-8-azaspiro[4.5]decane-8-carboxylate (0.165 g, 0.533 mmol) from Step I in ethanol (5 mL) was added ethyl hydrazine oxylate (0.096 g, 0.640 mmol). The reaction mixture was heated at 85° C. for 12 h, cooled, and then concentrated. The residue was taken up in a minimal amount of 40:40:20 acetonitrile/water/dimethyl sulfoxide solution and purified by Gilson reverse phase HPLC (Column: YMC-Pack Pro C18, 100×20 mm I.D.; Gradient Eluent: 10:90 to 90:10 v/v acetonitrile/water+0.1% trifluoroacetic acid over 12.5 min; Detection: PDA, 210–400 nm; Flow rate: 20 mL/min) to afford the title products as the trifluoroacetic acid salts, the faster eluting isomer by HPLC (0.220 g) and slower eluting isomer by HPLC (0.016 g). Note: The title compound can also be purified by flash chromatography eluting with 15% ethyl acetate in hexanes.

(faster HPLC Isomer):
$^1$H NMR (400 MHz, CDCl$_3$): δ 1.23 (t, 3 H), 1.42 (t, 3 H), 1.50 (s, 9 H), 1.60–1.63 (m, 2 H), 1.88–1.93 (m, 2 H), 2.42–2.47 (m, 2 H), 2.56–2.61 (m, 4 H), 2.86–2.89 (m, 2 H), 4.00 (q, 2 H), 4.10–4.13 (m, 2 H). MS/EI (acetonitrile/water): m/z 334 retention time=2.5 min.

(slower HPLC Isomer) $^1$H NMR (400 MHz, CDCl$_3$): δ 1.27 (t, 3 H), 1.38 (t, 3 H), 1.48 (s, 9 H), 1.51–1.57 (m, 2 H), 1.75–1.79 (m, 2 H), 2.22–2.45 (m, 2 H), 2.58–2.65 (m, 4 H), 3.51–3.60 (m, 2 H), 3.64–3.67 (m, 2 H), 4.03 (q, 2 H). MS/EI (acetonitrile/water): m/z 334 retention time=3.1 min.

Step K: 1,3-Diethyl-4,5-dihydrospiro[cyclopentapyrazole-6(1H),4'-piperidine]dihydrochloride To a solution of 1'-(tert-butoxycarbonyl)-1,3-diethyl-4,5-dihydrospiro[cyclopentapyrazole-6(1H),4'-piperidine] (0.547 g, 1.64 mmol, the faster eluting isomer from Step J) in methanol (16 mL) at 0° C. was added acetyl chloride (1.17 mL, 16.4 mmol). The reaction mixture was allowed to warm to room temperature, stirred for 60 h and then concentrated to afford the title compound as the dihydrochloride salt.

$^1$H NMR (400 MHz, CDCl$_3$): δ 1.32 (t, 3 H), 1.54 (t, 3 H), 2.00 (d, 2 H), 2.37–2.45 (m, 2 H), 2.66–2.69 (m, 2 H), 2.73–2.82 (m, 4 H), 3.18–3.24 (m, 2 H), 3.47–3.52 (d, 2 H), 4.41 (q, 2 H).

Procedure 2

2,3-Diethyl-4,5-dihydrospiro[cyclopentapyrazole-6(2H),4'-piperidine]dihydrochloride

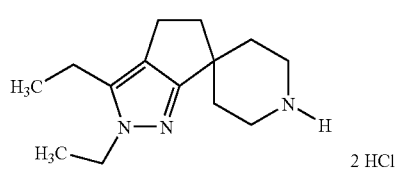

2 HCl

The title compound was prepared essentially the same as in Procedure 1, Step K, but using 1'-(tert-butoxycarbonyl)-2,3-diethyl-4,5-dihydrospiro-[cyclopentapyrazole-6(2H),4'-piperidine] (the slower eluting isomer from Procedure 1, Step J). MS/EI (acetonitrile/water) m/z 234 retention time=1.3 min.

Procedure 3

3-Ethyl-1-methyl-4,5-dihydrospiro[cyclopentapyrazole-6(1H),4'-piperidine]dihydrochloride

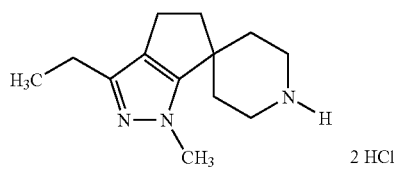

Step A: 1'-(tert-Butoxycarbonyl)-3-ethyl-1-methyl-4,5-dihydrospiro[cyclopentapyrazole-6(1H),4'-piperidine] (faster isomer) and 1'-(tert-butoxycarbonyl)-3-ethyl-2-methyl-4,5-dihydrospiro[cyclopentapyrazole-6(2H),4'-piperidine] (slower isomer)

To a solution of tert-butyl 2-(1-oxoprop-1-yl)-1-oxo-8-azaspiro[4.5]decane-8-carboxylate (0.517 g, 1.67 mmol) from Procedure 1, Step I in ethanol (17 mL) was added methyl hydrazine (0.107 mL, 2.00 mmol). The reaction mixture was heated at 85° C. for 12 h, cooled, and then concentrated. The residue was taken up in 40:40:20 acetonitrile/water/dimethyl sulfoxide solution (4 mL) and purified by Gilson reverse phase HPLC (Column: YMC-Pack Pro C18, 100×20 mm I.D.; Gradient Eluent: 10:90 to 90:10 v/v acetonitrile/water+0.1% trifluoroacetic acid over 12.5 min; Detection: PDA, 210–400 nm; Flow rate: 20 mL/min) to afford the title products as the trifluoroacetic acid salts, faster eluting isomer by HPLC (0.432 g) and slower eluting isomer by HPLC (0.090 g).

(faster isomer) $^1$H NMR (400 MHz, CDCl$_3$): δ 1.29 (t, 3 H), 1.49 (s, 9 H), 1.66–1.69 (m, 2 H), 1.88–1.92 (m, 2 H), 2.53–2.57 (m, 2 H), 2.69–2.73 (m, 4 H), 2.82–2.93 (m, 2 H), 3.99 (s, 3 H), 4.18–4.23 (m, 2 H). MS/EI (acetonitrile/water): m/z 320 retention time=2.1 min.

(slower isomer) $^1$H NMR (400 MHz, CDCl$_3$): δ 1.33 (t, 3 H), 1.49 (s, 9 H), 1.59–1.64 (m, 2 H), 1.87–1.92 (m, 2 H), 2.38–2.41 (m, 2 H), 2.66 (q, 2 H), 2.73 (t, 2 H), 3.24–3.31 (m, 2 H), 3.77–3.83 (m, 2 H), 3.94 (s, 3 H). MS/EI (acetonitrile/water): m/z 320 retention time=2.6 min.

Step B: 3-Ethyl-1-methyl-4,5-dihydrospiro[cyclopentapyrazole-6(1H),4'-piperidine]dihydrochloride To a solution of 1'-(tert-butoxycarbonyl)-3-ethyl-1-methyl-4,5-dihydrospiro[cyclopentapyrazole-6(1H),4'-piperidine] (0.432 g, 0.789 mmol) the faster eluting isomer from Procedure 3, Step A in methanol (8 mL) at 0° C. was added acetyl chloride (0.561 mL, 7.89 mmol). The reaction mixture was allowed to warm to room temperature, stirred for 60 h and then concentrated to afford the title compound as the dihydrochloride salt. MS/EI (acetonitrile/water): m/z 220 retention time=0.3 min.

Procedure 4

3-Ethyl-2-methyl-4,5-dihydrospiro[cyclopentapyrazole-6(2H),4'-piperidine]dihydrochloride

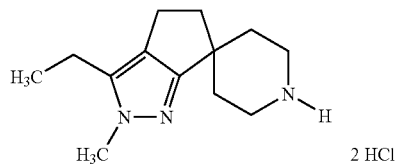

The title compound was prepared essentially the same as in Procedure 3, Step B, but using 1'-(tert-butoxycarbonyl)-3-ethyl-2-methyl-4,5-dihydrospiro-[cyclopentapyrazole-6(2H),4'-piperidine] the slower eluting isomer from Procedure 3, Step A.

Procedure 5

1,3-Dimethyl-4,5-dihydrospiro[cyclopentapyrazole-6(1H),4'-piperidine]dihydrochloride

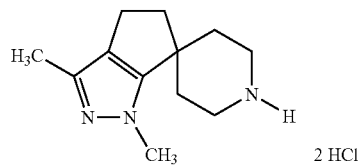

Step A: tert-Butyl 2-(1-hydroxyeth-1-yl)-1-oxo-8-azaspiro[4.5]decane 8-carboxylate tert-Butyl 1-oxo-8-azaspiro[4.5]decane-8-carboxylate from Procedure 1, Step G (1.2 g, 4.70 mmol) was dried by evaporating with toluene (5 mL) three times in vacuo, dissolved in tetrahydrofuran (50 mL), and cooled to −78° C. To this solution was added lithium diisopropylamide mono (tetrahydrofuran) (6.3 mL, 9.4 mmol, 1.5 M in cyclohexane). The reaction mixture was stirred for 35 min at −78° C. before adding acetaldehyde (0.527 mL, 9.4 mmol). After 10 min, the reaction mixture was diluted with diethyl ether, poured into saturated ammonium chloride, and extracted three times with diethyl ether. The organic layers were combined, washed with brine, dried over sodium sulfate, filtered, and concentrated to afford 6.7 g of a clear oil. The residue was purified by flash chromatography eluting with 20–40% ethyl acetate/hexanes to give the title compound (0.620 g).

$^1$H NMR (400 MHz, CDCl$_3$): δ 1.20 (d, 3 H), 1.31–1.37 (m, 2 H), 1.47 (s, 9 H), 1.52–1.81 (m, 4 H), 2.06–2.14 (m, 2 H), 2.25 (q, 1 H), 2.96–3.11 (m, 2 H), 3.79–3.96 (m, 3 H).

Step B: tert-Butyl 2-(1-oxoeth-1-yl)-1-oxo-8-azaspiro[4.5]decane-8-carboxylate To a solution of oxalyl chloride (0.556 mL, 6.37 mmol) in dichloromethane (80 mL) at −78° C. was slowly added dimethyl sulfoxide (0.905 mL, 37 mmol). After 15 min, a solution of tert-butyl 2-(1-hydroxyeth-1-yl)-1-oxo-8-aza-spiro[4.5]decane-8-carboxylate (1.58 g, 5.31 mmol) from Step A in dichloromethane (20 mL) was added dropwise. The reaction mixture was stirred for 45 min at −78° C. and then triethylamine (3.55 mL, 25.5 mmol) was added. After 5 min, the reaction mixture was removed from the cooling bath, allowed to warm to room temperature, poured into water, and extracted three times with dichloromethane. The organic layers were combined, washed with brine, dried over sodium sulfate, filtered, and concentrated. The residue was purified by flash chromatography eluting with 20% ethyl acetate/hexanes to give the title compound (39 g) as a pink oil.

$^1$H NMR (400 MHz, CDCl$_3$): δ 1.36–1.43 (m, 2 H), 1.48 (s, 9 H), 1.74–1.81 (m, 2 H), 1.86 (t, 2 H), 2.01 (s, 3 H), 2.50 (t, 2 H), 3.04–3.11 (m, 2 H), 3.89–3.95 (m, 2 H).

Step C: 1'-(tert-Butoxycarbonyl)-1,3-dimethyl-4,5-dihydrospiro[cyclopentapyrazole-6(1H),4'-piperidine] (faster isomer) and 1'-(tert-butoxycarbonyl)-2,3-dimethyl-4,5-dihydrospiro[cyclopentapyrazole-6(2H),4'-piperidine] (slower isomer)

To a solution of tert-butyl 2-(1-oxoeth-1-yl)-1-oxo-8-azaspiro[4.5]decane-8-carboxylate (0.477 g, 1.62 mmol) from Step B in ethanol (16 mL) was added methyl hydrazine (0.103 mL, 1.94 mmol). The reaction mixture was heated at 85° C. for 12 h, cooled, and then concentrated. The residue was taken up in a minimal amount of 40:40:20 acetonitrile/water/dimethyl sulfoxide solution and purified by Gilson reverse phase HPLC (Column: YMC-Pack Pro C18, 100×20 mm I.D.; Gradient Eluent: 10:90 to 90:10 v/v acetonitrile/water+0.1% trifluoroacetic acid over 12.5 min; Detection: PDA, 210–400 nm; Flow rate: 20 mL/min) to afford the title products as the trifluoroacetic acid salts, faster eluting isomer by HPLC (0.468 g) and slower eluting isomer by HPLC (0.100 g).

faster isomer: $^1$H NMR (400 MHz, CDCl$_3$): δ 1.49 (s, 9 H), 1.64–1.67 (m, 2 H), 1.86–1.94 (m, 2 H), 2.33 (s, 3 H), 2.52–2.56 (m, 2 H), 2.62–2.66 (m, 2 H), 2.84–2.89 (m, 2 H), 3.97 (s, 3 H), 4.19–4.21 (m, 2 H). MS/EI (acetonitrile/water) (faster isomer): m/z 306 retention time=2.2 min. MS/EI (acetonitrile/water) (slower isomer): m/z 306 retention time=2.5 min.

Step D: 1,3-Dimethyl-4,5-dihydrospiro[cyclopentapyrazole-6(1h),4'-piperidine]dihydrochloride To a solution of 1'-(tert-butoxycarbonyl)-1,3-dimethyl-4,5-dihydrospiro[cyclopentapyrazole-6(1H),4'-piperidine] (0.468 g, 0.877 mmol) the faster eluting isomer from Step C in methanol (8 mL) at 0° C. was added acetyl chloride (0.624 mL, 8.77 mmol). The reaction mixture was allowed to warm to room temperature, stirred for 12 h and then concentrated to afford the title compound as the dihydrochloride salt. MS/EI (acetonitrile/water): m/z 206 retention time=0.3 min.

Procedure 6

2,3-Dimethyl-4,5-dihydrospiro[cyclopentapyrazole-6(2H),4'-piperidine]dihydrochloride

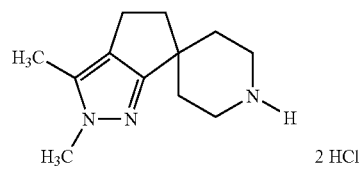

The title compound was prepared essentially the same as in Procedure 5, Step D, but using 1'-(tert-butoxycarbonyl)-2,3-dimethyl-4,5-dihydrospiro-[cyclopentapyrazole-6(2H),4'-piperidine] the slower eluting isomer from Procedure 5, Step C.

Procedure 7

1-Ethyl-3-methyl-4,5-dihydrospiro[cyclopentapyrazole-6(1H),4'-piperidine]dihydrochloride

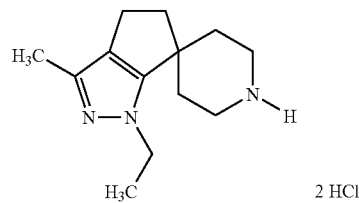

Step A: 1'-(tert-Butoxycarbonyl)-1-ethyl-3-methyl-4,5-dihydrospiro[cyclopentapyrazole-6(1H),4'-piperidine] (faster isomer) and 1'-(tert-butoxycarbonyl)-2-ethyl-3-methyl-4,5-dihydrospiro[cyclopentapyrazole-6(2H),4'-piperidine] (slower isomer)

To a solution of tert-butyl 2-(1-oxoeth-1-yl)-1-oxo-8-azaspiro[4.5]decane-8-carboxylate (0.394 g, 1.33 mmol) from Procedure 5, Step B in ethanol (13 mL) was added ethyl hydrazine oxylate (0.240 g, 1.60 mmol). The reaction mixture was heated at 85° C. for 36 h, cooled, and then concentrated. The residue was taken up in a minimal amount of 40:40:20 acetonitrile/water/dimethyl sulfoxide solution and purified by Gilson reverse phase HPLC (Column: YMC-Pack Pro C18, 100×20 mm I.D.; Gradient Eluent: 10:90 to 90:10 v/v acetonitrile/water+0.1% trifluoroacetic acid over 12.5 min; Detection: PDA, 210–400 nm; Flow rate: 20 mL/min) to afford the title products as the trifluoroacetic acid salts, faster eluting isomer by HPLC (0.414 g) and slower eluting isomer by HPLC (0.060 g).

Faster isomer: $^1$H NMR (400 MHz, CDCl$_3$): δ 1.51 (s, 9 H), 1.55 (t, 3 H), 1.68–1.72 (m, 2 H), 1.87–1.91 (m, 2 H), 2.37 (s, 3 H), 2.54–2.57 (m, 2 H), 2.64–2.68 (m, 2 H), 2.82–2.89 (m, 2 H), 4.19–4.23 (m, 2 H), 4.33 (q, 2 H). MS/EI (acetonitrile/water) (faster isomer): m/z 320 retention time=2.1 min. MS/EI (acetonitrile/water) (slower isomer): m/z 320 retention time=2.5 min.

Step B: 1-Ethyl-3-methyl-4,5-dihydrospiro[cyclopentapyrazole-6(1H),4'-piperidine]dihydrochloride To a solution of 1'-(tert-butoxycarbonyl)-1-ethyl-3-methyl-4,5-dihydrospiro[cyclopentapyrazole-6(1H),4'-piperidine] (0.414 g, 0.756 mmol) the faster eluting isomer from Step A in methanol (8 mL) at 0° C. was added acetyl chloride (0.538 mL, 7.56 mmol). The reaction mixture was allowed to warm to room temperature, stirred for 12 h and then concentrated to afford the title compound as the dihydrochloride salt. MS/EI (acetonitrile/water): m/z 220 retention time=0.3 min.

Procedure 8

2-Ethyl-3-methyl-4,5-dihydrospiro[cyclopentapyrazole-6(2H),4'-piperidine]dihydrochloride

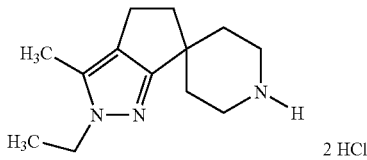

The title compound was prepared essentially the same as in Procedure 7, Step B, but using 1'-(tert-butoxycarbonyl)-2-ethyl-3-methyl-4,5-dihydrospiro-[cyclopentapyrazole-6(2H),4'-piperidine] the slower eluting isomer from Procedure 7, Step A.

Procedure 9

1-Ethyl-4,5-dihydrospiro[cyclopentapyrazole-6(1H),4'-piperidine]dihydrochloride

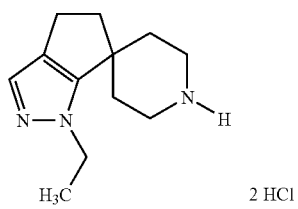

Step A: tert-Butyl 2-(hydroxymethyl)-1-oxo-8-azaspiro[4.5]decane-8-carboxylate tert-Butyl 1-oxo-8-azaspiro[4.5]decane-8-carboxylate from Procedure 1, Step G (0.526 g, 2.08 mmol) was dried by evaporating with toluene (10 mL) three times in vacuo, dissolved in methyl-tert-butyl ether (5 mL), and cooled to −78° C. To this solution was added ethyl formate (0.336 mL, 4.15 mmol) and then potassium t-butoxide (0.466 g, 4.16 mmol). After 2 days, the reaction mixture was diluted with diethyl ether, poured into 2N HCl, and extracted three times with diethyl ether. The organic layers were combined, washed with brine, dried over sodium sulfate, filtered, and concentrated to afford 0.575 g. The residue was purified by flash chromatography eluting with 45% ethyl acetate/hexanes to give the title compound (0.303 g). MS/EI (acetonitrile/water): m/z 304 (M+1+Na) retention time=2.9 min.

Step B: 1'-(tert-Butoxycarbonyl)-1-ethyl-4,5-dihydrospiro[cyclopentapyrazole-6(1H),4'-piperidine] (faster isomer) and 1'-(tert-butoxycarbonyl)-2-ethyl-4,5-dihydrospiro[cyclopentapyrazole-6(2H),4'-piperidine] (slower isomer)

To a solution of tert-butyl 2-(hydroxymethyl)-1-oxo-8-azaspiro[4.5]decane-8-carboxylate from Step A (0.303 g, 1.08 mmol) in ethanol (11 mL) was added ethyl hydrazine oxylate (0.194 g, 1.29 mmol). The reaction mixture was heated at 85° C. for 12 h, cooled, and then concentrated. The residue was taken up in a minimal amount of 40:40:20 acetonitrile/water/dimethyl sulfoxide solution and purified by Gilson reverse phase HPLC (Column: YMC-Pack Pro C18, 100×20 mm I.D.; Gradient Eluent: 10:90 to 90:10 v/v acetonitrile/water+0.1% trifluoroacetic acid over 12.5 min; Detection: PDA, 210–400 nm; Flow rate: 20 mL/min) to afford the title products as the trifluoroacetic acid salts, faster eluting isomer by HPLC (0.393 g) and slower eluting isomer by HPLC (0.050 g). MS/EI (acetonitrile/water) (faster isomer): m/z 306.3 retention time=2.4 min. MS/EI (acetonitrile/water) (slower isomer): m/z 306.3 retention time=2.9 min.

Step C: 1-Ethyl-4,5-dihydrospiro[cyclopentapyrazole-6(1H),4'-piperidine]dihydrochloride To a solution of 1'-(tert-butoxycarbonyl)-1-ethyl-4,5-dihydrospiro[cyclopentapyrazole-6(1H),4'-piperidine] (0.393 g, 0.737 mmol) the faster eluting isomer from Step B in methanol (7 mL) at 0° C. was added acetyl chloride (0.524 mL, 7.37 mmol). The reaction mixture was allowed to warm to room temperature, stirred for 12 h and then concentrated to afford the title compound as the dihydrochloride salt. MS/EI (acetonitrile/water): m/z 206.2 retention time=0.3 min.

Procedure 10

2-Ethyl-4,5-dihydrospiro[cyclopentapyrazole-6(2H),4'-piperidine]dihydrochloride

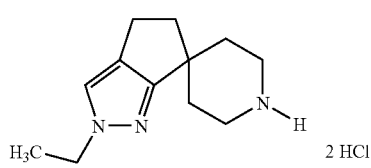

The title compound was prepared essentially the same as in Procedure 9, Step C, but using 1'-(tert-butoxycarbonyl)-2-ethyl-4,5-dihydrospiro[cyclopenta-pyrazole-6(2H),4'-piperidine] the slower eluting isomer from Procedure 9, Step B.

Procedure 11

1-Ethyl-3-methoxy-4,5-dihydrospiro[cyclopentapyrazole-6(1H),4'-piperidine]dihydrochloride

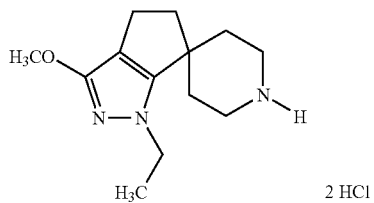

2 HCl

Step A: 1'-(tert-Butoxycarbonyl)-3-oxo-2,3,4,5-tetrahydrospiro[cyclopentapyrazole-6(1H),4'-piperidine]

To a solution of tert-butyl 2-(methoxycarbonyl)-1-oxo-8-azaspiro[4.5]decane-8-carboxate from Procedure 1, Step F (0.448 g, 1.46 mmol) in toluene (15 mL) was added hydrazine (0.084 mL, 1.72 mmol). The reaction mixture was refluxed for 12 h, concentrated and the residue was purified by flash chromatography eluting with 5% MeOH/dichloromethane and 0.1% triethylamine to give the title compound (0.263 g). MS/EI (acetonitrile/water): m/z 294.3 retention time=2.0 min.

Step B: 1'-(tert-Butoxycarbonyl)-3-methoxy-1-methyl-4,5-dihydrospiro[cyclopentapyrazole-6(1H),4'-piperidine] (faster product) and 1'-(tert-butoxycarbonyl)-3-methoxy-4,5-dihydrospiro[cyclopentapyrazole-6(1H),4'-piperidine] (slower product)

To a solution of 1'-(tert-butoxycarbonyl)-3-oxo-2,3,4,5-tetrahydrospiro[cyclopentapyrazole-6(1H),4'-piperidine] from Step A (2.78 g, 9.47 mmol) in diethyl ether (100 mL) at 0° C. was added a solution of diazomethane freshly prepared from Diazald (20.3 g, 94 mmol). The reaction mixture was stirred at 0° C. for 1 h, quenched with acetic acid, poured into a saturated sodium bicarbonate solution, extracted three times with diethyl ether, dried over sodium sulfate, and concentrated to afford 2.8 g. The residue was purified by flash chromatography eluting with 15–20% acetone/hexane to give the title products, faster eluting product (0.300 g) and slower eluting product (0.367 g).

Faster Product:
$^1$H NMR (400 MHz, CDCl$_3$): δ 1.49 (s, 9 H), 1.58–1.62 (m, 2 H), 1.85–1.93 (m, 2 H), 2.44 (t, 2 H), 2.58 (t, 2 H), 2.81–2.87 (m, 2 H), 3.69 (s, 3 H), 3.90 (s, 3 H), 4.14–4.21 (m, 2 H).

Slower Product: MS/EI (acetonitrile/water): m/z 308.3 retention time=2.5 min.

Step C: 1'-(tert-Butoxycarbonyl)-2-ethyl-3-methoxy4,5-dihydrospiro[cyclopentapyrazole-6(2H),4'-piperidine] (faster isomer) and 1'-(tert-butoxycarbonyl)-1-ethyl-3-methoxy-4,5-dihydrospiro[cyclopentapyrazole-6(1H),4'-piperidine] (slower isomer)

To a solution of 1'-(tert-butoxycarbonyl)-3-methoxy-4,5-dihydrospiro[cyclopentapyrazole-6(1H),4'-piperidine] (0.099 g, 0.320 mmol) the slower product from Step B in dimethylformamide (4 mL) at 0° C. was added sodium hydride 60% dispersion in mineral oil (0.018 g, 0.48 mmol) and ethyl iodide (0.038 mL, 0.481 mmol). The reaction mixture was stirred for 2 h, partitioned between saturated sodium chloride solution and diethyl ether, extracted three times with diethyl ether, dried over sodium sulfate, filtered and concentrated to afford 0.095 g. The residue was purified by flash chromatography eluting with 10% acetone/hexanes to afford the title products, the faster eluting isomer (0.059 g) and the slower eluting isomer (0.026 g). MS/EI (acetonitrile/water) (faster isomer): m/z 336.3 retention time=2.85 min. MS/EI (acetonitrile/water) (slower isomer): m/z 336.3 retention time=3.14 min.

Step D: 1-Ethyl-3-methoxy-4,5-dihydrospiro[cyclopentapyrazole-6(1H),4'-piperidine]dihydrochloride To a solution of 1'-(tert-butoxycarbonyl)-1-ethyl-3-methoxy-4,5-dihydrospiro[cyclopentapyrazole-6(1H),4'-piperidine] (0.026 g, 0.077 mmol) the slower eluting isomer from Step C in methanol (1 mL) at 0° C. was added acetyl chloride (0.055 mL, 0.775 mmol). The reaction mixture was allowed to warm to room temperature, stirred for 12 h and then concentrated to afford the title compound as a dihydrochloride salt. MS/EI (acetonitrile/water): m/z 236.2 retention time=1.12 min.

Procedure 12

2-Ethyl-3-methoxy-4,5-dihydrospiro[cyclopentapyrazole-6(2H),4'-piperidine]dihydrochloride

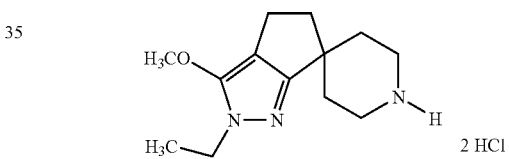

2 HCl

The title compound was prepared essentially the same as in Procedure 11, Step D, but using 1'-(tert-butoxycarbonyl)-2-ethyl-3-methoxy-4,5-dihydrospiro-[cyclopentapyrazole-6(2H),4'-piperidine] (0.059 g) the faster eluting isomer from Procedure 11, Step C.

Procedure 13

1-Methyl-3-methoxy-4,5-dihydrospiro[cyclopentapyrazole-6(1H),4'-piperidine]dihydrochloride

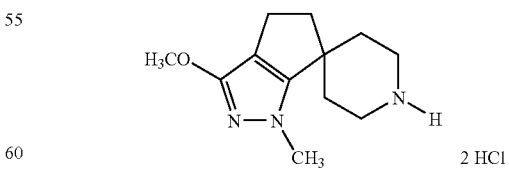

2 HCl

The title compound was prepared essentially the same as in Procedure 11, Step D, but using 1'-(tert-butoxycarbonyl)-1-methyl-3-methoxy-4,5-dihydrospiro-[cyclopentapyrazole-6(1H),4'-piperidine] (0.300 g) the faster eluting product from Procedure 11, Step B.

Procedure 14

3-Ethyl-4,5-dihydrospiro[6H-cyclopent[d]isoxazole-6,4'-piperidine]dihydrochloride

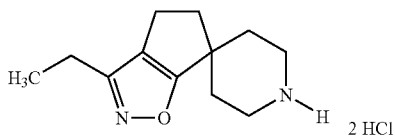

To a solution of tert-butyl 2-(1-oxoprop-1-yl)-1-oxo-8-azaspiro[4.5]decane-8-carboxylate (0.230 g, 0.743 mmol) from Procedure 1, Step I was added hydroxylamine (0.062 g, 0.892 mmol) and diisopropylethylamine (0.155 mL, 0.155 g, 0.892 mmol). The reaction mixture was heated at 100° C. for 12 h and concentrated. The residue was taken up in concentrated sulfuric acid (0.500 mL) and stirred for 2 h. The reaction mixture was diluted with dichloromethane and poured into 5% KOH and 5N NaOH was added until the pH of the reaction mixture was basic. The reaction mixture was then extracted three times with dichloromethane. The organic layers were combined, washed with saturated NaCl solution, dried over $Na_2SO_4$, filtered and concentrated. The residue was purified by prep TLC eluting with 10% MeOH/dichloromethane to give the title compound as the slower eluting isomer (0.026 g). MS/EI (acetonitrile/water): m/z 207 retention time=1.25 min.

Procedure 15

3-Ethyl-4,5-dihydrospiro[6H-cyclopent[c]isoxazole-6,4'-piperidine]dihydrochloride

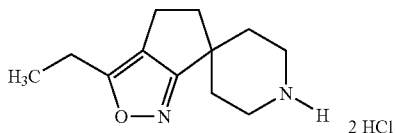

The title compound was prepared by the same method as in Procedure 14 except the title compound was the faster eluting isomer (0.005 g). MS/EI (acetonitrile/water): m/z 207 retention time=1.30 min.

Procedure 16

1,3-Diethyl-4,6-dihydrospiro[furo[3,4-c]pyrazole-6(1H),4'-piperidine]dihydrochloride

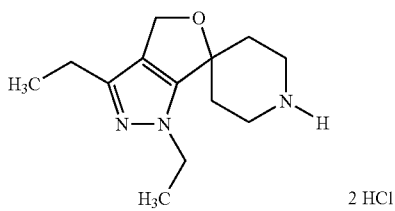

Step A: tert-Butyl 4-acetyl-4-methoxypiperidine-1-carboxylate

To a solution of 1-tert-butyl 4-methoxycarbonyl-4-methoxypiperidine-1-carboxylate (2.5 g, 9.05 mmol) dissolved in 100 mL of tetrahydrofuran at −78° C. was added trimethylsilylmethyl lithium (23 mL, 23 mmol). After 30 min additional trimethylsilylmethyl lithium (2.7 mL, 2.7 mmol) was added. The reaction mixture was then diluted with diethyl ether, poured into saturated ammonium chloride, and extracted three times with diethyl ether. The organic layers were combined, washed with saturated sodium chloride, dried over sodium sulfate, filtered and concentrated. The residue was purified by flash chromatography eluting with 10% ethyl acetate/hexanes to afford 1.7 g of silyl product which was taken up in tetrahydrofuran (50 mL) and tetrabutylammonium fluoride (6.1 mL, 6.1 mmol) was added. After 30 min at room temperature, the reaction mixture was diluted with ethyl acetate, poured into water, and extracted three times with ethyl acetate. The organic layers were combined, washed with sodium chloride solution, dried over $Na_2SO_4$, filtered and concentrated. The residue was purified by flash chromatography to afford the title compound (0.863 g).

$^1$H NMR (400 MHz, $CDCl_3$): δ 1.43 (s, 9 H), 1.66–1.86 (m, 4 H), 2.17 (s, 3 H), 3.06–3.13 (m 2 H), 3.17 (s, 3 H), 3.73–3.81 (m, 2 H).

Step B: tert-Butyl 4-(3-hydroxy-1-oxopent-1-yl)-4-methoxypiperidine-1-carboxylate To a solution of tert-butyl 4-acetyl-4-methoxypiperidine-1-carboxylate (0.589 g, 2.29 mmol) from Step A in tetrahydrofuran (20 mL) at −78° C. was added lithium diisopropylamine (0.650 mL, 0.974 mmol) followed by propionaldehyde (0.266 g, 0.330 mL, 4.58 mmol). After 5 min, the reaction mixture was poured into saturated ammonium chloride, and extracted three times with diethyl ether. The organic layers were combined, washed with saturated sodium chloride solution, dried over sodium sulfite, filtered, and concentrated. The residue was purified by flash chromatography eluting with 40% ethyl acetate/hexanes to afford the title compound (0.404 g). MS/EI (acetonitrile/water): m/z 216.1 (M+1−BOC) retention time=2.69 min.

Step C: tert-Butyl 4-methoxy4-(1,3-dioxopent-1-yl)piperidine-1-carboxylate

To a solution of oxalyl chloride (0.168 mL, 1.92 mmol) in dichloromethane (10 mL) at −78° C. was slowly added dimethyl sulfoxide (0.272 mL, 3.84 mmol). After 5 min, a solution of tert-butyl 4-(3-hydroxy-1-oxopent-1-yl)-4-methoxypiperidine-1-carboxylate (0.404 g, 1.28 mmol) from Step B in dichloromethane (5 mL) was added via syringe. The reaction mixture was stirred for 45 min at -78° C. and then triethylamine (1.1 mL, 7.68 mmol) was added. After 5 min, the reaction mixture was removed from the cooling bath, allowed to warm to room temperature for 1.5 h, poured into water, and extracted three times with dichloromethane. The organic layers were combined, washed with brine, dried over sodium sulfate, filtered, and concentrated. The residue was purified by flash chromatography eluting with 10% ethyl acetate/hexanes to afford the title compound (0.227 g).

$^1$H NMR (400 MHz, $CDCl_3$): δ 1.18 (t, 3 H), 1.47 (s, 9 H), 1.73–1.88 (m, 4 H), 2.37 (q, 2 H), 3.04–3.19 (m, 2 H), 3.22 (s, 3 H), 3.74–3.90 (m, 2 H), 5.87 (s, 1 H). MS/EI (acetonitrile/water): m/z 214 (M+1−BOC) retention time=2.95 min.

Step D: tert-Butyl 4-methoxy-4-(2-diazo-1,3-dioxopent-1-yl)piperidine-1-carboxylate To a solution of tert-butyl 4-methoxy-4-(1,3-dioxopent-1-yl)piperidine-1-carboxylate (0.227 g, 0.724 mmol) from Step C in dichloromethane (10 mL) was added triethylamine (0.101 mL, 0.724 mmol). Next, a solution of mesyl azide (0.087 g, 0.724 mmol) in dichloromethane (1 mL) was added. The reaction mixture was stirred for 3.5 h at room temperature. Additional mesyl azide (0.026 g, 0.217 mmol) was added. After 2 h, the reaction mixture was diluted with dichloromethane, poured into 1N sodium hydroxide solution, and extracted three times with dichloromethane. The organic layers were combined, washed with saturated sodium chloride, dried over sodium sulfite, filtered, and concentrated. The residue was purified by flash chromatography eluting with 5% ethyl acetate/dichloromethane to afford the title compound (0.174 g). MS/EI (acetonitrile/water): m/z 362 (M+Na) retention time=3.37 min.

Step E: tert-Butyl 4-oxo-3-(1-oxoprop-1-yl)-1-oxa-8-azaspiro[4.5]decane-8-carboxylate A solution of rhodium acetate dimer (0.002 g, 0.005 mmol) in dichloromethane (27 mL) was heated to 81° C. A solution of tert-butyl 4-methoxy-4-(2-diazo-1,3-dioxopent-1-yl)piperidine-1-carboxylate (0.092 g, 0.270 mmol) from Step D in dichloromethane (7 mL) was added slowly dropwise over 12 min. The reaction mixture was refluxed for 45 min then poured into 1N hydrochloric acid, and extracted three times with dichloromethane. The organic layers were combined, washed with saturated sodium chloride solution, dried over sodium sulfite, filtered, and concentrated. The residue was purified by flash chromatography eluting with 10% ethyl acetate/dichloromethane to afford the title compound (0.034 g).

$^1$H NMR (400 MHz, CDCl$_3$): δ 1.22–1.25 (t, 3 H), 1.45–1.59 (m, 2 H), 1.49 (s, 9 H), 1.85–1.91 (m, 2 H), 2.60 (q, 2 H), 3.12–3.22 (m, 2 H), 3.81 (s, 2 H), 4.03–4.13 (m, 2 H).

Step F: 1'-(tert-Butoxycarbonyl)-1,3-diethyl-4,6-dihydrospiro[furo[3,4-c]pyrazole-6(1H),4'-piperidine] and 1'-(tert-butoxycarbonyl)-2,3-diethyl-4,6-dihydrospiro[furo[3,4-c]pyrazole-6(2H),4'-piperidine]

To a solution of tert-butyl 4-oxo-3-(1-oxoprop-1-yl)-1-oxa-8-azaspiro[4.5]decane-8-carboxylate (0.034 g, 0.109 mmol) from Step E in ethanol (1.5 mL) was added ethyl hydrazine oxylate (0.016 g, Q. 109 mmol) and diisopropylethylamine (0.014 g, 0.019 mL, 0.109 mmol). The reaction mixture was heated at 80° C. for 12 h, cooled, and concentrated. The residue was dissolved in dichloromethane and saturated sodium bicarbonate, and extracted three times with dichloromethane. The organic layers were combined, washed with saturated sodium chloride solution, dried over sodium sulfate, filtered, and concentrated. The residue was purified by flash chromatography eluting with 20% acetonitrile/dichloromethane to afford the title compounds as a mixture (0.012 g). MS/EI (acetonitrile/water): m/z 336 retention time=3.1 min.

Step G: 1,3-Diethyl-4,6-dihydrospiro[furo[3,4-c]pyrazole-6(1H),4'-piperidine] and 2,3-diethyl-4,6-dihydrospiro[furo[3,4-c]pyrazole-6(2H),4'-piperidine]

To a solution of 1'-(tert-butoxycarbonyl)-1,3-diethyl-4,6-dihydrospiro[furo[3,4-c]pyrazole-6(1H),4'-piperidine] and 1'-(tert-butoxycarbonyl)-2,3-diethyl-4,6-dihydrospiro[furo[3,4-c]pyrazole-6(2H),4'-piperidine] (0.012 g, 0.034 mmol) from Step F in methanol (0.5 mL) at 0° C. was added acetyl chloride (0.040 mL, 0.698 mmol). The reaction mixture was allowed to warm to room temperature, stirred for 24 h and then concentrated. A mixture of title compounds was isolated as the free amines after elution from an ion exchange resin (0.0076 g). MS/EI (acetonitrile/water): m/z 236 retention times=1.1 and 1.4 min.

Procedure 17

1-Ethyl-5,6-dihydrospiro[cyclopentapyrazole-4(1H),4'-piperidine]dihydrochloride

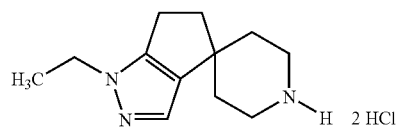

Step A: tert-Butyl 1-oxo-7-azaspiro[3.5]nonane-7-carboxylate

To a solution of cyclopropyldiphenylsulfonium tetrafluoroborate (3.44 g, 10.9 mmol) (B. Trost, *J. Am. Chem. Soc.*, 1975, 2218) in THF (100 mL) cooled to −40° C. was added solid potassium bis(trimethylsilyl)amide (KHMDS) (2.4 g, 11.9 mmol). After 5 min, BOC-piperidin-4-one (2.2 g, 10.9 mmol) was added and the reaction was stirred at −40° C. for 20 min, then allowed to warm to room temperature for 1 h. The reaction was quenched with water and extracted three times with ether. The organic layers were combined, washed with saturated sodium chloride solution, dried over sodium sulfate, filtered, and concentrated.

$^1$H NMR (400 MHz, CDCl$_3$): δ 1.458 (s, 9 H), 1.6–1.7 (m, 2 H), 1.8–1.9 (m, 2 H), 1.884 (t, 2 H), 3.032 (t, 2 H), 3.35–3.45 (m, 2 H), 3.5–3.6 (m, 2 H).

The residue was taken up in toluene (70 mL) and lithium tetrafluoroborate (81 mg, cat.) was added. The mixture was heated to 80° C. for 90 min, cooled, then quenched with water, and extracted three times with ether. The organic layers were combined, washed with saturated sodium chloride solution, dried over sodium sulfate, filtered, and concentrated. The residue was purified by flash chromatography eluting with 20% ethyl acetate in hexanes to afford the title compound as a white solid.

$^1$H NMR (400 MHz, CDCl$_3$): δ 0.932 (t, 2 H), 1.071 (t, 2 H), 1.484 (s, 9 H), 1.6–1.8 (m, 2 H), 1.8–1.95 (m, 2 H), 3.45–3.55 (m, 2 H), 3.65–3.75 (m, 2 H).

Step B: tert-Butyl 1-vinyl-2-oxo-8-azaspiro[4.5]decane-8-carboxylate

The tert-butyl 1-oxo-7-azaspiro[3.5]nonane-7-carboxylate (10.9 mmol) from Step A was taken up in methylene chloride (20 mL) and allyl tetrahydrothiophenium bromide (2.74 g, 13.1 mmol) (prepared from allyl bromide and tetrahydrothiophene in methanol according to *J. Chem. Soc., Perkin Trans. I*, 1993, 2979) and benzyltriethylammonium chloride (0.25 g, 1.1 mmol) were added. The mixture was cooled in an ice bath while 10N NaOH (17 mL) was added. The reaction was then stirred as it was allowed to warm to room temperature over 20 h. The reaction was diluted with water and extracted three times with methylene chloride. The organic layers were combined, washed with saturated sodium chloride solution, dried over sodium sulfate, filtered, and concentrated. The residue was purified by flash chromatography eluting with 10% ethyl acetate in hexanes to afford the intermediate spiro cyclobutyl/allyl epoxide (0.5 g) as a mixture of isomers along with starting material (1.74 g).

$^1$H NMR (400 MHz, CDCl$_3$): (partial spectrum) δ 1.464 (s, 9 H), 3.27 and 3.39 (2 d, 1 H), 5.25–5.3 and 5.32–5.36 (2 m, 1 H), 5.4–5.5 (m, 1 H) 5.5–5.56 and 5.58–5.68 (2 m, 1 H).

The above epoxide product (0.5 g, 1.79 mmol) was taken up in THF (18 mL) and 4-nitrophenol (0.25 g, 1.79 mmol) and tetrakis(triphenylphoshine) palladium (0) (0.10 g, 0.089 mmol) were added (according to the procedure of *Tetra. Lett.*, 1999, 3395). The reaction was stirred for 15 min and was then immediately diluted with ether and water and extracted twice with ether. The combined ether layers were washed three times with sat'd sodium carbonate to remove the 4-nitrophenol, then with brine, dried over sodium sulfate, filtered, and concentrated. The residue was purified by flash chromatography eluting with 20% ethyl acetate in hexanes to afford the title compound (0.30 g).

$^1$H NMR (400 MHz, CDCl$_3$): δ 1.472 (s, 9 H), 1.2–1.8 (3 m, 6 H), 2.65 (d, 1 H), 3.08 (br t, 2 H), 3.7–3.9 (m, 3 H), 5.19 (d, 1 H), 5.36 (d, 1 H) 5.63 (ddd, 1 H).

Step C: tert-Butyl 1-formyl-2-oxo-8-azaspiro[4.5]decane-8-carboxylate

Ozone was bubbled into a solution of tert-butyl 1-vinyl-2-oxo-8-azaspiro[4.5]decane-8-carboxylate (0.168 g, 0.599 mmol) from Step B in methanol (6 mL) at −70° C. until a blue color persisted. Excess ozone was removed with a stream of nitrogen and then dimethyl sulfide (0.5 mL) was added. The mixture was allowed to warm to room temperature for 1 h and was then concentrated in vacuo without heating to afford the crude title compound which was used directly in the next step.

Step D: 1-(tert-Butoxycarbonyl)-1-ethyl-5,6-dihydrospiro[cyclopentapyrazole-4(1H),4'-piperidine] (faster, minor isomer) and 1'-(tert-butoxycarbonyl)-2-ethyl-5,6-dihydrospiro[cyclopentapyrazole-4(2H), 4'-piperidine] (slower, major isomer)

The crude tert-butyl 1-formyl-2-oxo-8-azaspiro[4.5]decane-8-carboxylate (assumed 0.599 mmol) from Step C was taken up in methanol (6 mL) and ethyl hydrazine oxylate salt (0.089 g, 0.599 mmol) was added. The reaction was heated to 60° C. for 3 h and was then concentrated. The residue was purified by flash chromatography eluting with 1% methanol in methylene chloride to afford the title compounds (0.082 g) as a mixture of isomers. The mixture was taken up in a minimal amount of 40:40:20 acetonitrile/water/dimethyl sulfoxide solution (4 mL) and purified by Gilson reverse phase HPLC (Column: YMC-Pack Pro C18, 100×20 mm I.D.; Gradient Eluent: 10:90 to 90:10 v/v acetonitrile/water+ 0.1% trifluoroacetic acid over 12.5 min; Detection: PDA, 210–400 nm; Flow rate: 20 mL/min) to afford the title products as the trifluoroacetic acid salts, the faster eluting isomer by HPLC (6.28 min, 0.0075 g) and slower eluting isomer by HPLC (7.15 min, 0.017 g).

(faster HPLC isomer): MS/EI (acetonitrile/water): m/z 306 retention time=2.3 min.

(Slower HPLC Isomer) MS/EI (acetonitrile/water): m/z 306 retention time=2.7 min.

Step E: 1-Ethyl-5,6-dihydrospiro[cyclopentapyrazole-4(1H),4'-piperidine]dihydrochloride To a solution of 1'-(tert-butoxycarbonyl)-1-ethyl-5,6-dihydrospiro[cyclopentapyrazole-4(1H),4'-piperidine] (6 mg, 0.019 mmol) from the minor, faster isomer in Step D in methanol (0.5 mL) was added acetyl chloride (0.024 g, 0.4 mmol) and the solution was stirred at room temperature for 20 h. The volatiles were removed under a stream of nitrogen and then in vacuo to afford the title compound as a dihydrochloride salt. MS/EI (acetonitrile/water): m/z 206 (M+1); retention time=0.24 min.

Procedure 18

2-Ethyl-5,6-dihydrospiro[cyclopentapyrazole-4(2H), 4'-piperidine]dihydrochloride

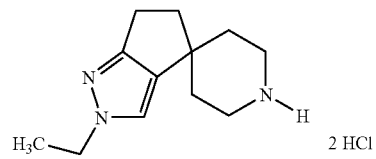

2 HCl

The title compound was prepared essentially the same as in Procedure 17, Step E, but using 1'-(tert-butoxycarbonyl)-2-ethyl-5,6-dihydrospiro[cyclopenta-pyrazole-4(2H),4'-piperidine] (0.011 g) the slower eluting product from Procedure 17, Step D. MS/EI (acetonitrile/water): m/z 206 (M+1); retention time=0.24 min.

Procedure 19

1,3-Diethyl-5,6-dihydrospiro[cyclopentapyrazole-4 (1H),4'-piperidine]dihydrochloride

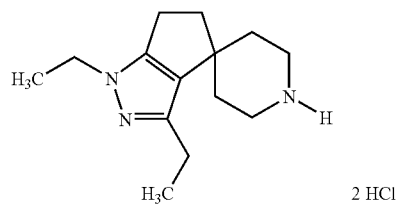

2 HCl

Step A: tert-Butyl 1-vinyl-2-hydroxy-8-azaspiro [4.5]decane-8-carboxylate

A solution of tert-butyl 1-vinyl-2-oxo-8-azaspiro[4.5]decane-8-carboxylate (0.59 g, 2.11 mmol) from Procedure 17, Step B in methanol (6 mL) was cooled to −70° C. and sodium borohydride (0.022 g, 0.60 mmol) was added. The reaction was allowed to warm to room temperature for 3 h and was then quenched with the addition of 1N hydrochloric acid. The mixture was diluted with water and extracted twice with ether. The combined ether layers were washed with brine, dried over sodium sulfate, filtered, and concentrated. The residue was purified by flash chromatography eluting with 20% ethyl acetate in hexanes to afford the title compound (0.621 g). $^1$H NMR (400 MHz, CDCl$_3$) indicated a mixture of isomers which was used in the next step.

Step B: tert-Butyl 1-vinyl-2-(tert-butyldimethylsilyloxy)-8-azaspiro[4.5]decane-8-carboxylate To a solution of tert-butyl 1-vinyl-2-hydroxy-8-azaspiro[4.5]decane-8-carboxylate (0.462 g, 1.64 mmoL) from Step A in DMF (8 mL) was added imidazole (0.335 mg, 4.92 mmol) and then tert-butyldimethylsilyl chloride (0.370 g, 2.4 mmol). The reaction was stirred at room temperature for 20 h and then diluted with ether and sodium bicarbonate solution. The mixture was extracted twice with ether. The combined ether layers were washed with brine, dried over sodium sulfate, filtered, and concentrated. The residue was purified by flash chromatography eluting with 5% ethyl acetate in hexanes to afford the title compound (0.56 g) as a mixture of isomers.

Step C: tert-Butyl 1-formyl-2-(tert-butyldimethylsilyloxy)-8-azaspiro[4.5]decane-8-carboxylate To a solution of tert-butyl 1-vinyl-2-(tert-butyldimethylsilyloxy)-8-azaspiro[4.5]decane-8-carboxylate (0.56 g, 1.42 mmol) from Step B in acetone (3 mL), t-butanol (6 mL), and water (1.5 mL) was added NMO (333 mg, 2.8 mmol) and 2.5% osmium tetroxide in t-butanol (0.268 mL, 0.855 mmol). After stirring at room temperature for 20 h, a second portion of osmium tetroxide was added and the reaction was stirred an additional 24 h. The reaction was quenched with the addition of aqueous sodium sulfite for 5 min and the mixture was extracted twice with ethyl acetate. The combined organic layers were washed with 1N HCl, sodium bicarbonate, and brine, dried over sodium sulfate, filtered, and concentrated. The residue was purified by flash chromatography eluting with 30% ethyl acetate in hexanes to afford a mixture of diols (0.356 g) which was used directly below.

The above diol mixture (0.356 g, 0.828 mmol) was taken up in THF (6 mL) and a solution of sodium periodate (0.213 g, 0.99 mmol) in water (1.2 mL) was added at room temperature. The reaction was stirred for 2 h and was then diluted with water and extracted twice with ethyl acetate. The combined organic layers were washed with brine, dried over sodium sulfate, filtered, and concentrated. The residue was purified by flash chromatography eluting with 10% ethyl acetate in hexanes to afford the title compound (0.284 g) as a mixture of isomers.

Step D: tert-Butyl 1-(1-hydroxyprop-1-yl)-2-(tert-butyldimethylsilyloxy)-8-azaspiro[4.5]decane-8-carboxylate A solution of tert-butyl 1-formyl-2-(tert-butyldimethylsilyloxy)-8-azaspiro[4.5]decane-8-carboxylate (0.284 g, 0.714 mmol) from Step C in THF (7 mL) was cooled to −70° C. and ethyl magnesium bromide (3.0M, 0.262 mL, 0.786 mmol) was added. The reaction was stirred for 30 min and then an additional aliquot of ethyl magnesium bromide (3.0M, 0.050 mL, 0.142 mmol) was added. After 5 min, the reaction was diluted with ether, poured into sodium bicarbonate, and extracted three times with ether. The combined organic layers were washed with brine, dried over sodium sulfate, filtered, and concentrated. The residue was purified by flash chromatography eluting with 10 to 20% ethyl acetate in hexanes to afford the title compound (0.248 g) as a mixture of isomers. MS/EI (acetonitrile/water): m/z 354 (100%, M+1−74 (t-BuOH)), 372 (M+1−56 (C$_4$H$_8$); 428 (M+1); retention time=4.29 min.

Step E: tert-Butyl 1-(1-hydroxyprop-1-yl)-2-hydroxy-8-azaspiro[4.5]decane-8-carboxylate To a solution of tert-butyl 1-(1-hydroxyprop-1-yl)-2-(tert-butyldimethylsilyloxy)-8-azaspiro[4.5]decane-8-carboxylate (0.248 g, 0.58 mmol) in THF (15 mL) was added 1M tetrabutylammonium fluoride in THF (2.3 mL, 2.3 mmol). The solution was stirred at room temperature for 4 h and was then diluted with ethyl acetate, poured into 1N HCl, and extracted twice with ethyl acetate. The combined organic layers were washed with brine, dried over sodium sulfate, filtered, and concentrated. The residue was purified by flash chromatography eluting with 50% ethyl acetate in hexanes to afford the title compound (0.18 g) as a mixture of isomers.

Step F: tert-Butyl 1-(1-oxoprop-1-yl)-2-oxo-8-azaspiro[4.5]decane-8-carboxylate

To a solution of tert-butyl 1-(1-hydroxyprop-1-yl)-2-hydroxy-8-azaspiro[4.5]decane-8-carboxylate (0.050 g, 0.16 mmol) from Step E in acetone (2 mL) at 0° C. was added 2.6M Jones reagent (0.122 mL, 0.32 mmol). The reaction was stirred at room temperature for 10 min and was then quenched with isopropanol. The mixture was diluted with water and extracted three times with methylene chloride. The combined organic layers were washed with brine, dried over sodium sulfate, filtered, and concentrated. The residue was purified by flash chromatography eluting with 20% ethyl acetate in hexanes to afford the title compound (0.033 g).

Step G: 1'-(tert-Butoxycarbonyl)-1,3-diethyl-5,6-dihydrospiro[cyclopentapyrazole-4(1H),4'-piperidine] (faster, minor isomer) and 1'-(tert-butoxycarbonyl)-2,3-diethyl-5,6-dihydrospiro[cyclopentapyrazole-4(2H),4'-piperidine] (slower, major isomer)

The tert-butyl 1-(1-oxoprop-1-yl)-2-oxo-8-azaspiro[4.5]decane-8-carboxylate (0.033 g, 0.11 mmol) from Step F was taken up in ethanol (1 mL) and ethyl hydrazine oxylate salt (0.018 g, 0.12 mmol) was added. The reaction was heated to 65° C. for 3 h and was then concentrated. The mixture was taken up in a minimal amount of 40:40:20 acetonitrile/water/dimethyl sulfoxide solution and purified by Gilson reverse phase HPLC (Column: YMC-Pack Pro C18, 100×20 mm I.D.; Gradient Eluent: 10:90 to 90:10 v/v acetonitrile/water+ 0.1% trifluoroacetic acid over 12.5 min; Detection: PDA, 210–400 nm; Flow rate: 20 mL/min) to afford the title products as the trifluoroacetic acid salts, the faster eluting minor isomer by HPLC (5.74 min, 0.0047 g) and slower eluting major isomer by HPLC (6.48 min, 0.012 g).

(Minor, Faster HPLC Isomer):
$^1$H NMR (400 MHz, CDCl$_3$): δ 1.246 (t, 3 H), 1.430 (t, 3 H), 1.499 (s, 9 H), 1.55 (m, 2 H) 1.8–1.95 (m, 4 H), 2.42 (t, 2 H), 2.59 (m, 2 H), 2.69 (t, 2 H), 2.96 (br t, 2 H), 4.00 (m, 2 H). MS/EI (acetonitrile/water): m/z 334 (M+1); retention time=2.24 min.

(Major, Slower HPLC Isomer)

$^1$H NMR (400 MHz, CDCl$_3$): δ 1.19 (m, 3 H), 1.45 (m, 3 H), 1.499 (s, 9 H), 1.5–9 (3 m, 6 H), 2.31 (m, 2 H), 2.60 (m, 2 H), 2.73 (m, 2 H), 2.90 (br m, 2 H), 4.03 (m, 2 H). MS/EI (acetonitrile/water): m/z 334 (M+1); retention time=2.53 min.

Step H: 1,3-Diethyl-5,6-dihydrospiro[cyclopentapyrazole-4(1H),4'-piperidine]dihydrochloride To a solution of 1'-(tert-butoxycarbonyl)-1,3-diethyl-5,6-dihydrospiro[cyclopentapyrazole-4(1H),4'-piperidine] (4.7 mg, 0.014 mmol) from the faster minor isomer in Step G in methanol (0.5 mL) at 0° C. was added acetyl chloride (0.016 g, 0.28 mmol) and the solution was then allowed to warm to room temperature and stirred for 20 h. The volatiles were removed under a stream of nitrogen and then in vacuo to afford the title compound as a dihydrochloride salt (6 mg). MS/EI (acetonitrile/water): m/z 234 (M+1) retention time=0.35 min.

Procedure 20

2,3-Diethyl-5,6-dihydrospiro[cyclopentapyrazole-4(2H),4'-piperidine]dihydrochloride

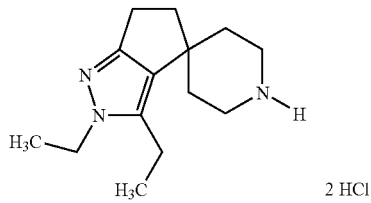

The title compound was prepared essentially the same as in Procedure 19, Step H, but using 1'-(tert-butoxycarbonyl)-2,3-diethyl-5,6-dihydrospiro[cyclopentapyrazole-4(2H),4'-piperidine] (0.011 g) the slower eluting major product from Procedure 19, Step G. $^1$H NMR (400 MHz, CDCl$_3$): δ 1.194 (t, 3 H), 1.353 (t, 3 H), 1.56 (m, 2 H), 1.91 (dt, 2 H), 2.34 (t, 2 H), 2.63 (t, 2 H), 2.69 (q, 2 H), 2.78 (dt, 2 H), 2.96 (dt, 2 H), 3.99 (q, 2 H). The 2,3-diethyl assignment was confirmed by nOe experiments. MS/EI (acetonitrile/water): m/z 233 (M+1) retention time=0.43 min.

Procedure 21

2'-Benzyl-5',6'-dihydrospiro[piperidine-4,4'-[4H]pyrrolo[1,2-b]pyrazole] dihydrochloride

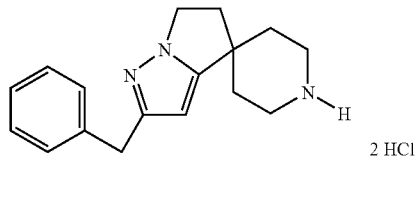

Step A: tert-Butyl 4-methoxycarbonyl-4-(2-(tert-butyldimethylsilyloxy)eth-1-yl)piperidine-1-carboxylate To a solution of KHMDS (8.72 g, 44 mmol) in THF (300 mL) at −70° C. was slowly added over 10 min a solution of tert-butyl 4-methoxycarbonylpiperidine-1-carboxylate (7.1 g, 29 mmol) in THF (70 mL). After 1 h, 2-bromo-1-(tert-butyldimethylsilyloxy)ethane (10 g, 47 mmol) was added and the reaction was allowed to warm to room temperature for 1 h. The mixture was poured into aq. sodium bicarbonate solution and extracted three times with ethyl acetate. The combined organic layers were washed with brine, dried over sodium sulfate, filtered, and concentrated. The residue was used directly in the next step. TLC (50% ethyl acetate in hexanes) indicated a mixture of bromide starting material and title product.

Step B: tert-Butyl 4-hydroxymethyl-4-(2-(tert-butyldimethylsilyloxy)eth-1-yl)piperidine-1-carboxylate The crude tert-butyl 4-methoxycarbonyl-4-(2-(tert-butyldimethylsilyloxy)eth-1-yl)piperidine-1-carboxylate (assumed 44 mmol) from Step A was taken up in THF (200 mL) and 2M lithium borohydride in THF (29 mL, 58 mmol) was added via syringe at room temperature. The reaction was stirred for 2 days at room temperature and then at 50° C. for 20 h after addition of more 2M lithium borohydride in THF (2.9 mL, 5.8 mmol). The mixture was then quenched with acetic acid, diluted with ether and aq. sodium bicarbonate solution, and extracted three times with ether. The combined organic layers were washed with brine, dried over sodium sulfate, filtered, and concentrated. The residue was purified by flash chromatography (20% ethyl acetate in hexanes) to afford recovered starting material (2.5 g) and the title product (7.1 g).

$^1$H NMR (400 MHz, CDCl$_3$): δ 0.115 (s, 6 H), 0.926 (s, 9 H), 1.36 (ddd, 2 H), 1.467 (s, 9 H), 1.55 (ddd, 2 H), 1.62 (dd, 2 H), 3.345 (ddd, 2 H), 3.40–3.47 m, 2 H), 3.478 (s, 2 H), 3.740 (dd, 2 H).

Step C: tert-Butyl 4-formyl-4-(2-(tert-butyldimethylsilyloxy)eth-1-yl)piperidine-1-carboxylate To a solution of oxalyl chloride (3.3 mL, 38 mmol) in methylene chloride (500 mL) at −70° C. was added DMSO (5.4 mL, 76 mmol) over 5 min. After 15 min, a solution of tert-butyl 4-hydroxymethyl-4-(2-(tert-butyldimethylsilyloxy)eth-1-yl)piperidine-1-carboxylate (7.1 g, 19 mmol) in methylene chloride (125 mL) was slowly added over 15 min. After 1 h, triethylamine (21.2 mL, 152 mmol) was added and the reaction was allowed to warm to room temperature for 1 h. The mixture was poured into water and extracted three times with methylene chloride. The combined organic layers were washed with brine, dried over sodium sulfate, filtered, and concentrated. The residue was purified by flash chromatography (40% ethyl acetate in hexanes) to afford the title product (6.3 g).

$^1$H NMR (400 MHz, CDCl$_3$): δ 0.032 (s, 6 H), 0.878 (s, 9 H), 1.462 (s, 9 H), 1.4–1.5 (m, 2 H), 1.78 (t, 2 H), 1.96 (dt, 2 H), 3.0–3.1 (m, 2 H), 3.63 (t, 2 H), 3.76 (dt, 2 H), 9.515 (s, 1 H).

Step D: tert-Butyl 4-(1-hydroxyeth-1-yl)-4-(2-(tert-butyldimethylsilyloxy)eth-1-yl)piperidine-1-carboxylate To a solution of tert-butyl 4-formyl-4-(2-(tert-butyldimethylsilyloxy)eth-1-yl)piperidine-1-carboxylate (6.3 g, 17 mmol) in THF (170 mL) at −70° C. was added 1.4M methyl lithium in ether (13.3 mL, 19 mmol). After 2 h, an additional amount of 1.4M methyl lithium in ether (2.5 mL) was added. After an additional 30 min, the reaction was poured into aq. sodium bicarbonate and extracted three times with ether. The combined organic layers were washed with brine, dried over sodium sulfate, filtered, and concentrated to afford the title product (6.6 g) which was used directly in the next step.

$^1$H NMR (400 MHz, CDCl$_3$): δ 0.117 and 0.119 (2 s, 6 H), 0.929 (s, 9 H), 1.175 (d, 3 H), 1.32 (m, 1 H), 1.43 (m, 1 H), 1.469 (s, 9 H), 1.48–1.7 (m, 3 H), 1.76–1.84 (m, 1 H), 3.0–3.2 (m, 2 H), 3.55 (q, 1 H), 3.6–3.73 (m, 2 H), 3.73–3.8 (m, 2 H).

Step E: tert-Butyl 4-acetyl-4-(2-(tert-butyldimethylsilyloxy)eth-1-yl)piperidine-1-carboxylate To a solution of oxalyl chloride (3.0 mL, 34 mmol) in methylene chloride (400 mL) at −70° C. was added DMSO (4.8 mL, 68 mmol) over 5 min. After 15 min, a solution of tert-butyl 4-(1-hydroxyeth-1-yl)-4-(2-(tert-butyldimethylsilyloxy)eth-1-yl)piperidine-1-carboxylate (6.6 g, 17 mmol) in methylene chloride (125 mL) was slowly added over 15 min. After 1 h, triethylamine (19 mL, 136 mmol) was added and the reaction was allowed to warm to room temperature for 1 h. The mixture was poured into water and extracted three times with methylene chloride. The combined organic layers were washed with brine, dried over sodium sulfate, filtered, and concentrated. The residue was purified by flash chromatography (10% ethyl acetate in hexanes) to afford the title product (4.5 g).

$^1$H NMR (400 MHz, CDCl$_3$): δ 0.027 (s, 6 H), 0.876 (s, 9 H), 1.4–1.5 (m, 2 H), 1.458 (s, 9 H), 1.85 (t, 2 H), 2.0–2.05 (m, 2 H), 2.157 (s, 3 H), 3.0–3.1 (m, 2 H), 3.58 (t, 2 H), 3.65–3.72 (m, 2 H).

Step F: tert-Butyl 4-(4-phenyl-3-hydroxy-1-oxobut-1-yl)-4-(2-(tert-butyldimethylsilyloxy)eth-1-yl)piperidine-1-carboxylate To a solution of tert-butyl 4-acetyl-4-(2-(tert-butyldimethylsilyloxy)eth-1-yl)piperidine-1-carboxylate (4.6 g, 12 mmol) in THF (120 mL) at −70° C. was added HMPA (20.7 mL, 120 mmol) and 1M LHMDS in THF (12 mL, 12 mmol). After 1 h, phenylacetaldehyde (5.7 g, 48 mmol) was added in THF (80 mL) over 10 min and the reaction was stirred for 1 h. The mixture was then poured into ether and aq. ammonium chloride solution and extracted three times with ether. The combined organic layers were washed with brine, dried over sodium sulfate, filtered, and concentrated. The residue was purified by flash chromatography (10 to 30% ethyl acetate in hexanes) to afford recovered starting material (2.15 g) and the title product (2.2 g).

$^1$H NMR (400 MHz, CDCl$_3$): δ 0.013 (s, 6 H), 0.876 (s, 9 H), 1.4–1.5 (m, 2 H), 1.455 (s, 9 H), 1.83 (t, 2 H), 1.85–2.05 (m, 2 H), 2.64 (d, 2 H), 2.74 and 2.85 (d Abq, 2 H), 3.05–3.15 (m, 2 H), 3.56 (q, 2 H), 3.58–3.66 (m, 2 H), 4.35 (m, 1 H), 7.2–7.4 (m, 5 H).

Step G: tert-Butyl 4-(4-phenyl-1,3-dioxobut-1-yl)-4-(2-(tert-butyldimethylsilyloxy)eth-1-yl)piperidine-1-carboxylate To a solution of tert-butyl 4-(4-phenyl-3-hydroxy-1-oxobut-1-yl)-4-(2-(tert-butyldimethylsilyloxy)eth-1-yl)piperidine-1-carboxylate (494 mg, 0.98 mmol) from Step F in methylene chloride (10 mL) at room temperature was added Dess-Martin reagent (621 mg, 1.5 mmol). After 3 h, the reaction was diluted with ether and quenched with 1N sodium hydroxide. After stirring for 30 min, the mixture was diluted with water and extracted twice with ether. The combined organic layers were washed with brine, dried over sodium sulfate, filtered, and concentrated. The residue was purified by flash chromatography (10% ethyl acetate in hexanes) to afford the title product (343 mg).

Step H: 1-(tert-Butoxycarbonyl)-4-(2-tert-butyldimethylsilyloxyeth-1-yl)-4-(3-benzyl-(1H)-pyrazol-5-yl)piperidine To a solution of tert-butyl 4-(4-phenyl-1,3-dioxobut-1-yl)-4-(2-(tert-butyldimethylsilyloxy)eth-1-yl)piperidine-1-carboxylate (343 mg, 0.68 mmol) from Step G in ethanol (7 mL) was added hydrazine hydrate (0.040 mL, 0.82 mmol). The reaction was heated at 85° C. for 3 h and was then concentrated in vacuo. The residue was purified by flash chromatography (30% ethyl acetate in hexanes) to afford the title product (243 mg).

$^1$H NMR (400 MHz, CDCl$_3$): δ 31 0.021 (s, 6 H), 0.854 (s, 9 H), 1.453 (s, 9 H), 1.6–1.75 (m, 2 H), 1.79 (t, 2 H), 2.0–2.15 (m, 2 H), 3.05–3.15 (m, 2 H), 3.46 (t, 2 H), 3.65–3.8 (m, 2 H), 3.997 (s, 2 H), 7.2–7.4 (m, 5 H).

Step I: 1-(tert-Butoxycarbonyl)-4-(2-hydroxyeth-1-yl)-4-(3-benzyl-(1H)-pyrazol-5-yl)piperidine To a solution of 1-(tert-butoxycarbonyl)-4-(2-tert-butyldimethylsilyloxyeth-1-yl)-4-(3-benzyl-(1H)-pyrazol-5-yl)piperidine (243 mg, 0.49 mmol) from Step H in THF (5 mL) was added 1M tetrabutylammonium fluoride in THF (0.63 mL, 0.63 mmol). The reaction was stirred at room temperature for 1 h and was then diluted with ethyl acetate, poured into 1N HCl, and extracted twice with ethyl acetate. The combined organic layers were washed with brine, dried over sodium sulfate, filtered, and concentrated. The residue was purified by flash chromatography eluting with 5% methanol in methylene chloride to afford the title compound (125 mg).

Step J: 1-(tert-Butoxycarbonyl)-2'-benzyl-5',6'-dihydrospiro[piperidine-4,4'-[4H]pyrrolo[1,2-b]pyrazole]

To a solution of 1-(tert-butoxycarbonyl)-4-(2-hydroxyeth-1-yl)-4-(3-benzyl-(1H)-pyrazol-5-yl)piperidine (125 mg, 0.32 mmol) from Step I in THF (4 mL) at 0° C. was added triphenylphosphine (85 mg, 0.32 mmol) and DEAD (0.051 mL, 0.32 mmol). The reaction was stirred for 20 min and was then allowed to warm to room temperature for 2 h. The mixture was concentrated and purified by flash chromatography eluting with 80% ethyl acetate in hexanes, then 5% methanol in methylene chloride to afford the title compound (100 mg).

$^1$H NMR (400 MHz, CDCl$_3$): δ 1.478 (s, 9 H), 1.58–1.76 (2 m, 4 H), 2.40 (t, 2 H), 3.3–3.4 (m, 2 H), 3.6–3.7 (m, 2 H), 3.971 (s, 2 H), 4.23 (t, 2 H), 5.800 (s, 1 H), 7.2–7.4 (m, 5 H). MS/EI (acetonitrile/water): m/z 312 retention time=3.55 min.

Step K: 2'-Benzyl-5',6'-dihydrospiro[piperidine-4,4'-[4H]pyrrolo[1,2-b]pyrazole]

To a solution of 1-(tert-butoxycarbonyl)-2'-benzyl-5',6'-dihydrospiro[piperidine-4,4'-[4H]pyrrolo[1,2-b]pyrazole] (100 mg, 0.27 mmol) from Step J in methanol (3 mL) was added acetyl chloride (0.20 mL, 2.7 mmol). The solution was stirred at room temperature for 20 h and then the volatiles were removed under a stream of nitrogen. The residue was taken up in a minimal amount of 40:40:20 acetonitrile/water/dimethyl sulfoxide solution and purified by Gilson reverse phase HPLC (Column: YMC-Pack Pro C18, 100×20 mm I.D.; Gradient Eluent: 10:90 to 90:10 v/v acetonitrile/water+0.1% trifluoroacetic acid over 12.5 min; Detection: PDA, 210–400 nm; Flow rate: 20 mL/min) to afford the title products as the trifluoroacetic acid salt (150 mg). This was converted to the free amine by elution from an ion exchange resin (30 mg).

$^1$H NMR (400 MHz, CDCl$_3$): δ 2.0–2.05 (m, 4 H), 2.54 (t, 2 H), 3.2–3.35 (m, 4 H), 4.002 (s, 2 H), 4.30 (t, 2 H), 5.988 (s, 1 H), 7.2–7.4 (m, 5 H). MS/EI (acetonitrile/water): m/z 268 retention time=1.49 min.

EXAMPLE 1

N-Methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine trihydrochloride salt

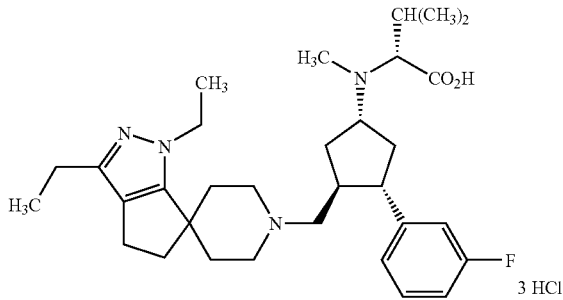

Step A: Methyl (±)-trans-4-methylene-2-(3-fluorophenyl)cyclopentanoate

A mixture of methyl trans-3-fluorocinnamate (41.25 g, 229 mmol), tetrakis(triphenylphosphine) palladium(0) (18.5 g, 16 mmol), 1,2-bis(diphenylphosphino)ethane (5.5 g, 13.7 mmol), and 2-((trimethylsilyl)methyl)-2-propen-1-yl acetate (42.66 g, 229 mmol) in THF (300 mL) under nitrogen was heated to reflux for 6 h and then stirred at room temperature for 16 h. The reaction was diluted with hexane and filtered to remove the yellow precipitate. The volatiles were then removed in vacuo and the residue was purified by FC (3 to 5% ethyl acetate in hexanes) to afford the title compound (45 g).

NMR (CDCl$_3$) δ: 2.52 (m, 1 H), 2.68 (m, 1 H), 2.8–2.9 (m, 2 H), 2.95 (ddd, 1 H), 3.45 (ddd, 1 H), 3.63 (s, 3 H), 4.96 (m, 2 H), 6.9–7.0 (m, 2 H), 7.03 (d, 1 H), 7.2–7.3 (m, 1 H).

Step B: (+−)-trans-4-Methylene-2-(3-fluorophenyl)cyclopentanoic acid

To a solution of methyl (+−)-trans-4-methylene-2-(3-fluoro)phenylcyclopentanoate (47 g, 200 mmol) from Step A in methanol (500 mL) was added 5N sodium hydroxide (200 mL, 1000 mmol). The reaction was stirred at room temperature for 60 h then concentrated in vacuo. The residue was taken up in water, acidified with 2M hydrochloric acid and extracted twice with methylene chloride. The organic layers were each washed with brine, dried over sodium sulfate, combined and concentrated in vacuo to give the crude title acid (40.8 g) which was used directly in Step C.

Step C: (+)-trans-1-(S)-Hydroxymethyl-4-methylene-2-(S)-(3-fluorophenyl)cyclopentane and (−)-trans-1-(R)-hydroxymethyl-4-methylene-2-(R)-(3-fluorophenyl)cyclopentane Method A:

A solution of (±)-trans-4-methylene-2-(3-fluorophenyl)cyclopentanoic acid (5.2 g, 23.6 mmol) from Step B in THF (100 mL) was cooled to 0° C. under nitrogen and 1M lithium aluminum hydride (LAH) in THF (35.4 mL) was added dropwise over 10 min. The reaction was stirred at room temperature for 16 h, the excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (25% ethyl acetate in hexanes) to afford the racemic title product (4.1 g) as a an oil. Chiral Prep HPLC on a 2 cm×25 cm Chiracel OD column eluting with 5% isopropanol in hexanes (25 injections) afforded the (−)-enantiomer, [α]$_D$=−44.5 (MeOH, c=0.9), as the first eluting peak (R$_t$=17.5 min) and the (+)-enantiomer (1.87 g), [α]$_D$=+44.7 (MeOH, c=1.0), as the second peak (R$_t$=22.0 min).

NMR (CDCl$_3$) δ: 2.2–2.35 (m, 2 H), 2.5 (m, 1 H), 2.65–2.85 (m, 2 H), 2.9 (m, 1 H), 3.51 and 3.68 (dABq, 2 H), 4.93 (m, 2 H), 6.9–7.0 (m, 2 H), 7.06 (d, 1 H), 7.3–7.4 (m, 1 H).

Method B:

Step B-1: 1-(S)-(((S)-(−)-4-Benzyl-2-oxazolidin-1-yl)carbonyl)-3-methylene-2-(S)-(3-fluorophenyl)cyclopentane (higher R$_f$) and 1-(R)-(((S)-(−)-4-benzyl-2-oxazolidin-1-yl)carbonyl)-3-methylene-2-(R)-(3-fluorophenyl)cyclopentane (lower R$_f$)

To a solution of N-(trans-3-fluorocinnamoyl)-(S)-(−)-4-benzyl-2-oxazolidine (34.4 g, 112 mmol) and 2-((trimethylsilyl)methyl)-2-propen-1-yl acetate (25 g, 135 mmol) in THF (100 mL) under nitrogen was added tetrakis(triphenylphosphine) palladium(0) (18.5 g, 16 mmol) and 1,2-bis(diphenylphosphino)ethane (5.5 g, 13.7 mmol). The mixture was again purged with nitrogen and stirred at room temperature for 3.5 days. The catalyst was precipitated with 5% ethyl acetate in hexanes and then filtered through Celite. The filtrate was evaporated and the residue was taken up in 10% ethyl acetate in hexanes and the 1-(R) lower R$_f$ title compound was allowed to precipitate and was then filtered (10 g). The filtrate was concentrated and purified by Prep LC (8% ethyl acetate in hexanes) to afford the 1-(S) higher R$_f$ title compound (26.3 g) as an oil.

Alternatively, the above title compounds were prepared from the racemic acid from Step B. To a solution of (±)-trans-4-methylene-2-(3-fluorophenyl)cyclopentanoic acid (10.5 g, 52 mmol) in ether (200 mL) at −10° C. was added pivaloyl chloride (6.3 g, 52 mmol) and DIPEA (10.8 mL, 62 mmol). The reaction was stirred for 30 min, warmed to room temperature for 2 h, and then recooled to −50° C. Simultaneously in a separate reaction, (S)-(−)-4-benzyl-2-oxazolidinone (11.5 g, 65 mmol) in THF (100 mL) at −70° C. was treated with 2.5M n-butyl lithium in THF (24 mL, 60 mmol). The mixture was stirred at −70° C. for 30 min and then at −50° C. for 1 h. This solution was slowly added to the above mixed anhydride mixture at −50° C. via a double tipped needle. After 30 min, the reaction was warmed to room temperature for 16 h. The mixture was diluted with aq. sodium bicarbonate solution and extracted twice with ether. The organic layers were each washed with a portion of brine, dried over sodium sulfate, combined, and evaporated. The residue was taken up in 10% ethyl acetate in hexanes at which time most of the 1-(R) lower $R_f$ isomer title compound precipitated and was filtered (1.87 g). The mother liquor was purified by prep LC eluting with 10% ethyl acetate in hexanes to afford the 1-(S) higher $R_f$ isomer title compound (5.1 g) and additional lower $R_f$ isomer.

Step B-2: (+)-trans4-Methylene-2-(3-fluorophenyl) cyclopentanoic acid and (−)-trans-4-methylene-2-(3-fluorophenyl)cyclopentanoic acid A solution of 1-(S)-(((S)-(−)-4-benzyl-2-oxazolidin-1-yl)carbonyl)-3-methylene-2-(S)-(3-fluorophenyl)cyclopentane (36 g, 100 mmol) (higher $R_f$ isomer) from Step B-1 in THF (900 mL):water (200 mL) was cooled to 10° C. and 30% hydrogen peroxide (68 mL, 600 mmol) was added slowly. A solution of lithium hydroxide (8.2 g, 200 mmol) in water (100 mL) was added over 1 h with cooling to maintain the temperature below 10° C. The reaction was stirred at 0–10° C. for 2 h and then diluted with water. A solution of sodium sulfite (75 g) in water (500 mL) was added over 1 h while the temperature was maintained at less than 20° C. with a water bath. After an additional 1 h with ice bath cooling, most of the THF was removed in vacuo, water was added to dissolve the solids, sodium bicarbonate was added, and the mixture was extracted four times with ether. The aq. layer was acidified with 2N HCl and extracted twice with ethyl acetate. The organic layers were each washed with brine, dried over sodium sulfate, combined and concentrated. The residue afforded the (+) title compound (22 g) contaminated with a trace of oxazolidinone by-product, but was used directly in the next step. $[\alpha]_D$=+93.0 (MeOH, c=1.0), Similarly, the hydrolysis of 1-(R)-(((S)-(−)-4-benzyl-2-oxazolidin-1-yl)carbonyl)-3-methylene-2-(R)-(3-fluorophenyl)cyclopentane (lower $R_f$ isomer from Step B-1) afforded the (−) title compound.

Step B-3: (+)-trans-1-(S)-Hydroxymethyl-4-methylene-2-(S)-(3-fluorophenyl)cyclopentane and (−)-trans-1-(R)-hydroxymethyl-4-methylene-2-(R)-(3-fluorophenyl)cyclopentane A solution of (+)-trans-4-methylene-2-(3-fluorophenyl) cyclopentanoic acid (22.5 g, 98 mmol) from Step B-2 in THF (500 mL) was cooled to 0° C. under nitrogen and 1M lithium aluminum hydride (LAH) in THF (35.4 mL) was added dropwise over 10 min. The reaction was stirred at room temperature for 16 h, the excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (10–40% ethyl acetate in hexanes) to afford the non-racemic title product (19.6 g) as a an oil which was the same as the slower eluting enantiomer of Method A. $[\alpha]_D$=+44.6 (MeOH, c=1.0), Similarly, LAH reduction of (−)-trans-4-methylene-2-(3-fluorophenyl)cyclopentanoic acid from Step B-2 afforded the (−) title compound.

Step D: (+)-trans-3-(S)-Hydroxymethyl-4-(S)-(3-fluorophenyl)cyclopentanone

A solution of (+)-trans-1-hydroxymethyl-4-methylene-2-(3-fluorophenyl)cyclopentane from Step C (1.87 g, 9.0 mmol) in methanol (75 mL) was cooled in a dry ice/acetone bath and ozone was bubbled into the solution until the blue color persisted. The excess ozone was removed with a stream of nitrogen and then dimethylsulfide (5 mL) was added. After 10 min, the bath was removed and the reaction was allowed to warm to room temperature over 2 h. The mixture was treated with 10 drops of sulfuric acid (c) in water (20 mL) for 1 h before most of the methanol was removed in vacuo. The mixture was diluted with water and extracted twice with ethyl acetate and the organic layers were washed with brine, dried over sodium sulfate, combined and concentrated. The residue was purified by FC (50% ethyl acetate in hexanes) to give the title compound (1.87 g). $[\alpha]_D$ =+132 (MeOH, c=1.2).

NMR (CDCl$_3$) δ: 2.3–2.45 (m, 2 H), 2.5 (m, 1 H), 2.61 and 2.77 (dABq, 2 H), 2.28 (ddd, 1 H), 3.61 and 3.75 (dABq, 2 H), 6.9–7.0 (m, 2 H), 7.06 (d, 1 H), 7.3–7.4 (m, 1 H).

Step E: N-(1-(R and S)-3-(S)-Hydroxymethyl-4-(S)-(3-fluorophenyl)cyclopent-1-yl)-(R)-valine t-butyl ester To a solution of (+)-trans-3-(S)-hydroxymethyl-4-(S)-(3-fluorophenyl)cyclopentanone from Step D (1.0 g, 4.8 mmol) in 1,2-dichloroethane (50 mL) was added (R)-valine t-butyl ester (0.90 g, 5.2 mmol) and acetic acid (0.330 mL, 5.8 mmol). After 15 min, sodium triacetoxyborohydride (2.0 g, 5.6 mmol) was added and the reaction was stirred at room temperature for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by FC eluting with 30% ethyl acetate in hexanes to give the title products (1.62 g) as a mixture of the major, slightly higher $R_f$ title 1-(R) compound and the minor, 1-(S) isomer as the free amines.

Step F: N-Methyl-N-(1-(R)-3-(S)-hydroxymethyl-4-(S)-(3-fluorophenyl)cyclopent-1-yl)-(R)-valine t-butyl ester (higher $R_f$) and N-methyl-N-(1-(S)-3-(S)-hydroxymethyl-4-(S)-(3-fluorophenyl)cyclopent-1-yl)-(R)-valine t-butyl ester (lower $R_f$)

Method A:
To a solution of N-(1-(R and S)-3-(S)-hydroxymethyl-4-(S)-(3-fluorophenyl)cyclopent-1-yl)-(R)-valine t-butyl ester from Step E (1.62 g, 4.44 mmol) and 37 wt % formaldehyde in water (2.1 mL, 27 mmol) in methanol (35 mL) was added 10% Pd/C (200 mg). After 10 min, the mixture was placed under hydrogen and stirred at atmospheric pressure for 60 h. The catalyst was removed by filtration and the filtrate was evaporated. The residue was purified by FC eluting with a gradient of 15 to 50% ethyl acetate in hexanes to give the 1-(R), higher $R_f$ title product (1.44 g) and the 1-(S), lower C-1 isomer (0.17 g) as the free amines.

Method B:

To a solution of (+)-trans-3-(S)-hydroxymethyl-4-(S)-(3-fluorophenyl)cyclopentanone from Step D (6.6 g, 32 mmol) in 1,2-dichloroethane (80 mL) was added (R)-valine t-butyl ester hydrochloride salt (6.1 g, 35 mmol) and DIPEA (5.7 mL, 32 mmol). After 5 min, sodium triacetoxyborohydride (10.2 g, 48 mmol) was added and the reaction was stirred at room temperature for 16 h. Aq. formaldehyde (37%, 5.2 mL, 64 mmol) and additional sodium triacetoxyborohydride (6.8 g, 32 mmol) were added and the reaction was stirred another 2 h. The mixture was diluted with methylene chloride, quenched with aq. sodium carbonate and extracted 3 times with methylene chloride. The organic layers were each washed with brine, dried over sodium sulfate, combined and concentrated in vacuo. The residue was purified by Prep LC eluting with 17% ethyl acetate in hexanes to give the 1-(R), higher $R_f$ title product (9.7 g) and then the 1-(S), lower C-1 isomer (3.5 g) as the free amines.

Step G: N-Methyl-N-(1-(R)-3-(S)-formyl-4-(S)-(3-fluorophenyl)cyclopent-1-yl)-(R)-valine t-butyl ester To a solution of oxalyl chloride (0.235 mL, 2.65 mmol) in methylene chloride (10 mL) at −70° C. was added dropwise DMSO (0.385 mL, 5.3 mmol). After 15 min, a solution of N-methyl-N-(1-(R)-3-(S)-hydroxymethyl-4-(S)-(3-fluorophenyl)cyclopent-1-yl)-(R)-valine t-butyl ester (higher $R_f$ isomer from Step F) (400 mg, 1.05 mmol) in methylene chloride (10 mL) was added. The reaction was stirred at −70° C. for 1 h and then DIPEA (1.8 mL, 11 mmol) in methylene chloride (5 mL) was added dropwise over 5 min. After a further 10 min at −70° C., the mixture was allowed to warm to room temperature for 1 h and was then diluted with methylene chloride and water. The layers were separated and the aq. layer was reextracted with a second portion of methylene chloride and the organic layers were each washed with brine, dried over sodium sulfate, combined and concentrated in vacuo. The residue was purified by FC (15% ethyl acetate in hexanes) to give the title product (378 mg) as an oil.

Step H: N-Methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine t-butyl ester TFA salt To a solution of N-methyl-N-(1-(R)-3-(S)-formyl-4-(S)-(3-fluorophenyl)cyclopent-1-yl)-(R)-valine t-butyl ester (30 mg, 0.0795 mmol) from Step G in 1,2-dichloroethane (2 mL) was added 1,3-diethyl-4,5-dihydrospiro[cyclopentapyrazole-6(1H),4'-piperidine]dihydrochloride (24 mg, 0.0795 mmol) from Procedure 1 and DIPEA (0.031 mL, 0.18 mmol). After 15 min, sodium triacetoxyborohydride (34 mg, 0.16 mmol) was added and the reaction was stirred at room temperature for 16 h. The reaction was diluted with methylene chloride, quenched with aq. sodium carbonate and extracted 3 times with methylene chloride. The organic layers were each washed with brine, dried over sodium sulfate, combined, and concentrated in vacuo. The residue was taken up in a minimal amount of 40:40:20 acetonitrile/water/dimethyl sulfoxide solution (4 mL) and purified by Gilson reverse phase HPLC (Column: YMC-Pack Pro C18, 100×20 mm I.D.; Gradient Eluent: 10:90 to 90:10 v/v acetonitrile/water+0.1% trifluoroacetic acid over 12.5 min; Detection: PDA, 210–400 nm; Flow rate: 20 mL/min) to afford the title product as the TFA salt.

HPLC/MS (ESI): m/z 595.6 (M+1); retention time=2.08 min.

Step I: N-Methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine trihydrochloride salt The N-methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine t-butyl ester from Step H was taken up in TFA (2 mL) and stirred at room temperature for 16 h. The volatiles were evaporated under a stream of nitrogen. The residue was taken up in methanol and adsorbed onto a 500 mg Varian SCX ion-exchange resin cartridge. The resin was first eluted with 2×3 mL of methanol, then the product was eluted with 2×3 mL of 2M ammonia in methanol. The product solution was concentrated under nitrogen, then 2 volumes of methylene chloride were evaporated to remove methanol and ammonia to give the free amine. The hydrochloride salt was prepared by dissolving the free amine in methylene chloride, adding excess (>3-fold) 1M hydrogen chloride in ether and evaporating to dryness.

HPLC/MS (ESI): m/z 539.6 (M+1); retention time=1.57 min.

Using essentially the same procedure as in Example 1, Steps G and H, but substituting the appropriate 4-substituted spiropiperidine from Procedures 2–21 (or analogous piperidines), the following compounds of Examples 2–17 were prepared:

EXAMPLE 2

N-Methyl-N-(1-(R)-3-(S)-((2,3-diethyl-4,5-dihydrospiro[cyclopentapyrazole-6(2H),4'-piperidin-1'-yl])methyl)-4-(S)-(3-fluorophenyl)cyclopent-1-yl)-(R)-valine trihydrochloride salt

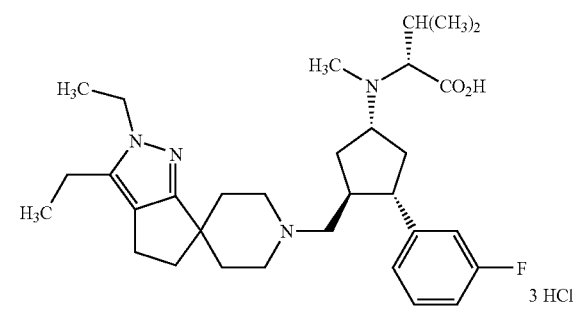

HPLC/MS (ESI): m/z 539.6 (M+1); retention time=1.90 min.

EXAMPLE 3

N-Methyl-N-(1-(R)-3-(S)-((3-ethyl-1-methyl-4,5-dihydrospiro[cyclopentapyrazole-6(1H),4'-piperidin-1'-yl])methyl)4-(S)-(3-fluorophenyl)cyclopent-1-yl)-(R)-valine trihydrochloride salt

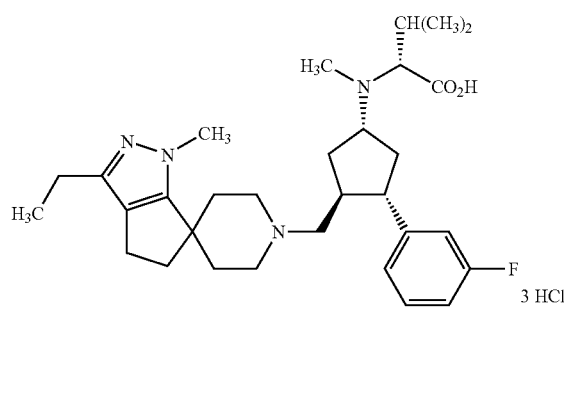

HPLC/MS (ESI): m/z 525.5 (M+1); retention time=1.57 min.

EXAMPLE 4

N-Methyl-N-(1-(R)-3-(S)-((1,3-dimethyl-4,5-dihydrospiro[cyclopentapyrazole-6(1H),4'-piperidin-1'-yl])methyl)-4-(S)-(3-fluorophenyl)cyclopent-1-yl)-(R)-valine trihydrochloride salt

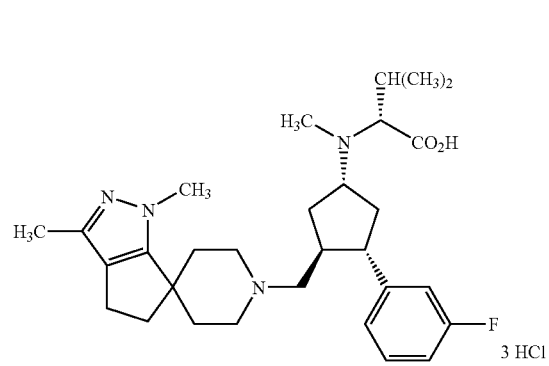

HPLC/MS (ESI): m/z 511.5 (M+1); retention time=1.71 min.

EXAMPLE 5

N-Methyl-N-(1-(R)-3-(S)-((1-ethyl-3-methyl-4,5-dihydrospiro[cyclopentapyrazole-6(1H),4'-piperidin-1'-yl])methyl)-4-(S)-(3-fluorophenyl)cyclopent-1-yl)-(R)-valine trihydrochloride salt

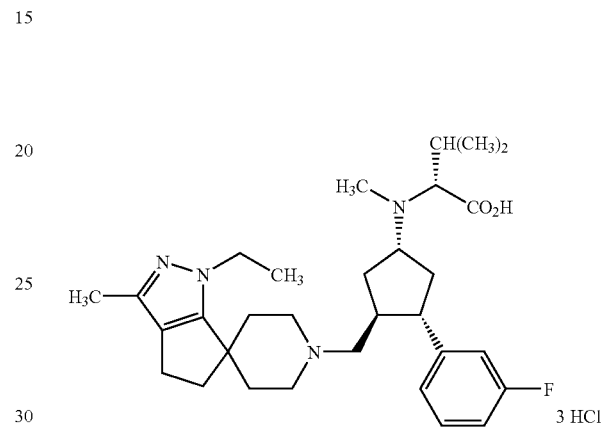

HPLC/MS (ESI): m/z 525.5 (M+1); retention time=1.50 min.

EXAMPLE 6

N-Methyl-N-(1-(R)-3-(S)-((1-ethyl-4,5-dihydrospiro[cyclopentapyrazole-6(1H),4'-piperidin-1'-yl])methyl)-4-(S)-(3-fluorophenyl)cyclopent-1-yl)-(R)-valine trihydrochloride salt

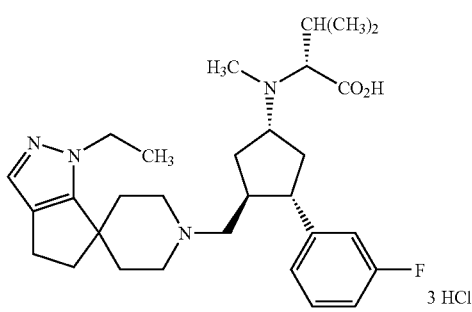

HPLC/MS (ESI): m/z 511.5 (M+1); retention time=1.60 min.

EXAMPLE 7

N-Methyl-N-(1-(R)-3-(S)-((3-methyl-4,5-dihydrospiro[cyclopentapyrazole-6(1H),4'-piperidin-1'-yl])methyl)-4-(S)-(3-fluorophenyl)cyclopent-1-yl)-(R)-valine trihydrochloride salt

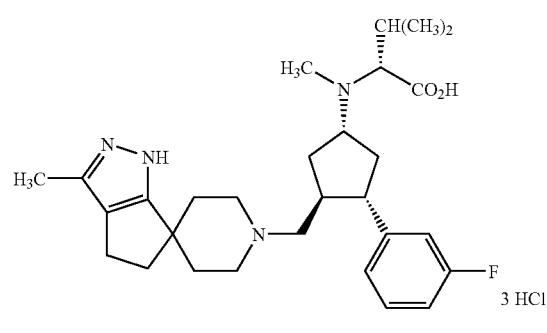

HPLC/MS (ESI): m/z 497.5 (M+1); retention time=1.50 min.

EXAMPLE 8

N-Methyl-N-(1-(R)-3-(S)-((1-ethyl-3-methoxy-4,5-dihydrospiro[cyclopentapyrazole-6(1H),4'-piperidin-1'-yl])methyl)-4-(S)-(3-fluorophenyl)cyclopent-1-yl)-(R)-valine trihydrochloride salt

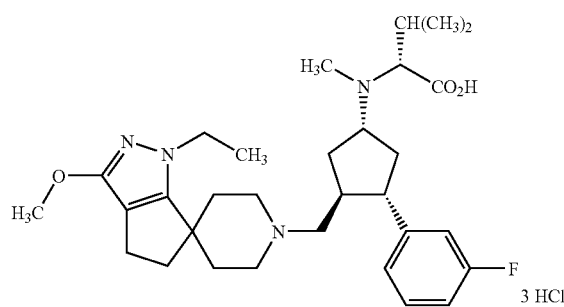

HPLC/MS (ESI): m/z 541.5 (M+1); retention time=1.89 min.

EXAMPLE 9

N-Methyl-N-(1-(R)-3-(S)-((2-ethyl-3-methoxy-4,5-dihydrospiro[cyclopentapyrazole-6(2H),4'-piperidin-1'-yl])methyl)-4-(S)-(3-fluorophenyl)cyclopent-1-yl)-(R)-valine trihydrochloride salt

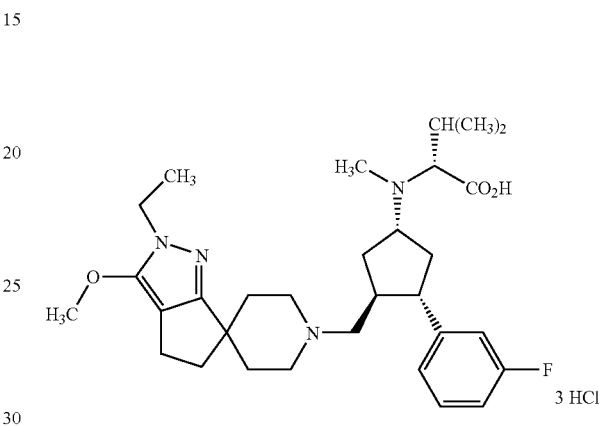

HPLC/MS (ESI): m/z 541.5 (M+1); retention time=2.03 min.

EXAMPLE 10

N-Methyl-N-(1-(R)-3-(S)-((1-methyl-3-methoxy-4,5-dihydrospiro[cyclopenta-pyrazole-6(1H),4'-piperidin-1'-yl])methyl)-4-(S)-(3-fluorophenyl)cyclopent-1-yl)-(R)-valine trihydrochloride salt

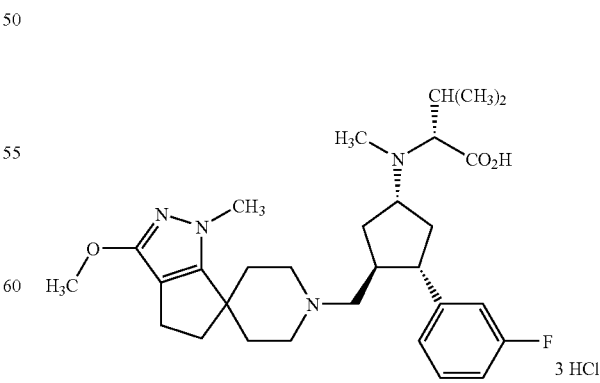

HPLC/MS (ESI): m/z 527.5 (M+1); retention time=1.8 min.

EXAMPLE 11

N-Methyl-N-(1-(R)-3-(S)-((3-ethyl-4,5-dihydrospiro[6H-cyclopent[d]isoxazole-6,4'-piperidin-1'-yl])methyl)-4-(S)-(3-fluorophenyl)cyclopent-1-yl)-(R)-valine trihydrochloride salt

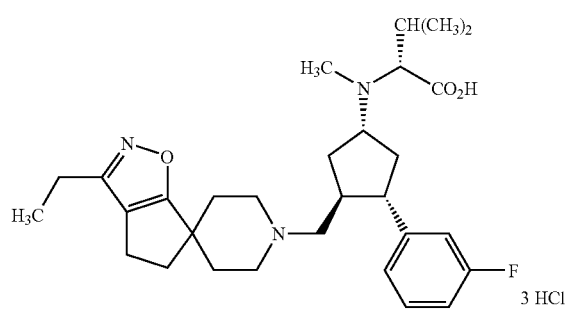

HPLC/MS (ESI): m/z 512.5 (M+1); retention time=1.97 min.

EXAMPLE 12

N-Methyl-N-(1-(R)-3-(S)-((3-ethyl-4,5-dihydrospiro[6H-cyclopent[c]isoxazole-6,4'-piperidin-1'-yl])methyl)-4-(S)-(3-fluorophenyl)cyclopent-1-yl)-(R)-valine trihydrochloride salt

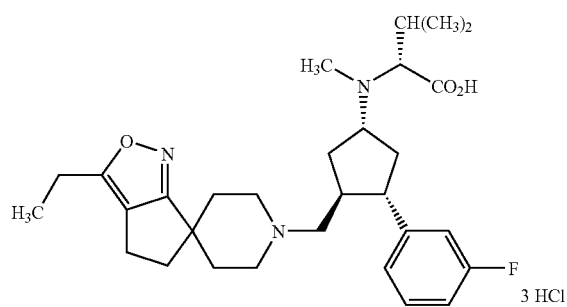

HPLC/MS (ESI): m/z 512.5 (M+1); retention time=2.0 min.

EXAMPLE 13

N-Methyl-N-(1-(R)-3-(S)-((1,3-diethyl-4,6-dihydrospiro[furo[3,4-c]pyrazole-6(1H),4'-piperidin-1'-yl])methyl)-4-(S)-(3-fluorophenyl)cyclopent-1-yl)-(R)-valine trihydrochloride salt

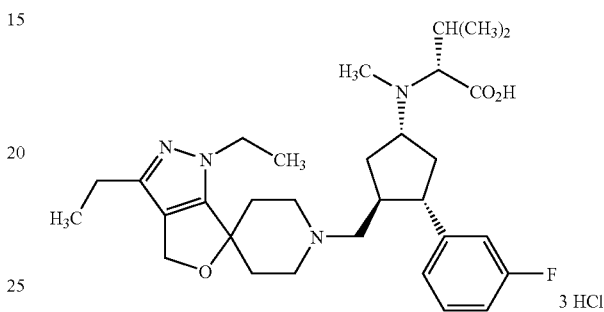

HPLC/MS (ESI): m/z 541.1 (M+1); retention time=2.0 min.

and

N-Methyl-N-(1-(R)-3-(S)-((2,3-diethyl-4,6-dihydrospiro[furo[3,4-c]pyrazole-6(1H),4'-piperidin-1'-yl])methyl)-4-(S)-(3-fluorophenyl)cyclopent-1-yl)-(R)-valine trihydrochloride salt

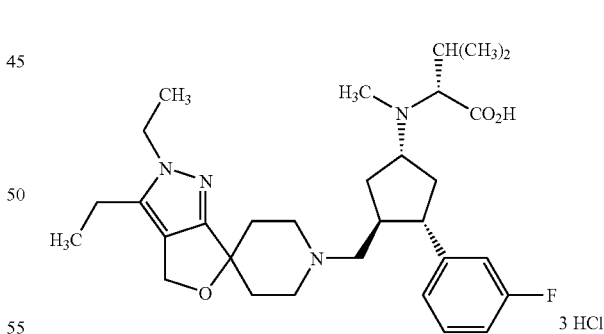

HPLC/MS (ESI): m/z 541.1 (M+1); retention time=2.1 min.

Reaction of the piperidine mixture from Procedure 16 as in Example 1, Step H, followed by separation of the piperidine isomers by prep HPLC, afforded the individual t-butyl esters. Each was individually treated with TFA as in Example 1, Step I, to afford the title compounds.

EXAMPLE 14

N-Methyl-N-(1-(R)-3-(S)-((1-ethyl-5,6 dihydrospiro[cyclopentapyrazole-4(1H),4'-piperidin-1'-yl])methyl)-4-(S)-(3-fluorophenyl)cyclopent-1-yl)-(R)-valine trihydrochloride salt

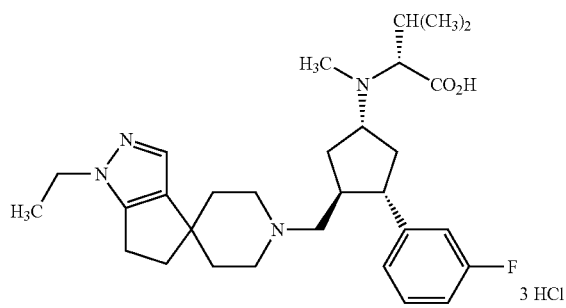

HPLC/MS (ESI): m/z 511.5 (M+1); retention time=1.41 min.

EXAMPLE 15

N-Methyl-N-(1-(R)-3-(S)-((2-ethyl-5,6 dihydrospiro[cyclopentapyrazole-4(2H),4'-piperidin-1'-yl])methyl)-4-(S)-(3-fluorophenyl)cyclopent-1-yl)-(R)-valine trihydrochloride salt

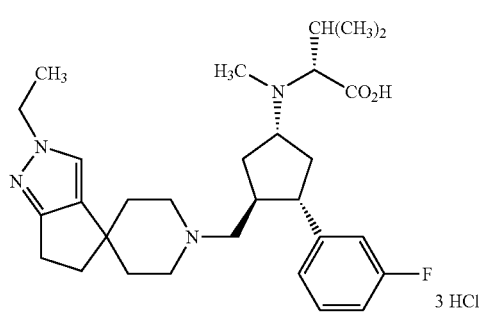

HPLC/MS (ESI): m/z 511.5 (M+1); retention time=1.5 min.

EXAMPLE 16

N-Methyl-N-(1-(R)-3-(S)-((1,3-diethyl-5,6 dihydrospiro[cyclopentapyrazole-4(1H),4'-piperidin-1'-yl])methyl)-4-(S)-(3-fluorophenyl)cyclopent-1-yl)-(R)-valine trihydrochloride salt

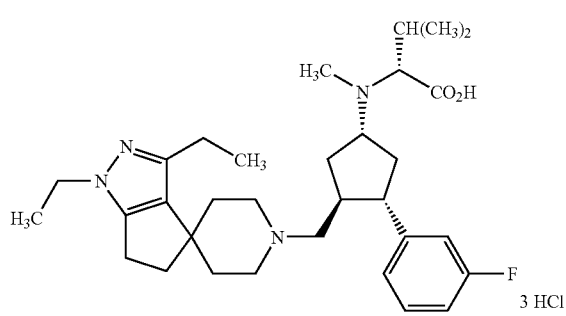

HPLC/MS (ESI): m/z 539.5 (M+1); retention time=1.44 min.

EXAMPLE 17

N-Methyl-N-(1-(R)-3-(S)-((2'-benzyl-5',6'-dihydrospiro[piperidin-1-yl-4,4'-[4H]pyrrolo[1,2-b]pyrazole])methyl)-4-(S)-(3-fluorophenyl)cyclopent-1-yl)-(R)-valine trihydrochloride salt

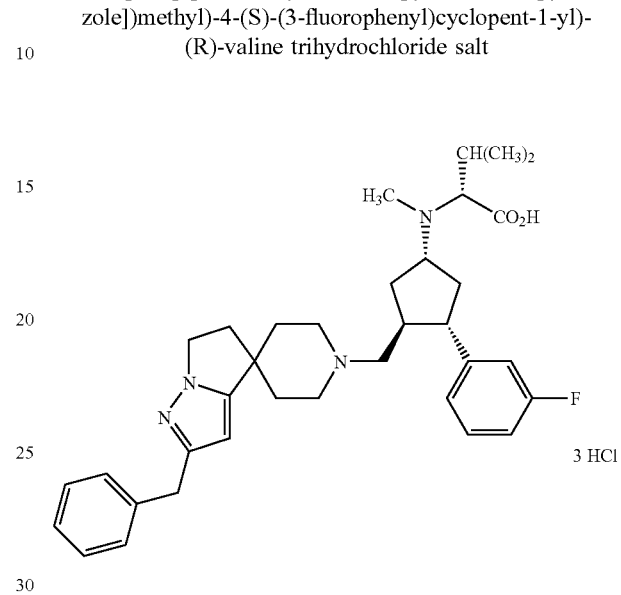

HPLC/MS (ESI): m/z 573.5 (M+1); retention time=2.13 min.

EXAMPLE 18

N-Ethyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine trihydrochloride salt

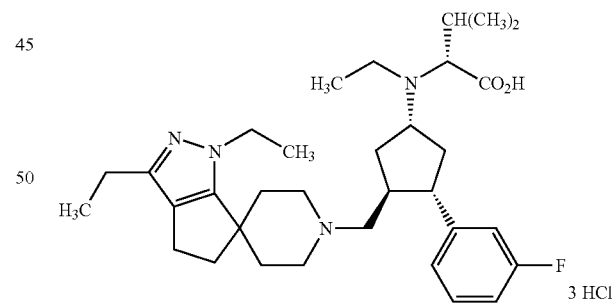

Step A: N-Ethyl-N-(1-(R)-3-(S)-hydroxymethyl-4-(S)-(3-fluorophenyl)cyclopent-1-yl)-(R)-valine t-butyl ester Using essentially the same procedure as Example 1, Step F, Method B, but using acetaldehyde in place of formaldehyde, the title compound was prepared as the higher $R_f$ isomer.

HPLC/MS (ESI): m/z 609.6 (M+1).

Step B: N-Ethyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine trihydrochloride salt Using essentially the same procedures as Example 1, Steps G–I, N-ethyl-N-(1-(R)-3-(S)-hydroxymethyl-4-(S)-(3-fluorophenyl)cyclopent-1-yl)-(R)-valine t-butyl ester from Step A was converted to the title compound.

HPLC/MS (ESI): m/z 553.6 (M+1); retention time=1.68 min.

EXAMPLE 19

N-Methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-leucine trihydrochloride salt

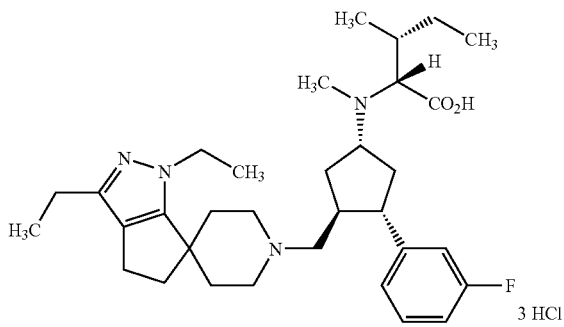

Step A: N-Methyl-N-(1-(R)-3-(S)-hydroxymethyl-4-(S)-(3-fluorophenyl)cyclopent-1-yl)-(R)-leucine t-butyl ester Using essentially the same procedure as Example 1, Step F, Method B, but using (R)-leucine t-butyl ester in place of (R)-valine t-butyl ester, the title compound was prepared as the higher $R_f$ isomer.

Step B: N-Methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-leucine trihydrochloride salt Using essentially the same procedures as Example 1, Steps G-I, N-methyl-N-(1-(R)-3-(S)-hydroxymethyl-4-(S)-(3-fluorophenyl)cyclopent-1-yl)-(R)-leucine t-butyl ester from Step A was converted to the title compound.

HPLC/MS (ESI): m/z 553.6 (M+1); retention time=1.73 min.

EXAMPLE 20

N-Methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-t-butylglycine trihydrochloride salt

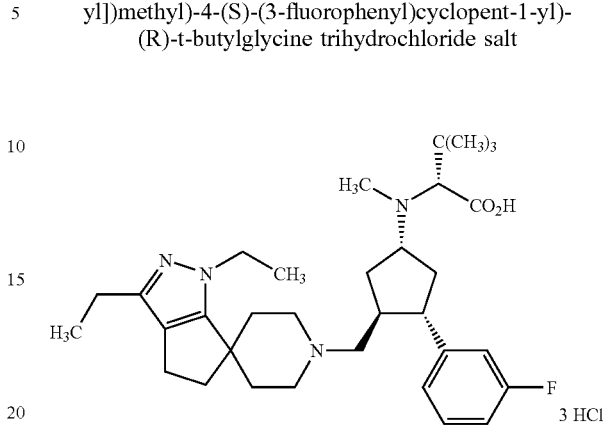

Step A: N-Methyl-N-(1-(R)-3-(S)-hydroxymethyl-4-(S)-(3-fluorophenyl)cyclopent-1-yl)-(R)-t-butylglycine t-butyl ester Using essentially the same procedure as Example 1, Step F, Method B, but using (R)-t-butylglycine t-butyl ester in place of (R)-valine t-butyl ester, the title compound was prepared as the higher $R_f$ isomer.

Step B: N-Methyl-N-(1-(R)-3-(S)-((1,3-diethyl-4,5-dihydrospiro[cyclopenta-pyrazole-6(1H),4'-piperidin-1'-yl])methyl)-4-(S)-(3-fluorophenyl)cyclopent-1-yl)-(R)-t-butylglycine trihydrochloride salt Using essentially the same procedures as Example 1, Steps G-I, N-methyl-N-(1-(R)-3-(S)-hydroxymethyl-4-(S)-(3-fluorophenyl)cyclopent-1-yl)-(R)-t-butylglycine t-butyl ester from Step A was converted to the title compound.

HPLC/MS (ESI): m/z 553.6 (M+1); retention time=1.71 min.

EXAMPLE 21

N-Methyl-N-(1-(R)-3-(S)-((1-methyl-3-ethyl-4,5-dihydrospiro[cyclopentapyrazole-6(1H),4'-piperidin-1'-yl])methyl)-4-(S)-(3-fluorophenyl)cyclopent-1-yl)-(R)-t-butylglycine trihydrochloride salt

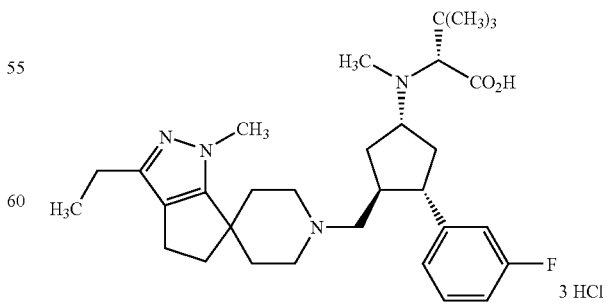

Using essentially the same procedures as Example 1, Steps G-I, but using N-methyl-N-(1-(R)-3-(S)-hydroxymethyl-4-(S)-(3-fluorophenyl)cyclopent-1-yl)-(R)-t-butylglycine t-butyl ester from Example 20, Step A in Step G and 1-methyl-3-ethyl-4,5-dihydrospiro[cyclopentapyrazole-6(1H),4'-piperidine from Procedure 3 in Step H, the title compound was prepared.

HPLC/MS (ESI): m/z 539.6 (M+1); retention time=1.80 min.

EXAMPLE 22

N-Methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R,S)-α-methylvaline trihydrochloride salt

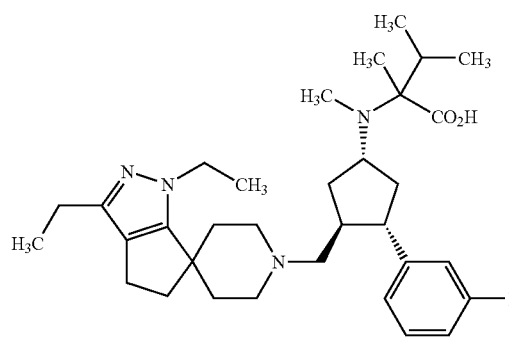

3 HCl

Step A: N-Methyl-N-(1-(R)-3-(S)-hydroxymethyl-4-(S)-(3-fluorophenyl)cyclopent-1-yl)-(R,S)-α-methylvaline t-butyl ester Using essentially the same procedure as Example 1, Step F, Method B, but using (R,S)-α-methylvaline t-butyl ester in place of (R)-valine t-butyl ester, the title compound was prepared as the higher $R_f$ isomer.

Step B: N-Methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R,S)-α-methylvaline trihydrochloride salt Using essentially the same procedures as Example 1, Steps G-I, N-methyl-N-(1-(R)-3-(S)-hydroxymethyl-4-(S)-(3-fluorophenyl)cyclopent-1-yl)-(R,S)-α-methylvaline t-butyl ester from Step A was converted to the title compound.

HPLC/MS (ESI): m/z 553.6 (M+1); retention time=1.68 min.

EXAMPLE 23

N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R,S)-α-methylvaline trihydrochloride salt and N-(1-(S)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R,S)-α-methylvaline trihydrochloride salt

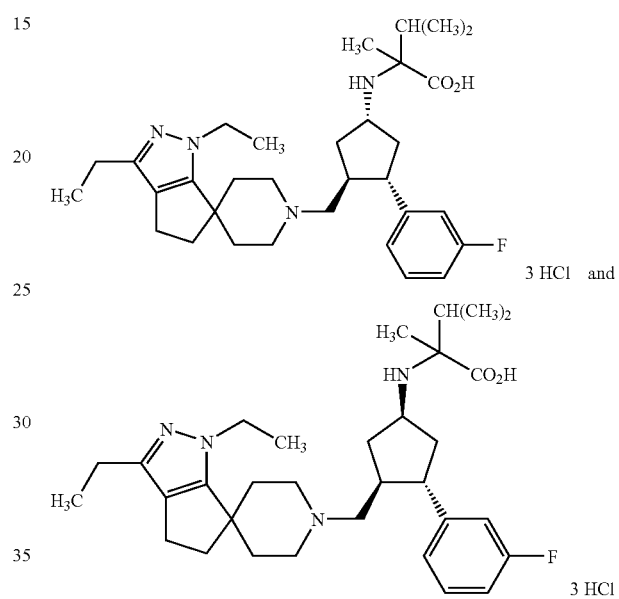

3 HCl and

3 HCl

Step A: N-(1-(RS)-3-(S)-hydroxymethyl-4-(S)-(3-fluorophenyl)cyclopent-1-yl)-(R,S)-α-methylvaline t-butyl ester Using essentially the same procedure as Example 1, Step E, but using (R,S)-α-methylvaline t-butyl ester in place of (R)-valine t-butyl ester, the title compound was prepared as a mixture of four C-1 and α-methylvaline isomers.

Step B: N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R,S)-α-methylvaline trihydrochloride salt and
N-(1-(S)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R,S)-α-methylvaline trihydrochloride salt Using essentially the same procedures as Example 1, Steps G-I, N-(1-(RS)-3-(S)-hydroxymethyl-4-(S)-(3-fluorophenyl)cyclopent-1-yl)-(R,S)-α-methylvaline t-butyl ester from Step A was converted to the title compounds after HPLC separation of the C-1 isomers.

HPLC/MS (ESI): m/z 539.6 (M+1); retention time=1.76 and 1.78 min.

EXAMPLE 24

N-Methyl-N-(1-(R)-3-(S)-((1,3-diethyl-4,5-dihydrospiro[cyclopentapyrazole-6(1H),4'-piperidin-1'-yl])methyl)-4-(S)-(3,5-difluorophenyl)cyclopent-1-yl)-(R)-valine trihydrochloride salt

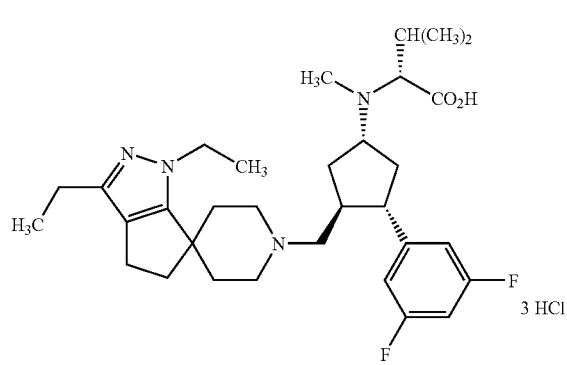

Using essentially the same procedures as Example 1, Step C, Method B, to I, but using N-(trans-3,5-difluorocinnamoyl)-(S)-(−)-4-benzyl-2-oxazolidine in place of N-(trans-3-fluorocinnamoyl)-(S)-(−)-4-benzyl-2-oxazolidine, the title compound was prepared.

HPLC/MS (ESI): m/z 557.6 (M+1); retention time=1.73 min.

EXAMPLE 25

N-Methyl-N-(1-(R)-3-(S)-((1,3-diethyl-4,5-dihydrospiro[cyclopentapyrazole-6(1H),4'-piperidin-1'-yl])methyl)-4-(S)-(3,4-difluorophenyl)cyclopent-1-yl)-(R)-valine trihydrochloride salt

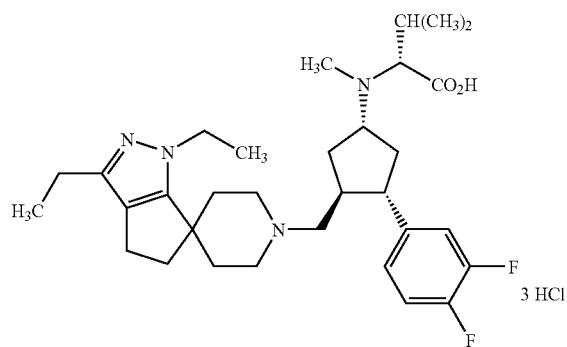

Using essentially the same procedures as Example 1, Step C, Method B, to I, but using N-(trans-3,4-difluorocinnamoyl)-(S)-(−)-4-benzyl-2-oxazolidine in place of N-(trans-3-fluorocinnamoyl)-(S)-(−)-4-benzyl-2-oxazolidine, the title compound was prepared.

HPLC/MS (ESI): m/z 557.6 (M+1); retention time=1.73 min.

EXAMPLE 26

N-Methyl-N-(1-(R)-3-(S)-((1,3-diethyl-4,5-dihydrospiro[cyclopentapyrazole-6(1H),4'-piperidin-1'-yl])methyl)-4-(S)-(3,4-dichlorophenyl)cyclopent-1-yl)-(R)-valine trihydrochloride salt

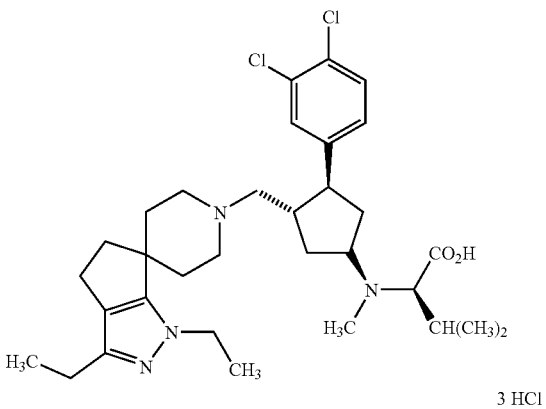

Using essentially the same procedures as Example 1, Step C, Method B, to I, but using N-(trans-3,4-dichlorocinnamoyl)-(S)-(−)-4-benzyl-2-oxazolidine in place of N-(trans-3-fluorocinnamoyl)-(S)-(−)-4-benzyl-2-oxazolidine, the title compound was prepared.

HPLC/MS (ESI): n/z 589.3 (M+1) and 591.3 (M+3); retention time=2.05 min.

EXAMPLE 27

N-Methyl-N-(1-(R)-3-(S)-((1,3-diethyl-4,5-dihydrospiro[cyclopentapyrazole-6(1H),4'-piperidin-1'-yl])methyl)-4-(S)-(3-fluoro-4-methylphenyl)cyclopent-1-yl)-(R)-valine trihydrochloride salt

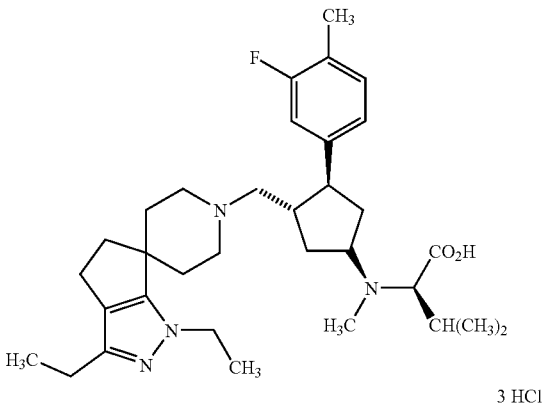

Using essentially the same procedures as Example 1, Step C, Method B, to I, but using N-(trans-3-fluoro4-methylcinnamoyl)-(S)-(−)-4-benzyl-2-oxazolidine in place of N-(trans-3-fluorocinnamoyl)-(S)-(−)-4-benzyl-2-oxazolidine, the title compound was prepared.

HPLC/MS (ESI): m/z 553.2 (M+1); retention time=1.92 min.

EXAMPLE 28

N-Methyl-N-(1-(R)-3-(S)-((1,3-diethyl-4,5-dihydrospiro[cyclopentapyrazole-6(1H),4'-piperidin-1'-yl])methyl)-4-(S)-(4-fluorophenyl)cyclopent-1-yl)-(R)-valine trihydrochloride salt

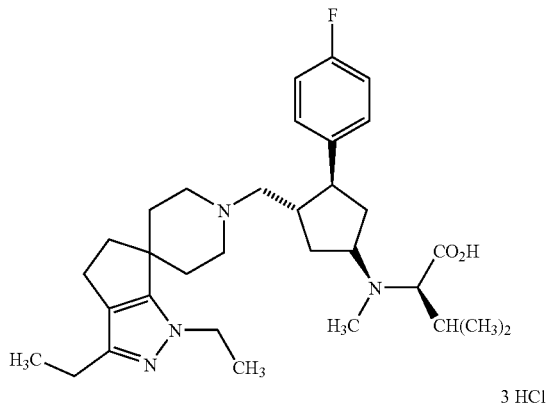

Using essentially the same procedures as Example 1, Step C, Method B, to I, but using N-(trans4-fluorocinnamoyl)-(S)-(−)-4-benzyl-2-oxazolidine in place of N-(trans-3-fluorocinnamoyl)-(S)-(−)-4-benzyl-2-oxazolidine, the title compound was prepared.

HPLC/MS (ESI): m/z 539.65 (M+1); retention time=2.16 min.

EXAMPLE 29

N-Methyl-N-(1-(R)-3-(S)-((3-ethyl-1-methyl-4,5-dihydrospiro[cyclopentapyrazole-6(1H),4'-piperidin-1'-yl])methyl)-4-(S)-(3,5-difluorophenyl)cyclopent-1-yl)-(R)-valine trihydrochloride salt

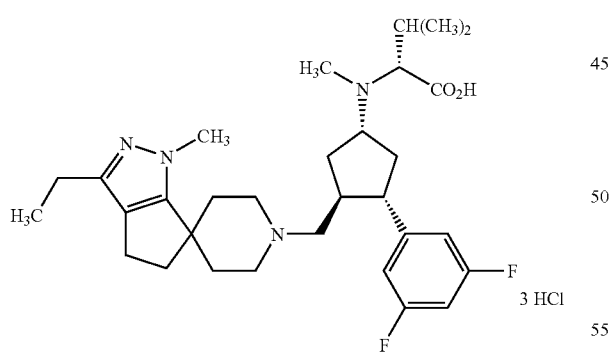

Using essentially the same procedures as Example 1, Step C, Method B, to I, but using N-(trans-3,5-difluorocinnamoyl)-(S)-(−)-4-benzyl-2-oxazolidine in place of N-(trans-3-fluorocinnamoyl)-(S)-(−)-4-benzyl-2-oxazolidine in Step C, Method B, and 3-ethyl-1-methyl-4,5-dihydrospiro[cyclopentapyrazole-6(1H),4'-piperidine]dihydrochloride from Procedure 3 in Step H in the place of 1,3-diethyl-4,5-dihydrospiro[cyclopentapyrazole-6(1H),4'-piperidine]dihydrochloride, the title compound was prepared.

HPLC/MS (ESI): n/z 543.6 (M+1); retention time=1.81 min.

EXAMPLE 30

N-Methyl-N-(1-(R)-3-(S)-((1,3-diethyl-4,5-dihydrospiro[cyclopentapyrazole-6(1H),4'-piperidin-1'-yl])methyl)-4-(S)-(3,5-difluorophenyl)cyclopent-1-yl)-(R)-t-butylglycine trihydrochloride salt

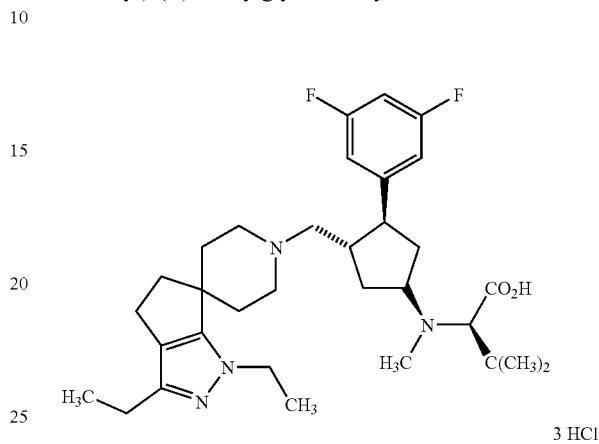

Using essentially the same procedures as Example 1, Step C, Method B, to I, but using N-(trans-3,5-difluorocinnamoyl)-(S)-(−)-4-benzyl-2-oxazolidine in place of N-(trans-3-fluorocinnamoyl)-(S)-(−)-4-benzyl-2-oxazolidine in Step C, Method B, and (R)-t-butylglycine t-butyl ester in Step F, Method B in the place of (R)-valine t-butyl ester, the title compound was prepared.

HPLC/MS (ESI): m/z 571.5 (M+1); retention time=2.11 min.

EXAMPLE 31

N-Methyl-N-(1-(R)-3-(S)-((3-ethyl-1-methyl-4,5-dihydrospiro[cyclopentapyrazole-6(1H),4'-piperidin-1'-yl])methyl)-4-(S)-(3,5-difluorophenyl)cyclopent-1-yl)-(R)-t-butylglycine trihydrochloride salt

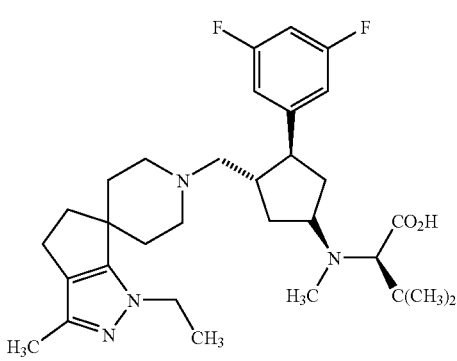

Using essentially the same procedures as Example 1, Step C, Method B, to I, but using N-(trans-3,5-difluorocinnamoyl)-(S)-(−)-4-benzyl-2-oxazolidine in place of N-(trans-3-fluorocinnamoyl)-(S)-(−)-4-benzyl-2-oxazolidine in Step C, Method B, (R)-t-butylglycine t-butyl ester in Step F, Method B in the place of (R)-valine t-butyl ester, and 3-ethyl-1-methyl-4,5-dihydrospiro[cyclopentapyrazole-6(1H),4'-piperidine]dihydrochloride from Procedure 3 in Step H in the place of 1,3-diethyl-4,5-dihydrospiro[cyclopentapyrazole-6(1H),4'-piperidine]dihydrochloride, the title compound was prepared.

HPLC/MS (ESI): m/z 557.5 (M+1); retention time=1.97 min.

EXAMPLE 32

N-Methyl-N-(1-(R)-3-(S)-((1-ethyl-3-methoxy-4,5-dihydrospiro[cyclopentapyrazole-6(1H),4'-piperidin-1'-yl])methyl)-4-(S)-(3,5-difluorophenyl)cyclopent-1-yl)-(R)-t-butylglycine trihydrochloride salt

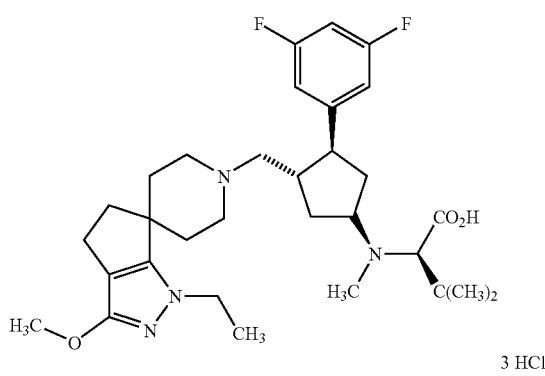

3 HCl

Using essentially the same procedures as Example 1, Step C, Method B, to I, but using N-(trans-3,5-difluorocinnamoyl)-(S)-(−)-4-benzyl-2-oxazolidine in place of N-(trans-3-fluorocinnamoyl)-(S)-(−)-4-benzyl-2-oxazolidine in Step C, Method B, (R)-t-butylglycine t-butyl ester in Step F, Method B in the place of (R)-valine t-butyl ester, and 1-ethyl-3-methoxy-4,5-dihydrospiro[cyclopentapyrazole-6(1H),4'-piperidine]dihydrochloride from Procedure 3 in Step H in the place of 1,3-diethyl-4,5-dihydrospiro[cyclopentapyrazole-6(1H),4'-piperidine]dihydrochloride, the title compound was prepared.

HPLC/MS (ESI): m/z 573.6 (M+1); retention time=2.19 min.

EXAMPLE 33

N-Methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-valine trihydrochloride salt

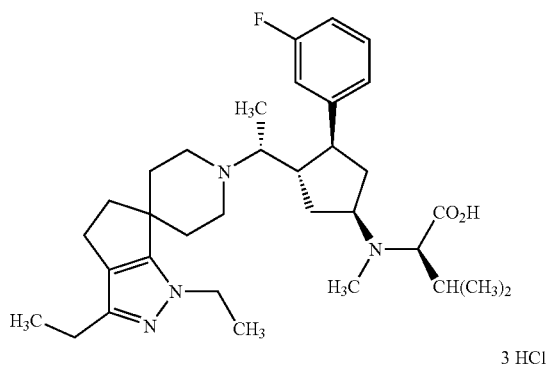

3 HCl

Step A: 1-(S)-4-Methylene-2-(S)-(3-fluorophenyl)cyclopentane carboxaldehyde

To a solution of oxalyl chloride (3.8 mL, 43 mmol) in methylene chloride (250 mL) was added dropwise at −70° C. DMSO (6.1 mL, 86 mmol). The reaction was stirred for 15 min, afterwhich a solution of (+)-trans-1-(S)-hydroxymethyl-4-methylene-2-(S)-(3-fluorophenyl)cyclopentane (5.9 g, 29 mmol) from Example 1, Step C in methylene chloride (50 mL) was added slowly at −70° C. After 1 h, TEA (24 mL, 172 mmol) was added and the reaction was allowed to warm to room temperature for 1 h and was then diluted with methylene chloride and water. The layers were separated and the aq. layer was reextracted with a second portion of methylene chloride and the organic layers were each washed with brine, dried over sodium sulfate, combined and concentrated in vacuo. The residue was purified by FC (5% ethyl acetate in hexanes) to give the title product (2.8 g) as an oil.

Step B: 1-(S)-((R and S)-(1,3-Diethyl-4,5-dihydrospiro[cyclopentapyrazole-6(1H),4'-piperidin-1'-yl])cyanomethyl)-4-methylene-2-(S)-(3-fluorophenyl)cyclopentane To a solution of 1-(S)-4-methylene-2-(S)-(3-fluorophenyl)cyclopentane carboxaldehyde (2.2 g, 10.8 mmol) from Step A and 1,3-diethyl-4,5-dihydrospiro[cyclopentapyrazole-6(1H),4'-piperidine]dihydrochloride (3.3 g, 10.8 mmol) from Procedure 1 in acetic acid (27 mL) was added trimethylsilyl cyanide (2.2 mL, 16 mmol). The reaction was warmed to 60° C. for 90 min and was then cooled to room temperature, poured into ammonium hydroxide (70 mL) and ice water, and extracted three times with ether. The organic layers were each washed with brine, dried over sodium sulfate, combined and concentrated in vacuo. The residue was purified by FC (15% ethyl acetate in hexanes) to give a mixture of the title products (2.96 g).

Step C: 1-(S)-(1-(R and S)-(1,3-Diethyl-4,5-dihydrospiro[cyclopentapyrazole-6(1H),4'-piperidin-1'-yl])eth-1-yl)-4-methylene-2-(S)-(3-fluorophenyl)cyclopentane To a solution of 1-(S)-((R and S)-(1,3-diethyl-4,5-dihydrospiro[cyclopentapyrazole-6(1H),4'-piperidin-1'-yl])cyanomethyl)-4-methylene-2-(S)-(3-fluorophenyl)cyclopentane (2.9 g, 6.63 mmol) from Step B in THF (60 mL) at 0° C. was added 1.4M methyl magnesium bromide in THF (71 mL, 99 mmol). The reaction was stirred at room temperature for 16 h and then quenched with aq. ammonium chloride and extracted twice with ether. The organic layers were each washed with brine, dried over sodium sulfate, combined and concentrated in vacuo. The residue was purified by FC (40% ethyl acetate in hexanes) to give the title products, first a mixture of (S) and (R) isomers (0.35 g) and then pure lower $R_f$ (R) isomer (2.1 g).

HPLC/MS (ESI): m/z 436.4 (M+1); retention time=2.54 min.

Step D: 3-(S)-(1-(R)-(1,3-Diethyl-4,5-dihydrospiro[cyclopentapyrazole-6(1H),4'-piperidin-1'-yl])eth-1-yl)-4-(S)-(3-fluorophenyl)cyclopentan-1-one Method A:

To a solution of 1-(S)-(1-(R)-(1,3-diethyl-4,5-dihydrospiro[cyclopentapyrazole-6(1H),4'-piperidin-1'-yl])eth-1-yl)-4-methylene-2-(S)-(3-fluorophenyl)cyclopentane (1.74 g, 4.0 mmol) from Step C in t-butanol (25 mL) and water (25 mL) at room temperature was added potassium carbonate (1.65 g, 12 mmol), potassium ferricyanide (III) (3.94 g, 12 mmol), hydroquinine 1,4-phthalazinediyl diether ((DHQ)$_2$PHAL) (311 mg, 0.40 mmol), and potassium osmate dihydrate (150 mg, 0.40 mmol). The reaction was stirred at room temperature for 20 h and was then quenched with sodium sulfite, diluted with water, and extracted three times with ethyl acetate. The organic layers were each washed with brine, dried over sodium sulfate, combined and concentrated in vacuo. The residue was purified by FC (5% methanol in methylene chloride) to give the intermediate diol as a mixture of diastereomers (1.88 g).

HPLC/MS (ESI): m/z 470.5 (M+1); retention time=1.78 min.

The above diol mixture (1.88 g, 4.0 mmol) was taken up in THF (40 mL) and an aq. solution (10 mL) of sodium periodate (1.71 g, 8.0 mmol) was added at room temperature. After 2 h, the mixture was diluted with water and extracted three times with ethyl acetate. The organic layers were each washed with brine, dried over sodium sulfate, combined and concentrated in vacuo. The residue was purified by FC (30–60% acetonitrile in methylene chloride) to give the title product (0.86 g).

HPLC/MS (ESI): m/z 438.4 (M+1); retention time=2.00 min.

Method B:

To a solution of 1-(S)-(1-(R)-(1,3-diethyl-4,5-dihydrospiro[cyclopentapyrazole-6(1H),4'-piperidin-1'-yl])eth-1-yl)-4-methylene-2-(S)-(3-fluorophenyl)cyclopentane (0.75 g, 1.7 mmol) from Step C in methanol (35 mL) was added 2N HCl in ether (4 mL, 8 mmol). The solution was cooled to −70° C. and ozone was bubbled through until a blue color persisted. The excess ozone was removed with a stream of nitrogen and then dimethyl sulfide (7 mL) was added. The mixture was allowed to warm to room temperature for 1 h. The reaction was concentrated in vacuo and the residue was diluted with aq. sodium bicarbonate and extracted twice with ethyl acetate. The organic layers were each washed with brine, dried over sodium sulfate, combined and concentrated in vacuo. The residue was purified by FC (75–85% ethyl acetate in hexanes) to give the title product (0.450 g).

HPLC/MS (ESI): m/z 438.3 (M+1); retention time=2.05 min.

Step E: N-Methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-valine t-butyl ester (lower $R_f$) and N-Methyl-N-(1-(S)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-valine t-butyl ester (higher $R_f$)

To a solution of 3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentan-1-one from Step D (250 mg, 0.57 mmol) in 1,2-dichloroethane (3 mL) was added (R)-valine t-butyl ester hydrochloride salt (240 mg, 1.14 mmol) and DIPEA (0.210 mL, 1.2 mmol). After 15 min, sodium triacetoxyborohydride (250 mg, 1.2 mmol) was added and the reaction was stirred at room temperature for 16 h and then at 50° C. for 3 h. The reaction was cooled to room temperature.

HPLC/MS (ESI): m/z 595.5 (M+1); retention time=2.37 min.

Aq. formaldehyde (37%, 1.5 mL, 1.8 mmol) and additional sodium triacetoxyborohydride (250 mg, 1.2 mmol) were added. The reaction was stirred another 20 h before the mixture was diluted with methylene chloride, quenched with aq. sodium carbonate and extracted 3 times with methylene chloride. The organic layers were each washed with brine, dried over sodium sulfate, combined and concentrated in vacuo. The residue was purified by Prep LC eluting with 35% ethyl acetate in hexanes to give the a mixture of C-1 isomers (300 mg). The isomers were then separated by Prep TLC (20% acetone in hexanes) to afford the higher $R_f$ title 1-(S) product and lower $R_f$ 1-(R) product as the free amines.

HPLC/MS (ESI): m/z 609.5 (M+1); retention time=2.45 min.

Step F: N-Methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-valine trihydrochloride salt he N-methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-valine t-butyl ester (lower $R_f$) (25 mg, 0.041 mmol) from Step E was taken up in TFA (2 mL) and aged at room temperature for 16 h. The volatiles were then evaporated under a stream of nitrogen. The residue was taken up in methanol and adsorbed onto a 500 mg Varian SCX ion-exchange resin cartridge. The resin was first eluted with 2×3 mL of methanol, then the product was eluted with 2×3 mL of 2M ammonia in methanol. The product solution was concentrated under nitrogen, then 2 volumes of methylene chloride were evaporated to remove methanol and ammonia to give the free amine. The hydrochloride salt was prepared by dissolving the free amine in methylene chloride, adding excess (>3-fold) 1M hydrogen chloride in ether and evaporating to dryness.

HPLC/MS (ESI): n/z 553.4 (M+1); retention time=1.65 min.

EXAMPLE 34

N-Methyl-N-(1-(S)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-valine trihydrochloride salt

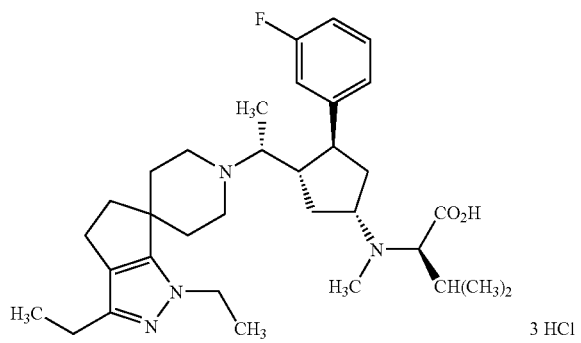

3 HCl

Using essentially the same procedure as in Example 33, Step F, but using the higher R$_f$ product from Example 33, Step E, the title compound was obtained.

HPLC/MS (ESI): m/z 553.4 (M+1); retention time=1.68 min.

EXAMPLE 35

N-Methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-t-butylglycine trihydrochloride salt

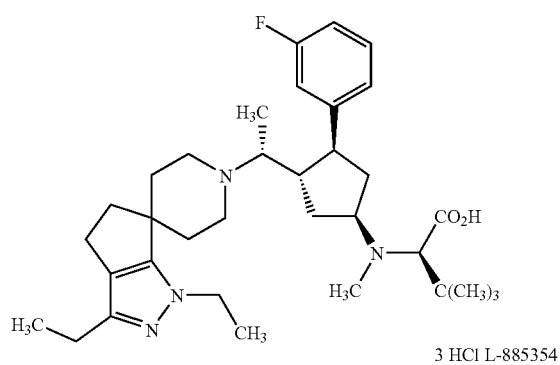

3 HCl L-885354

Using essentially the same procedures as in Example 33, but using (R)-t-butylglycine t-butyl ester in Step E in the place of (R)-valine t-butyl ester, the title compound was prepared using the lower R$_f$ product from Step E.

HPLC/MS (ESI): m/z 567.3 (M+1); retention time=1.79 min.

EXAMPLE 36

N-Methyl-N-(1-(S)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-t-butylglycine trihydrochloride salt

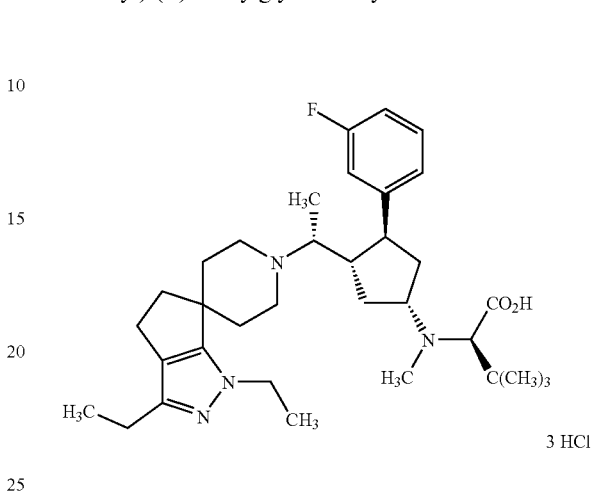

3 HCl

Using essentially the same procedure as in Example 33, Step F, but using the higher R$_f$ product from Example 35, Step E, the title compound was obtained.

HPLC/MS (ESI): m/z 567.3 (M+1); retention time=1.84 min.

EXAMPLE 37

N-Methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3,5-difluorophenyl)cyclopent-1-yl)-(R)-valine trihydrochloride salt

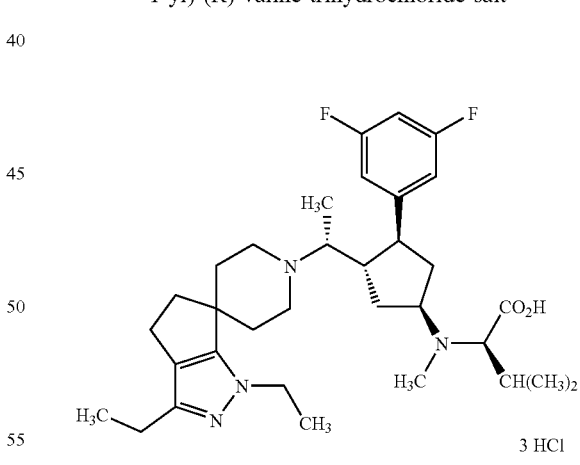

3 HCl

Using essentially the same procedures as in Example 33, but starting with (+)-trans-1-hydroxymethyl-4-methylene-2-(3,5-difluorophenyl)cyclopentane prepared as in Example 24 in place of (+)-trans-1-hydroxymethyl-4-methylene-2-(3-fluorophenyl)cyclopentane, the title compound was prepared using the lower R$_f$ product from Step E.

HPLC/MS (ESI): n/z 571.3 (M+1); retention time=1.73 min.

EXAMPLE 38

N-Methyl-N-(1-(S)-3-(S)-(1-(R)-(1,3-diethyl-4,5-dihydrospiro[cyclopentapyrazole-6(1H),4'-piperidin-1'-yl])eth-1-yl)-4-(S)-(3,5-difluorophenyl)cyclopent-1-yl)-(R)-valine trihydrochloride salt

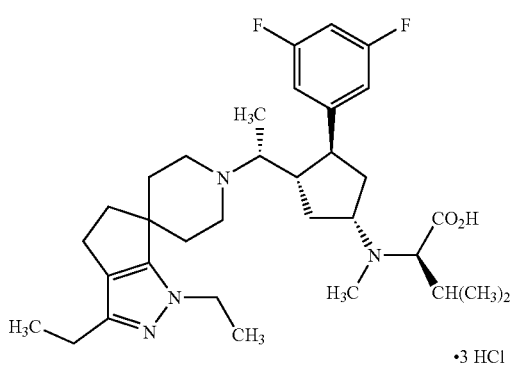

•3 HCl

Using essentially the same procedure as in Example 33, Step F, but using the higher $R_f$ product from Example 37, Step E, the title compound was obtained.

HPLC/MS (ESI): m/z 571.3 (M+1); retention time=1.79 min.

EXAMPLE 39

N-Methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3,5-difluorophenyl)cyclopent-1-yl)-(R)-t-butylglycine trihydrochloride salt

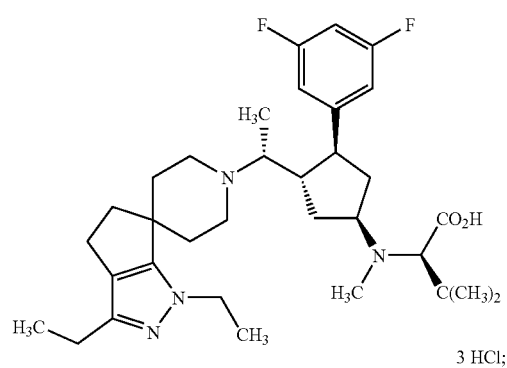

3 HCl;

Using essentially the same procedures as in Example 33, but starting with (+)-trans-1-hydroxymethyl-4-methylene-2-(3,5-difluorophenyl)cyclopentane prepared as in Example 24 in place of (+)-trans-1-hydroxymethyl-4-methylene-2-(3-fluorophenyl)cyclopentane and (R)-t-butylglycine t-butyl ester in Step E in the place of (R)-valine t-butyl ester, the title compound was prepared using the lower $R_f$ product from Step E.

HPLC/MS (ESI): m/z 585.3 (M+1); retention time=1.89 min.

EXAMPLE 40

N-Methyl-N-(1-(S)-3-(S)-(1-(R)-(1,3-diethyl-4,5-dihydrospiro[cyclopentapyrazole-6(1H),4'-piperidin-1'-yl])eth-1-yl)-4-(S)-(3,5-difluorophenyl)cyclopent-1-yl)-(R)-t-butylglycine trihydrochloride salt

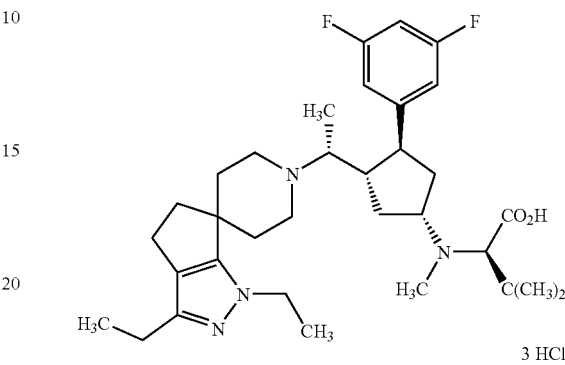

3 HCl

Using essentially the same procedure as in Example 33, Step F, but using the higher $R_f$ product from Example 39, Step E, the title compound was obtained.

HPLC/MS (ESI): m/z 585.3 (M+1); retention time=1.89 min.

EXAMPLE 41

2-(S)-(1-(R)-3-(S)-((1,3-Diethyl-4,5-dihydrospiro[cyclopentapyrazole-6(1H),4'-piperidin-1'-yl])methyl)-4-(S)-(3-fluorophenyl)cyclopent-1-yl)-3-(cyclopropyl)propionic acid di-hydrochloride salt, Method A

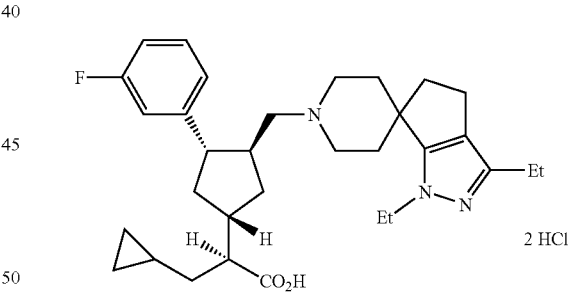

2 HCl

Step A: (+)-trans-1-t-Butyldimethylsilyloxymethyl-4-oxo-2-(3-fluorophenyl)cyclopentane To a solution of (+)-trans-3-hydroxymethyl-4-(3-fluorophenyl)cyclopentan-1-one from Example 1, Step D (6.23 g, 29.9 mmol) in methylene chloride (100 mL) was added DIPEA (16.0 mL, 11.6 g, 89.7 mmol) and t-butyldimethylsilyl chloride (6.80 g, 44.8 mmol). The reaction mixture was stirred at room temperature for 48 h, poured into aqueous sodium bicarbonate, and extracted three times with methylene chloride. The organic layers were combined, washed with brine, dried over sodium sulfate, filtered and concentrated. The residue (12 g) was purified by FC (5% ethyl acetate in hexanes) to afford the title product (8.99 g) as a oil.

¹H NMR (CDCl₃) δ 0.02 (s 3 H), 0.03 (s, 3 H), 0.90 (s, 9 H), 2.36–2.55 (m, 4 H), 2.73 (dd, 1 H), 3.31–3.38 (m, 1 H), 3.54 (dd, 1 H), 3.62 (dd, 1 H), 6.93–7.05 (m, 3 H), 7.27–7.34 (m, 1 H).

Step B: Ethyl (E and Z)-3-(S)-t-butyldimethylsilyloxymethyl-4-(S)-(3-fluorophenyl)cyclopent-1-ylideneacetate To a solution of 60% sodium hydride in mineral oil (3.0 g, 76 mmol) in THF (100 mL) was added triethyl phosphonoacetate (19 mL, 21 g, 95 mmol). The reaction mixture was stirred at room temperature for 30 min. To this solution was added via canula a solution of (+)-trans-1-t-butyldimethylsilyloxymethyl-4-oxo-2-(3-fluorophenyl)cyclopentane from Step A (6.13 g, 19 mmol) in THF (20 mL). The reaction mixture was stirred at room temperature for 12 h, diluted with diethyl ether, poured into water and extracted three times with diethyl ether. The organic layers were combined, washed with brine, dried over sodium sulfate, filtered and concentrated in vacuo. The crude residue (7.45 g) was taken on to Step C without further purification.

Step C: Ethyl (E and Z)-3-(S)-hydroxymethyl-4-(S)-(3-fluorophenyl)cyclopent-1-ylideneacetate To a solution of ethyl (E and Z)-3-(S)-t-butyldimethylsilyloxymethyl-4-(S)-(3-fluorophenyl)cyclopent-1-ylideneacetate from Step B (7.45 g, 19 mmol) in THF (100 mL) was added a 1.0 M solution of tetrabutylammonium fluoride in THF (39 mL, 39 mmol) and the reaction mixture was stirred at room temperature for 4 h. The reaction mixture was diluted with ethyl acetate, poured into 1 N aqueous hydrochloric acid solution, extracted three times with ethyl acetate, combined organic layers, washed with brine, dried over sodium sulfate and concentrated in vacuo. The residue was purified by FC (5% ethyl acetate in hexanes) to afford the title compound (3.03 g).

¹H NMR (CDCl₃): δ 1.25 and 1.28 (2 t, 3 H), 2.05–2.39 (m, 1 H), 2.49–2.57 (m, 0.5 H), 2.65–2.74 (m, 1 H), 2.79–2.92 (m, 1 H), 2.95–3.01 (m, 1 H), 3.22 (d, 0.5 H), 3.33 (dd, 0.5 H), 3.47–3.59 (m, 1.5 H), 3.63–3.74 (m, 1 H), 4.13 and 4.17 (2 q, 2 H), 5.83 (br s, 1 H), 6.90–7.00 (m, 2 H), 7.15 (d, 1 H), 7.23–7.35 (m, 1 H).

Step D: Ethyl (1-(R)-3-(S)-hydroxymethyl-4-(S)-(3-fluorophenyl)cyclopent-1-yl)acetate A solution of ethyl (E and Z)-3-(S)-hydroxymethyl-4-(S)-(3-fluorophenyl)cyclopent-1-ylideneacetate from Step C (3.62 g, 13 mmol) in methylene chloride (150 mL) was hydrogenated at atmospheric pressure using (1,5-cyclooctadiene)(pyridine)(tricyclohexylphosphine)iridium(I) hexafluorophosphate (0.250 g) for 12 h. The volatiles were removed in vacuo to afford the title compound (3.64 g) as essentially a single cyclopentyl C-1 isomer which then was used crude in Step E.

¹H NMR (CDCl₃): δ 1.27 (t, 3 H), 1.41–1.54 (m, 1 H), 1.65–1.73 (m, 1 H), 1.88–1.95 (m, 1 H), 2.22–2.32 (m, 2 H), 2.41–2.50 (m, 3 H), 2.78–2.85 (m, 1 H), 3.51 (dd, 1 H), 3.63 (dd, 1 H), 4.14 (m, 2 H), 6.87–6.97 (m, 2 H), 7.02 (d, 1 H), 7.23–7.29 (m, 1 H).

Step E: Ethyl (1-(R)-3-(S)-t-butyldimethylsilyloxymethyl-4-(S)-(3-fluorophenyl)cyclopent-1-yl)acetate To a solution of ethyl (1-(R)-3-(S)-hydroxymethyl-4-(S)-(3-fluorophenyl)cyclopent-1-yl)acetate from Step D (3.64 g, 13.0 mmol) in methylene chloride (130 mL) was added DIPEA (6.8 mL, 5.0 g, 39 mmol) and t-butyldimethylsilyl chloride (2.94 g, 19.5 mmol). The reaction mixture was stirred at room temperature for 3 days, poured into aqueous sodium bicarbonate, and extracted three times with methylene chloride. The organic layers were combined, washed with brine, dried over sodium sulfate, filtered and concentrated. The residue was purified by FC (3% ethyl acetate in hexanes) to afford the title compound (4.55 g).

Step F: (1-(R)-3-(S)-t-Butyldimethylsilyloxymethyl-4-(S)-(3-fluorophenyl)cyclopent-1-yl)acetic acid To a solution of ethyl (1-(R)-3-(S)-t-butyldimethylsilyloxymethyl-4-(S)-(3-fluorophenyl)cyclopent-1-yl)acetate from Step E (4.55 g, 11.5 mmol) in MeOH (100 mL) was added 5.0 N sodium hydroxide solution (12 mL, 58 mmol). The reaction mixture was stirred at room temperature for 12 h, acidified with 18% citric acid until the pH=4, diluted with methylene chloride, poured into water, and extracted three times with methylene chloride. The organic layers were combined, washed with brine, dried over sodium sulfate, filtered and concentrated to afford the title compound (4.23 g) which was used in Step G without purification.

Step G: 4-Methoxybenzyl (1-(R)-3-(S)-t-butyldimethylsilyloxymethyl-4-(S)-(3-fluorophenyl)cyclopent-1-yl)acetate To a solution of (1-(R)-3-(S)-t-butyldimethylsilyloxymethyl-4-(S)-(3-fluorophenyl)cyclopent-1-yl)acetic acid from Step F (4.23 g, 11.5 mmol) in DMF (100 mL) was added pulverized potassium carbonate (4.8 g, 35 mmol) and 4-methoxybenzyl chloride (2.3 mL, 2.7 g, 17 mmol). The reaction mixture was stirred at room temperature for 12 h, diluted with diethyl ether, poured into saturated sodium bicarbonate, and extracted three times with diethyl ether. The organic layers were combined, washed with brine, dried over sodium sulfate, filtered, and concentrated. The residue was purified by FC (5% ethyl acetate in hexane) to afford the title product (0.300 g). Note: a significant amount of 4-methoxybenzyl (1-(R)-3-(S)-hydroxymethyl-4-(S)-(3-fluorophenyl)cyclopent-1-yl)acetate (4.71 g) was recovered from this reaction.

¹H NMR (CDCl₃): δ −0.01 (s, 3 H), −0.00 (s, 3 H), 0.87 (s, 9 H), 1.37–1.47 (m, 1 H), 1.56–1.63 (m, 1 H), 1.87–1.95 (m, 1 H), 2.13–2.27 (m, 2 H), 2.40–2.48 (m, 3 H), 2.82–2.89 (m, 1 H), 3.44 (dd, 1 H), 3.52 (dd, 1 H), 3.83 (s, 3 H), 5.07 (s, 2 H), 6.85–6.94 (m, 4 H), 6.98 (d, 1 H), 7.20–7.33 (m, 3 H).

Step H: 4-Methoxybenzyl 2-(R and S)-(1-(R)-3-(S)-t-butyldimethylsilyloxymethyl-4-(S)-(3-fluorophenyl)cyclopent-1-yl)-3-(cyclopropyl)propionate To a solution of 5:1 THF/hexamethylphosphoramide (6 mL) at −78° C. was added 1.5 M lithium diisopropylamide mono(tetrahydrofuran) solution in cyclohexane (0.534 mL, 0.801 mmol). To this solution was then added a solution of 4-methoxybenzyl (1-(R)-3-(S)-t-butyldimethylsilyloxymethyl-4-(S)-(3-fluorophenyl)cyclopent-1-yl)acetate from Step G (0.300 g, 0.616 mmol) in THF (1 mL) and the reaction mixture was stirred at −78° C. for 40 min. To the reaction mixture was then added (bromomethyl)cyclopropane (0.299 mL, 0.416 g, 3.08 mmol). The reaction mixture was stirred for 3 h as it was allowed to warm to room temperature and then diluted with diethyl ether, poured into saturated sodium bicarbonate and extracted three times with diethyl ether. The organic layers were combined, washed with brine, dried over sodium sulfate, filtered and concentrated. The residue was purified by FC (3% ethyl acetate in hexanes) to afford the title products (0.232 g) as 1:1 mixture of diastereomers.

$^1$H NMR (CDCl$_3$): δ −0.02, −0.01 and −0.00 (3 s, 6 H), 0.02–0.05 (m, 2 H), 0.36–0.42 (m, 2 H), 0.61–0.65 (m, 1 H), 0.86 and 0.86 (2 s, 9 H), 1.21–1.50 (m, 3 H), 1.52–1.62 (m, 2 H), 1.64–1.75 (m, 0.5 H), 1.82–1.89 (m, 0.5 H), 1.95–2.01 (m, 0.5 H), 2.08–2.26 (m, 2.5 H), 2.38–2.47 (m, 1 H), 3.38–3.44 (m, 1 H), 3.47–3.52 (m, 1 H), 3.80 and 3.83 (s, 3 H), 5.04–5.32 (m, 2 H), 6.85–6.96 (m, 5 H), 7.22 (dd, 1 H), 7.27–7.35 (m, 2 H).

Step I: 4-Methoxybenzyl 2-(R)-(1-(R)-3-(S)-hydroxymethyl-4-(S)-(3-fluorophenyl)cyclopent-1-yl)-3-(cyclopropyl)propionate (higher R$_f$) and 4-methoxybenzyl 2-(S)-(1-(R)-3-(S)-hydroxymethyl-4-(S)-(3-fluorophenyl)cyclopent-1-yl)-3-(cyclopropyl)propionate (lower R$_f$)

To a solution of 4-methoxybenzyl 2-(R and S)-(1-(R)-3-(S)-t-butyldimethylsilyloxymethyl-4-(S)-(3-fluorophenyl)cyclopent-1-yl)-3-(cyclopropyl)propionate from Step H (0.026 g, 0.048 mmol) in THF (1 mL) was added a 1.0M solution of tetrabutylammonium fluoride in THF (0.072 mL, 0.072 mmol) and the reaction mixture was stirred at room temperature for 12 h. The reaction mixture was diluted with ethyl acetate, poured into 1N aqueous hydrochloric acid solution, extracted three times with ethyl acetate, combined organic layers, washed with brine, dried over sodium sulfate and concentrated to afford 0.018 g. The residue was purified by FC (5% ethyl acetate in methylene chloride) to afford separation at the 2-position of the 3-(cyclopropyl)propionate to give the higher R$_f$ (0.008 g) and lower R$_f$ (0.009 g) title compounds. The stereochemistries were assigned as determined in Example 43.

(higher R$_f$ isomer) $^1$H NMR (CDCl$_3$): δ −0.01–0.01 (m, 2 H), 0.38–0.42 (m, 2 H), 0.60–0.68 (m, 1 H), 1.42–1.50 (m, 2 H), 1.53–1.70 (m, 3 H), 1.80–1.88 (m, 1 H), 1.99–2.06 (m, 1 H), 2.10–2.29 (m, 1 H), 2.45 (td, 1 H), 2.68–2.75 (m, 1 H), 3.45 (dd, 1 H), 3.59 (dd, 1 H), 3.80 (s, 3 H), 5.07 (s, 2 H), 6.92–6.96 (m, 3 H), 6.98 (d, 1 H), 7.10–7.16 (m, 4 H). (lower R$_f$ isomer) $^1$H NMR (CDCl$_3$): δ −0.02–0.02 (m, 2 H), 0.38–0.40 (m, 2 H), 0.58–0.68 (m, 1 H), 1.38–1.44 (m, 2 H), 1.54–1.60 (m, 2 H), 1.63–1.78 (m, 2 H), 2.13–2.33 (m, 2 H), 2.45 (td, 1 H), 2.70–2.78 (m, 1 H), 3.46 (dd, 1 H), 3.56 (dd, 1 H), 3.83 (s, 3 H), 5.11 (d, 2 H), 6.93–6.96 (m, 3 H), 6.99 (d, 1 H), 7.10–7.18 (m, 4 H).

Step J: 4-Methoxybenzyl 2-(S)-(1-(R)-3-(S)-formyl-4-(S)-(3-fluorophenyl)cyclopent-1-yl)-3-(cyclopropyl)propionate To a solution of oxalyl chloride (0.008 mL, 0.011 g, 0.089 mmol) in methylene chloride (0.5 mL) at −70° C. was added DMSO (0.013 mL, 0.014 g, 0.180 mmol). After 10 min, a solution of 4-methoxybenzyl 2-(S)-(1-(R)-3-(S)-hydroxymethyl-4-(S)-(3-fluorophenyl)cyclopent-1-yl)-3-(cyclopropyl)propionate, the lower R$_f$ isomer from Step I, (0.008 g, 0.018 mmol) in methylene chloride (0.5 mL) was added dropwise. The reaction was stirred at −70° C. for 40 min and then triethylamine (0.037 mL, 0.027 g, 0.268 mmol) was added. The reaction mixture was allowed to warm to room temperature for 10 min and then diluted with methylene chloride, poured into water, and extracted three times with methylene chloride. The organic layers were combined, washed with brine, dried over sodium sulfate, filtered and concentrated in vacuo. The crude title compound was used directly in Step K.

Step K: 4-Methoxybenzyl 2-(S)-(1-(R)-3-(S)-((1,3-diethyl-4,5-dihydrospiro[cyclopentapyrazole-6(1H), 4'-piperidin-1'-yl])methyl)-4-(S)-(3-fluorophenyl) cyclopent-1-yl)-3-(cyclopropyl)propionate To a solution of 4-methoxybenzyl 2-(S)-(1-(R)-3-(S)-formyl-4-(S)-(3-fluorophenyl)cyclopent-1-yl)-3-(cyclopropyl)propionate from Step J (0.008 g, 0.018 mmol) in 1,2-dichloroethane (1 mL) was added 1,3-diethyl-4,5-dihydrospiro[cyclopentapyrazole-6(1H),4'-piperidine] dihydrochloride (0.007 g, 0.020 mmol) from Procedure 1 and DIPEA (0.007 mL, 0.005 g, 0.039 mmol). After 10 min, sodium triacetoxyborohydride (0.007 g, 0.036 mmol) was added. The reaction mixture was stirred at room temperature for 12 h, diluted with methylene chloride, poured into aqueous sodium bicarbonate and extracted three times with methylene chloride. The organic layers were combined, washed with brine, dried over sodium sulfate, filtered and concentrated in vacuo. The residue was purified by prep TLC eluting with 5% MeOH in methylene chloride to afford the title compound (0.009 g).

HPLC/MS (ESI): m/z 642.6 (M+1); retention time=2.98 min.

Step L: 2-(S)-(1-(R)-3-(S)-((1,3-Diethyl-4,5-dihydrospiro[cyclopentapyrazole-6(1H),4'-piperidin-1'-yl])methyl)-4-(S)-(3-fluorophenyl)cyclopent-1-yl)-3-(cyclopropyl)propionate 4-Methoxybenzyl 2-(S)-(1-(R)-3-(S)-((1,3-diethyl-4,5-dihydrospiro[cyclopentapyrazole-6(1H),4'-piperidin-1'-yl]) methyl)-4-(S)-(3-fluorophenyl)cyclopent-1-yl)-3-(cyclopropyl)propionate from Step K (0.009 g, 0.018 mmol) was taken up in 96% formic acid (1 mL) and stirred at room temperature for 12 h. The formic acid was removed under a stream of nitrogen. The residue was purified by ion exchange chromatography (0.5 g Varian SCX resin, eluting with 100% MeOH, then with 2.0 M NH$_3$/MeOH) to afford to the title compound (0.008 g).

HPLC/MS (ESI): m/z 522.5 (M+1); retention time=2.42 min.

Step M: 2-(S)-(1-(R)-3-(S)-((1,3-Diethyl-4,5-dihydrospiro[cyclopentapyrazole-6(1H),4'-piperidin-1'-yl])methyl)-4-(S)-(3-fluorophenyl)cyclopent-1-yl)-3-(cyclopropyl)propionic acid di-hydrochloride salt 2-(S)-(1-(R)-3-(S)-((4-(3-Benzyl-1-ethyl-(1H)-pyrazol-5-yl)piperidin-1-yl)methyl)-4-(S)-(3-fluorophenyl)cyclopent-1-yl)-3-(cyclopropyl)propionic acid from Step L (0.008 g, 0.014 mmol) was taken up in 1:1 methylene chloride:ether (0.5 mL) and 1.0 N hydrochloric acid in diethyl ether was added (0.086 mL, 0.086 mmol). The volatiles were removed under a stream of nitrogen to give the title compound as a white solid.

HPLC/MS (ESI): m/z 522.5 (M+1); retention time=2.42 min.

EXAMPLE 42

2-(R)-(1-(R)-3-(S)-((1,3-Diethyl-4,5-dihydrospiro[cyclopentapyrazole-6(1H),4'-piperidin-1'-yl])methyl)-4-(S)-(3-fluorophenyl)cyclopent-1-yl)-3-(cyclopropyl)propionic acid di-hydrochloride salt

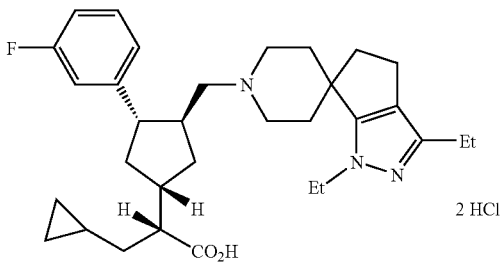

Using essentially the same procedure as in Example 41, Steps J–M, the higher $R_f$ isomer from Example 41, Step I can be elaborated to afford the title compound.

EXAMPLE 43

2-(S)-(1-(R)-3-(S)-((1,3-Diethyl-4,5-dihydrospiro[cyclopentapyrazole-6(1H),4'-piperidin-1'-yl])methyl)-4-(S)-(3-fluorophenyl)cyclopent-1-yl)-3-(cyclopropyl)propionic acid di-hydrochloride salt, Method B

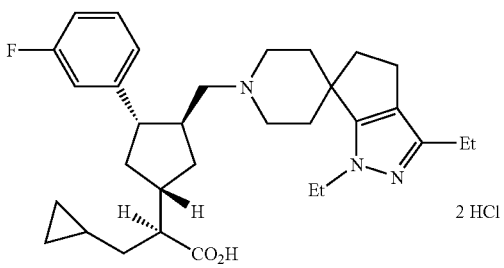

Step A: 2-(Diethoxyphosphoryl)acetic acid para-methoxybenzyl ester

To a solution of diethyl phosphonoacetic acid (6.0 g, 30.5 mmol) in 100 ml of DMF was added pulverized potassium carbonate (12.6 g, 91.5 mmol) and 4-methoxybenzyl chloride (6.2 mL, 45.8 mmol). The reaction mixture was stirred 12 h then diluted with diethyl ether, poured into water, and extracted three times with diethyl ether. The organic phases were combined, washed with saturated sodium chloride, dried over sodium sulfate, and filtered. The volatiles were removed in vacuo to afford 11 g. The residue was purified by FC (40–60% ethyl acetate in hexanes) to afford the title compound (6.04 g).

$^1$H NMR (CDCl$_3$): δ 1.30 (t, 6 H), 2.96 (s, 1 H), 3.02 (s, 1 H), 3.81 (s, 3 H), 4.09–4.17 (m, 4 H), 5.12 (s, 2 H), 6.89 (d, 2 H), 7.32 (d, 2 H).

Step B: 2-(Diethoxyphosphoryl)-3-cyclopropylproprionic acid 4-methoxybenzyl ester To a suspension of 60% sodium hydride in mineral oil (0.840 g, 21.0 mmol) in DMF (100 mL) was added a solution of 2-(diethoxyphosphoryl)acetic acid 4-methoxybenzyl ester (6.04 g, 19.1 mmol) from Step A in DMF (10 mL). The reaction mixture was stirred for 30 min at room temperature. Bromomethylcyclopropane (2.4 mL, 24.8 mmol) was added and the reaction mixture was stirred at room temperature for 12 h. The reaction mixture was diluted with diethyl ether, poured into saturated sodium bicarbonate, and extracted three times with diethyl ether. The organic layers were combined, washed with saturated sodium chloride, dried over sodium sulfate, and filtered. The volatiles were removed in vacuo and the residue was purified by FC (40% ethyl acetate in hexanes) to afford 4.31 g of the title compound.

$^1$H NMR (CDCl$_3$): δ 0.04–0.13 (m, 2 H), 0.37–0.45 (m, 2 H), 0.68–0.73 (m, 1 H), 1.25–1.29 (m, 6 H), 1.65–1.72 (m, 1 H), 1.85–2.02 (m, 1 H), 3.10 (dd, 1 H), 3.80 (s, 3 H), 4.07–4.13 (m, 4 H), 5.14 (s, 2 H), 6.88 (d, 2 H), 7.31 (d, 2 H).

Step C: 4-Methoxybenzyl 2-(E and Z)-(3-(S)-(t-butyldimethylsilyloxymethyl)-4-(S)-(3-fluorophenyl)cyclopent-1-ylidenyl-3-(cyclopropyl)propionate To a solution of 60% sodium hydride in mineral oil (0.318 g, 7.9 mmol) in THF (15 mL) was added 2-(diethoxyphosphoryl)-3-cyclopropylproprionic acid 4-methoxybenzyl ester (3.7 g, 9.99 mmol) from Step B. The reaction mixture was stirred at room temperature for 30 min. To this solution was added a solution of (+)-trans-1-t-butyldimethylsilyloxymethyl-4-oxo-2-(3-fluorophenyl)cyclopentane from Example 41 Step A (0.645 g, 1.99 mmol) in THF (5 mL). The reaction mixture was stirred at room temperature for 2 days, diluted with diethyl ether (20 mL), poured into water (50 mL) and extracted three times with diethyl ether (3×20 mL). The organic layers were combined, washed with brine (50 mL), dried over sodium sulfate, filtered and concentrated in vacuo. The residue (3.7 g) was purified by FC (5% ethyl acetate in hexanes) to afford the title compound as a 1:1 mixture of E:Z double bond isomers (0.398 g) as an oil.

$^1$H NMR (CDCl$_3$): δ −0.02–0.03 (br s, 6 H), 0.10–0.14 (m, 2 H), 0.39 (br s, 2 H), 0.89 (s, 9 H), 0.87–0.91 (m, 1H), 2.19 (br s, 1 H), 2.27–2.31 (m, 2 H), 2.42–2.57 (m, 1.5 H), 2.66–2.85 (m, 2 H), 2.92–3.06 (m, 1 H), 3.14–3.17 (m, 0.5 H), 3.34–3.37 (m, 1 H), 3.41–3.46 (m, 1 H), 3.82 (s, 3 H), 5.13 (s, 1 H), 5.17 (s, 1 H), 6.89–7.00 (m, 5 H), 7.27–7.35 (m, 3 H).

Step D: 4-Methoxybenzyl 2-(E)-(3-(S)-(hydroxymethyl)-4-(S)-(3-fluorophenyl)cyclopent-1-ylidenyl-3-(cyclopropyl)propionate and 4-methoxybenzyl 2-(Z)-(3-(S)-(hydroxymethyl)-4-(S)-(3-fluorophenyl)cyclopent-1-ylidenyl-3-(cyclopropyl)propionate 4-Methoxybenzyl 2-(Z)-(3-(S)-(t-butyldimethylsilyloxymethyl)-4-(S)-(3-fluorophenyl)cyclopent-1-ylidenyl-3-(cyclopropyl)propionate from Step C (0.398 g, 0.74 mmol) in THF (8 mL) was added a 1.0 M solution of tetrabutylammonium fluoride in THF (1.1 mL, 1.1 mmol) and the reaction mixture was stirred at room temperature for 12 h. The reaction mixture was diluted with ethyl acetate, poured into 5% aqueous HCl solution, extracted three times with ethyl acetate, combined organic layers, washed with brine, dried over sodium sulfate and concentrated. The residue was purified by prep TLC eluting with 3% ethyl acetate in methylene chloride to afford separation of the E and Z isomers to give the higher $R_f$ (0.108 g) and lower $R_f$ (0.078 g) chiral title compounds. The higher $R_f$ isomer was assigned as the E double bond isomer and the lower $R_f$ isomer was assigned as the Z double bond isomer based on nOe NMR experiments.

(Higher $R_f$ isomer): $^1$H NMR ($C_6D_6$): δ 0.20–0.30 (m, 2 H), 0.38–0.41 (m, 2 H), 0.90–1.00 (m, 1 H), 1.71–1.78 (m, 1 H), 2.10–2.16 (m, 1 H), 2.28–2.33 (m, 1 H), 2.28–2.33 (m, 1 H), 2.34–2.41 (m, 1 H), 2.42–2.47 (m, 1 H), 2.55 (dd, 1 H), 2.72–2.79 (m, 1 H), 2.98 (dd, 1 H), 3.14 (dd, 1 H), 3.19 (s, 3 H), 3.40 (dd, 1 H), 5.12 (s, 2 H), 6.65–6.80 (m, 4 H), 6.83–6.93 (m, 1 H), 7.20 (d, 3 H).

(Lower $R_f$ isomer): $^1$H NMR (CDCl$_3$): δ 0.08–0.14 (m, 2 H), 0.34–0.40 (m, 2 H), 0.79–0.86 (m, 1 H), 2.26–2.28 (m, 2 H), 2.26–2.33 (m, 1 H), 2.55–2.67 (m, 2 H), 2.92–3.04 (m, 2 H), 3.25 (dd, 1 H), 3.48–3.61 (dd, 1 H), 3.62–3.67 (dd, 1 H), 3.83 (s, 3 H), 5.16 (s, 2 H), 6.86–6.99 (m 4 H), 7.02 (d, 1 H), 7.03–7.37 (m, 3 H).

Step E: 4-Methoxybenzyl 2-(S)-(1-(R)-3-(S)-hydroxymethyl-4-(S)-(3-fluorophenyl)cyclopent-1-yl)-3-(cyclopropyl)propionate A solution of the higher $R_f$ E double bond isomer from Step D (0.003 g, 0.007 mmol) in methylene chloride (1 mL) was hydrogenated at atmospheric pressure using (1,5-cyclooctadiene) (pyridine) (tricyclohexyl-phosphine)iridium (I) hexafluorophosphate (0.001 g) for 12 h. The volatiles were removed in vacuo to afford the lower $R_f$ isomer at the 2-position of the 3-(cyclopropyl)propionate with 1,3 trans C-1 stereochemistry as the title compound which is the same as the lower $R_f$ isomer from Example 41, Step I.

Step F: 2-(S)-(1-(R)-3-(S)-((1,3-Diethyl-4,5-dihydrospiro[cyclopentapyrazole-6(1H),4'-piperidin-1'-yl])methyl)-4-(S)-(3-fluorophenyl)cyclopent-1-yl)-3-(cyclopropyl)propionic acid di-hydrochloride salt Using essentially the same procedure as in Example 41, Steps J-M, 4-methoxybenzyl 2-(S)-(1-(R)-3-(S)-hydroxymethyl-4-(S)-(3-fluorophenyl)cyclopent-1-yl)-3-(cyclopropyl)propionate from Step E was converted to the title compound.
HPLC/MS (ESI): m/z 522.5 (M+1) Rt=2.40 min.

EXAMPLE 44

2-(R)-(1-(R)-3-(S)-((1,3-Diethyl-4,5-dihydrospiro[cyclopentapyrazole-6(1H),4'-piperidin-1'-yl])methyl)-4-(S)-(3-fluorophenyl)cyclopent-1-yl)-3-(cyclopropyl)propionic acid di-hydrochloride salt, Method B

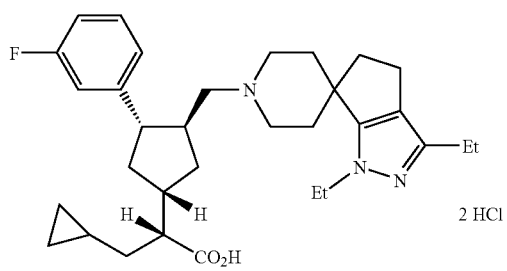

Using essentially the same procedure as in Example 43, Steps E–F, but substituting the lower $R_f$ Z double bond isomer from Example 43, Step D, the title compound can be obtained.

EXAMPLE 45

2-(S)-(1-(R)-3-(S)-((1,3-Diethyl-4,5-dihydrospiro[cyclopentapyrazole-6(1H),4'-piperidin-1'-yl])methyl)-4-(S)-(3-fluorophenyl)cyclopent-1-yl)-2-(1,1-dimethylprop-1-ylamino)acetic acid trihydrochloride salt

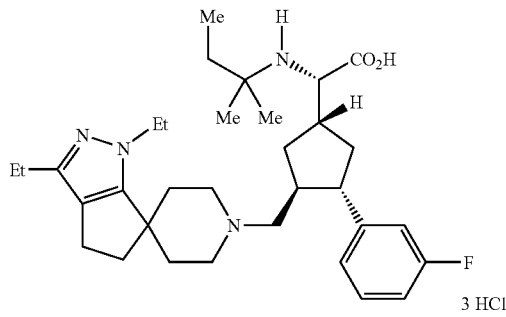

Step A: 4-Methoxybenzyl (R)-(1-(R)-3-(S)-t-butyldimethylsilyloxymethyl-4-(S)-(3-fluorophenyl)cyclopent-1-yl)hydroxyacetate (major isomer) and 4-methoxybenzyl (S)-(1-(R)-3-(S)-t-butyldimethylsilyloxymethyl-4-(S)-(3-fluorophenyl)cyclopent-1-yl) hydroxyacetate (minor isomer)

According to the procedure of Davis, et. al., *J. Org. Chem.* 1986, 2402, to a solution of 4-methoxybenzyl (1-(R)-3-(S)-t-butyldimethylsilyloxymethyl-4-(S)-(3-fluorophenyl)cyclopent-1-yl)acetate (0.50 g, 1.0 mmol) from Example 41, Step G in THF (20 mL) at –70° C. was added 1.5M LDA in cyclohexane (1.0 mL, 1.5 mmol). After 30 min, (1S)-(+)-(10-camphorsulfonyl)oxaziridine (468 mg, 2.0 mmol) in THF (5 mL) was added dropwise. After 2 h at –70° C., 5% aq. ammonium chloride was added and the mixture was extracted twice with ethyl acetate. The organic layers were combined, washed with brine, dried over sodium sulfate, filtered and concentrated in vacuo. The residue was purified by FC (5–10% ethyl acetate in hexanes) to afford the title compounds (530 mg) as a 2.5:1 mixture of (R):(S) hydroxy isomers as a white solid. The isomers were then separated by Chiral Prep HPLC on a 2 cm×25 cm Chiracel OD column eluting with 16% isopropanol in hexanes to afford the major, slower eluting (R) isomer (180 mg) and the minor, faster eluting (S) isomer. The assignment of the hydroxy stereochemistry was achieved by a single crystal x-ray structure determination on (R)-(1-(R)-3-(S)-hydroxymethyl-4-(S)-(3-fluorophenyl)cyclopent-1-yl)hydroxyacetic acid derived from the major, slower eluting isomer.

Step B: 4-Methoxybenzyl 2-(R)-(1-(R)-3-(S)-t-bu-tyldimethylsilyloxymethyl-4-(S)-(3-fluorophenyl)cyclopent-1-yl)-2-(trifluoromethanesulfonyloxy)acetate A solution of 4-methoxybenzyl 2-(R)-(1-(R)-3-(S)-t-butyldimethylsilyloxymethyl-4-(S)-(3-fluorophenyl)cyclopent-1-yl)-2-hydroxyacetate (316 mg, 0.63 mmol) from Step A (major faster isomer) and lutidine (0.117 mL, 1.0 mmol) in methylene chloride (7 mL) was cooled to −70° C. and triflic anhydride (0.127 mL, 0.75 mmol) was added. After 20 min, the reaction was warmed to 0° C. for 1 h and was then quenched with aq. sodium bicarbonate and extracted twice with methylene chloride. The organic layers were combined, washed with brine, dried over sodium sulfate, filtered and concentrated in vacuo. The residue was purified by FC (5% ethyl acetate in hexanes) to afford the title compound (343 mg) as a clear oil. This was used immediately in the next step.

Step C: 4-Methoxybenzyl 2-(S)-(1-(R)-3-(S)-t-bu-tyldimethylsilyloxymethyl-4-(S)-(3-fluorophenyl)cyclopent-1-yl)-2-(1,1-dimethylprop-1-ylamino)acetate A solution of 4-methoxybenzyl 2-(R)-(1-(R)-3-(S)-t-butyldimethylsilyloxymethyl-4-(S)-(3-fluorophenyl)cyclopent-1-yl)-2-(trifluoromethanesulfonyloxy)acetate (340 mg, 0.53 mmol) from Step B and t-amyl amine (1.2 mL, 10 mmol) in DCE (4 mL) was heated to 65° C. for 20 h. The reaction was cooled, dilute with aq. sodium bicarbonate and extracted twice with methylene chloride. The organic layers were combined, washed with brine, dried over sodium sulfate, filtered and concentrated in vacuo. The residue was purified by FC (4% ethyl acetate in hexanes containing 0.5% TEA) to afford the title compound (275 mg).

HPLC/MS (ESI): m/z 572.5 (M+1) Rt=3.47 min; (−TB-DMS group) m/z 458.4 (M+1) Rt=2.40 min

Step D: 4-Methoxybenzyl 2-(S)-(1-(R)-3-(S)-hy-droxymethyl-4-(S)-(3-fluorophenyl)cyclopent-1-yl)-2-(1,1-dimethylprop-1-ylamino)acetate A solution of 4-methoxybenzyl 2-(R)-(1-(R)-3-(S)-t-butyldimethylsilyloxymethyl-4-(S)-(3-fluorophenyl)cyclopent-1-yl)-2-(1,1-dimethylprop-1-ylamino)acetate (275 mg, 0.48 mmol) from Step C in THF (6 ML) was added 1M TBAF in THF (0.72 mL, 0.72 mmol). The solution was stirred at room temperature for 16 h and was then diluted with ethyl acetate, poured into aq. sodium bicarbonate and extracted twice with ethyl acetate. The organic layers were combined, washed with brine, dried over sodium sulfate, filtered and concentrated in vacuo. The residue was purified by FC (25–40% ethyl acetate in hexanes containing 0.5% TEA) to afford the title compound (200 mg).

Step E: 4-Methoxybenzyl 2-(S)-(1-(R)-3-(S)-formyl-4-(S)-(3-fluorophenyl)cyclopent-1-yl)-2-(1,1-dimethylprop-1-ylamino)acetate A solution of 4-methoxybenzyl 2-(R)-(1-(R)-3-(S)-hydroxymethyl-4-(S)-(3-fluorophenyl)cyclopent-1-yl)-2-(1,1-dimethylprop-1-ylamino)acetate (200 mg, 0.43 mmol) from Step D in methylene chloride (2 mL) was added TPAP (8 mg, 0.022 mmol) and N-methylmorpholine-N-oxide (76 mg, 0.65 mmol). The solution was stirred at room temperature for 90 min and was then placed directly on 2 Prep TLC plates. The plates were eluted with 25% ethyl acetate in hexanes to afford the title compound (100 mg).

Step F: 2-(S)-(1-(R)-3-(S)-((1,3-Diethyl-4,5-dihy-drospiro[cyclopentapyrazole-6(1H),4'-piperidin-1'-yl])methyl)-4-(S)-(3-fluorophenyl)cyclopent-1-yl)-2-(1,1-dimethylprop-1-ylamino)acetate trihydrochloride salt Using essentially the same procedures as in Example 1, Steps H-I, 4-methoxybenzyl 2-(S)-(1-(R)-3-(S)-formyl-4-(S)-(3-fluorophenyl)cyclopent-1-yl)-2-(1,1-dimethylprop-1-ylamino)acetate (30 mg) was converted to the title compound (20 mg).

HPLC/MS (ESI): m/z 553.6 (M+1) Rt=2.19 min.

EXAMPLE 46

2-(S)-(1-(R)-3-(S)-((1,3-Diethyl-4,5-dihydrospiro[cyclopentapyrazole-6(1H),4'-piperidin-1'-yl])methyl)-4-(S)-(3-fluorophenyl)cyclopent-1-yl)-2-((1,1-dimethylprop-1-yl)methylamino)acetic acid trihydrochloride salt

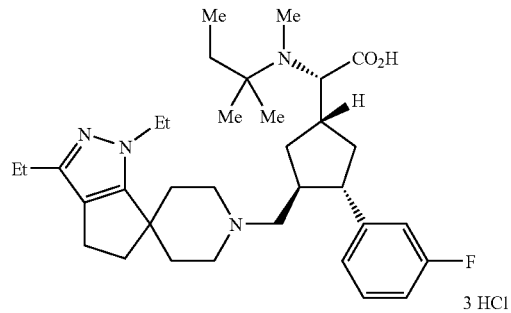

To a solution of 2-(S)-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-2-(1,1-dimethylprop-1-ylamino)acetate (9 mg, 0.016 mmol) from Example 45, Step F in DCE was added 37% aq. formaldehyde (0.00043 mL, 0.016 mmol) and DIPEA (0.0054 mL, 0.031 mmol). After 5 min, sodium triacetoxyborohydride (10 mg, 0.045 mmol) was added and the reaction was stirred at room temperature for 16 h. The mixture was concentrated and the residue was loaded onto a 250 mg Varian SCX ion-exchange resin cartridge. The resin was eluted with 2×3 mL of methanol, then the product was eluted with 2×3 mL of 2M ammonia in methanol. The product solution was concentrated under nitrogen, then 2 volumes of methylene chloride were evaporated to remove methanol and ammonia to give the title compound as the free amine. The hydrochloride salt was prepared by dissolving the free amine in methylene chloride, adding excess (>3-fold) 1M hydrogen chloride in ether and evaporating to dryness.

HPLC/MS (ESI): m/z 567.6 (M+1); retention time=1.80 min.

EXAMPLE 47

1-(R or S)-(2,2-Dimethylprop-1-ylamino)-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylic acid trihydrochloride salt

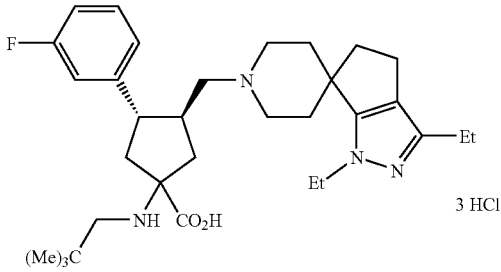

Step A: 3-(S)-(t-Butyldimethylsilyloxymethyl)-4-(S)-(3-fluorophenyl)-1-(R and S)-(trichloromethyl)cyclopentanol To a solution of (+)-trans-1-t-butyldimethylsilyloxymethyl-4-oxo-2-(3-fluorophenyl)cyclopentane (2.0 g, 6.2 mmol) from Example 41, Step A and chloroform (0.990 mL, 12.4 mmol) in THF (60 mL) at −70° C. was added via a double-tipped needle 1M LHMDS in THF (12.4 mL, 12.4 mmol) also pre-cooled to −70° C. The reaction was stirred at −70° C. for one h and was then diluted with ether, quenched by addition of aq. ammonium chloride, and extracted twice with ether. The organic layers were combined, washed with brine, dried over sodium sulfate, filtered and concentrated in vacuo. The residue was purified by FC (5% ethyl acetate in hexanes) to afford the title compound (1.96 g) as a mixture of C-1 isomers.

Step B: Methyl 1-(R and S)-azido-3-(S)-(t-butyldimethylsilyloxymethyl)-4-(S)-(3-fluorophenyl)cyclopentane carboxylate To a solution of 3-(S)-(t-butyldimethylsilyloxymethyl)-4-(S)-(3-fluorophenyl)-1-(R and S)-(trichloromethyl)cyclopentanol (1.96 g, 4.45 mmol) from Step A in methanol (90 mL) at room temperature was added sodium azide (2.89 g, 44.5 mmol), then 18-crrown-6 (58 mg, 0.22 mmol), and then DBU (3.3 mL, 22.2 mmol). The reaction was stirred at room temperature for 20 h, and was then diluted with ether, quenched by addition of aq. ammonium chloride, and extracted three times with ether. The organic layers were combined, washed with brine, dried over sodium sulfate, filtered and concentrated in vacuo. The residue was purified by FC (20% methylene chloride in hexanes) to afford the title compound (1.13 g) as a mixture of C-1 isomers.

Step C: Methyl 1-(S or R)-azido-3-(S)-(hydroxymethyl)-4-(S)-(3-fluorophenyl)cyclopentane carboxylate (minor, higher $R_f$) and methyl 1-(R or S)-azido-3-(S)-(hydroxymethyl)-4-(S)-(3-fluorophenyl)cyclopentane carboxylate (major, lower $R_f$)

To a solution of 1-(R and S)-azido-3-(S)-(t-butyldimethylsilyloxymethyl)-4-(S)-(3-fluorophenyl)cyclopentanol (1.96 g, 4.45 mmol) from Step B in methanol (13 mL) at room temperature was added acetyl chloride (0.890 mL, 12.5 mmol). The solution was stirred at room temperature for 16 h and was then concentrated in vacuo. The residue was purified by FC (20% ethyl acetate in hexanes) to afford the higher $R_f$, minor C-1 isomer (84 mg) and lower $R_f$, major C-1 isomer (262 mg) of the title compound.

Step D: Methyl 1-(R or S)-azido-3-(S)-(formyl)-4-(S)-(3-fluorophenyl)cyclopentane carboxylate Using essentially the same procedure as Example 1, Steps G, methyl 1-(R or S)-azido-3-(S)-(hydroxymethyl)-4-(S)-(3-fluorophenyl)cyclopentane carboxylate (262 mg) from Step C major, lower $R_f$ isomer was converted to the title compound (213 mg).

Step E: Methyl 1-(R or S)-azido-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylate Using essentially the same procedure as Example 1, Steps H, methyl 1-(R or S)-azido-3-(S)-(formyl)-4-(S)-(3-fluorophenyl)cyclopentane carboxylate (50 mg) from Step D and 1,3-diethyl-4,5-dihydrospiro[cyclopentapyrazole-6(1H),4'-piperidine] from Procedure 1 were converted to the title compound (48 mg).

HPLC/MS (ESI): m/z 509.6 (M+1)

Step F: Methyl 1-(R or S)-amino-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylate To a solution of methyl 1-(R or S)-azido-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylate (48 mg, 0.09 mmol) from Step E in ethyl acetate (1 mL) was added 10% Pd/C (20 mg). The mixture was stirred under a hydrogen balloon for 40 h and was then filtered and concentrated to afford the title compound (39 mg).

HPLC/MS (ESI): m/z 483.5 (M+1); retention time=1.76 min.

Step G: Methyl 1-(R or S)-(2,2-dimethylprop-1-ylamino)-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylate To a solution of methyl 1-(R or S)-amino-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylate (39 mg, 0.080 mmol) from Step F in DCE (2 mL) was added trimethylacetaldehyde (0.010 mL. 0.088 mmol), acetic acid (0.005 mL, 0.088 mmol). After 5 min, sodium triacetoxyborohydride (34 mg, 0.16 mmol) was added and the mixture was stirred at room temperature for 20 h. The mixture was then quenched with aq. sodium carbonate and extracted three times with methylene chloride. The organic layers were combined, washed with brine, dried over sodium sulfate, filtered and concentrated in vacuo. The residue was purified by Prep TLC (5% methanol in methylene chloride) to afford the title compound (30 mg).

HPLC/MS (ESI): m/z 553.6 (M+1); retention time=2.16 min.

Step H: 1-(R or S)-(2,2-Dimethylprop-1-ylamino)-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylic acid trihydrochloride salt To a solution of methyl 1-(R or S)-(2,2-dimethylprop-1-ylamino)-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylate (16 mg, 0.030 mmol) from Step G in methanol (2 mL) was added 5N sodium hydroxide (0.090 mL. 0.45 mmol). The solution was stirred at 80° C. for 24 h and was then acidified with 2N HCl and concentrated. The residue was loaded onto a 250 mg Varian SCX ion-exchange resin cartridge. The resin was eluted with 2×3 mL of methanol, then the product was eluted with 2×3 mL of 2M ammonia in methanol. The product solution was concentrated under nitrogen, then 2 volumes of methylene chloride were evaporated to remove methanol and ammonia to give the title compound as the free amine. The hydrochloride salt was prepared by dissolving the free amine in methylene chloride, adding excess (>3-fold) 1M hydrogen chloride in ether and evaporating to dryness.

HPLC/MS (ESI): m/z 539.6 (M+1); retention time=2.00 min.

EXAMPLE 48

1-(R or S)-((2,2-Dimethylprop-1-yl)methylamino)-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylic acid trihydrochloride salt

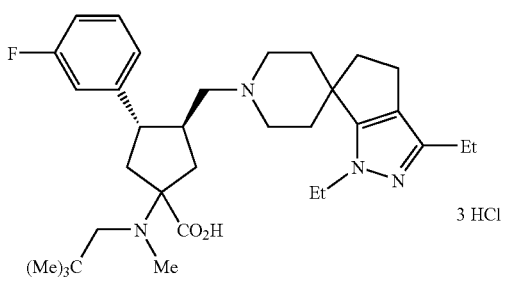

Step A: Methyl 1-(R or S)-((2,2-dimethylprop-1-yl)methylamino)-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylate To a solution of methyl 1-(R or S)-(2,2-dimethylprop-1-ylamino)-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylate (14 mg, 0.025 mmol) from Example 47, Step G in DCE was added 37% aq. formaldehyde (0.0021 mL, 0.075 mmol) and acetic acid (0.0016 mL, 0.028 mmol). After 5 min, sodium triacetoxyborohydride (11 mg, 0.050 mmol) was added and the reaction was stirred at room temperature for 2 h. The mixture was quenched with aq. sodium bicarbonate and extracted three times with methylene chloride. The organic layers were combined, washed with brine, dried over sodium sulfate, filtered and concentrated in vacuo. The residue was purified by Prep TLC (5% methanol in methylene chloride) to afford the title compound (11.5 mg).

HPLC/MS (ESI): m/z 567.6 (M+1); retention time=2.18 min.

Step B: 1-(R or S)-((2,2-Dimethylprop-1-yl)methylamino)-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylic acid trihydrochloride salt Using essentially the same procedure as Example 47, Step H, methyl 1-(R or S)-((2,2-dimethylprop-1-yl)methylamino)-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylate (11.5 mg) from Step A was converted to the title compound (14 mg)

HPLC/MS (ESI): m/z 553.6 (M+1); retention time=1.95 min.

EXAMPLE 49

1-(R or S)-((2,2-Dimethylprop-1-yl)amino)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylic acid trihydrochloride salt

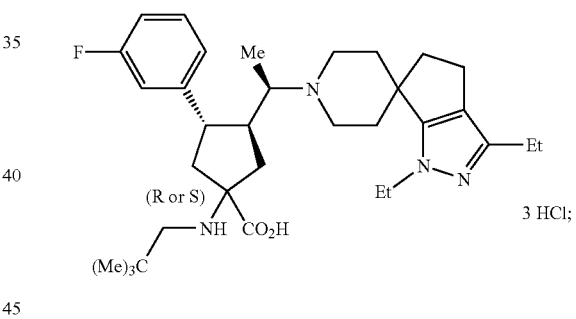

Step A: Methyl 1-(R and S)-(Trichloromethyl)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentanol Using essentially the same procedure as Example 47, Steps A, 3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentan-1-one (1.71 g, 3.9 mmol) from Example 33, Step D was converted into the title compounds. The C-1 isomers were separated by FC (18% acetone in hexanes) to give the higher $R_f$ C-1 isomer (295 mg) and lower C-1 isomer (283 mg).

Higher $R_f$ Isomer

HPLC/MS (ESI): m/z 556.0 (M+1) and 558 (M+3); retention time=2.59 min.

Lower $R_f$ Isomer

HPLC/MS (ESI): m/z 556.0 (M+1) and 558 (M+3); retention time=2.56 min.

Step B: Methyl 1-(R or S)-azido-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylate Using essentially the same procedures as Example 47, Step B, methyl 1-(R or S)-(trichloromethyl)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentanol (295 mg, 0.53 mmol) from Step A (higher $R_f$ isomer) was converted into the title compound (100 mg).

HPLC/MS (ESI): m/z 523.2 (M+1); retention time=2.61 min.

Step C: 1-(R or S)-((2,2-Dimethylprop-1-yl)methylamino)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylic acid trihydrochloride salt Using essentially the same procedures as Example 47, Step F–H, methyl 1-(R or S)-azido-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylate (100 mg, 0.53 mmol) from Step B was converted into the title compound (13 mg).

HPLC/MS (ESI): m/z 553.4 (M+1); retention time=1.95 min.

EXAMPLE 50

1-(S or R)-((2,2-Dimethylprop-1-yl)amino)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylic acid trihydrochloride salt

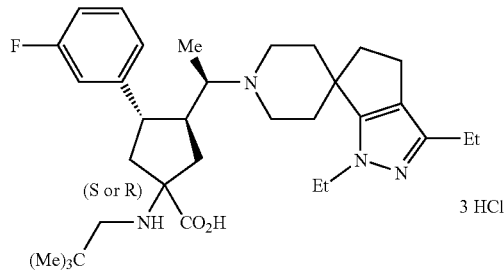

Using essentially the same procedures as Example 49, Steps B-C, methyl 1-(S or R)-(trichloromethyl)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentanol (100 mg, 0.53 mmol) from Example 49, Step A was converted into the title compound.

HPLC/MS (ESI): m/z 553.2 (M+1); retention time=2.0 min.

EXAMPLE 51

1-(R and S)-(Dimethylamino)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylic acid trihydrochloride salt

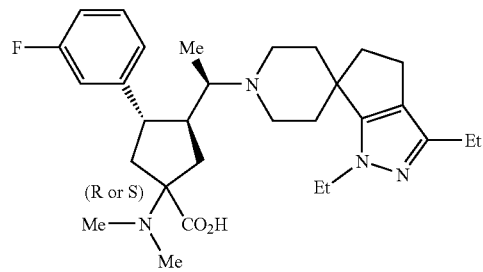

Using essentially the same procedures as Example 48, both methyl 1-(R or S)-(amino)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylates from Example 49, Step B can be converted into the title compounds.

HPLC/MS (ESI): m/z 511.2 (M+1); retention time=1.73 min.

EXAMPLE 52

N-(1-(R or S)-Methyl-3-(S)-(1-(R)-(1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine trihydrochloride salt

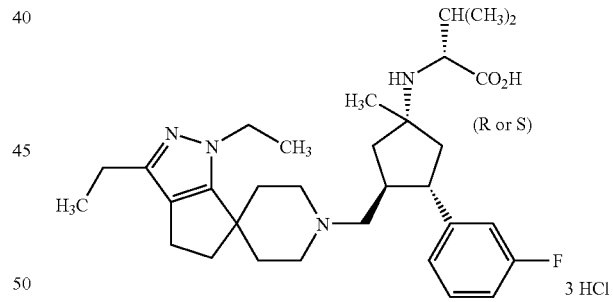

Step A: 1-(S)-Benzyloxymethyl-2-(S)-(3-fluorophenyl)-4-methylenecyclopentane

To a solution of (+)-trans-1-hydroxymethyl-4-methylene-2-(3-fluorophenyl)cyclopentane (5.0 g, 26.5 mmol) from Example 1, Step C and benzyl bromide (4.7 mL, 40 mmol) in DMF (130 mL) was added 60% sodium hydride in mineral oil (0.77 g, 32 mmol). The reaction was stirred at room temperature for 24 h was then diluted with ether and slowly quenched into aq. sodium bicarbonate. After three ether extractions, the organic layers were combined, washed with brine, dried over sodium sulfate, filtered and concentrated in vacuo. The residue was purified by FC (2–5% ethyl acetate in hexanes) to afford the title compound (7.1 g).

Step B: 3-(S)-Benzyloxymethyl-4-(S)-(3-fluorophenyl)cyclopentanone

A solution of 1-(S)-benzyloxymethyl-2-(S)-(3-fluorophenyl)-4-methylenecyclopentane from Step A (7.1 g, 25.5 mmol) in methanol (300 mL) was cooled in a dry ice/acetone bath and ozone was bubbled into the solution until the blue color persisted. The excess ozone was removed with a stream of nitrogen and then dimethylsulfide (10 mL) was added. After 10 min, the bath was removed and the reaction was allowed to warm to room temperature over 2 h. The mixture was treated with 10 drops of sulfuric acid (c) in water (2 mL) for 1 h before most of the methanol was removed in vacuo. The mixture was diluted with water and extracted twice with ethyl acetate and the organic layers were washed with brine, dried over sodium sulfate, combined and concentrated. The residue was purified by FC (15% ethyl acetate in hexanes) to give the title compound (4.74 g).

Step C: 3-(S)-Benzyloxymethyl-4-(S)-(3-fluorophenyl)-1-(R and S)-methylcyclopentanol A solution of 3-(S)-benzyloxymethyl-4-(S)-(3-fluorophenyl)cyclopentanone from Step B (2.54 g, 8.5 mmol) in THF (85 mL) was cooled in a dry ice/acetone bath and 1.4M methyl lithium in THF (8.0 mL, 11.2 mmol) was added. After 10 min, the bath was removed and the reaction was allowed to warm to 0° C. over 2 h in an ice bath. The mixture was diluted with aq. ammonium chloride and extracted twice with ether. The organic layers were washed with brine, dried over sodium sulfate, combined and concentrated. The residue was purified by FC (20% ethyl acetate in hexanes) to give the title compound (1.4 g) as a mixture of C-1 isomers.

Step D: N-(3-(S)-Benzyloxymethyl-4-(S)-(3-fluorophenyl)-1-(R and S)-methylcyclopent-1-yl)acetamide A solution of 3-(S)-benzyloxymethyl-4-(S)-(3-fluorophenyl)-1-(R and S)-methylcyclopentanol from Step C (1.81 g, 5.75 mmol) in acetonitrile (3 mL) was cooled to 0° C. and concentrated sulfuric acid (1.2 mL) was added. After 5 min, the bath was removed and the mixture was stirred at room temperature for 1 h. The mixture was then poured into ice water and extracted three times with methylene chloride. The organic layers were washed with brine, dried over sodium sulfate, combined and concentrated. The residue was purified by FC (50% ethyl acetate in hexanes) to give the title compounds (2.4 g) as a mixture of C-1 isomers.

HPLC/MS (ESI): m/z 356.3 (M+1); retention time=3.52 min.

Step E: (3-(S)-Benzyloxymethyl-4-(S)-(3-fluorophenyl)-1-(R and S)-methylcyclopent-1-yl)amine A solution of N-(3-(S)-benzyloxymethyl-4-(S)-(3-fluorophenyl)-1-(R and S)-methylcyclopent-1-yl)acetamide from Step D (1.81 g, 5.75 mmol) in water (2.5 mL) and ethylene glycol containing 50% sodium hydroxide (2.5 mL) was heated to 145° C. for 12 days. The dark mixture was diluted with water and extracted three times with methylene chloride. The organic layers were washed with brine, dried over sodium sulfate, combined and concentrated. The residue was purified by FC (10% methanol in methylene chloride) to give the title compounds (0.233 g) as a 4:1 mixture of C-1 isomers.

HPLC/MS (ESI): m/z 314.2 (M+1); retention time=2.53 min.

Step F: N-(3-(S)-Benzyloxymethyl-4-(S)-(3-fluorophenyl)-1-(R and S)-methylcyclopent-1-yl)-(R)-valine benzyl ester A sample of (3-(S)-benzyloxymethyl-4-(S)-(3-fluorophenyl)-1-(R and S)-methylcyclopent-1-yl)amine (0.315 g, 1.0 mmol) from Step E was rigorously dried via evaporation of three times 10 mL of toluene. The residue was taken up in dry DCE (8 mL) and DIPEA (0.130 mL, 2.0 mmol) and benzyl 3-methyl-2-(S)-trifluorosulfonyloxybutanoate (0.340 g, 1.0 mmol) was added under nitrogen. The reaction was heated at 65° C. for 50 h. The reaction was cooled, diluted with methylene chloride, poured into aq. sodium bicarbonate, and extracted three times with methylene chloride. The organic layers were washed with brine, dried over sodium sulfate, combined and concentrated. The residue was purified by FC (10% ethyl acetate in hexanes) to give the title compounds (0.24 g) as a 4:1 mixture of C-1 isomers.

HPLC/MS (ESI): m/z 504.1 (M+1); retention time=3.36 min.

Step G: N-(3-(S)-Hydroxymethyl-4-(S)-(3-fluorophenyl)-1-(R and S)-methylcyclopent-1-yl)-(R)-valine To a solution of N-(3-(S)-benzyloxymethyl-4-(S)-(3-fluorophenyl)-1-(R and S)-methylcyclopent-1-yl)-(R)-valine benzyl ester (0.24 g, 0.48 mmol) from Step F in methanol (5 mL) was added a drop of acetic acid and 10% Pd/C (100 mg). The mixture was hydrogenated on a Parr shaker at 50 psi for 14 days. The catalyst was filtered and the filtrate was evaporated to afford the title compound as a 4:1 mixture of C-1 isomers.

HPLC/MS (ESI): m/z 324.1 (M+1); retention time=1.73 min.

Step H: N-(3-(S)-Hydroxymethyl-4-(S)-(3-fluorophenyl)-1-(R and S)-methylcyclopent-1-yl)-(R)-valine methyl ester To a solution of N-(3-(S)-hydroxymethyl-4-(S)-(3-fluorophenyl)-1-(R and S)-methylcyclopent-1-yl)-(R)-valine benzyl ester (0.14 g, 0.44 mmol) from Step G in methanol (0.750 mL) and methylene chloride (2 mL) at 0° C. was added a dropwise 2M trimethylsilyldiazomethane until the yellow color persisted. The mixture was concentrated and the residue was purified by Prep TLC (2% methanol in methylene chloride) to afford the title compounds as the higher $R_f$ C-1 isomer (71 mg) and lower C-1 isomer (0.022 mg).

Higher isomer: HPLC/MS (ESI): m/z 338.1 (M+1); retention time=1.97 min.

Lower isomer: HPLC/MS (ESI): m/z 338.1 (M+1); retention time=1.81 min.

Step I: N-(3-(S)-Formyl-4-(S)-(3-fluorophenyl)-1-(R and S)-methylcyclopent-1-yl)-(R)-valine methyl ester Using essentially the same procedure as Example 45, Step E, N-(3-(S)-hydroxymethyl-4-(S)-(3-fluorophenyl)-1-(R and S)-methylcyclopent-1-yl)-(R)-valine methyl ester (67 mg, 0.20 mmol) from Step H (higher $R_f$ isomer) was converted with TPAP (3.5 mg) and NMO (35 mg) to the title compound (45 mg).

Step J: N-(1-(R or S)-Methyl-3-(S)-(1-(R)-(1,3-diethyl-4,5-dihydrospiro[cyclopentapyrazole-6(1H), 4'-piperidin-1'-yl])methyl)-4-(S)-(3-fluorophenyl)cyclopent-1-yl)-(R)-valine methyl ester Using essentially the same procedure as Example 1, Step H, N-(3-(S)-formyl-4-(S)-(3-fluorophenyl)-1-(R or S)-methylcyclopent-1-yl)-(R)-valine methyl ester (45 mg, 0.13 mmol) from Step I was converted into the title compound (61 mg).

HPLC/MS (ESI): m/z 553.4 (M+1); retention time=1.88 min.

Step K: N-(1-(R or S)-Methyl-3-(S)-(1-(R)-(1,3-diethyl-4,5-dihydrospiro[cyclopentapyrazole-6(1H), 4'-piperidin-1'-yl])methyl)-4-(S)-(3-fluorophenyl)cyclopent-1-yl)-(R)-valine trihydrochloride salt Using essentially the same procedure as Example 47, Step H, N-(1-(R or S)-methyl-3-(S)-(1-(R)-(1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine methyl ester (30 mg, 0.054 mmol) from Step J was converted into the title compound (15 mg).

HPLC/MS (ESI): m/z 539.4 (M+1); retention time=1.81 min.

EXAMPLE 53

N-(1-(S or R)-Methyl-3-(S)-(1-(R)-(1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine trihydrochloride salt

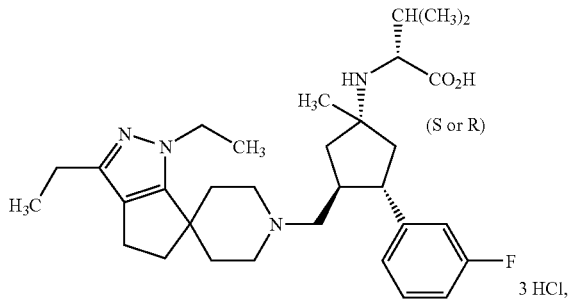

Using essentially the same procedures as in Example 52, Steps I–K, but starting with the lower $R_f$ isomer from Example 52, Step H, the title compound was prepared.

HPLC/MS (ESI): m/z 539.4 (M+1); retention time=1.84 min.

EXAMPLE 54

N-Methyl-N-(1-(R or S)-Methyl-3-(S)-(1-(R)-(1,3-diethyl-4,5-dihydrospiro[cyclopentapyrazole-6(1H), 4'-piperidin-1'-yl])methyl)-4-(S)-(3-fluorophenyl)cyclopent-1-yl)-(R)-valine trihydrochloride salt

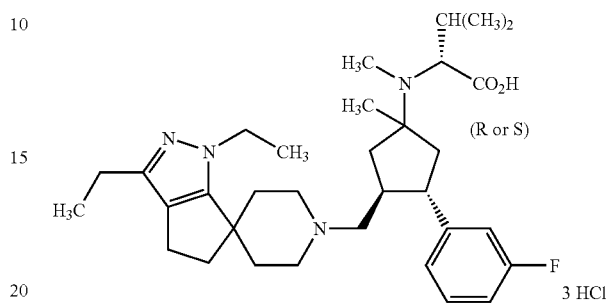

Using essentially the same procedures as in Example 48, Steps A and Example 47, Step H, but starting with N-(1-(R or S)-methyl-3-(S)-(1-(R)-(1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine methyl ester derived from the higher $R_f$ isomer from Example 52, Step H, the title compound was prepared.

HPLC/MS (ESI): m/z 553.4 (M+1); retention time=1.75 min.

EXAMPLE 55

N-Methyl-N-(1-(S or R)-Methyl-3-(S)-(1-(R)-(1,3-diethyl-4,5-dihydrospiro[cyclopentapyrazole-6(1H), 4'-piperidin-1'-yl])methyl)-4-(S)-(3-fluorophenyl)cyclopent-1-yl)-(R)-valine trihydrochloride salt

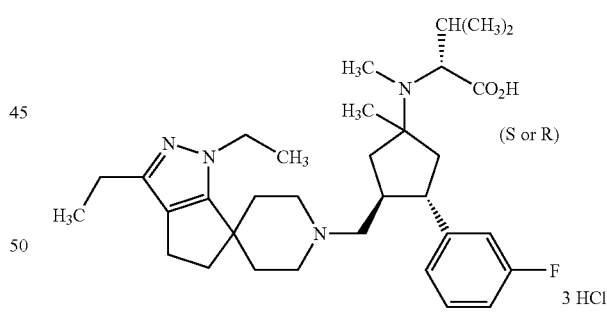

Using essentially the same procedures as in Example 54, but starting with N-(1-(S or R)-methyl-3-(S)-(1-(R)-(1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine methyl ester derived from the lower $R_f$ isomer from Example 52, Step H, the title compound was prepared.

HPLC/MS (ESI): m/z 553.3 (M+1); retention time=1.78 min.

EXAMPLE 56

Using essentially the same procedures as in Example 1, Step H and/or Step I, but utilizing other available piperdine isomers as prepared using Procedures 1 to 21, other compounds within the scope of the present invention have been prepared including the following compounds:

N-methyl-N-(1-(R)-3-(S)-((2,3-diethyl-5,6 dihydrospiro[cyclopentapyrazole-4(1H),4'-piperidin-1'-yl])methyl)-4-(S)-(3-fluorophenyl)cyclopent-1-yl)-(R)-valine:

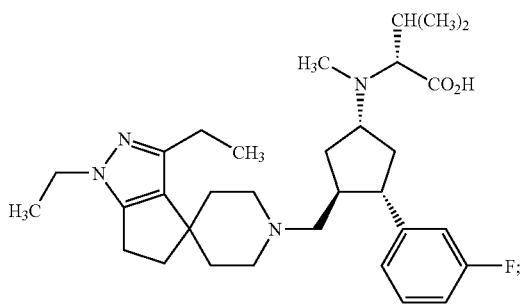

N-methyl-N-(1-(R)-3-(S)-((1-ethyl-3-methoxy-5,6-dihydrospiro[cyclopenta-pyrazole-4(2H),4'-piperidin-1'-yl])methyl)-4-(S)-(3-fluorophenyl)cyclopent-1-yl)-(R)-valine:

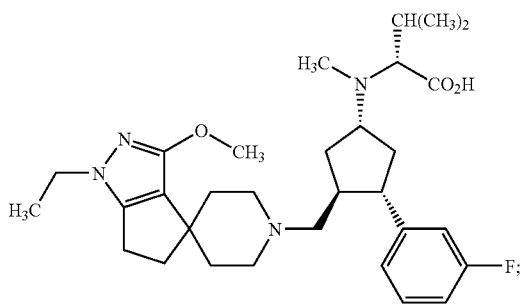

N-methyl-N-(1-(R)-3-(S)-((2-ethyl-3-methoxy-5,6-dihydrospiro[cyclopenta-pyrazole-4(2H),4'-piperidin-1'-yl])methyl)-4-(S)-(3-fluorophenyl)cyclopent-1-yl)-(R)-valine:

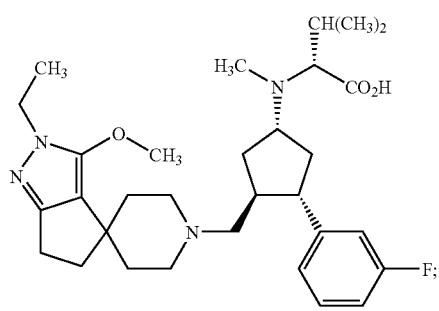

N-methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valinamide:

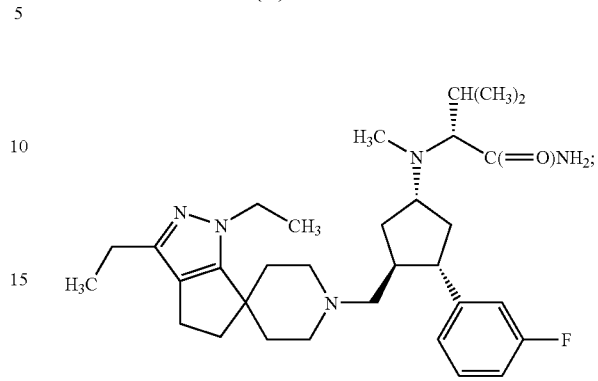

N-methyl-N-(1-(S)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valinamide:

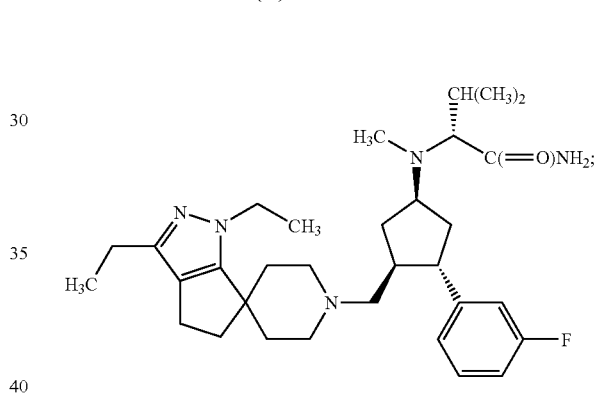

and

N-methyl-N-(1-(R)-3-(S)-((2'-ethyl-5',6'-dihydrospiro[piperidin-1-yl-4,4'-[4H]pyrrolo[1,2-b]pyrazole])methyl)-4-(S)-(3-fluorophenyl)cyclopent-1-yl)-(R)-valine:

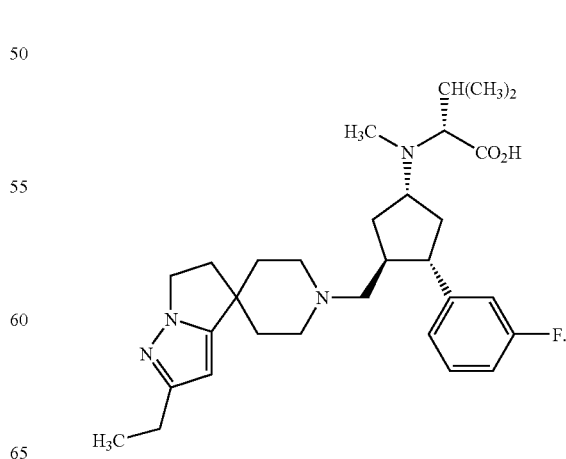

EXAMPLE 57

Using essentially the same procedures as set forth in Examples 1–56, but utilizing the enantiomeric product from Example 1, Step C (i.e., (−)-trans-1-(R)-hydroxymethyl-4-methylene-2-(R)-(3-fluorophenyl)cyclopentane), in conjuction with the appropriate piperidines as prepared using Procedures 1 to 21, the corresponding enantiomeric compounds within the scope of this invention are prepared.

EXAMPLE 58

Assay for Determining CCR3 Binding Activity

The CCR3 binding activity of representative compounds of the present invention can be determined via the assay disclosed in U.S. Pat. No. 6,303,593 or U.S. Pat. No. 6,538,002. Certain compounds of the invention (e.g., the compounds prepared in Examples 1, 2, 3, 6, 12, 15, 16, 18, 20, 25, 45, and 46) tested with this assay were found to have $IC_{50}$ values less than 10 micromolar.

EXAMPLE 59

Assay for Determining CCR5 Binding Activity

The CCR5 binding activity of compounds of the present invention can be determined by testing the ability of the compounds to displace [$^{125}$I]-MIP-1α from the CCR5 receptor expressed on Chinese Hamster Ovary cell membranes. The assay can be conducted in the manner described in Siciliano et al., *J. Biol. Chem.*, 1999, 274, 1905 Hale et al., *Bioorg. Med. Chem. Lett.* 2001, 11: 1437–1440 (see endnote 20). Representative compounds of the invention, including the compounds prepared in Examples 1–56, were tested with this assay and were found to have $IC_{50}$ values less than 1 micromolar.

EXAMPLE 60

Assay for Inhibition of HIV Replication

The ability of representative compounds of the present invention to inhibit a single HIV-1 infectin cycle was determined using a CCR5 expressing HeLa Magi cell line in the manner described in Hazuda et al., *Science* 2000, 287: 646–650 (see endnote 10). Representative compounds of the invention, including the compounds prepared in Examples 1–56, were tested with this assay and were found to have $IC_{95}$ values less than 1 micromolar.

While the foregoing specification teaches the principles of the present invention, with examples provided for the purpose of illustration, the practice of the invention encompasses all of the usual variations, adaptations and/or modifications that come within the scope of the following claims.

What is claimed is:
1. A compound of Formula (I):

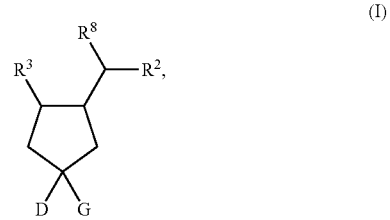

or a pharmaceutically acceptable salt and/or an individual diastereomer thereof, wherein:

D and G are defined as follows:
  (A) D is —H and G is

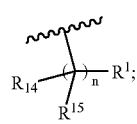

(B) D is $R^7$ and G is

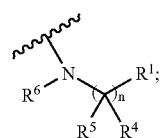

or
  (C) D is $R^{15}$ and G is $R^1$;
  (D) D is —H and G is

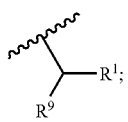

or
  (E) D and G together form

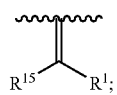

$R^1$ is:
  (1) —CO$_2$H,
  (2) —C(=O)NR$^y$R$^z$,
  (3) tetrazolyl,
  (4) —SO$_2$NHCO—R$^u$, or
  (5) —P(O)(OH)$_2$;

$R^2$ is:

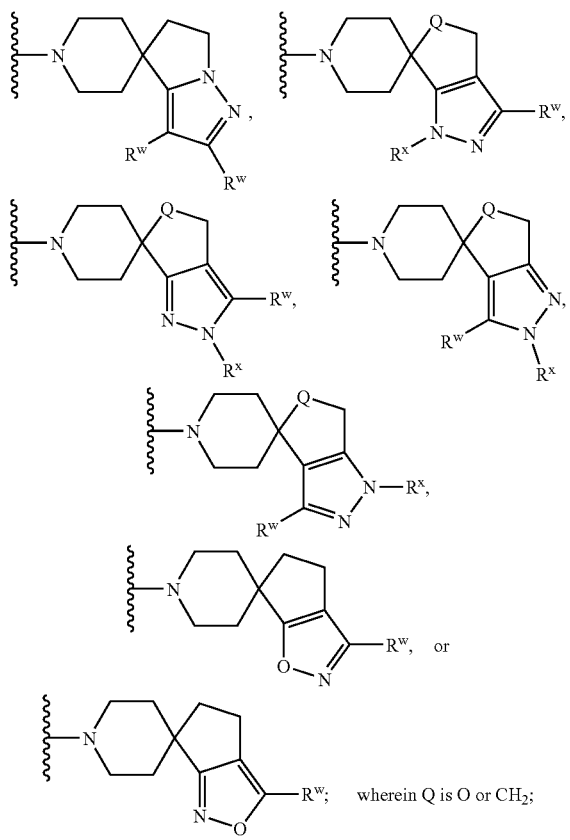

wherein Q is O or CH$_2$;

$R^3$ is phenyl which is optionally substituted with from 1 to 5 substituents each of which is independently:
(a) halo,
(b) —C$_{1-3}$ haloalkyl,
(c) —OH,
(d) —C$_{1-3}$ alkyl,
(e) —O—C$_{1-3}$ alkyl,
(f) —CO$_2$R$^u$,
(g) —NR$^u$R$^v$, or
(h) —C(=O)NR$^u$R$^v$;

$R^4$, $R^5$ and $R^6$ are defined as follows:
(A) each of $R^4$, $R^5$ and $R^6$ is independently —H, —C$_{1-10}$ alkyl, —C$_{3-8}$ cycloalkyl, —C$_{2-10}$ alkenyl, —C$_{2-10}$ alkynyl, phenyl, —C$_{1-6}$ alkyl-phenyl, —C$_{1-6}$ alkyl-C$_{3-8}$ cycloalkyl, naphthyl, or biphenyl; and wherein the alkyl, cycloalkyl, alkenyl, alkynyl, phenyl, phenylalkyl, cycloalkylalkyl, naphthyl, or biphenyl, is optionally subsituted with from 1 to 5 substituents each of which is independently:
(a) halo,
(b) —C$_{1-3}$ haloalkyl,
(c) —OH,
(d) —C$_{1-3}$ alkyl,
(e) —O—C$_{1-3}$ alkyl,
(f) —CO$_2$R$^u$,
(g) —NR$^u$R$^v$, or
(h) —C(=O)NR$^u$R$^v$; or
(B) with the proviso that n is 1, $R^6$ is as defined in (A); and $R^4$ and $R^5$ are joined together to form with the carbon atom to which both are attached a 3- to 8-membered saturated carbocyclic ring which is optionally substituted with from 1 to 5 substituents each of which is independently:
(a) halo,
(b) —C$_{1-3}$ haloalkyl,
(c) —OH,
(d) —C$_{1-3}$ alkyl,
(e) —O—C$_{1-3}$ alkyl,
(f) —CO$_2$R$^u$,
(g) —NR$^u$R$^v$, or
(h) —C(=O)NR$^u$R$^v$;

$R^7$ is —H or —C$_{1-6}$ alkyl;
$R^8$ is —H or —C$_{1-6}$ alkyl;
$R^9$ is —NR$^s$R$^t$,
$R^{14}$ is —H or —C$_{1-10}$ alkyl;
$R^{15}$ is —H, —NR$^s$R$^t$, —C$_{1-10}$ alkyl, —C$_{2-10}$ alkenyl, —C$_{3-8}$ cycloalkyl, —C$_{5-8}$ cycloalkenyl, or —C$_{1-6}$ alkyl-C$_{3-8}$ cycloalkyl; wherein the alkyl, alkenyl, cycloalkyl, cycloalkenyl, or the cycloalkylalkyl is optionally subsituted with from 1 to 5 substituents each of which is independently:
(a) halo,
(b) —C$_{1-3}$ haloalkyl,
(c) —OH,
(d) —C$_{1-3}$ alkyl, or
(e) —O—C$_{1-3}$ alkyl;

$R^s$ and $R^t$ are each independently —H, —C$_{1-6}$ alkyl, or —C$_{1-6}$ alkyl-C$_{3-8}$ cycloalkyl;

each $R^u$ is independently —H, —C$_{1-6}$ alkyl, —C$_{5-6}$ cycloalkyl, benzyl or phenyl, wherein the alkyl, cycloalkyl, benzyl, or phenyl is optionally substituted with from 1 to 3 substituents each of which is independently halo, —C$_{1-3}$ alkyl, —O—C$_{1-3}$ alkyl, or —C$_{1-3}$ haloalkyl;

each $R^v$ is independently —H, —C$_{1-6}$ alkyl, —C$_{5-6}$ cycloalkyl, benzyl or phenyl, wherein the alkyl, cycloalkyl, benzyl, or phenyl is optionally substituted with from 1 to 3 substituents each of which is independently halo, —C$_{1-3}$ alkyl, —O—C$_{1-3}$ alkyl, or —C$_{1-3}$ haloalkyl;

each $R^w$ is independently —H, —C$_{1-6}$ alkyl, —C$_{1-6}$ haloalkyl, —O—C$_{1-6}$ alkyl, —O—C$_{1-6}$ haloalkyl, or —C$_{1-6}$ alkyl-aryl; wherein the aryl in the arylalkyl group is optionally substituted with from 1 to 5 substituents each of which is independently halo, —C$_{1-6}$ alkyl, or —O—C$_{1-6}$ alkyl;

$R^x$ is —H, —C$_{1-6}$ alkyl, —C$_{1-6}$ haloalkyl, or —C$_{1-6}$ alkyl-aryl; wherein the aryl in the arylalkyl group is optionally substituted with from 1 to 5 substituents each of which is independently halo, —C$_{1-6}$ alkyl, or —O—C$_{1-6}$ alkyl;

$R^y$ and $R^z$ are each independently —H or —C$_{1-6}$ alkyl; and
n is an integer which is equal to 1, 2, 3, or 4.

2. The compound according to claim 1, or a pharmaceutically acceptable salt and/or an individual diastereomer thereof, wherein $R^1$ is —CO$_2$H, —C(=O)NR$^y$R$^z$, or tetrazolyl.

3. The compound according to claim 1, or a pharmaceutically acceptable salt and/or an individual diastereomer thereof, wherein $R^1$ is —CO$_2$H or —C(=O)NH$_2$.

4. The compound according to claim 1, or a pharmaceutically acceptable salt and/or an individual diastereomer thereof, wherein $R^1$ is —CO$_2$H.

5. The compound according to claim 1, or a pharmaceutically acceptable salt and/or an individual diastereomer thereof, wherein $R^2$ is:

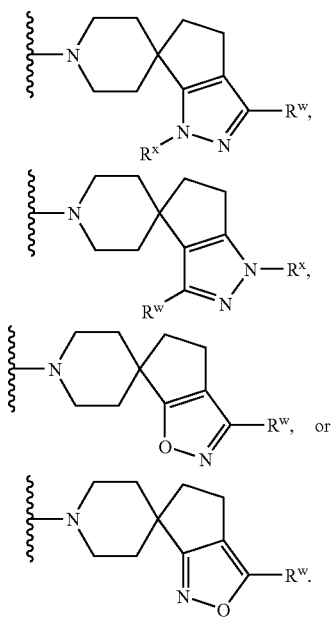

6. The compound according to claim 1, or a pharmaceutically acceptable salt and/or an individual diastereomer thereof, wherein R² is:

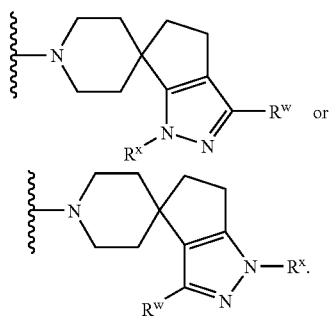

7. The compound according to claim 6, or a pharmaceutically acceptable salt and/or an individual diastereomer thereof, wherein:

R^w is —H, —C_{1-4} alkyl, —C_{1-4} fluoroalkyl, —O—C_{1-4} alkyl, —O—C_{1-4} fluoroalkyl, or —C_{1-3} alkyl-phenyl; wherein the phenyl in the phenylalkyl group is optionally substituted with from 1 to 4 substituents each of which is independently halo, —C_{1-4} alkyl, or —O—C_{1-4} alkyl; and R^x is —H, —C_{1-4} alkyl, —C_{1-4} fluoroalkyl, or —C_{1-3} alkyl-phenyl; wherein the phenyl in phenylalkyl group is optionally substituted with from 1 to 4 substituents each of which is independently halo, —C_{1-4} alkyl, or —O—C_{1-4} alkyl.

8. The compound according to claim 7, or a pharmaceutically acceptable salt and/or an individual diastereomer thereof, wherein:

R^w is —H, —C_{1-3} alkyl, —CF_3, —O—C_{1-3} alkyl, —O—CF_3, or benzyl; wherein the benzyl ring is optionally substituted with from 1 to 3 substituents each of which is independently bromo, chloro, fluoro, —C_{1-3} alkyl, or —O—C_{1-3} alkyl; and R^x is —H, —C_{1-3} alkyl, or —CF_3.

9. The compound according to claim 1, or a pharmaceutically acceptable salt and/or an individual diastereomer thereof, wherein R³ is phenyl which is optionally substituted with from 1 to 3 substituents each of which is independently:
(a) halo,
(b) —C_{1-3} fluoroalkyl,
(c) —OH,
(d) —C_{1-3} alkyl, or
(e) —O—C_{1-3} alkyl.

10. The compound according to claim 1, or a pharmaceutically acceptable salt and/or an individual diastereomer thereof, wherein R³ is phenyl which is optionally substituted with from 1 to 3 substituents each of which is independently:
(a) halo,
(b) —CF_3,
(c) —OH,
(d) —C_{1-3} alkyl, or
(e) —O—C_{1-3} alkyl.

11. The compound according to claim 1, or a pharmaceutically acceptable salt and/or an individual diastereomer thereof, wherein R³ is phenyl which is optionally substituted with from 1 to 3 substituents each of which is independently:
(a) fluoro,
(b) chloro,
(c) —CF_3,
(d) —OH, or
(e) —C_{1-3} alkyl.

12. The compound according to claim 1, or a pharmaceutically acceptable salt and/or an individual diastereomer thereof, wherein R³ is phenyl opitionally substituted with from 1 to 4 substituents each of which is independently fluoro or chloro.

13. The compound according to claim 1, or a pharmaceutically acceptable salt and/or an individual diastereomer thereof, wherein R³ is phenyl, 3-fluorophenyl, 3,4-difluorophenyl, or 3,5-difluorophenyl.

14. The compound according to claim 1, or a pharmaceutically acceptable salt and/or an individual diastereomer thereof, wherein R⁸ is —H or —CH_3.

15. The compound according to claim 1, or a pharmaceutically acceptable salt and/or an individual diastereomer thereof, wherein R⁸ is —H.

16. The compound according to claim 1, or a pharmaceutically acceptable salt and/or an individual diastereomer thereof, wherein R^{15} is —NR^sR^t, —C_{1-10} alkyl, or —C_{1-6} alkyl-C_{3-8} cycloalkyl; wherein the alkyl or the cycloalkylalkyl is optionally subsituted with from 1 to 5 substituents each of which is independently:
(a) halo,
(b) —C_{1-3} haloalkyl,
(c) —OH,
(d) —C_{1-3} alkyl, or
(e) —O—C_{1-3} alkyl.

17. The compound according to claim 1, or a pharmaceutically acceptable salt and/or an individual diastereomer thereof, which is a compound of Formula XA or XB:

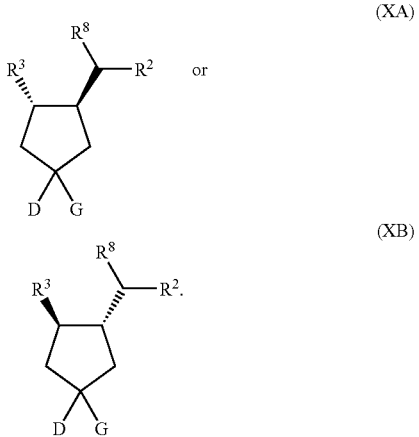

18. A compound selected from the group consisting of
N-methyl-N-(1-(R)-3-(S)-((2'-benzyl-5',6'-dihydrospiro[piperidin-1-yl-4,4'-[4H]pyrrolo[1,2-b]pyrazole])methyl)-4-(S)-(3-fluorophenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((2-ethyl-5,6 dihydrospiro[cyclopentapyrazole-4(2H),4'-piperidin-1'-yl])methyl)-4-(S)-(3-fluorophenyl)cyclopent-1-yl)-(R)-valine;

N-methyl-N-(1-(R)-3-(S)-((2,3-diethyl-4,5-dihydrospiro[cyclopentapyrazole-6(2H),4'-piperidin-1'-yl])methyl)-4-(S)-(3-fluorophenyl)cyclopent-1-yl)-(R)-valine;

N-methyl-N-(1-(R)-3-(S)-((1-ethyl-5,6 dihydrospiro[cyclopentapyrazole-4(1H),4'-piperidin-1'-yl])methyl)-4-(S)-(3-fluorophenyl)cyclopent-1-yl)-(R)-valine;

N-methyl-N-(1-(R)-3-(S)-((1-ethyl-3-methyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((1,3-dimethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((3-methyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((2,3-diethyl-5,6 dihydrospiro[cyclopentapyrazole-4(1H),4'-piperidin-1'-yl])methyl)-4-(S)-(3-fluorophenyl)cyclopent-1-yl)-(R)-valine;

N-methyl-N-(1-(R)-3-(S)-((1,3-diethyl-5,6 dihydrospiro[cyclopentapyrazole-4(1H),4'-piperidin-1'-yl])methyl)-4-(S)-(3-fluorophenyl)cyclopent-1-yl)-(R)-valine;

N-methyl-N-(1-(R)-3-(S)-((3-ethyl-1-methyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R,S)-α-methylvaline;

N-methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-t-butylglycine;

N-methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-leucine;

N-ethyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3,5-difluorophenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3,4-difluorophenyl)cyclopent-1-yl)-(R)-valine;

N-methyl-N-(1-(R)-3-(S)-((1-ethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((1-methyl-3-ethyl-4,5-dihydrospiro[cyclopentapyrazole-6(1H),4'-piperidin-1'-yl])methyl)-4-(S)-(3-fluorophenyl)cyclopent-1-yl)-(R)-t-butylglycine;

N-methyl-N-(1-(R)-3-(S)-((3-ethyl-1-methyl-4,5-dihydrospiro[cyclopentapyrazole-6(1H),4'-piperidin-1'-yl])methyl)-4-(S)-(3,5-difluorophenyl)cyclopent-1-yl)-(R)-valine;

N-methyl-N-(1-(R)-3-(S)-((3-ethyl-4,5-dihydrospiro[6H-cyclopent[d]isoxazole-6,4'-piperidin-1'-yl])methyl)-4-(S)-(3-fluorophenyl)cyclopent-1-yl)-(R)-valine;

N-methyl-N-(1-(R)-3-(S)-((3-ethyl-4,5-dihydrospiro[6H-cyclopent[c]isoxazole-6,4'-piperidin-1'-yl])methyl)-4-(S)-(3-fluorophenyl)cyclopent-1-yl)-(R)-valine;

N-methyl-N-(1-(R)-3-(S)-((1-ethyl-3-methoxy-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(R)-3-(S)-((2-ethyl-3-methoxy-4,5-dihydrospiro[cyclopentapyrazole-6(2H),4'-piperidin-1'-yl])methyl)-4-(S)-(3-fluorophenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3-fluoro-4-methylphenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3,4-dichlorophenyl)cyclopent-1-yl)-(R)-valine;

N-methyl-N-(1-(R)-3-(S)-((1,3-diethyl-4,5-dihydrospiro[cyclopentapyrazole-6(1H),4'-piperidin-1'-yl])methyl)-4-(S)-(3,5-difluorophenyl)cyclopent-1-yl)-(R)-t-butylglycine;

N-methyl-N-(1-(R)-3-(S)-((1,3-diethyl-4,5-dihydrospiro[cyclopentapyrazole-6(1H),4'-piperidin-1'-yl])methyl)-4-(S)-(4-fluorophenyl)cyclopent-1-yl)-(R)-valine;

N-methyl-N-(1-(R)-3-(S)-((1-ethyl-3-methoxy-5,6-dihydrospiro[cyclopenta-pyrazole-4(2H),4'-piperidin-1'-yl])methyl)-4-(S)-(3-fluorophenyl)cyclopent-1-yl)-(R)-valine;

N-methyl-N-(1-(R)-3-(S)-((2-ethyl-3-methoxy-5,6-dihydrospiro[cyclopenta-pyrazole-4(2H),4'-piperidin-1'-yl])methyl)-4-(S)-(3-fluorophenyl)cyclopent-1-yl)-(R)-valine;

N-methyl-N-(1-(R)-3-(S)-((1-methyl-3-methoxy-4,5-dihydrospiro[cyclopenta-pyrazole-6(1H),4'-piperidin-1'-yl])methyl)-4-(S)-(3-fluorophenyl)cyclopent-1-yl)-(R)-valine;

N-methyl-N-(1-(R)-3-(S)-((1-ethyl-3-methoxy-4,5-dihydrospiro[cyclopentapyrazole-6(1H),4'-piperidin-1'-yl])methyl)-4-(S)-(3,5-difluorophenyl)cyclopent-1-yl)-(R)-t-butylglycine;

N-methyl-N-(1-(R)-3-(S)-((3-ethyl-1-methyl-4,5-dihydrospiro[cyclopentapyrazole-6(1H),4'-piperidin-1'-yl])methyl)-4-(S)-(3,5-difluorophenyl)cyclopent-1-yl)-(R)-t-butylglycine;

N-methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-valine;

N-methyl-N-(1-(S)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-valine;

N-methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-t-butylglycine;

N-methyl-N-(1-(S)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopent-1-yl)-(R)-t-butylglycine;

N-methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3,5-difluorophenyl)cyclopent-1-yl)-(R)-valine;

N-methyl-N-(1-(S)-3-(S)-(1-(R)-(1,3-diethyl-4,5-dihydrospiro[cyclopentapyrazole-6(1H),4'-piperidin-1'-yl])eth-1-yl)-4-(S)-(3,5-difluorophenyl)cyclopent-1-yl)-(R)-valine;

N-methyl-N-(1-(R)-3-(S)-(1-(R)-(1,3-diethyl-4,5-dihydrospiro[cyclopentapyrazole-6(1H),4'-piperidin-1'-yl])eth-1-yl)-4-(S)-(3,5-difluorophenyl)cyclopent-1-yl)-(R)-t-butylglycine;

N-methyl-N-(1-(S)-3-(S)-(1-(R)-(1,3-diethyl-4,5-dihydrospiro[cyclopentapyrazole-6(1H),4'-piperidin-1'-yl])eth-1-yl)-4-(S)-(3,5-difluorophenyl)cyclopent-1-yl)-(R)-t-butylglycine;

N-methyl-N-(1-(R)-methyl-3-(S)-(1-(R)-(1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-methyl-N-(1-(S)-methyl-3-(S)-(1-(R)-(1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-(1-(R)-methyl-3-(S)-(1-(R)-(1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-(1-(S)-methyl-3-(S)-(1-(R)-(1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valine;

N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R,S)-α-methylvaline;

N-(1-(S)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R,S)-α-methylvaline;

N-methyl-N-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valinamide;

N-methyl-N-(1-(S)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-(R)-valinamide;

N-methyl-N-(1-(R)-3-(S)-((2'-ethyl-5',6'-dihydrospiro[piperidin-1-yl-4,4'-[4H]pyrrolo[1,2-b]pyrazole])methyl)-4-(S)-(3-fluorophenyl)cyclopent-1-yl)-(R)-valine;

N-methyl-N-(1-(R)-3-(S)-((1,3-diethyl-4,6-dihydrospiro[furo[3,4-c]pyrazole-6(1H),4'-piperidin-1'-yl])methyl)-4-(S)-(3-fluorophenyl)cyclopent-1-yl)-(R)-valine;

N-methyl-N-(1-(R)-3-(S)-((2,3-diethyl-4,6-dihydrospiro[furo[3,4-c]pyrazole-6(1H),4'-piperidin-1'-yl])methyl)-4-(S)-(3-fluorophenyl)cyclopent-1-yl)-(R)-valine;

2-(S)-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-2-(1,1-dimethylprop-1-ylamino)acetic acid;

2-(S)-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-2-((1,1-dimethylprop-1-yl)methylamino)acetic acid;

2-(S)-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-3-(cyclopropyl)propionic acid;

2-(R)-(1-(R)-3-(S)-((1,3-diethyl-4,5-dihydrospiro[cyclopentapyrazole-6(1H),4'-piperidin-1'-yl])methyl)-4-(S)-(3-fluorophenyl)cyclopent-1-yl)-3-(cyclopropyl)propionic acid;

1-(R or S)-(2,2-dimethylprop-1-ylamino)-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylic acid;

1-(R or S)-((2,2-dimethylprop-1-yl)methylamino)-3-(S)-((1,3-diethyl-4,5-dihydrospiro[cyclopentapyrazole-6(1H),4'-piperidin-1'-yl])methyl)-4-(S)-(3-fluorophenyl)cyclopentane carboxylic acid;

1-(S)-((2,2-dimethylprop-1-yl)amino)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylic acid;

1-(R)-((2,2-dimethylprop-1-yl)amino)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylic acid;

1-(R)-(dimethylamino)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylic acid;

1-(S)-(dimethylamino)-3-(S)-(1-(R)-(1,3-diethyl-4,5-dihydrospiro[cyclopentapyrazole-6(1H),4'-piperidin-1'-yl])eth-1-yl)-4-(S)-(3-fluorophenyl)cyclopentane carboxylic acid;

and pharmaceutically acceptable salts thereof.

19. A pharmaceutical composition which comprises an effective amount of a compound according to claim 1, or a pharmaceutically acceptable salt and/or an individual diastereomer thereof, and a pharmaceutically acceptable carrier.

20. A method for treating infection by HIV, delaying of the onset of AIDS, or inhibit progression to AIDS in a subject in need thereof, which comprises administering to the subject a therapeutically effective amount of a compound according to claim 1, or a pharmaceutically acceptable salt and/or an individual diastereomer thereof.

* * * * *